(12) United States Patent
Mihara et al.

(10) Patent No.: US 9,227,923 B2
(45) Date of Patent: Jan. 5, 2016

(54) PESTICIDAL CARBOXAMIDES

(75) Inventors: Jun Mihara, Osaka (JP); Koichi Araki, Ibaraki (JP); Takuma Mori, Tokyo (JP); Tetsuya Murata, Osaka (JP); Yasushi Yoneta, Saitama (JP); Yukiyoshi Watanabe, Osaka (JP); Eiichi Shimojo, Osaka (JP); Teruyuki Ichihara, Tochigi (JP); Masashi Ataka, Saitama (JP); Katsuhiko Shibuya, Tochigi (JP); Ulrich Gorgens, Ratingen (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/390,302

(22) PCT Filed: Aug. 3, 2010

(86) PCT No.: PCT/EP2010/004739
§ 371 (c)(1),
(2), (4) Date: Feb. 13, 2012

(87) PCT Pub. No.: WO2011/018170
PCT Pub. Date: Feb. 17, 2011

(65) Prior Publication Data
US 2012/0149910 A1 Jun. 14, 2012

(30) Foreign Application Priority Data

Aug. 14, 2009 (JP) .................................. 2009-188049
Mar. 12, 2010 (JP) .................................. 2010-055470

(51) Int. Cl.
*C07C 233/65* (2006.01)
*A01N 37/18* (2006.01)
*C07C 233/66* (2006.01)
(Continued)

(52) U.S. Cl.
CPC ............. *C07C 233/66* (2013.01); *A01N 37/42* (2013.01); *A01N 37/44* (2013.01); *A01N 37/48* (2013.01); *A01N 37/50* (2013.01); *A01N 43/40* (2013.01); *A01N 43/56* (2013.01); *C07C 235/84* (2013.01); *C07C 237/40* (2013.01); *C07C 237/42* (2013.01); *C07C 237/48* (2013.01); *C07C 251/44* (2013.01); *C07C 251/48* (2013.01); *C07C 255/19* (2013.01); *C07C 255/57* (2013.01); *C07C 271/22* (2013.01); *C07C 275/24* (2013.01); *C07C 309/66* (2013.01); *C07C 311/06* (2013.01); *C07C 323/60* (2013.01); *C07D 209/48* (2013.01); *C07D 213/61* (2013.01); *C07D 213/81* (2013.01); *C07D 213/82* (2013.01); *C07D 213/84* (2013.01); *C07D 213/85* (2013.01); *C07D 231/12* (2013.01); *C07D 231/16* (2013.01); *C07D 249/08* (2013.01); *C07D 249/18* (2013.01); *C07D 249/20* (2013.01); *C07D 257/04* (2013.01); *C07D 295/155* (2013.01); *C07D 401/12* (2013.01); *C07C 2101/02* (2013.01); *C07C 2101/04* (2013.01); *C07C 2101/08* (2013.01); *C07C 2101/10* (2013.01); *C07C 2101/14* (2013.01); *C07C 2102/08* (2013.01)

(58) Field of Classification Search
CPC .. C07C 237/42; C07C 255/60; C07C 237/40; C07C 233/64; C07D 231/12; C07D 207/327; C07D 233/61; C07D 249/18; C07D 213/82; C07D 249/08; C07D 257/04; A01N 37/42; A01N 37/44; A01N 37/48; A01N 37/50; A01N 43/40; A01N 43/56
USPC .......... 564/155, 158, 164, 180, 184; 514/616, 514/352, 383, 403, 520; 546/352; 548/253, 548/262.4, 265.8, 343.5, 377.1, 563; 558/416
See application file for complete search history.

(56) References Cited

U.S. PATENT DOCUMENTS 7,662,972 B2    2/2010   Mita et al.
7,964,735 B2 *  6/2011   Yanagi et al. ................. 546/316
(Continued)

FOREIGN PATENT DOCUMENTS

EP    1 649 852 A1   4/2006
EP    1 932 836 A1   6/2008
(Continued)

OTHER PUBLICATIONS

Angyal, S.J., "The Sommelet Reaction," in *Organic Reactions*, vol. 8, pp. 197-217, John Wiley & Sons, United States., United States (1954).
Caddick, S., et al., "A generic approach for the catalytic reduction of nitriles," *Tetrahedron* 59:5417-5423, Elsevier Science Ltd, England (2003).
(Continued)

*Primary Examiner* — Shailendra Kumar
(74) *Attorney, Agent, or Firm* — Sterne, Kessler, Goldstein & Fox P.L.L.C.

(57) ABSTRACT

The object of the present invention is to provide novel carboxamides which exhibit an excellent pesticidal activity as pesticides. Disclosed are the carboxamides represented by the following Formula (I):

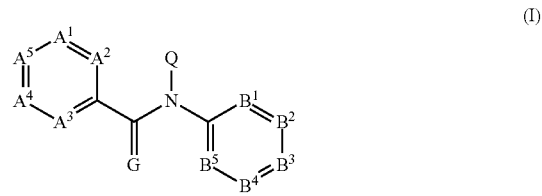

(I)

wherein each substituent is as defined in the specification, and use thereof as pesticides and animal parasite controlling agents.

8 Claims, No Drawings

(51) Int. Cl.

| | | |
|---|---|---|
| *A01N 37/42* | (2006.01) | |
| *A01N 37/44* | (2006.01) | |
| *A01N 37/48* | (2006.01) | |
| *A01N 37/50* | (2006.01) | |
| *A01N 43/40* | (2006.01) | |
| *A01N 43/56* | (2006.01) | |
| *C07C 235/84* | (2006.01) | |
| *C07C 237/40* | (2006.01) | |
| *C07C 237/42* | (2006.01) | |
| *C07C 237/48* | (2006.01) | |
| *C07C 251/44* | (2006.01) | |
| *C07C 251/48* | (2006.01) | |
| *C07C 255/19* | (2006.01) | |
| *C07C 255/57* | (2006.01) | |
| *C07C 271/22* | (2006.01) | |
| *C07C 275/24* | (2006.01) | |
| *C07C 309/66* | (2006.01) | |
| *C07C 311/06* | (2006.01) | |
| *C07C 323/60* | (2006.01) | |
| *C07D 209/48* | (2006.01) | |
| *C07D 213/61* | (2006.01) | |
| *C07D 213/81* | (2006.01) | |
| *C07D 213/82* | (2006.01) | |
| *C07D 213/84* | (2006.01) | |
| *C07D 213/85* | (2006.01) | |
| *C07D 231/12* | (2006.01) | |
| *C07D 231/16* | (2006.01) | |
| *C07D 249/08* | (2006.01) | |
| *C07D 249/18* | (2006.01) | |
| *C07D 249/20* | (2006.01) | |
| *C07D 257/04* | (2006.01) | |
| *C07D 295/155* | (2006.01) | |
| *C07D 401/12* | (2006.01) | |

(56) References Cited

U.S. PATENT DOCUMENTS

| | | | | |
|---|---|---|---|---|
| 8,202,858 B2* | 6/2012 | Batt et al. | | 514/217 |
| 8,247,594 B2* | 8/2012 | Jung et al. | | 560/29 |
| 2002/0198399 A1 | 12/2002 | Onishi et al. | | |
| 2004/0102492 A1 | 5/2004 | Cogan et al. | | |
| 2004/0248947 A1* | 12/2004 | Bold et al. | | 514/352 |
| 2007/0027154 A1 | 2/2007 | Yoshida et al. | | |
| 2007/0275980 A1 | 11/2007 | Yoshida et al. | | |
| 2008/0182837 A1 | 7/2008 | Steurer et al. | | |
| 2009/0099204 A1 | 4/2009 | Yoshida et al. | | |
| 2009/0192175 A1 | 7/2009 | Jung et al. | | |
| 2009/0233962 A1 | 9/2009 | Kai et al. | | |
| 2010/0234409 A1* | 9/2010 | Yang et al. | | 514/278 |

FOREIGN PATENT DOCUMENTS

| | | |
|---|---|---|
| EP | 2 201 946 A1 | 6/2010 |
| JP | H0892224 A | 4/1996 |
| JP | H9-59236 | 3/1997 |
| JP | 2001-064268 A | 3/2001 |
| JP | 2003034673 A | 2/2003 |
| JP | 2003040864 A | 2/2003 |
| JP | 2004-534098 | 11/2004 |
| JP | 2006-514940 | 5/2006 |
| JP | 2006-306771 A | 11/2006 |
| JP | 2007-099761 A | 4/2007 |
| JP | 2007-302617 A | 11/2007 |
| JP | 2007306471 A | 11/2007 |
| JP | 2009-518442 | 5/2009 |
| JP | 2009209090 A | 9/2009 |
| JP | 2011-524365 | 9/2011 |
| JP | 2012-504114 | 2/2012 |
| WO | WO 03/006456 A1 | 1/2003 |
| WO | WO 03/011028 A1 | 2/2003 |
| WO | WO 2005/007151 A1 | 1/2005 |
| WO | WO 2006/024412 A2 | 3/2006 |
| WO | WO 2007/017075 A1 | 2/2007 |
| WO | WO 2007/051560 A1 | 5/2007 |
| WO | WO 2007/067836 A2 | 6/2007 |
| WO | WO 2008/000438 A1 | 1/2008 |
| WO | WO 2008/012027 A1 | 1/2008 |
| WO | WO 2008/031534 A1 | 3/2008 |
| WO | WO 2008/074427 A1 | 6/2008 |
| WO | WO 2008/107091 A1 | 9/2008 |
| WO | WO 2009/049844 A1 | 4/2009 |
| WO | WO 2009/049845 A2 | 4/2009 |
| WO | WO 2009/054439 A1 | 4/2009 |
| WO | WO 2009/152356 A2 | 12/2009 |
| WO | WO 2010/034838 A2 | 4/2010 |
| WO | WO 2010/127927 A1 | 11/2010 |
| WO | WO 2011/009540 A2 | 1/2011 |

OTHER PUBLICATIONS

Caddick, S., et al., "Convenient synthesis of protected primary amines from nitriles," *Tetrahedron Letters* 41:3513-3516, Elsevier Science Ltd., England (2000).

Delépine, M., "Sur l'hexaméthylène-amine (suite). Solubilités, hydrate, bromure, sulfate, phosphate," *Bull. Soc. Chim.* 13:352-355, Bulletin de la Société Chimique de Paris, France (1895).

Henry, R. A., et al., "Anomalous Reaction of Pentafluorophenacyl Bromide with Hexamethylenetetramine. Structure of the Product," *J. Org. Chem.*, 55(6):1796-1801, American Chemical Society, USA (1990).

Kornblum, N. and Ungnade, H.E. "1-Nitroöctane," in *Organic Syntheses Coll.*, vol. 4, pp. 724-727, John Wiley & Sons, United States., United States (1963).

Kornblum, N., "The Synthesis of Aliphatic and Alicyclic Nitro Compounds," in *Organic Reactions*, vol. 12, pp. 101-156, John Wiley & Sons, United States., United States (1962).

Scriven, E.F.V. and Turnbull, K., "Azides: Their Preparation and Synthetic Uses," *Chemical Review*, 88(2):297-368, American Chemical Society, United States (1988).

Thompson, A.S., et al., "Direct Conversion of Activated Alcohols to Azides Using Diphenyl Phosphorazidate. A Practical Alternative to Mitsunobu Conditions," *J. Org. Chem.*, 58(22): 5886-5888, American Chemical Society, United States (1993).

Warmus, J.S., et al., A Modified Procedure for the Preparation of 2,5-Dihydropyrrole (3-Pyrroline), *J. Org. Chem.* 58 (1):270-271, American Chemical Society, United States (1993).

English language Abstract of Japanese Patent Publication No. 2007-099761 A, Japanese Patent Office, Patent & Utility Model Gazette DB, Patent Abstracts of Japan (2007).

English language Abstract of Japanese Patent Publication No. 2007-302617 A, Japanese Patent Office, Patent & Utility Model Gazette DB, Patent Abstracts of Japan (2007).

English language Abstract of Japanese Patent Publication No. 2006-306771 A, Japanese Patent Office, Patent & Utility Model Gazette DB, Patent Abstracts of Japan (2006).

Chemical Abstracts Service, Database Registry, CAS Registry No. 930462-65-0, Benzamide, N-[4-(difluoromethoxy)-3-(phenylmethyl)phenyl]-3-nitro-4-(1H-1,2,4-triazol-1-yl)-, retrieved from STN, Jan. 25, 2008.

Chemical Abstracts Service, Database Registry, CAS Registry No. 338407-82-2, Benzamide, 3-nitro-4-(1H-1,2,4-triazol-1-yl)-N-[3-(trifluoromethyl)phenyl]-, retrieved from STN, Jan. 25, 2008.

International Search Report for International Application No. PCT/EP2010/004739, European Patent Office, The Hague, Netherlands, mailed on Jun. 3, 2011.

Bhattacharjee, A.K. and Karle, J.M., "Molecular Electronic Properties of a Series of 4-Quinolinecarbinolamines Define Antimalarial Activity Profile," *J. Med. Chem.* 39:4622-4629, American Chemical Society, United States (1996).

English language Abstract of Japanese Patent No. JPH 9-59236 A. 2008.

* cited by examiner

PESTICIDAL CARBOXAMIDES

This application is a 371 of PCT/EP2010/004739, filed Aug. 3, 2010.

TECHNICAL FIELD

The present invention relates to pesticidal carboxamides and their use as pesticides.

BACKGROUND ART

Pesticidal carboxamide compounds are useful as agents for controlling harmful organisms.

EP 1 661 886 A1 (WO 2005/021488), EP 1 714 958 A1 (WO 2005/073165), EP 1 916 236 A1 (WO 2006/137395), EP 1 911 7510 A1 (WO 2006/137376), WO 2008/000438, WO 2008/012027, WO 2008/031534, WO 2008/074427, WO 2008/107091, WO 2009/049844, WO 2009/049845, WO 2007/017075, JP 2006/306771, JP2007/302617 and JP 2007/099761 A refer to insecticidal compounds. WO 2007/128410, WO 2007/051560 discloses insecticidal compounds having a 5 membered ring-system in the core structure.

SUMMARY OF THE INVENTION

Inventors of the present invention extensively studied to develop novel compounds which are highly active as pesticides and have a broad spectrum use. As a result, the inventors found that the novel carboxamides represented by the following Formula (I) have a high activity, a broad spectrum use and safety, and also are effective against harmful pests that are resistant to organic phosphorous agents or carbamate agents.

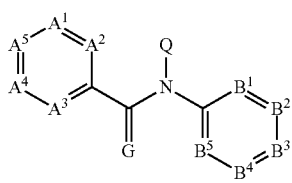

(I)

wherein $A^1$, $A^2$, $A^3$, $A^4$ and $A^5$ each independently represent nitrogen, C—$X^1$ or C-T, provided that at least one of $A^1$, $A^2$, $A^3$, $A^4$ and $A^5$ is C-T;

$B^1$, $B^2$, $B^3$, $B^4$ and $B^5$ each independently represent nitrogen, C—$X^2$ or C-J, provided that at least one of B', $B^2$, $B^3$, $B^4$ and $B^5$ is C-J;

G represents oxygen or sulfur;

Q represents hydrogen, $C_{1-12}$ alkyl, $C_{1-12}$ haloalkyl, ($C_{1-12}$ alkyl)carbonyl, ($C_{1-12}$ haloalkyl)carbonyl, ($C_{1-12}$ alkoxy)carbonyl or ($C_{1-12}$ haloalkoxy)carbonyl;

$X^1$ and $X^2$ each independently represent hydrogen, cyano, halogen, nitro, hydroxy, mercapto, amino, formyl, oxide, $C_{1-12}$ alkyl, $C_{1-12}$ haloalkyl, aryl-($C_{1-12}$)alkyl, heterocyclyl-($C_{1-12}$)alkyl, $C_{1-12}$ alkyl-O—, $C_{1-12}$ alkyl-NH—, $C_{1-12}$ alkyl-S—, $C_{1-12}$ alkyl-S(O)—, $C_{1-12}$ alkyl-S(O)$_2$—, $C_{1-12}$ alkyl-S(O)$_2$O—, $C_{1-12}$ haloalkyl-O—, $C_{1-12}$ haloalkyl-NH—, $C_{1-12}$ haloalkyl-S—, $C_{1-12}$ haloalkyl-S(O)—, $C_{1-12}$ haloalkyl-S(O)$_2$—, $C_{1-12}$ haloalkyl-S(=O)$_2$O—, aryl-O—, aryl-NH—, aryl-S—, aryl-S(O)—, aryl-S(O)$_2$—, aryl-S(O)$_2$O—, heterocyclyl-O—, heterocyclyl-NH—, heterocyclyl-S—, heterocyclyl-S(O)—, heterocyclyl-S(O)$_2$—, heterocyclyl-S(O)$_2$O—, $C_{1-12}$ alkyl-O—($C_{1-12}$)alkyl, $C_{1-12}$ alkyl-NH—($C_{1-12}$)alkyl, $C_{1-12}$ alkyl-S—($C_{1-12}$)alkyl, $C_{1-12}$ alkyl-S(O)—($C_{1-12}$)alkyl, $C_{1-12}$ alkyl-S(O)$_2$—($C_{1-12}$)alkyl, $C_{1-12}$ alkyl-S(O)$_2$O—($C_{1-12}$)alkyl, $C_{1-12}$ haloalkyl-O—($C_{1-12}$)alkyl, $C_{1-12}$ haloalkyl-NH—($C_{1-12}$)alkyl, $C_{1-12}$ haloalkyl-S—($C_{1-12}$)alkyl, $C_{1-12}$ haloalkyl-S(O)—($C_{1-12}$)alkyl, $C_{1-12}$ haloalkyl-S(O)$_2$—($C_{1-12}$)alkyl, $C_{1-12}$ haloalkyl-S(O)$_2$O—($C_{1-12}$)alkyl, aryl-O—($C_{1-12}$)alkyl, aryl-NH—($C_{1-12}$)alkyl, aryl-S—($C_{1-12}$)alkyl, aryl-S(O)—($C_{1-12}$)alkyl, aryl-S(O)$_2$—($C_{1-12}$)alkyl, aryl-S(O)$_2$O—($C_{1-12}$)alkyl, heterocyclyl-O—($C_{1-12}$)alkyl, heterocyclyl-NH—($C_{1-12}$)alkyl, heterocyclyl-S—($C_{1-12}$)alkyl, heterocyclyl-S(O)—($C_{1-12}$)alkyl, heterocyclyl-S(O)$_2$—($C_{1-12}$)alkyl, heterocyclyl-S(O)$_2$O—($C_{1-12}$)alkyl, $C_{3-8}$ cycloalkyl, $C_{3-8}$ cycloalkyl-($C_{1-12}$)alkyl-, $C_{3-8}$ halocycloalkyl, $C_{3-8}$ halocycloalkyl-($C_{1-12}$)alkyl-, $C_{2-12}$ alkenyl, $C_{2-12}$ haloalkenyl, $C_{2-12}$ alkynyl, $C_{2-12}$ haloalkynyl, di($C_{1-12}$ alkyl)amino, di($C_{1-12}$ haloalkyl)amino, $C_{3-36}$ trialkylsilyl, hydroxyimino($C_{1-12}$)alkyl, $C_{1-12}$ alkyl-O—N=($C_{1-12}$)alkyl, $C_{1-12}$ alkyl-NH—N=($C_{1-12}$)alkyl, $C_{1-12}$ alkyl-S—N=($C_{1-12}$)alkyl, $C_{1-12}$ alkyl-S(O)—N=($C_{1-12}$)alkyl, $C_{1-12}$ alkyl-S(O)$_2$—N=($C_{1-12}$)alkyl, $C_{1-12}$ alkyl-S(O)$_2$O—N=($C_{1-12}$)alkyl, $C_{1-12}$ haloalkyl-O—N=($C_{1-12}$)alkyl, $C_{1-12}$ haloalkyl-NH—N=($C_{1-12}$)alkyl, $C_{1-12}$ haloalkyl-S—N=($C_{1-12}$)alkyl, $C_{1-12}$ haloalkyl-S(O)—N=($C_{1-12}$)alkyl, $C_{1-12}$ haloalkyl-S(O)$_2$—N=($C_{1-12}$)alkyl, $C_{1-12}$ haloalkyl-S(O)$_2$O—N=($C_{1-12}$)alkyl, ($C_{1-12}$ alkoxy)carbonyl, ($C_{1-12}$ haloalkoxy)carbonyl, ($C_{3-8}$ cycloalkoxy)carbony, ($C_{3-8}$ halocycloalkoxy)carbony, $C_{3-8}$ cycloalkyl-($C_{1-12}$ alkoxy)carbony, $C_{3-8}$ halocycloalkyl-($C_{1-12}$ alkoxy)carbony, ($C_{1-12}$ alkyl)carbonyl, ($C_{1-12}$ haloalkyl)carbonyl, ($C_{3-8}$ cycloalkyl)carbonyl, ($C_{3-8}$ halocycloalkyl)carbonyl, $C_{3-8}$ cycloalkyl-($C_{1-12}$)alkyl-carbonyl, ($C_{3-8}$ halocycloalkyl)-($C_{1-12}$)alkyl-carbonyl, an aryl group, a heterocyclic group, sulfur pentafluoride, or one of the substituents represented by the following Formulae (X1-1) to (X1-5):

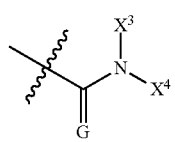

X1-1

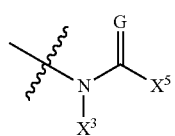

X1-2

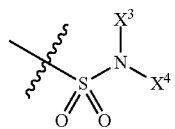

X1-3

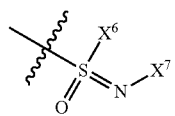

X1-4

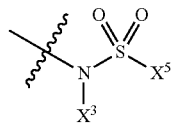

X1-5 wherein G independently has the same meaning as G described above;

$X^3$, $X^4$ and $X^5$ each independently represent hydrogen, cyano, halogen, nitro, hydroxy, mercapto, amino, formyl, $C_{1-12}$ alkyl, $C_{1-12}$ haloalkyl, aryl-($C_{1-12}$)alkyl, heterocyclyl-($C_{1-12}$)alkyl, $C_{1-12}$ alkyl-O—, $C_{1-12}$ alkyl-NH—, $C_{1-12}$ alkyl-S—, $C_{1-12}$ alkyl-S(O)—, $C_{1-12}$ alkyl-S(O)$_2$—, $C_{1-12}$ alkyl-S(O)$_2$O—, $C_{1-12}$ haloalkyl-O—, $C_{1-12}$ haloalkyl-NH—, $C_{1-12}$ haloalkyl-S—, $C_{1-12}$ haloalkyl-S(O)—, $C_{1-12}$ haloalkyl-S(O)$_2$—, $C_{1-12}$ haloalkyl-S(O)$_2$O—, aryl-O—, aryl-NH—, aryl-S—, aryl-S(O)—, aryl-S(O)$_2$—, aryl-S(O)$_2$O—, heterocyclyl-O—, heterocyclyl-NH—, heterocyclyl-S—, heterocyclyl-S(O)—, heterocyclyl-S(O)$_2$—, heterocyclyl-S(O)$_2$O—, $C_{1-12}$ alkyl-O—($C_{1-12}$)alkyl, $C_{1-12}$ alkyl-NH—($C_{1-12}$)alkyl, $C_{1-12}$ alkyl-S—($C_{1-12}$)alkyl, $C_{1-12}$ alkyl-S(O)—($C_{1-12}$)alkyl, $C_{1-12}$ alkyl-S(O)$_2$—($C_{1-12}$)alkyl, $C_{1-12}$ alkyl-S(O)$_2$O—($C_{1-12}$)alkyl, $C_{1-12}$ haloalkyl-O—($C_{1-12}$)alkyl, $C_{1-12}$ haloalkyl-NH—($C_{1-12}$)alkyl, $C_{1-12}$ haloalkyl-S—($C_{1-12}$)alkyl, $C_{1-12}$ haloalkyl-S(O)—($C_{1-12}$)alkyl, $C_{1-12}$ haloalkyl-S(O)$_2$—($C_{1-12}$)alkyl, $C_{1-12}$ haloalkyl-S(O)$_2$O—($C_{1-12}$)alkyl, aryl-O—($C_{1-12}$)alkyl, aryl-NH—($C_{1-12}$)alkyl, aryl-S—($C_{1-12}$)alkyl, aryl-S(O)—($C_{1-12}$)alkyl, aryl-S(O)$_2$—($C_{1-12}$)alkyl, aryl-S(O)$_2$O—($C_{1-12}$)alkyl, heterocyclyl-O—($C_{1-12}$)alkyl, heterocyclyl-NH—($C_{1-12}$)alkyl, heterocyclyl-S—($C_{1-12}$)alkyl, heterocyclyl-S(O)—($C_{1-12}$)alkyl, heterocyclyl-S(O)$_2$—($C_{1-12}$)alkyl, heterocyclyl-S(O)$_2$O—($C_{1-12}$)alkyl, $C_{3-8}$ cycloalkyl, $C_{3-8}$ cycloalkyl-($C_{1-12}$)alkyl-, $C_{3-8}$ halocycloalkyl, $C_{3-8}$ halocycloalkyl-($C_{1-12}$)alkyl-, $C_{2-12}$ alkenyl, $C_{2-12}$ haloalkenyl, $C_{2-12}$ alkynyl, $C_{2-12}$ haloalkynyl, di($C_{1-12}$ alkyl)amino, di($C_{1-12}$ haloalkyl)amino, $C_{3-36}$ trialkylsilyl, hydroxyimino($C_{1-12}$)alkyl, $C_{1-12}$ alkyl-O—N=($C_{1-12}$)alkyl, $C_{1-12}$ alkyl-NH—N=($C_{1-12}$)alkyl, $C_{1-12}$ alkyl-S—N=($C_{1-12}$)alkyl, $C_{1-12}$ alkyl-S(O)—N=($C_{1-12}$)alkyl, $C_{1-12}$ alkyl-S(O)$_2$—N=($C_{1-12}$)alkyl, $C_{1-12}$ alkyl-S(O)$_2$O—N=($C_{1-12}$)alkyl, $C_{1-12}$ haloalkyl-O—N=($C_{1-12}$)alkyl, $C_{1-12}$ haloalkyl-NH—N=($C_{1-12}$)alkyl, $C_{1-12}$ haloalkyl-S—N=($C_{1-12}$)alkyl, $C_{1-12}$ haloalkyl-S(O)—N=($C_{1-12}$)alkyl, $C_{1-12}$ haloalkyl-S(O)$_2$—N=($C_{1-12}$)alkyl, $C_{1-12}$ haloalkyl-S(O)$_2$O—N=($C_{1-12}$)alkyl, ($C_{1-12}$ alkoxy)carbonyl, ($C_{1-12}$ haloalkoxy)carbonyl, ($C_{3-8}$ cycloalkoxy)carbony, ($C_{3-8}$ halocycloalkoxy)carbony, $C_{3-8}$ cycloalkyl-($C_{1-12}$ alkoxy)carbony, $C_{3-8}$ halocycloalkyl-($C_{1-12}$ alkoxy)carbony, ($C_{1-12}$ alkyl)carbonyl, ($C_{1-12}$ haloalkyl)carbonyl, ($C_{3-8}$ cycloalkyl) carbonyl, ($C_{3-8}$ halocycloalkyl)carbonyl, $C_{3-8}$ cycloalkyl-($C_{1-12}$)alkyl-carbonyl, $C_{3-8}$ halocycloalkyl-($C_{1-42}$)alkyl-carbonyl, aryl-carbonyl, heterocyclyl-carbonyl, aryl-($C_{1-12}$) alkyl-carbonyl, heterocyclyl-($C_{1-12}$)alkyl-carbonyl, sulfur pentafluoride, an aryl group or a heterocyclic group, $X^3$ and $X^4$ may form a heterocycle together with the nitrogen atom, carbon atom, oxygen atom or sulfur atom to which they are bonded, $X^3$ and $X^5$ may form a heterocycle together with the nitrogen atom, carbon atom, oxygen atom or sulfur atom to which they are bonded;

$X^6$ each independently represents hydrogen, $C_{1-12}$ alkyl, $C_{1-12}$ haloalkyl, $C_{3-8}$ cycloalkyl, $C_{2-12}$ alkenyl, $C_{2-12}$ haloalkenyl, an aryl group, a heterocyclic group, aryl-($C_{1-12}$)alkyl or heterocyclyl-($C_{1-12}$)alkyl;

$X^7$ each independently represents hydrogen, nitro, cyano, formyl, $X^8$-carbonyl or $X^8$-oxycarbonyl, wherein $X^8$ independently has the same meaning as $X^6$ described above;

J each independently represents $C_{1-12}$ haloalkyl, $C_{1-12}$ haloalkyl-O—, $C_{1-12}$ haloalkyl-S—, $C_{1-12}$ haloalkyl-S(=O)—, $C_{1-12}$ haloalkyl-S(=O)$_2$—, $C_{3-8}$ halocycloalkyl, —C($J^1$)($J^2$)($J^3$) or —C ($J^1$)($J^2$)(O$J^4$), wherein $J^1$ and $J^2$ each independently represent $C_{1-12}$ haloalkyl, $J^3$ represents a heterocyclic group, $J^4$ represents hydrogen, $C_{1-12}$ alkyl, $C_{1-12}$ haloalkyl, $C_{1-12}$ alkylsulfonyl, $C_{1-12}$ haloalkylsulfonyl, arylsulfonyl, an aryl group or a heterocyclic group;

T represents a 5- to 6-membered heterocycle or any one of the substituents represented by the following Formulae (X2-1) to (X2-4):

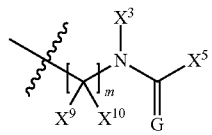

X2-1

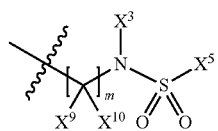

X2-2

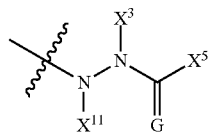

X2-3

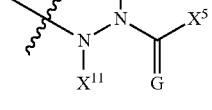

X2-4 or

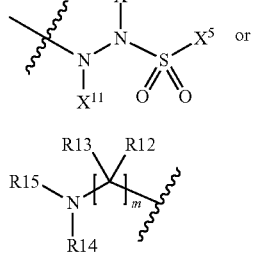

X2-5 wherein $X^3$, $X^5$ and G independently have the same meaning as $X^3$, $X^5$ and G defined above, respectively;

$X^9$, $X^{10}$ and $X^{11}$ each independently have the same meaning as $X^3$, $X^4$ and $X^5$ defined above, respectively, $X^9$ and $X^{10}$ may form a 3- to 8-membered carbon ring or heterocycle, together with the carbon atom to which they are bonded, $X^9$ and $X^5$, $X^{10}$ and $X^5$, or $X^{11}$ and $X^5$ may together form $C_{1-4}$ alkylene;

R12 and R13 have the same meaning as $X^9$ and $X^{10}$, respectively,

R14 has the same meaning as $X^3$ described above, and

R15 represents hydrogen;

when $A^1$, $A^2$, $A^3$, $A^4$ or $A^5$ is C-T and T represents any one of the substituents represented by Formulae (X2-1) to (X2-4), then $X^9$, $X^{10}$, $X^{11}$ or $X^3$ in T may form $C_{1-4}$ alkylene together with $X^1$ if $A^1$, $A^2$, $A^3$, $A^4$ or $A^5$ that is adjacent to the carbon atom to which T in C-T is bonded is C—$X^1$, and one —CH$_2$— at any position in the alkylene may be replaced by —O—, —S— or —NH—;

when both $A^1$ and $A^2$ represent C—$X^1$ then $X^1$'s in the C—$X^1$'s may form a 5- to 6-membered saturated or unsaturated carbon ring or heterocycle, together with the carbon atoms to which $X^1$'s in C—$X^1$'s are bonded, and when both $A^3$ and $A^4$ represent C—$X^1$, then $X^1$'s in the C—$X^1$'s may form a 5- to 6-membered saturated or unsaturated carbon ring or heterocycle, together with the carbon atoms to which $X^1$'s in C—$X^1$'s are bonded;
m each independently represents an integer of 1 to 4; and
each substituent defined above may be further substituted with any substituent.

The compounds of Formula (I) of the present invention can be obtained according to the following Preparation method (a) to (g), for example.

Preparation Method (a)

A method comprising reacting the compounds represented by Formula (II):

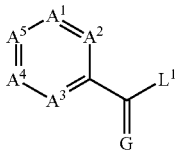
(II)

(wherein $A^1, A^2, A^3, A^4, A^5$ and G are as defined above, and $L^1$ represents hydroxy or an appropriate leaving group, for example chlorine, bromine, a $C_{1-4}$ alkyl-carbonyloxy group, a $C_{1-4}$ alkoxy-carbonyloxy group, an azolyl group, a $C_{1-4}$ alkyl-sulfonyloxy group, a $C_{1-4}$ haloalkylsulfonyloxy group, or an arylsulfonyloxy group)
with the compounds represented by Formula (III):

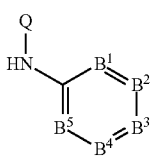
(III)

(wherein $B^1$ to $B^5$ and Q are as defined above) in the presence of a condensing agent, a base or an appropriate diluent, if necessary.

Preparation Method (b) (when at Least one of $A^1$, $A^2$, $A^3$, $A^4$ and $A^5$ in Formula (I) is any one of C-W1 to C-W9 as Defined herein (see, paragraph [0035])

A method comprising reacting the compounds represented by Formula (IV):

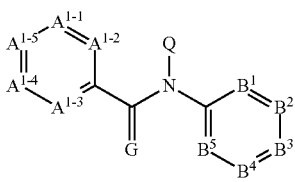
(IV)

(wherein $B^1$ to $B^5$, G and Q are as defined above, and $A^{1-1}$, $A^{1-2}, A^{1-3}, A^{1-4}$ and $A^{1-5}$ independently have the same meaning as $A^1$ to $A^5$ defined above, respectively, with the proviso that at least one of $A^{1-2}, A^{1-3}, A^{1-4}$ and $A^{1-5}$ is C-halogen) with the compounds represented by W1-H, W2-H, W3-H, W4-H, W5-H, W6-H, W7-H, W8-H or W9-H (wherein W1 to W9 are as defined below) in the presence of an appropriate base, a catalyst or a diluent, if necessary.

Preparation Method (c) [when at Least One of $A^1$, $A^2, A^3, A^4$ and $A^5$ in Formula (I) is C—(X2-1) or C—(X2-2) Having the Same Meaning as Defined Above]

A method comprising reacting the compounds represented by Formula (I-c1):

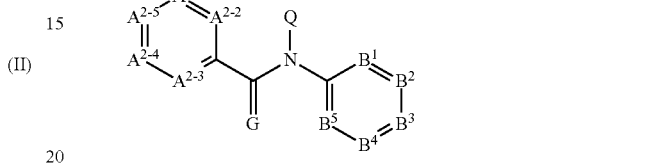
(I-c1)

[wherein $B^1$ to $B^5$, G and Q are as defined above, and $A^{2-1}$, $A^{2-2}, A^{2-3}, A^{2-4}$ and $A^{2-5}$ independently have the same meaning as $A^1$ to $A^5$ defined above, respectively, with the proviso that at least one of $A^{2-1}, A^{2-2}, A^{2-3}, A^{2-4}$ and $A^{2-5}$ is Formula (X3-1):

(X3-1)

and $X^9, X^{10}$ and m are as defined above]
with the compounds represented by Formula (r-1-1):

(r-1-1)

(wherein $X^5$ and $L^1$ are as defined above), or
with the compounds represented by Formula (r-1-2):

(r-1-2)

(wherein $X^5$ and $L^1$ are as defined above) or
with acid anhydrides of the respective compounds in the presence of an appropriate base, a condensing agent or a diluent, if necessary, and
further, with the compounds represented by Formula (r-2):

(r-2)

(wherein $X^3$ and $L^1$ are as defined above) or
with their acid anhydrides when the compounds represented by Formula (r-2) are carboxylic acids or sulfonic acids, in the presence of an appropriate base, a condensing agent or a diluent, if necessary.

Preparation Method (d) [when A⁵ in Formula (I) is C—(X2-1) or (X2-2), X¹⁰ in Formula (X2-1) or X2-2 is a Hydrogen, m is 1, A⁴ is C—X¹, X¹ and X¹⁰ together Form C₃ alkylene]

A method comprising reacting the compounds represented by Formula (I-d1):

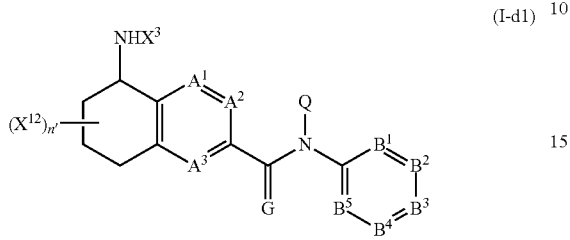

(wherein $A^1$ to $A^3$ each independently represent nitrogen, C—$X^1$ or C-T, $B^1$ to $B^5$, G, Q and $X^3$ are as defined above, $X^{12}$ independently has the same meaning as $X^1$ defined above, and n' represent an integer from 1 to 4)
with the compounds represented by Formula (r-1-1) mentioned above or the compounds represented by Formula (r-1-2) mentioned above, or
with acid anhydrides of the respective compounds, in the presence of an appropriate base, a condensing agent or a diluent, if necessary, and
further, with the compounds represented by Formula (r-2) mentioned above, or
with their acid anhydrides when the compounds represented by Formula (r-2) are carboxylic acids or sulfonic acids in the presence of an appropriate base, a condensing agent or a diluent, if necessary.

Preparation Method (e) [when A5 in Formula (I) is C—(X2-1) or (X2-2), X10 in Formula (X2-1) or (X2-2) is hydrogen, m is 1, A4 is C—X1, X1 and X10 together Form C2 alkylene]

A method comprising reacting the compounds represented by Formula (I-e1):

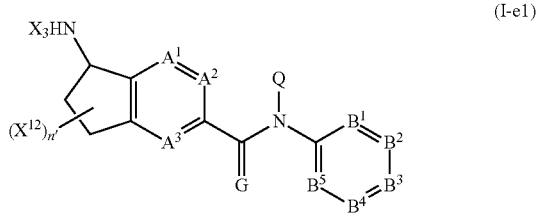

(wherein $A^1$ to $A^3$, $B^1$ to $B^5$, G, Q, $X^3$ and $(X^{12})_{n'}$ are as defined above)
with the compounds represented by Formula (r-1-1) mentioned above or the compounds represented by Formula (r-1-2) mentioned above, or
with acid anhydrides of the respective compounds, in the presence of an appropriate base, a condensing agent or a diluent, if necessary, and
further, with the compounds represented by Formula (r-2) mentioned above, or with their acid anhydrides when the compounds represented by Formula (r-2) are carboxylic acids or sulfonic acids in the presence of an appropriate base, a condensing agent or a diluent, if necessary.

Preparation Method (f)

A method comprising reacting the compounds represented by Formula (1-f1):

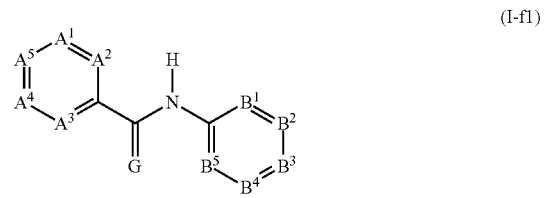

(wherein $A^1$ to $A^5$, $B^1$ to $B^5$ and G are as defined above) with the compounds represented by Formula (r-3):

$$Q\text{-}L^2 \qquad (r\text{-}3)$$

(wherein Q is as defined above and $L^2$ represents fluorine, chlorine, bromine, a $C_{1-4}$ alkyl-carbonyloxy group, a $C_{1-4}$ alkoxy-carbonyloxy group, an azolyl group, a $C_{1-4}$ alkylsulfonyloxy group, a $C_{1-4}$ haloalkylsulfonyloxy group, or an arylsulfonyloxy group) in the presence of a base or an appropriate diluent, if necessary.

Preparation Method (2) [when G in Formula (I) Represents Sulfur]

A method comprising reacting the compounds represented by Formula (I-g1):

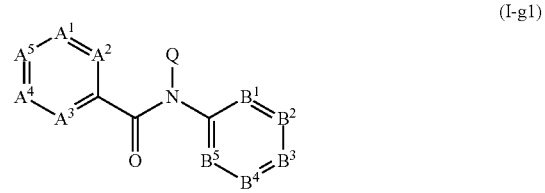

(wherein $A^1$ to $A^5$, $B^1$ to $B^5$ and Q are as defined above)
with appropriate sulfurizing reagents in the presence of an appropriate diluent.

The compounds of Formulas (I-c1), (1-d1), (1-e1), (1-f1) and (1-g1) are encompassed by the compounds of Formula (I) of the present invention.

According to the present invention, carboxamides of Formula (I) of the present invention have a potent pesticidal activity.

In the present specification, "alkyl" represents linear or branched $C_{1-12}$ alkyl such as methyl, ethyl, n- or iso-propyl, n-, iso-, sec- or tert-butyl, n-pentyl, n-hexyl, n-heptyl, n-octyl, n-nonyl, n-decyl, n-undecyl and n-dodecyl, preferably $C_{1-6}$ alkyl, and more preferably $C_{1-4}$ alkyl.

Further, for each alkyl moiety included in a group which includes the alkyl as a part of its constitution, those that are the same as "alkyl" described above can be exemplified.

"Haloalkyl" represents carbon chains in which at least one hydrogen of linear or branched $C_{1-12}$ alkyl, preferably $C_{1-6}$ alkyl, more preferably $C_{1-4}$ alkyl is substituted with haloge, for example, $CH_2F$, $CHF_2$, $CF_3$, $CF_2Cl$, $CFCl_2$, $CF_2Br$, $CF_2CF_3$, $CFHCF_3$, $CH_2CF_3$, $CFClCF_3$, $CCl_2CF_3$, $CF_2CH_3$, $CF_2CH_2F$, $CF_2CHF_2$, $CF_2CF_2Cl$, $CF_2CF_2Br$, $CFHCH_3$, CFHCHF$_2$, CFHCHF$_2$, CHFCF$_3$, CHFCF$_2$Cl, CHFCF$_2$Br, CFClCF$_3$, CCl$_2$CF$_3$, CF$_2$CF$_2$CF$_3$, CH$_2$CF$_2$CF$_3$, CF$_2$CH$_2$CF$_3$, CF$_2$CF$_2$CH$_3$, CHFCF$_2$CF$_3$, CF$_2$CHFCF$_3$, CF$_2$CF$_2$CHF$_2$, CF$_2$CF$_2$CH$_2$F, CF$_2$CF$_2$CH$_2$Cl, CF$_2$CF$_2$CF$_2$Br, CH(CHF$_2$)CF$_3$, CH(CF$_3$)CF$_3$, CF(CF$_3$)CF$_3$, CF(CF$_3$)CF$_2$Br, CF$_2$CF$_2$CF$_2$CF$_3$, CH(CF$_3$)CF$_2$F$_3$ or CF(CF$_3$)CF$_2$CF$_3$. The haloalkyl also includes perfluoroalkyl in which every substitutable hydrogen on the alkyl is substituted with fluorine. Further, monobromoperfluoroalkyl, which represents an alkyl in which one substitutable hydrogen on the alkyl is substituted with bromo and the rest of every substitutable hydrogen is substituted with fluorine, is also encompassed by "haloalkyl." The haloalkyl may be further substituted with any substituent.

"Alkoxy" represents alkoxy of linear or branched C$_{1-12}$, preferably C$_{1-6}$, more preferably C$_{1-4}$, for example, methoxy, ethoxy, n-propoxy, i-propoxy, n-, iso-, sec- or tert-butoxy, pentyloxy or hexyloxy. The alkoxy may be further substituted with any substituent.

"Halogen" and each halogen moiety included in a group substituted with halogen represent fluorine, chlorine, bromine or iodine, preferably fluorine, chlorine or bromine "Cycloalkyl" represents C$_{3-8}$ cycloalkyl including cyclopropyl, cyclobutyl, cyclopentyl, cyclohexyl, cycloheptyl, cyclooctyl, preferably C$_{3-7}$ cycloalkyl, and more preferably C$_{3-6}$ cycloalkyl.

Further, for each cycloalkyl moiety included in a group which has cycloalkyl as a part of its constitution, those that are the same as "cycloalkyl" described above can be exemplified.

"Halocycloalkyl" represents a cycloalkyl at least one hydrogen on which is substituted by halogen, and examples thereof include fluorocyclopropyl, chlorocyclopropyl, difluorocyclopropyl, dichlorocyclopropyl and undecafluorocyclohexyl.

"Alkenyl" represents C$_{2-12}$ alkenyl, preferably C$_{2-5}$ alkenyl, such as vinyl, allyl, 1-propenyl, 1-(or 2-, or 3butenyl, 1-pentenyl and the like, and more preferably C$_{2-4}$ alkenyl.

"Alkynyl" represents C$_{2-12}$ alkynyl, preferably C$_{2-5}$ alkynyl, such as ethynyl, propargyl, 1-propynyl, butan-3-ynyl, pentan-4-ynyl and the like, and more preferably C$_{2-4}$ alkynyl.

"Aryl" represents a C$_{6-12}$ aromatic hydrocarbon group, and examples thereof include phenyl, naphthyl, biphenyl, preferably a C$_{6-10}$ aromatic hydrocarbon group, and more preferably a C$_6$ aromatic hydrocarbon group, i.e., phenyl.

"Heterocycle" represents a 3 to 6-membered heterocyclic group having, as a hetero atom, at least one of N, O and S. In preferred embodiments, a heterocycle refers to a 3, a 5 or a 6 membered heterocyclic group. "Heterocycle" also represents a fused heterocyclic group which may be a benzo-fused heterocycle. Further, the carbon atom in the heterocycle may be substituted with oxo or thioxo.

Specific examples of the heterocycle include pyrrolidinyl, piperidinyl, morpholinyl, thiomorpholinyl, aziridinyl, oxiranyl, thiiranyl, azetidinyl, oxetanyl, thietanyl, pyrrolidinyl, tetrahydrofuranyl, tetrahydrothiophenyl, tetrahydropyranyl, tetrahydrothiopyranyl (as examples of a saturated heterocycle), dihydropyrrolyl, dihydroisoxazolyl, dihydropyrazolyl, dihydrooxazolyl, dihydrothiazolyl (as examples of a partially saturated heterocycle), furyl, thienyl, pyrrolyl, isoxazolyl, pyrazolyl, oxazolyl, isothiazolyl, thiazolyl, imidazolyl, triazolyl, oxadiazolyl, thiadiazolyl, tetrazolyl, pyridyl, pyrimidinyl, pyridazinyl, pyrazinyl, triazinyl, indolyl, benzoxazolyl, benzothiazolyl, quinolyl and the like. Furthermore, the heterocycle may be substituted with any substituent.

Examples of the substituent described in the expression "may be substituted with any substituent" include amino, hydroxy, oxo, thioxo, halogen, nitro, cyano, isocyano, mercapto, isothiocyanate, carboxy, carboamide, SF$_5$, aminosulfonyl, alkyl, cycloalkyl, alkenyl, cycloalkenyl, alkynyl, monoalkylamino, dialkylamino, N-alkylcarbonyl-amino, alkoxy, alkenyloxy, alkynyloxy, cycloalkyloxy, cycloalkenyloxy, alkoxycarbonyl, alkenyloxycarbonyl, alkynyloxycarbonyl, aryloxycarbonyl, alkylcarbonyl, alkenylcarbonyl, alkynylcarbonyl, arylcarbonyl, alkylthio, cycloalkylthio, alkenylthio, cycloalkenylthio, alkynylthio, alkylsulfenyl, alkylsulfinyl, alkylsulfinyl including isomers, alkylsulfonyl, monoalkylaminosulfonyl, dialkylaminosulfonyl, alkylphosphinyl, alkylphosphonyl, alkylphosphinyl including isomers, alkylphosphonyl including isomers, N-alkyl-aminocarbonyl, N,N-dialkyl-aminocarbonyl, N-alkylcarbonyl-aminocarbonyl, N-alkylcarbonyl-N-alkylaminocarbonyl, aryl, aryloxy, benzyl, benzyloxy, benzylthio, arylthio, arylamino, benzylamino, heterocycle, trialkylsilyl, alkoxyalkyl, alkylthioalkyl, alkylthioalkoxy, alkoxyalkoxy, phenethyl, benzyloxy, haloalkyl, haloalkoxy, haloalkylthio, haloalkylcarbonyl, haloalkoxycarbonyl, haloalkoxyalkoxy, haloalkoxyalkylthio, haloalkoxyalkylcarbonyl and haloalkoxyalkyl, and preferably chloro, fluoro, bromo, iodo, amino, nitro, cyano, hydroxy, thio and carboxy.

In a preferred embodiment of the present invention, at least one of X$^1$, X$^2$, T or J$^3$ represents a nitrogen-containing heterocycle, i.e., the core of the heterocycle contains only C and N. More preferably, the nitrogen-containing heterocycle is a 5 membered heterocycle.

In an even more preferred embodiment of the present invention, at least one of X$^1$, X$^2$, T or J$^3$ is selected from one of the following substituents W1-W9:

W1

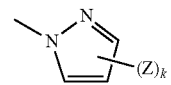

W2

W3

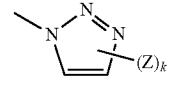

W4

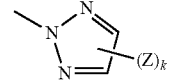

W5

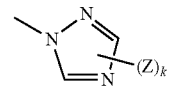

W6

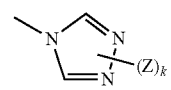

W7

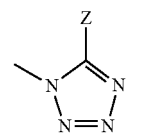

W8

-continued

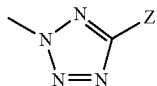

W9 wherein Z each independently represents hydrogen, halogen, nitro, cyano, hydroxy, thio, $C_{1-6}$ haloalkyl, $C_{1-6}$ haloalkoxy, $C_{1-6}$ alkylthio, $C_{1-6}$ alkylsulfinyl, $C_{1-6}$ alkylsulfonyl, $C_{1-6}$ haloalkylthio, $C_{1-6}$ haloalkylsulfinyl or $C_{1-6}$ haloalkylsulfonyl, and k represents an integer from 1 to 4. In a preferred embodiments Z is hydrogen.

In another preferred embodiment of the present invention, all alkyl or alkyl-containing substituents (e.g. haloalkyl, alkyl-O— etc.) of compounds of the present invention are $C_{1-6}$ alkyl or $C_{1-6}$ alkyl-containing substituents, respectively, more preferably said alkyl or alkyl-containing substituents are $C_{1-4}$ alkyl or $C_{1-4}$ alkyl-containing-substituents, respectively.

In yet another preferred embodiment, T represents any one of the substituents represented by the following Formulae (X2-1) to (X2-4):

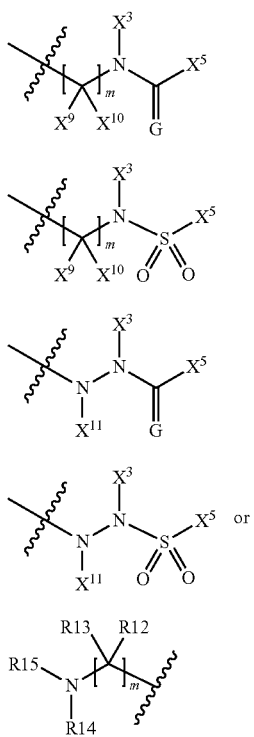

wherein
$X^3$, $X^5$ and G independently have the same meaning as $X^3$, $X^5$ and G defined above, respectively;
$X^9$, $X^{10}$ and $X^{11}$ each independently have the same meaning as $X^3$, $X^4$ and $X^5$ defined above, respectively,
$X^9$ and $X^{10}$ may form a 3- to 8-membered carbon ring or heterocycle, together with the carbon atom to which they are bonded,
$X^9$ and $X^5$, $X^{10}$ and $X^5$, or $X^{11}$ and $X^5$ may together form $C_{1-4}$ alkylene;

R12 and R13 have the same meaning as $X^9$ and $X^{10}$, respectively,
R14 has the same meaning as $X^3$ described above, and
R15 represents hydrogen;

Among the compounds represented by Formula (I) of the present invention, the following compounds may be referred to as preferred compounds.

The compounds represented by formula (I) wherein
$A^1$, $A^2$, $A^3$, $A^4$ and $A^5$ each independently represent nitrogen, C—$X^1$ or C-T, provided that at least one of $A^1$, $A^2$, $A^3$, $A^4$ and $A^5$ is C-T;
$B^1$, $B^2$, $B^3$, $B^4$ and $B^5$ each independently represent nitrogen, C—$X^2$ or C-J, provided that at least one of $B^1$, $B^2$, $B^3$, $B^4$ and $B^5$ is C-J;
G represents oxygen or sulfur;
Q represents hydrogen, $C_{1-6}$ alkyl, $C_{1-6}$ haloalkyl, ($C_{1-6}$ alkyl) carbonyl, ($C_{1-6}$ haloalkyl)carbonyl, ($C_{1-6}$ alkoxy)carbonyl or ($C_{1-6}$ haloalkoxy)carbonyl;
$X^1$ and $X^2$ each independently represent hydrogen, cyano, halogen, nitro, hydroxy, mercapto, amino, formyl, oxide, $C_{1-6}$ alkyl, $C_{1-6}$ haloalkyl, aryl-($C_{1-6}$)alkyl, heterocyclyl-($C_{1-6}$)alkyl, $C_{1-6}$ alkyl-O—, $C_{1-6}$ alkyl-NH—, $C_{1-6}$ alkyl-S—, $C_{1-6}$ alkyl-S(O)—, $C_{1-6}$ alkyl-S(O)$_2$—, $C_{1-6}$ alkyl-S(O)$_2$O—, $C_{1-6}$ haloalkyl-O—, $C_{1-6}$ haloalkyl-NH—, $C_{1-6}$ haloalkyl-S—, $C_{1-6}$ haloalkyl-S(O)—, $C_{1-6}$ haloalkyl-S(O)$_2$—, $C_{1-6}$ haloalkyl-S(=O)$_2$O—, aryl-O—, aryl-NH—, aryl-S—, aryl-S(O)—, aryl-S(O)$_2$—, aryl-S(O)$_2$O—, heterocyclyl-O—, heterocyclyl-NH—, heterocyclyl-S—, heterocyclyl-S(O)—, heterocyclyl-S(O)$_2$—, heterocyclyl-S(O)$_2$O—, $C_{1-6}$ alkyl-O—($C_{1-6}$)alkyl, $C_{1-6}$ alkyl-NH—($C_{1-6}$)alkyl, $C_{1-6}$ alkyl-S—($C_{1-6}$)alkyl, $C_{1-6}$ alkyl-S(O)—($C_{1-6}$)alkyl, $C_{1-6}$ alkyl-S(O)$_2$—($C_{1-6}$)alkyl, $C_{1-6}$ alkyl-S(O)$_2$O—($C_{1-6}$)alkyl, $C_{1-6}$ haloalkyl-O—($C_{1-6}$) alkyl, $C_{1-6}$ haloalkyl-NH—($C_{1-6}$)alkyl, $C_{1-6}$ haloalkyl-S—($C_{1-6}$)alkyl, $C_{1-6}$ haloalkyl-S(O)—($C_{1-6}$)alkyl, $C_{1-6}$ haloalkyl-S(O)$_2$—($C_{1-6}$)alkyl, $C_{1-6}$ haloalkyl-S(O)$_2$O—($C_{1-6}$)alkyl, aryl-O—($C_{1-6}$)alkyl, aryl-NH—($C_{1-6}$)alkyl, aryl-S—($C_{1-6}$)alkyl, aryl-S(O)—($C_{1-6}$)alkyl, aryl-S(O)$_2$—($C_{1-6}$)alkyl, aryl-S(O)$_2$O—($C_{1-6}$)alkyl, heterocyclyl-O—($C_{1-6}$)alkyl, heterocyclyl-NH—($C_{1-6}$)alkyl, heterocyclyl-S—($C_{1-6}$)alkyl, heterocyclyl-S(O)—($C_{1-6}$)alkyl, heterocyclyl-S(O)$_2$—($C_{1-6}$)alkyl, heterocyclyl-S(O)$_2$O—($C_{1-6}$)alkyl, $C_{3-7}$ cycloalkyl, $C_{3-7}$ cycloalkyl-($C_{1-6}$)alkyl-, $C_{3-7}$ halocycloalkyl, $C_{3-7}$ halocycloalkyl-($C_{1-6}$)alkyl-, $C_{2-6}$ alkenyl, $C_{2-6}$ haloalkenyl, $C_{2-6}$ alkynyl, $C_{2-6}$ haloalkynyl, di($C_{1-6}$ alkyl)amino, di($C_{1-6}$ haloalkyl)amino, $C_{3-18}$ trialkylsilyl, hydroxyimino($C_{1-6}$)alkyl, $C_{1-6}$ alkyl-O—N=($C_{1-6}$)alkyl, $C_{1-6}$ alkyl-NH—N=($C_{1-6}$)alkyl, $C_{1-6}$ alkyl-S—N=($C_{1-6}$)alkyl, $C_{1-6}$ alkyl-S(O)—N=($C_{1-6}$)alkyl, $C_{1-6}$ alkyl-S(O)$_2$—N=($C_{1-6}$)alkyl, $C_{1-6}$ alkyl-S(O)$_2$O—N=($C_{1-6}$)alkyl, $C_{1-6}$ haloalkyl-O—N=($C_{1-6}$)alkyl, $C_{1-6}$ haloalkyl-NH—N=($C_{1-6}$)alkyl, $C_{1-6}$ haloalkyl-S—N=($C_{1-6}$)alkyl, $C_{1-6}$ haloalkyl-S(O)—N=($C_{1-6}$)alkyl, $C_{1-6}$ haloalkyl-S(O)$_2$—N=($C_{1-6}$)alkyl, $C_{1-6}$ haloalkyl-S(O)$_2$O—N=($C_{1-6}$)alkyl, ($C_{1-6}$ alkoxy)carbonyl, ($C_{1-6}$ haloalkoxy)carbonyl, ($C_{3-7}$ cycloalkoxy)carbony, ($C_{3-7}$ halocycloalkoxy)carbony, $C_{3-7}$ cycloalkyl-($C_{1-6}$ alkoxy)carbony, $C_{3-7}$ halocycloalkyl-($C_{1-6}$ alkoxy)carbony, ($C_{1-6}$ alkyl)carbonyl, ($C_{1-6}$ haloalkyl)carbonyl, ($C_{3-7}$ cycloalkyl) carbonyl, ($C_{3-7}$ halocycloalkyl)carbonyl, $C_{3-7}$ cycloalkyl-($C_{1-6}$)alkyl-carbonyl, ($C_{3-7}$ halocycloalkyl)-($C_{1-6}$)alkyl-carbonyl, an aryl group, sulfur pentafluoride, one of the substituents represented by the following Formulae (X1-1) to (X1-5):

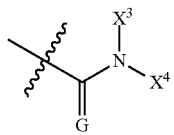
X1-1

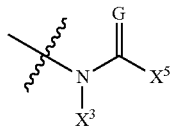
X1-2

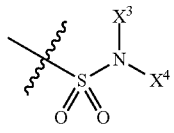
X1-3

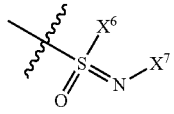
X1-4

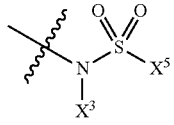
X1-5 wherein G independently has the same meaning as G described above;

or $X^1$ and $X^2$ each independently represent a heterocyclic group represented by any one of W1 to W9 as described above;

$X^3$, $X^4$ and $X^5$ each independently represent hydrogen, cyano, halogen, nitro, hydroxy, mercapto, amino, formyl, $C_{1-6}$ alkyl, $C_{1-6}$ haloalkyl, aryl-$(C_{1-6})$alkyl, heterocyclyl-$(C_{1-6})$alkyl, $C_{1-6}$ alkyl-O—, $C_{1-6}$ alkyl-NH—, $C_{1-6}$ alkyl-S—, $C_{1-6}$ alkyl-S(O)—, $C_{1-6}$ alkyl-S(O)$_2$—, $C_{1-6}$ alkyl-S(O)$_2$O—, $C_{1-6}$ haloalkyl-O—, $C_{1-6}$ haloalkyl-NH—, $C_{1-6}$ haloalkyl-S—, $C_{1-6}$ haloalkyl-S(O)—, $C_{1-6}$ haloalkyl-S(O)$_2$—, $C_{1-6}$ haloalkyl-S(O)$_2$O—, aryl-O—, aryl-NH—, aryl-S—, aryl-S(O)—, aryl-S(O)$_2$—, aryl-S(O)$_2$O—, heterocyclyl-O—, heterocyclyl-NH—, heterocyclyl-S—, heterocyclyl-S(O)—, heterocyclyl-S(O)$_2$—, heterocyclyl-S(O)$_2$O—, $C_{1-6}$ alkyl-O—$(C_{1-6})$alkyl, $C_{1-6}$ alkyl-NH—$(C_{1-6})$alkyl, $C_{1-6}$ alkyl-S—$(C_{1-6})$alkyl, $C_{1-6}$ alkyl-S(O)—$(C_{1-6})$alkyl, $C_{1-6}$ alkyl-S(O)$_2$—$(C_{1-6})$alkyl, $C_{1-6}$ alkyl-S(O)$_2$O—$(C_{1-6})$alkyl, $C_{1-6}$ haloalkyl-O—$(C_{1-6})$alkyl, $C_{1-6}$ haloalkyl-NH—$(C_{1-6})$alkyl, $C_{1-6}$ haloalkyl-S—$(C_{1-6})$alkyl, $C_{1-6}$ haloalkyl-S(O)—$(C_{1-6})$alkyl, $C_{1-6}$ haloalkyl-S(O)$_2$—$(C_{1-6})$alkyl, $C_{1-6}$ haloalkyl-S(O)$_2$O—$(C_{1-6})$alkyl, aryl-O—$(C_{1-6})$alkyl, aryl-NH—$(C_{1-6})$alkyl, aryl-S—$(C_{1-6})$alkyl, aryl-S(O)—$(C_{1-6})$alkyl, aryl-S(O)$_2$—$(C_{1-6})$alkyl, aryl-S(O)$_2$O—$(C_{1-6})$alkyl, heterocyclyl-O—$(C_{1-6})$alkyl, heterocyclyl-NH—$(C_{1-6})$alkyl, heterocyclyl-S—$(C_{1-6})$alkyl, heterocyclyl-S(O)—$(C_{1-6})$alkyl, heterocyclyl-S(O)$_2$—$(C_{1-6})$alkyl, heterocyclyl-S(O)$_2$O—$(C_{1-6})$alkyl, $C_{3-7}$ cycloalkyl, $C_{3-7}$ cycloalkyl-$(C_{1-6})$alkyl-, $C_{3-7}$ halocycloalkyl, $C_{3-7}$ halocycloalkyl-$(C_{1-6})$alkyl-, $C_{2-6}$ alkenyl, $C_{2-6}$ haloalkenyl, $C_{2-6}$ alkynyl, $C_{2-6}$ haloalkynyl, di($C_{1-6}$ alkyl)amino, di($C_{1-6}$ haloalkyl)amino, $C_{3-18}$ trialkylsilyl, hydroxyimino($C_{1-6}$)alkyl, $C_{1-6}$ alkyl-O—N=$(C_{1-6})$alkyl, $C_{1-6}$ alkyl-NH—N=$(C_{1-6})$alkyl, $C_{1-6}$ alkyl-S—N=$(C_{1-6})$alkyl, $C_{1-6}$ alkyl-S(O)—N=$(C_{1-6})$alkyl, $C_{1-6}$ alkyl-S(O)$_2$—N=$(C_{1-6})$alkyl, $C_{1-6}$ alkyl-S(O)$_2$O—N=$(C_{1-6})$alkyl, $C_{1-6}$ haloalkyl-O—N=$(C_{1-6})$alkyl, $C_{1-6}$ haloalkyl-NH—N=$(C_{1-6})$alkyl, $C_{1-6}$ haloalkyl-S—N=$(C_{1-6})$alkyl, $C_{1-6}$ haloalkyl-S(O)—N=$(C_{1-6})$alkyl, $C_{1-6}$ haloalkyl-S(O)$_2$—N=$(C_{1-6})$alkyl, $C_{1-6}$ haloalkyl-S(O)$_2$O—N=$(C_{1-6})$alkyl, ($C_{1-6}$ alkoxy)carbonyl, ($C_{1-6}$ haloalkoxy)carbonyl, ($C_{3-7}$ cycloalkoxy)carbony, ($C_{3-7}$ halocycloalkoxy)carbony, $C_{3-7}$ cycloalkyl-($C_{1-6}$ alkoxy)carbony, $C_{3-7}$ halocycloalkyl-($C_{1-6}$ alkoxy)carbony, ($C_{1-6}$ alkyl)carbonyl, ($C_{1-6}$ haloalkyl)carbonyl, ($C_{3-7}$ cycloalkyl)carbonyl, ($C_{3-7}$ halocycloalkyl)carbonyl, $C_{3-7}$ cycloalkyl-$(C_{1-6})$alkyl-carbonyl, $C_{3-7}$ halocycloalkyl-$(C_{1-6})$alkyl-carbonyl, aryl-carbonyl, heterocyclyl-carbonyl, aryl-$(C_{1-6})$alkyl-carbonyl, heterocyclyl-$(C_{1-6})$alkyl-carbonyl, sulfur pentafluoride, an aryl group or a heterocyclic group, $X^3$ and $X^4$ may form a heterocycle together with the nitrogen atom, carbon atom, oxygen atom or sulfur atom to which they are bonded, $X^3$ and $X^5$ may form a heterocycle together with the nitrogen atom, carbon atom, oxygen atom or sulfur atom to which they are bonded;

$X^6$ each independently represents hydrogen, $C_{1-6}$ alkyl, $C_{1-6}$ haloalkyl, $C_{3-7}$ cycloalkyl, $C_{2-6}$ alkenyl, $C_{2-6}$ haloalkenyl, an aryl group, a heterocyclic group, aryl-$(C_{1-6})$alkyl or heterocyclyl-$(C_{1-6})$alkyl;

$X^7$ each independently represents hydrogen, nitro, cyano, formyl, $X^8$-carbonyl or $X^8$-oxycarbonyl, wherein $X^8$ independently has the same meaning as $X^6$ described above;

J each independently represents $C_{1-6}$ haloalkyl, $C_{1-6}$ haloalkyl-O—, $C_{1-6}$ haloalkyl-S—, $C_{1-6}$ haloalkyl-S(=O)—, $C_{1-6}$ haloalkyl-S(=O)$_2$—, $C_{3-7}$ halocycloalkyl, —C($J^1$)($J^2$)($J^3$) or —C($J^1$)($J^2$)(O$J^4$), wherein $J^1$ and $J^2$ each independently represent $C_{1-6}$ haloalkyl, $J^3$ independently represents any one of the above W1 to W9;

$J^4$ represents hydrogen, $C_{1-6}$ alkyl, $C_{1-6}$ haloalkyl, $C_{1-6}$ alkylsulfonyl, $C_{1-6}$ haloalkylsulfonyl, arylsulfonyl, an aryl group or a heterocyclic group;

T represents any one of the substituents represented by W1 to W9 mentioned above or any one of the substituents represented by the following Formulae (X2-1) to (X2-4):

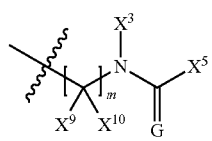
X2-1

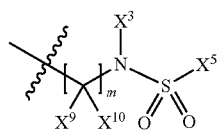
X2-2

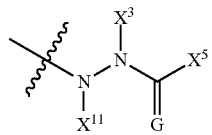
X2-3

-continued

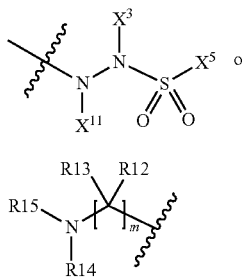

wherein
- m each independently represents an integer of 1 to 4;
- $X^3$, $X^5$ and G independently have the same meaning as $X^3$, $X^5$ and G defined above, respectively;
- $X^9$, $X^{10}$ and $X^{11}$ each independently have the same meaning as $X^3$, $X^4$ and $X^5$ defined above, respectively,
- $X^9$ and $X^{10}$ may form a 3- to 8-membered carbon ring or heterocycle, together with the carbon atom to which they are bonded,
- $X^9$ and $X^5$, $X^{10}$ and $X^5$, or $X^{11}$ and $X^5$ may together form $C_{1-4}$ alkylene
- R12 and R13 have the same meaning as $X^9$ and $X^{10}$, respectively,
- R14 has the same meaning as $X^3$ described above, and
- R15 represents hydrogen;
- when $A^1$, $A^2$, $A^3$, $A^4$ or $A^5$ is C-T and T represents any one of the substituents represented by Formulae (X2-1) to (X2-4), then $X^9$, $X^{10}$, $X^{11}$ or $X^3$ in T may form $C_{1-4}$ alkylene together with $X^1$ if $A^1$, $A^2$, $A^3$, $A^4$ or $A^5$ that is adjacent to the carbon atom to which T in C-T is bonded is C—$X^1$, and one —CH$_2$— at any position in the alkylene may be replaced by —O—, —S— or —NH—;
- when both $A^1$ and $A^2$ represent C—$X^1$ then $X^1$'s in the C—$X^1$'s may form a 5- to 6-membered saturated or unsaturated carbon ring or heterocycle, together with the carbon atoms to which $X^1$'s in C—$X^1$'s are bonded, and when both $A^3$ and $A^4$ represent C—$X^1$, then $X^1$'s in the C—$X^1$'s may form a 5- to 6-membered saturated or unsaturated carbon ring or heterocycle, together with the carbon atoms to which $X^1$'s in C—$X^1$'s are bonded; and
- each substituent defined above may be further substituted with any substituent.

Among the compounds represented by formula (I) the following compounds are especially suitable.

The compounds of formula (I) wherein
- $A^1$, $A^2$, $A^3$, $A^4$ and $A^5$ each independently represent nitrogen, C—$X^1$ or C-T, provided that at least one of $A^1$, $A^2$, $A^3$, $A^4$ and $A^5$ is C-T;
- $B^1$, $B^2$, $B^3$, $B^4$ and $B^5$ each independently represent nitrogen, C—$X^2$ or C-J, provided that at least one of B', $B^2$, $B^3$, $B^4$ and $B^5$ is C-J;
- G represents oxygen or sulfur;
- Q represents hydrogen, $C_{1-4}$ alkyl, $C_{1-4}$ haloalkyl, ($C_{1-4}$ alkyl)carbonyl, ($C_{1-4}$ haloalkyl)carbonyl, ($C_{1-4}$ alkoxy)carbonyl or ($C_{1-4}$ haloalkoxy)carbonyl;
- $X^1$ and $X^2$ each independently represent hydrogen, cyano, halogen, nitro, hydroxy, mercapto, amino, formyl, oxide, $C_{1-4}$ alkyl, $C_{1-4}$ haloalkyl, aryl-($C_{1-4}$)alkyl, heterocyclyl-($C_{1-4}$ alkyl, $C_{1-4}$ alkyl-O—, $C_{1-4}$ alkyl-NH—, $C_{1-4}$ alkyl-S—, $C_{1-4}$ alkyl-S(O)—, $C_{1-4}$ alkyl-S(O)$_2$—, $C_{1-4}$ alkyl-S(O)$_2$O—, $C_{1-4}$ haloalkyl-O—, $C_{1-4}$haloalkyl-NH—, $C_{1-4}$ haloalkyl-S—, $C_{1-4}$ haloalkyl-S(O)—, $C_{1-4}$ haloalkyl-S(O)$_2$—, $C_{1-4}$ haloalkyl-S(=O)$_2$O—, aryl-O—, aryl-NH—, aryl-S—, aryl-S(O)—, aryl-S(O)$_2$—, aryl-S(O)$_2$O—, heterocyclyl-O—, heterocyclyl-NH—, heterocyclyl-S—, heterocyclyl-S(O)—, heterocyclyl-S(O)$_2$—, heterocyclyl-S(O)$_2$O—, $C_{1-4}$ alkyl-O—($C_{1-4}$)alkyl, $C_{1-4}$ alkyl-NH—($C_{1-4}$)alkyl, $C_{1-4}$ alkyl-S—($C_{1-4}$)alkyl, $C_{1-4}$ alkyl-S(O)—($C_{1-4}$)alkyl, $C_{1-4}$ alkyl-S(O)$_2$—($C_{1-4}$)alkyl, $C_{1-4}$ alkyl-S(O)$_2$O—($C_{1-4}$)alkyl, $C_{1-4}$ haloalkyl-O—($C_{1-4}$ alkyl, $C_{1-4}$ haloalkyl-NH—($C_{1-4}$)alkyl, $C_{1-4}$ haloalkyl-S—($C_{1-4}$)alkyl, $C_{1-4}$ haloalkyl-S(O)—($C_{1-4}$ alkyl, $C_{1-4}$ haloalkyl-S(O)$_2$—($C_{1-4}$)alkyl, $C_{1-4}$ haloalkyl-S(O)$_2$O—($C_{1-4}$)alkyl, aryl-O—($C_{1-4}$)alkyl, aryl-NH—($C_{1-4}$)alkyl, aryl-S—($C_{1-4}$)alkyl, aryl-S(O)—($C_{1-4}$)alkyl, aryl-S(O)$_2$—($C_{1-4}$)alkyl, aryl-S(O)$_2$O—($C_{1-4}$)alkyl, heterocyclyl-O—($C_{1-4}$)alkyl, heterocyclyl-NH—($C_{1-4}$)alkyl, heterocyclyl-S—($C_{1-4}$ alkyl, heterocyclyl-S(O)—($C_{1-4}$ alkyl, heterocyclyl-S(O)$_2$—($C_{1-4}$)alkyl, heterocyclyl-S(O)$_2$O—($C_{1-4}$)alkyl, $C_{3-6}$ cycloalkyl, $C_{3-6}$ cycloalkyl-($C_{1-4}$)alkyl-, $C_{3-6}$ halocycloalkyl, $C_{3-6}$ halocycloalkyl-($C_{1-4}$)alkyl-, $C_2$ alkenyl, $C_{2-4}$ haloalkenyl, $C_{2-4}$ alkynyl, $C_{2-4}$ haloalkynyl, di($C_{1-4}$ alkyl)amino, di($C_{1-4}$ haloalkyl)amino, $C_{3-12}$ trialkylsilyl, hydroxyimino($C_{1-4}$)alkyl, $C_{1-4}$ alkyl-O—N=($C_{1-4}$)alkyl, $C_{1-4}$ alkyl-NH—N=($C_{1-4}$)alkyl, $C_{1-4}$ alkyl-S—N=($C_{1-4}$)alkyl, $C_{1-4}$ alkyl-S(O)—N=($C_{1-4}$)alkyl, $C_{1-4}$ alkyl-S(O)$_2$—N=($C_{1-4}$)alkyl, $C_{1-4}$ alkyl-S(O)$_2$O—N=($C_{1-4}$)alkyl, $C_{1-4}$ haloalkyl-O—N=($C_{1-4}$)alkyl, $C_{1-4}$ haloalkyl-NH—N=($C_{1-4}$)alkyl, $C_{1-4}$ haloalkyl-S—N=($C_{1-4}$)alkyl, $C_{1-4}$ haloalkyl-S(O)—N=($C_{1-4}$)alkyl, $C_{1-4}$ haloalkyl-S(O)$_2$—N=($C_{1-4}$)alkyl, $C_{1-4}$ haloalkyl-S(O)$_2$O—N=($C_{1-4}$)alkyl, ($C_{1-4}$ alkoxy)carbonyl, ($C_{1-4}$ haloalkoxy)carbonyl, ($C_{3-6}$ cycloalkoxy)carbony, ($C_{3-6}$ halocycloalkoxy)carbony, $C_{3-6}$ cycloalkyl-($C_{1-4}$ alkoxy)carbony, $C_{3-6}$ halocycloalkyl-($C_{1-4}$ alkoxy)carbony, ($C_{1-4}$ alkyl)carbonyl, ($C_{1-4}$ haloalkyl)carbonyl, ($C_{3-6}$ cycloalkyl)carbonyl, ($C_{3-6}$ halocycloalkyl)carbonyl, $C_{3-6}$ cycloalkyl-($C_{1-4}$ alkyl-carbonyl, ($C_{3-6}$ halocycloalkyl)-($C_{1-4}$)alkyl-carbonyl, an aryl group, sulfur pentafluoride, one of the substituents represented by the following Formulae (X1-1) to (X1-5):

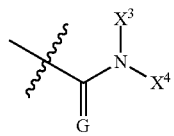

X1-1

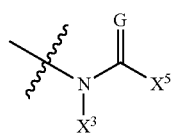

X1-2

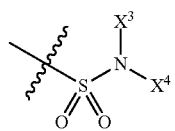

X1-3

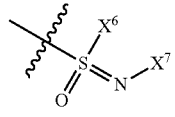

X1-4

-continued

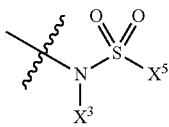
X1-5 wherein G independently has the same meaning as G described above; or

X¹ and X² each independently represent a heterocyclic group represented by any one of W1 to W9;

X³, X⁴ and X⁵ each independently represent hydrogen, cyano, halogen, nitro, hydroxy, mercapto, amino, formyl, $C_{1-4}$ alkyl, $C_{1-4}$ haloalkyl, aryl-($C_{1-4}$)alkyl, heterocyclyl-($C_{1-4}$)alkyl, $C_{1-4}$ alkyl-O—, $C_{1-4}$ alkyl-NH—, $C_{1-4}$ alkyl-S—, $C_{1-4}$ alkyl-S(O)—, $C_{1-4}$ alkyl-S(O)$_2$—, $C_{1-4}$ alkyl-S(O)$_2$O—, $C_{1-4}$ haloalkyl-O—, $C_{1-4}$ haloalkyl-NH—, $C_{1-4}$ haloalkyl-S—, $C_{1-4}$haloalkyl-S(O)—, $C_{1-4}$haloalkyl-S(O)$_2$—, $C_{1-4}$ haloalkyl-S(O)$_2$O—, aryl-O—, aryl-NH—, aryl-S—, aryl-S(O)—, aryl-S(O)$_2$—, aryl-S(O)$_2$O—, heterocyclyl-O—, heterocyclyl-NH—, heterocyclyl-S—, heterocyclyl-S(O)—, heterocyclyl-S(O)$_2$—, heterocyclyl-S(O)$_2$O—, $C_{1-4}$ alkyl-O—($C_{1-4}$)alkyl, $C_{1-4}$ alkyl-NH—($C_{1-4}$)alkyl, $C_{1-4}$ alkyl-S—($C_{1-4}$)alkyl, $C_{1-4}$ alkyl-S(O)—($C_{1-4}$)alkyl, $C_{1-4}$ alkyl-S(O)$_2$—($C_{1-4}$)alkyl, $C_{1-4}$ alkyl-S(O)$_2$O—($C_{1-4}$)alkyl, $C_{1-4}$ haloalkyl-O—($C_{1-4}$)alkyl, $C_{1-4}$ haloalkyl-NH—($C_{1-4}$)alkyl, $C_{1-4}$ haloalkyl-S—($C_{1-4}$)alkyl, $C_{1-4}$ haloalkyl-S(O)—($C_{1-4}$ alkyl, $C_{1-4}$ haloalkyl-S(O)$_2$—($C_{1-4}$)alkyl, $C_{1-4}$ haloalkyl-S(O)$_2$O—($C_{1-4}$)alkyl, aryl-O—($C_{1-4}$)alkyl, aryl-NH—($C_{1-4}$)alkyl, aryl-S—($C_{1-4}$)alkyl, aryl-S(O)—($C_{1-4}$)alkyl, aryl-S(O)$_2$—($C_{1-4}$) alkyl, aryl-S(O)$_2$O—($C_{1-4}$)alkyl, heterocyclyl-O—($C_{1-4}$) alkyl, heterocyclyl-NH—($C_{1-4}$)alkyl, heterocyclyl-S—($C_{1-4}$)alkyl, heterocyclyl-S(O)—($C_{1-4}$ alkyl, heterocyclyl-S(O)$_2$—($C_{1-4}$)alkyl, heterocyclyl-S(O)$_2$O—($C_{1-4}$)alkyl, $C_{3-6}$ cycloalkyl, $C_{3-6}$ cycloalkyl-($C_{1-4}$)alkyl-, $C_{3-6}$ halocycloalkyl, $C_{3-6}$ halocycloalkyl-($C_{1-4}$)alkyl-, $C_2$ alkenyl, $C_{2-4}$ haloalkenyl, $C_{2-4}$ alkynyl, $C_{2-4}$ haloalkynyl, di($C_{1-4}$ alkyl) amino, di($C_{1-4}$ haloalkyl)amino, $C_{3-12}$ trialkylsilyl, hydroxyimino($C_{1-4}$)alkyl, $C_{1-4}$ alkyl-O—N=($C_{1-4}$)alkyl, $C_{1-4}$ alkyl-NH—N=($C_{1-4}$)alkyl, $C_{1-4}$ alkyl-S—N=($C_{1-4}$) alkyl, $C_{1-4}$ alkyl-S(O)—N=($C_{1-4}$)alkyl, $C_{1-4}$ alkyl-S(O)$_2$—N=($C_{1-4}$)alkyl, $C_{1-4}$ alkyl-S(O)$_2$O—N=($C_{1-4}$) alkyl, $C_{1-4}$ haloalkyl-O—N=($C_{1-4}$)alkyl, $C_{1-4}$ haloalkyl-NH—N=($C_{1-4}$)alkyl, $C_{1-4}$ haloalkyl-S—N=($C_{1-4}$)alkyl, $C_{1-4}$ haloalkyl-S(O)—N=($C_{1-4}$)alkyl, $C_{1-4}$ haloalkyl-S(O)$_2$—N=($C_{1-4}$)alkyl, $C_{1-4}$ haloalkyl-S(O)$_2$O—N=($C_{1-4}$)alkyl, ($C_{1-4}$ alkoxy)carbonyl, ($C_{1-4}$ haloalkoxy)carbonyl, ($C_{3-6}$ cycloalkoxy)carbony, ($C_{3-6}$ halocycloalkoxy) carbony, $C_{3-6}$ cycloalkyl-($C_{1-4}$ alkoxy)carbony, $C_{3-6}$ halocycloalkyl-($C_{1-4}$ alkoxy)carbony, ($C_{1-4}$ alkyl)carbonyl, ($C_{1-4}$ haloalkyl)carbonyl, ($C_{3-6}$ cycloalkyl)carbonyl, ($C_{3-6}$ halocycloalkyl)carbonyl, $C_{3-6}$ cycloalkyl-($C_{1-4}$ alkyl-carbonyl, $C_{3-6}$ halocycloalkyl-($C_{1-4}$ alkyl-carbonyl, aryl-carbonyl, heterocyclyl-carbonyl, aryl-($C_{1-4}$)alkyl-carbonyl, heterocyclyl-($C_{1-4}$)alkyl-carbonyl, sulfur pentafluoride, an aryl group or a heterocyclic group, X³ and X⁴ may form a heterocycle together with the nitrogen atom, carbon atom, oxygen atom or sulfur atom to which they are bonded, X³ and X⁵ may form a heterocycle together with the nitrogen atom, carbon atom, oxygen atom or sulfur atom to which they are bonded;

X⁶ each independently represents hydrogen, $C_{1-4}$ alkyl, $C_{1-4}$ haloalkyl, $C_{3-6}$ cycloalkyl, $C_{2-4}$ alkenyl, $C_{2-4}$ haloalkenyl, an aryl group, a heterocyclic group, aryl-($C_{1-4}$)alkyl or heterocyclyl-($C_{1-4}$)alkyl;

X⁷ each independently represents hydrogen, nitro, cyano, formyl, X⁸-carbonyl or X⁸-oxycarbonyl,
wherein X⁸ independently has the same meaning as X⁶ described above;

J each independently represents $C_{1-4}$ haloalkyl, $C_{1-4}$ haloalkyl-O—, $C_{1-4}$ haloalkyl-S—, $C_{1-4}$ haloalkyl-S(=O)—, $C_{1-4}$ haloalkyl-S(=O)$_2$—, $C_{3-6}$ halocycloalkyl, —C(J¹)(J²)(J³) or —C(J¹)(J²)(OJ⁴),
wherein J¹ and J² each independently represent $C_{1-4}$ haloalkyl,
J³ independently represents any one of the above W1 to W9;
J⁴ represents hydrogen, $C_{1-4}$ alkyl, $C_{1-4}$ haloalkyl, $C_{1-4}$ alkylsulfonyl, $C_{1-4}$ haloalkylsulfonyl, arylsulfonyl, an aryl group or a heterocyclic group;

T represents any one of the substituents represented by W1 to W9 mentioned above or any one of the substituents represented by the following Formulae (X2-1) to (X2-4):

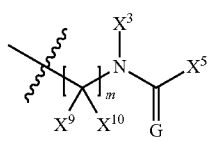
X2-1

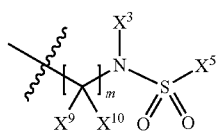
X2-2

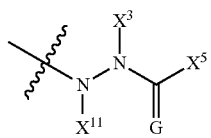
X2-3

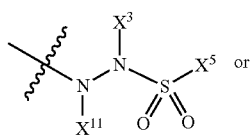
X2-4 or

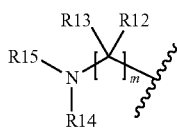
X2-5 wherein
m each independently represents an integer of 1 to 4;
X³, X⁵ and G independently have the same meaning as X³, X⁵ and G defined above, respectively;
X⁹, X¹⁰ and X¹¹ each independently have the same meaning as X³, X⁴ and X⁵ defined above, respectively,
X⁹ and X¹⁰ may form a 3- to 8-membered carbon ring or heterocycle, together with the carbon atom to which they are bonded,
X⁹ and X⁵, X¹⁰ and X⁵, or X¹¹ and X⁵ may together form $C_{1-4}$ alkylene
R12 and R13 have the same meaning as X⁹ and X¹⁰, respectively,
R14 has the same meaning as X³ described above, and
R15 represents hydrogen;
when A¹, A², A³, A⁴ or A⁵ is C-T and T represents any one of the substituents represented by Formulae (X2-1) to (X2-4), then X9, X$^{10}$, X$^{11}$ or X$^3$ in T may form C$_{1-4}$ alkylene together with X$^1$ if A$^1$, A$^2$, A$^3$, A$^4$ or A$^5$ that is adjacent to the carbon atom to which T in C-T is bonded is C—X$^1$, and one —CH$_2$— at any position in the alkylene may be replaced by —O—, —S— or —NH—;

when both A$^1$ and A$^2$ represent C—X$^1$ then X$^1$'s in the C—X$^1$'s may form a 5- to 6-membered saturated or unsaturated carbon ring or heterocycle, together with the carbon atoms to which X$^1$'s in C—X$^1$'s are bonded, and when both A$^3$ and A$^4$ represent C—X$^1$, then X$^1$'s in the C—X$^1$'s may form a 5- to 6-membered saturated or unsaturated carbon ring or heterocycle, together with the carbon atoms to which X$^1$'s in C—X$^1$'s are bonded; and each substituent defined above may be further substituted with any substituent.

In another preferred embodiment of the present invention, the compounds are preferred wherein in formula (I) the grouping

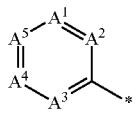

(Wherein the bond marked by (*) bonds to the carbon atom marked by (#) of the grouping

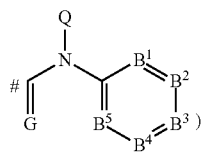

stands for a grouping selected among LH-1 to LH-13

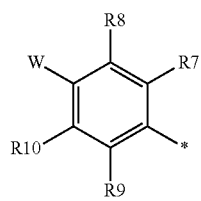
LH-1

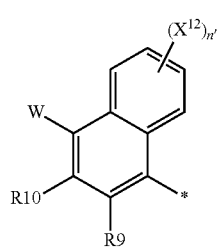
LH-2

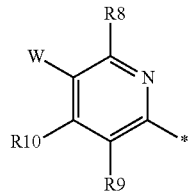
LH-3

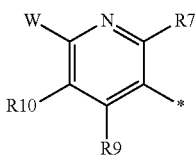
LH-4

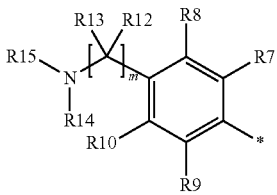
LH-5

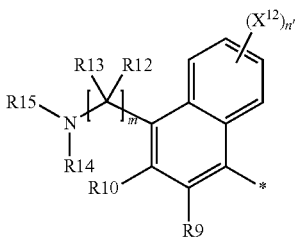
LH-6

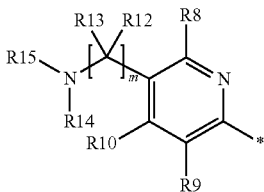
LH-7

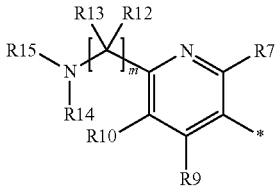
LH-8

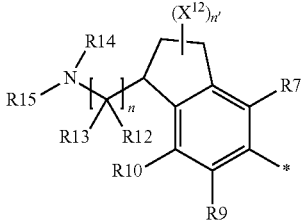
LH-9

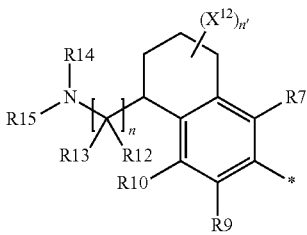
LH-10

-continued

LH-11

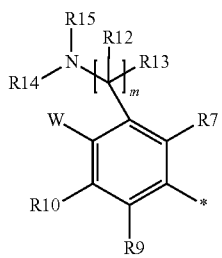

LH-12

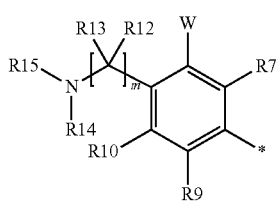

LH-13

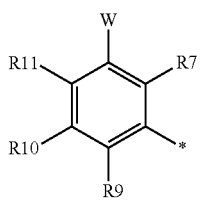

wherein W represents any one of W1 to W9 described above, R7, R8, R9, R10, R11 and $X^{12}$ each independently has the same meaning as $X^1$ defined above, R12 and R13 have the same meaning as $X^9$ and $X^{10}$ described above respectively, R14 has the same meaning as $X^3$ described above, R15 represents hydrogen or has the same meaning as $-C(=G)-X^5$; G and $X^5$ are as defined above, and n' represent an integer from 1 to 4.

Among the compounds of the Formula (I) of the present invention, the compounds are preferred wherein in formula (I) the grouping

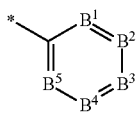

(Wherein the bond marked by (*) bonds to the nitrogen atom marked by (#) of the grouping

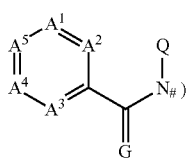

stands for a grouping:

LH-11

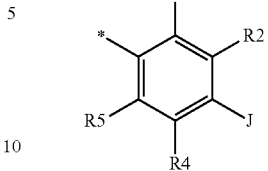

wherein,

R1, R2, R4 and R5 each independently has the same meaning as $X^2$ defined above, more preferably each independently represent hydrogen, cyano, halogen, oxygen, $C_{1-4}$ alkyl, $C_{1-4}$haloalkyl, $C_{1-4}$haloalkyl-O—, or haloalkyl-S(O)$_2$—, J each independently represents $C_{1-4}$ perfluoroalkyl, $C_{1-4}$ perfluoroalkyl-O—, $C_{1-4}$ monobromoperfluoroalkyl, $C_{1-4}$ perfluoroalkyl-S(O)$_2$—, $C_{3-6}$ perfluorocycloalkyl, —C(J$^1$)(J$^2$)(J$^3$) or —C(J$^1$)(J$^2$)(OJ$^4$), $J^1$ and $J^2$ each independently represent $C_{1-4}$ perfluoroalkyl, $J^3$ represents W2:

Z each independently represents hydrogen or halogen, k is 3, $J^4$ represents $C_{1-4}$ alkyl, or phenyl; and each group defined above may be further substituted with any substituent.

The following groups of the novel carboxamides are also preferred, and in any case they are understood as subgroups of the compounds of the Formula (I) described above.

Group 1: Carboxamides represented by Formula (I-I):

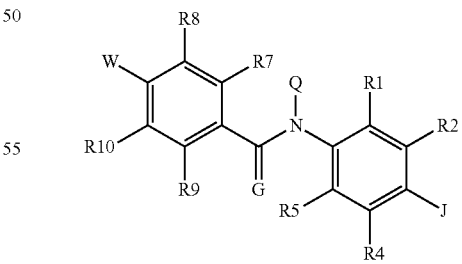

wherein G, Q and J are as defined above, W represents any one of W1 to W9 described above, R1, R2, R4 and R5 each independently has the same meaning as $X^2$ defined above, and R7, R8, R9 and R10 each independently has the same meaning as $X^1$ defined above.

Group 2: Carboxamides represented by Formula (I-II):

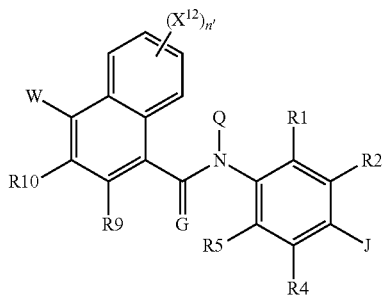

wherein W, G, Q, J, R1, R2, R4, R5, R9, R10 and $(X^{12})_{n'}$ are as defined above.

Group 3: Carboxamides represented by Formula (I-III):

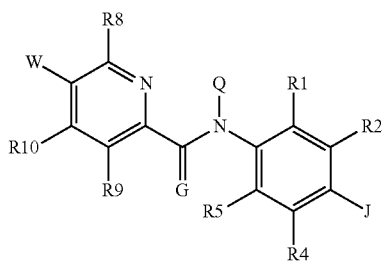

wherein W, G, Q, J, R1, R2, R4, R5, R8, R9 and R10 are as defined above.

Group 4: Carboxamides represented by Formula (I-IV)

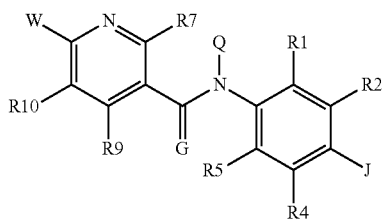

wherein W, G, Q, J, R1, R2, R4, R5, R7, R9 and R10 are as defined above.

Group 5: Carboxamides represented by Formula (I-V):

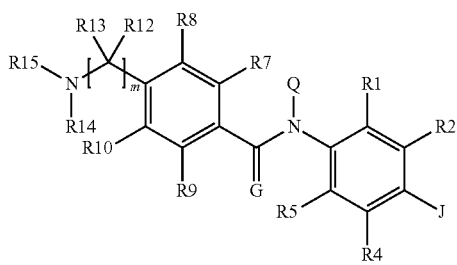

wherein G, Q, J, R1, R2, R4, R5, R7, R8, R9, R10 and m are as defined above, R12 and R13 have the same meaning as $X^9$ and $X^{10}$ described above, respectively, R14 has the same meaning as $X^3$ described above, R15 represents hydrogen or has the same meaning as —C (=G)-$X^5$, and G and $X^5$ are as defined above.

Group 6: Carboxamides represented by Formula (I-VI):

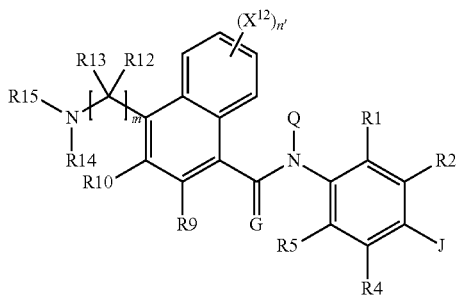

wherein G, Q, J, R1, R2, R4, R5, R9, R10, R12, R13, R14, R15, $(X^{12})_{n'}$ and m are as defined above.

Group 7: Carboxamides represented by Formula (I-VII):

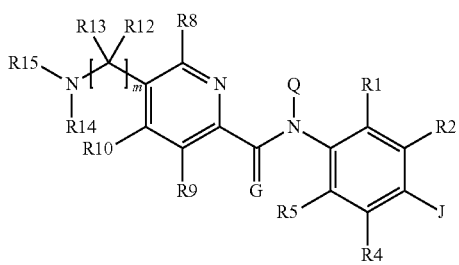

wherein G, Q, J, R1, R2, R4, R5, R8, R9, R10, R12, R13, R14, R15 and m are as defined above.

Group 8: Carboxamides represented by Formula (I-VIII):

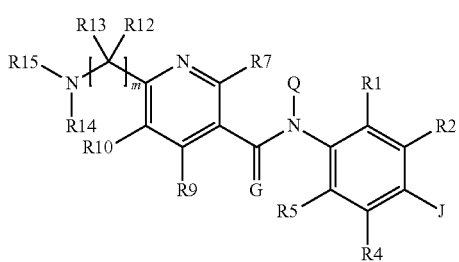

wherein G, Q, J, R1, R2, R4, R5, R7, R9, R10, R12, R13, R14, R15 and m are as defined above.

Group 9: Carboxamides represented by Formula (I-IX):

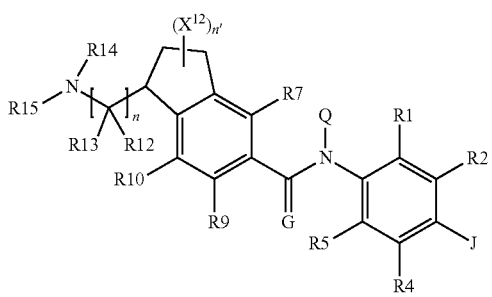

wherein G, Q, J, R1, R2, R4, R5, R7, R9, R10, R12, R13, R14, R15 and $(X^{12})_{n'}$ are as defined above, and n represents 0, 1 or 2.

Group 10: Carboxamides represented by Formula (I-X):

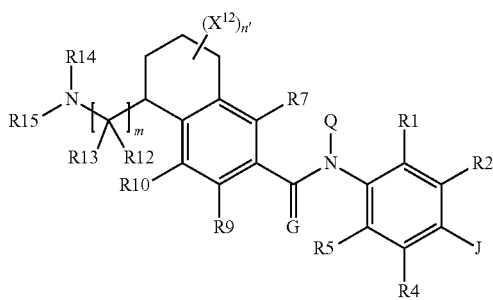

wherein G, Q, J, R1, R2, R4, R5, R7, R9, R10, R12, R13, R14, R15 and $X^{12}$ are as defined above, and n represents 0, 1 or 2.

Group 11: Carboxamides represented by Formula (I-XI):

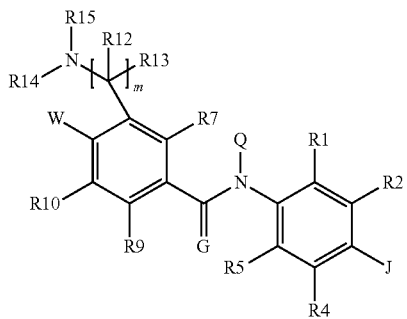

wherein W, G, Q, J, R1, R2, R4, R5, R7, R9, R10, R12, R13, R14, R15 and m are as defined above.

Group 12: Carboxamides represented by Formula (I-XII):

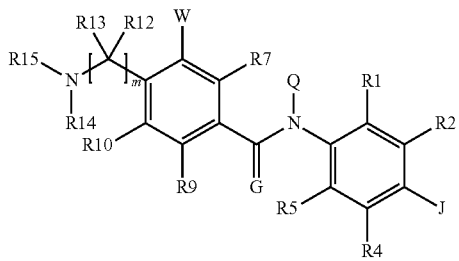

wherein W, G, Q, J, R1, R2, R4, R5, R7, R9, R10, R12, R13, R14, R15 and m are as defined above.

Group 13: Carboxamides represented by Formula (I-XIII):

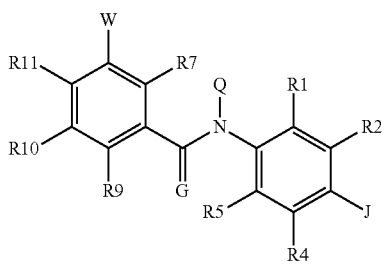

wherein G, Q and J are as defined above; W represents any one of the above W1 to W9; R1, R2, R4 and R5 independently have the same meaning as $X^2$ above; and R7, R9, R10 and R11 independently have the same meaning as $X^1$ above.

Herein, the carboxamides of Formula (I) and the carboxamides of Groups 1 to 13 satisfying the followings are preferable:

J each independently represents $C_{1-4}$ perfluoroalkyl, $C_{1-4}$ monobromoperfluoroalkyl, $C_{3-6}$ perfluorocycloalkyl, $-C(J^1)(J^2)(J^3)$ or $-C(J^1)(J^2)(OJ^4)$, $J^1$ and $J^2$ each independently represent $C_{1-4}$ perfluoroalkyl, $J^3$ represents any one of the substituents represented by Formulae W1 to W9 as described above, $J^4$ represents $C_{1-4}$ alkyl, $C_{1-4}$ haloalkyl or a phenyl group, and each group defined above may be substituted with any substituent.

The compounds of Formula (I) of the present invention may have an asymmetric carbon, and therefore optical isomers are included in such compounds.

Preparation method (a) can be represented by the following reaction formula when 4-(1H-1,2,4-triazolo-1-yl)benzoyl chloride and 2,6-dibromo-4-(1,1,1,2,3,3,3-heptafluoropropan-2-yl)aniline are used as startnig materials, for example.

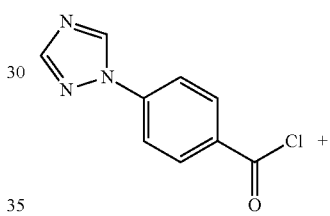

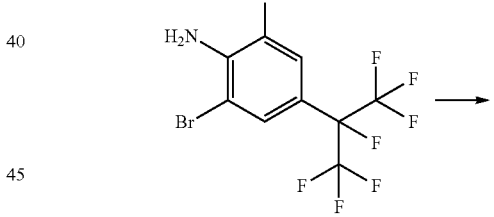

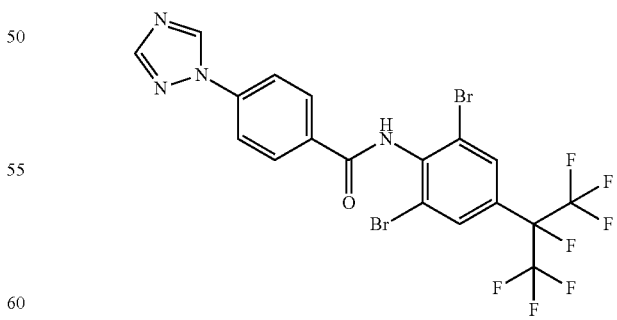

Preparation method (b) can be represented by the following reaction formula when N-[2-ethyl-4-(1, 1,1,2,3,3,3-heptafluoropropan-2-yl)-6-methylphenyl]-4-fluoro-3-nitrobenzamide and 1H-1,2,4-triazole are used as starting materials, for example.

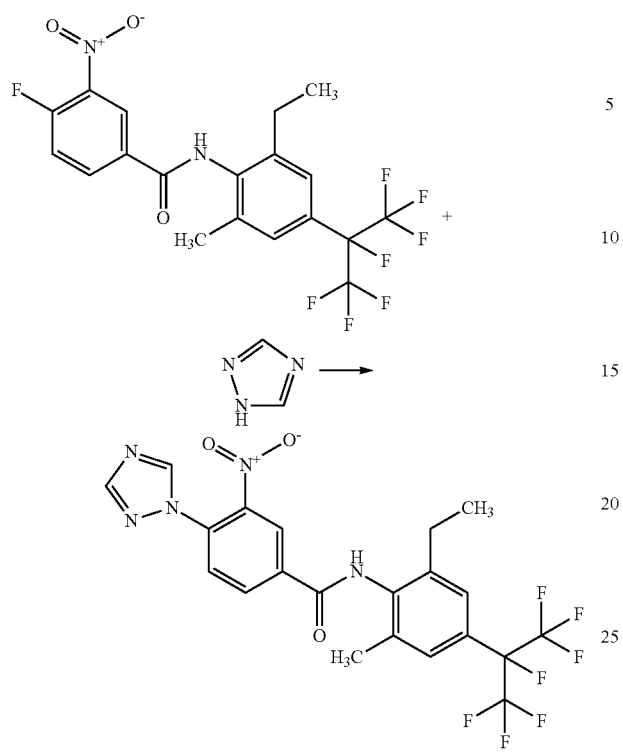

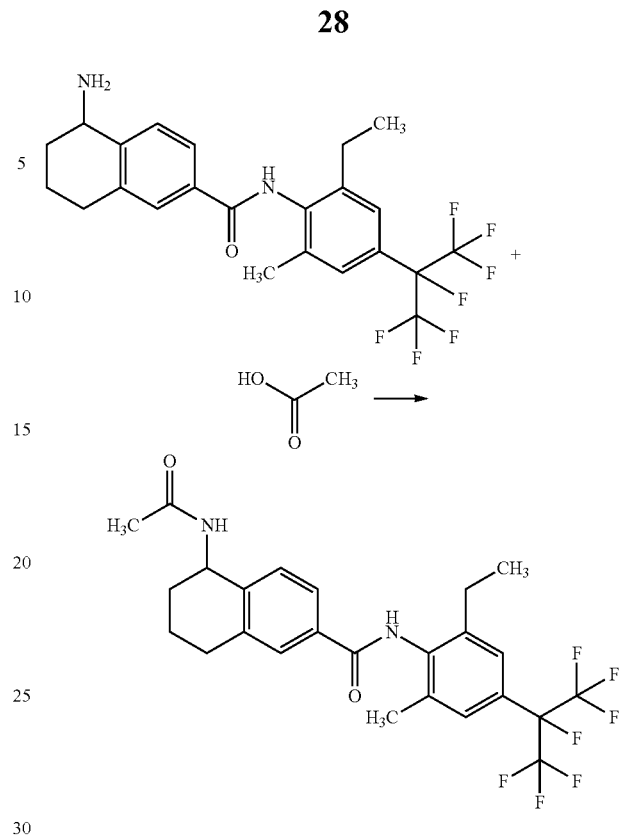

Preparation method (c) can be represented by the following reaction formula when 4-(aminomethyl)-N-[2-ethyl-4-(1,1,1,2,3,3,3-heptafluoropropan-2-yl)-6-methylphenyl]benzamide and acetic anhydride are used as starting materials, for example.

Preparation method (e) can be represented by the following reaction formula when 1-amino-N-[2-ethyl-4-(1,1,1,2,3,3,3-heptafluoropropan-2-yl)-6-methylphenyl]-indane-5-carboxamide and acetic acid are used as starting materials, for example.

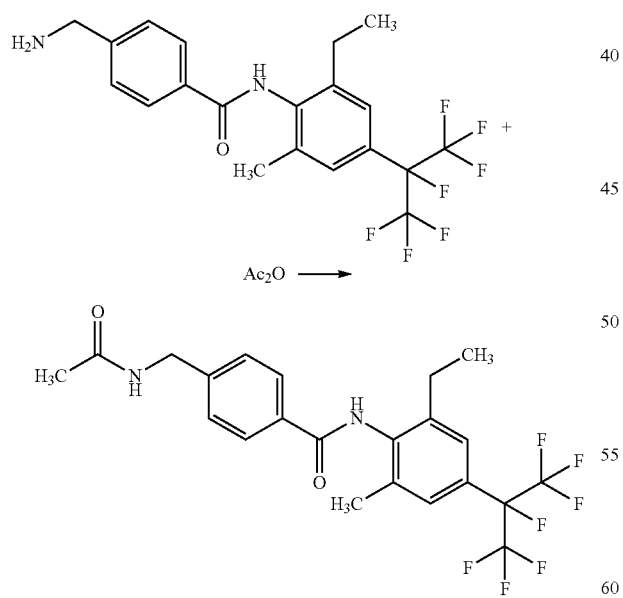

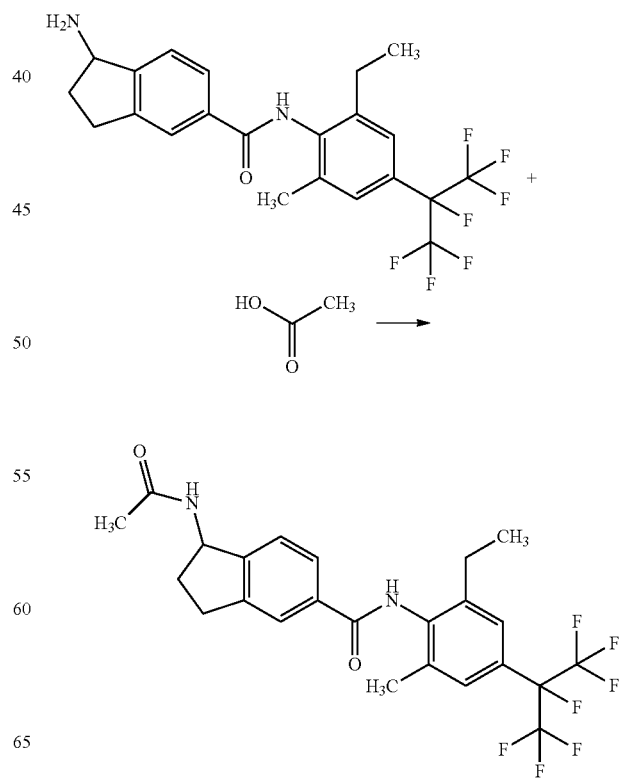

Preparation method (d) can be represented by the following reaction formula when 5-amino-N-[2-ethyl-4-(1,1,1,2,3,3,3-heptafluoropropan-2-yl)-6-methylphenyl]-5,6,7,8-tetrahydronaphthalene-2-carboxamide and acetic acid are used as starting materials, for example.

Preparation method (f) can be represented by the following reaction formula when N-[4-(1,1,1,2,3,3,3-heptafluoropropan-2-yl)-2,6-dimethylphenyl]-4-(1H-1,2,4-triazol-1-yl)benzamide and methyl iodide are used as starting materials, for example.

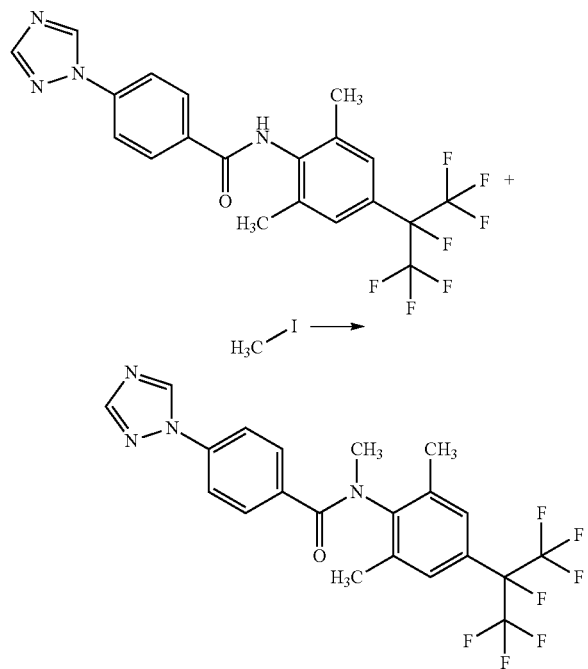

Preparation method (g) can be represented by the following reaction formula when N-[4-(1,1,1,2,3,3,3-heptafluoropropan-2-yl)-2,6-dimethylphenyl]-4-(1H-1,2,4-triazol-1-yl)benzamide and Lawesson reagent are used as starting materials, for example.

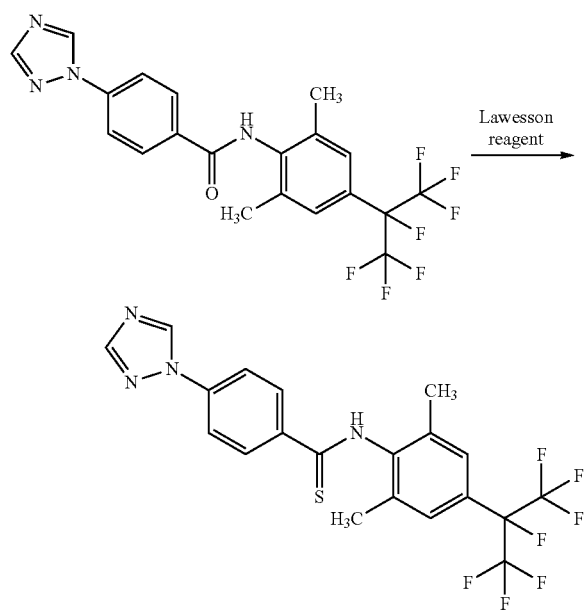

Explanation on the respective Preparation methods and intermediates will be provided below.

The compounds of Formula (II) which are starting materials in Preparation method (a) are publicly known and their representative examples are as follows:
4-(1H-pyrrol-1-yl)benzoyl chloride,
4-(1H-pyrazol-1-yl)benzoyl chloride,
3-chloro-4-(1H-pyrazol-1-yl)benzoyl chloride,
4-(1H-imidazol-1-yl)benzoyl chloride,
4-(1H-1,2,4-triazol-1-yl)benzoyl chloride,
4-(1H-tetrazol-1-yl)benzoyl chloride,
4-cyano-3-fluorobenzoyl chloride and the like.

When $L^1$ of Formula (II) represents hydroxy in the starting materials for Preparation method (a), they can be reacted with the compounds of Formula (III) in the presence of a condensing agent.

As the condensing agent, 1,3-dicyclohexylcarbodiimide (DCC), 1-ethyl-3-(3'-dimethylaminopropyl)-carbodiimide hydrochloride (WSCI), carbonyldiimidazole (CDI), diethyl phosphocyanate (DEPC), 2-chloro-1-methylpyridinium iodide (Mukaiyama reagent), etc. can be used for the reaction.

When $L^1$ of Formula (II) represents hydroxy in the starting materials for Preparation method (a), $L^1$ can be easily converted to an appropriate substituent by several methods including, pre-reacting with a chlorination agent, such as thionyl chloride, oxalyl chloride or phosphorous pentachloride, reacting with an organic acid halide, such as pyvaloyl chloride, or reacting with carbonyldiimidazole or sulfonylimidazole and the like.

Some of the compounds of Formula (III) as starting materials for Preparation method (a) are known and they can be synthesized according to the methods described in US 2002/0198399A1, WO 2005/021488A1, WO 2005/073165A1, WO 2006/024412A2 or Japanese Patent Application No. 2009-172800. Their representative examples are as follows:
4-(1,1,1,2,3,3,3-heptafluoropropan-2-yl)-2,6-dimethylaniline,
2-ethyl-4-(1,1,1,2,3,3,3-heptafluoropropan-2-yl)-6-methylaniline,
2,6-diethyl-4-(1,1,1,2,3,3,3-heptafluoropropan-2-yl)aniline,
2-bromo-4-(1,1,1,2,3,3,3-heptafluoropropan-2-yl)-6-methylaniline,
2-bromo-4-(1,1,1,2,3,3,3-heptafluoropropan-2-yl)-6-ethylaniline,
2,6-dichloro-4-(1,1,1,2,3,3,3-heptafluoropropan-2-yl)aniline,
2,6-dibromo-4-(1,1,1,2,3,3,3-heptafluoropropan-2-yl)aniline,
4-(1,1,1,2,3,3,3-heptafluoropropan-2-yl)-2,6-diiodoaniline,
4-(1,1,1,2,3,3,3-heptafluoropropan-2-yl)-2-(trifluoromethyl)aniline,
2-chloro-4-(1,1,1,2,3,3,3-heptafluoropropan-2-yl)-6-(trifluoromethyl)aniline,
2-bromo-4-(1,1,1,2,3,3,3-heptafluoropropan-2-yl)-6-(trifluoromethyl)aniline,
4-(1,1,1,2,3,3,3-heptafluoropropan-2-yl)-2-iodo-6-(trifluoromethyl)aniline,
4-(1,1,1,2,3,3,3-heptafluoropropan-2-yl)-2-(trifluoromethoxy)aniline,
2-chloro-4-(1,1,1,2,3,3,3-heptafluoropropan-2-yl)-6-(trifluoromethoxy)aniline,
2-bromo-4-(1,1,1,2,3,3,3-heptafluoropropan-2-yl)-6-(trifluoromethoxy)aniline,
4-(1,1,1,2,3,3,3-heptafluoropropan-2-yl)-2-iodo-6-(trifluoromethoxy)aniline,
4-(1,1,1,2,3,3,3-heptafluoropropan-2-yl)-2-[(trifluoromethyl)sulfanyl]aniline,
4-(1,1,1,2,3,3,3-heptafluoropropan-2-yl)-2-[(trifluoromethyl)sulfinyl]aniline, 4-(1,1,1,2,3,3,3-heptafluoropropan-2-yl)-2-[(trifluoromethyl)sulfonyl]aniline,
2-chloro-4-(1,1,1,2,3,3,3-heptafluoropropan-2-yl)-6-[(trifluoromethyl)-sulfanyl]aniline,
2-chloro-4-(1,1,1,2,3,3,3-heptafluoropropan-2-yl)-6-[(trifluoromethyl)-sulfinyl]aniline,
2-chloro-4-(1,1,1,2,3,3,3-heptafluoropropan-2-yl)-6-[(trifluoromethyl)-sulfonyl]aniline,
2-bromo-4-(1,1,1,2,3,3,3-heptafluoropropan-2-yl)-6-[(trifluoromethyl)-sulfanyl]aniline,
2-bromo-4-(1,1,1,2,3,3,3-heptafluoropropan-2-yl)-6-[(trifluoromethyl)-sulfinyl]aniline,
2-bromo-4-(1,1,1,2,3,3,3-heptafluoropropan-2-yl)-6-[(trifluoromethyl)-sulfonyl]aniline,
4-(1,1,1,2,3,3,3-heptafluoropropan-2-yl)-2-iodo-6-[(trifluoromethyl)-sulfanyl]aniline,
4-(1,1,1,2,3,3,3-heptafluoropropan-2-yl)-2-iodo-6-[(trifluoromethyl)-sulfinyl]aniline,
4-(1,1,1,2,3,3,3-heptafluoropropan-2-yl)-6-iodo-4-[(trifluoromethyl)-sulfonyl]aniline,
2-ethyl-4-(2-ethoxy-1,1,1,3,3,3-hexafluoropropan-2-yl)-6-methylaniline,
4-[2-(4-chlorophenoxy)-1,1,1,3,3,3-hexafluoropropan-2-yl]-2-ethyl-6-methylaniline,
4-[2-(4-chloro-1H-pyrazol-1-yl)-1,1,1,3,3,3-hexafluoropropan-2-yl]-2-ethyl-6-methylaniline,
4-(1,1,1,2,3,3,4,4,4-nonafluorobutan-2-yl)-2,6-dimethylaniline,
2-ethyl-4-(1,1,1,2,3,3,4,4,4-nonafluorobutan-2-yl)-6-methylaniline,
2,6-dichloro-4-(1,1,1,2,3,3,4,4,4-nonafluorobutan-2-yl) aniline,
2,6-dibromo-4-(1,1,1,2,3,3,4,4,4-nonafluorobutan-2-yl) aniline,
4-(1,1,1,2,3,3,4,4,4-nonafluorobutan-2-yl)-2,6-diiodoaniline,
2-ethyl-4-[2-ethoxy-1,1,1,3,3,4,4,4-octafluorobutan-2-yl]-6-methylaniline,
4-[2-(4-chlorophenoxy)-1,1,1,3,3,4,4,4-octafluorobutan-2-yl]-2-ethyl-6-methylaniline,
4-[2-(4-chloro-1H-pyrazol-1-yl)-1,1,1,3,3,4,4,4-octafluorobutan-2-yl]-2-ethyl-6-methylaniline,
2,6-dibromo-4-(trifluoromethoxy)aniline,
2,6-dibromo-4-[(trifluoromethyl)sulfanyl]aniline,
2,6-dibromo-4-[(trifluoromethyl)sulfinyl]aniline,
2,6-dibromo-4-[(trifluoromethyl)sulfonyl]aniline,
2,6-dibromo-4-[(pentafluoroethyl)sulfanyl]aniline,
2,6-dibromo-4-[(heptafluoropropyl)sulfanyl]aniline,
2,6-dibromo-4-[(nonafluorobutyl)sulfanyl]aniline,
2,6-dimethyl-4-(undecafluorocyclohexyl)aniline
2-ethyl-6-methyl-4-(undecafluorocyclohexyl)aniline
2,6-dichloro-4-(undecafluorocyclohexyl)aniline
2,6-dibromo-4-(undecafluorocyclohexyl)aniline
2,6-diiodo-4-(undecafluorocyclohexyl)aniline, and the like.

The reaction of Preparation method (a) can be carried out in the presence of an appropriate diluent, and examples thereof to be used include aliphatic hydrocarbons (hexane, cyclohexane, heptane, etc.), halogenated aliphatic hydrocarbons (dichloromethane, chloroform, carbon tetrachloride, dichloroethane, etc.), aromatic hydrocarbons (benezene, toluene, xylene, chlorobenzene, etc.), ethers (diethyl ether, dibutyl ether, dimethoxyethane (DME), tetrahydrofuran, dioxane, etc.), esters (ethyl acetate, ethyl propionate, etc.), acid amides (dimethyl formamide (DMF), dimethyl acetamide (DMA), N-methylpyrrolidone, etc.), nitriles (acetonitrile, propionitrile, etc), dimethyl sulfoxide (DMSO), water, a mixture thereof, and etc.

The reaction of Preparation method (a) can be carried out in the presence of an appropriate base, and examples thereof to be used include alkali metal bases, such as lithium hydride, sodium hydride, potassium hydride, butyllithium, tert-butyllithium, trimethylsilyllithium, lithium hexamethyldisilazide, sodium hydroxide, potassium hydroxide, sodium carbonate, potassium carbonate, cesium carbonate, tripotassium phosphate, sodium acetate, potassium acetate, sodium methoxide, sodium ethoxide, sodium tert-butoxide, and potassium tert-butoxide and organic bases, such as triethylamine, diisopropylethylamine, tributylamine, N-methylmorpholilne, N,N-dimethylaniline, N,N-diethylaniline, 4-tert-butyl-N,N-dimethylanilne, pyridine, picoline, lutidine, diazabicycloundecene, (1,8-diazabicyclo[5.4.0]undec-7-ene), diazabicyclooctane, imidazole and etc.

Preparation method (a) can be carried out within a substantially wide temperature range. It may be generally carried out at the temperature between about −78° C. and about 200° C., preferably between −10° C. and about 150° C. Said reaction is preferably carried out at normal pressure although it may be carried out under elevated or reduced pressure. The reaction time is 0.1 to 72 hours, preferably 0.1 to 24 hours.

For carrying out Preparation method (a), for example, 1 mole of the compound of formula (II) can be reacted with 1 to 3 moles of the compound of formula (III) using, when $L^1$ in Formula (II) represents hydroxy, 1 to 3 mole of a condensing agent in a diluent, e.g., DMF, or, when $L^1$ in Formula (II) represents an appropriate leaving group, in the presence of an appropriate base, e.g., pyridine, thereby to obtain the corresponding compound of Formula (I).

Some of the compounds of Formula (IV) as starting materials for Preparation method (b) include the publicly known compounds disclosed in WO 2005/021488 and WO 2005/073165 and their representative examples are as follows:
N-[2,6dimethyl-4-(1,1,1,2,3,3,3-heptafluoropropan-2-yl) phenyl]-4-fluoro-3-nitrobenzamide,
N-[2-ethyl-4-(1, 1,1,2,3,3,3-heptafluoropropan-2-yl)-6-methylphenyl]-4-fluoro-3-nitrobenzamide, and the like.

On the other hand, representative examples of the novel compounds encompassed by the compounds of Formula (IV) are as follows:
2-chloro-4-fluoro-N-[4-(1,1,1,2,3,3,3-heptafluoropropan-2-yl)-2,6-dimethylphenyl]benzamide,
4-fluoro-N-[4-(1,1,1,2,3,3,3-heptafluoropropan-2-yl)-2,6-dimethylphenyl]-2-(trifluoromethyl)benzamide,
4-fluoro-N-[4-(1,1,1,2,3,3,3-heptafluoropropan-2-yl)-2,6-dimethylphenyl]-2-nitrobenzamide,
N-[2-ethyl-4-(1,1,1,2,3,3,3-heptafluoropropan-2-yl)-6-methylphenyl]-3,4-difluorobenzamide,
3-chloro-N-[2-ethyl-4-(1,1,1,2,3,3,3-heptafluoropropan-2-yl)-6-methylphenyl]-4-fluorobenzamide,
3-bromo-N-[2-ethyl-4-(1,1,1,2,3,3,3-heptafluoropropan-2-yl)-6-methylphenyl]-4-fluorobenzamide,
N-[2-ethyl-4-(1,1,1,2,3,3,3-heptafluoropropan-2-yl)-6-methylphenyl]-4-fluoro-3-(trifluoromethyl)benzamide,
N-[2-ethyl-4-(1,1,1,2,3,3,3-heptafluoropropan-2-yl)-6-methylphenyl]-4-fluoro-1-naphthamide,
5-bromo-N-[2-ethyl-4-(1,1,1,2,3,3,3-heptafluoropropan-2-yl)-6-methyl-phenyl]pyridine-2-carboxamide,
6-chloro-N-[4-(1,1,1,2,3,3,3-heptafluoropropan-2-yl)-2,6-dimethylphenyl]-nicotinic acid amide,
6-chloro-N-[2-ethyl-4-(1,1,1,2,3,3,3-heptafluoropropan-2-yl)-6-methylphenyl]-nicotinic acid amide, and the like.

Novel intermediates among the compounds of Formula (IV) are shown in the following Formulae (V-1) to (V-5):

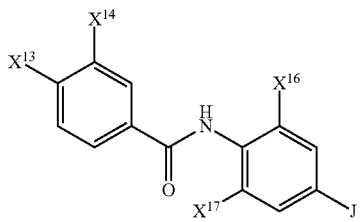
(V-1)

(wherein $X^{13}$ represents halogen, $X^{14}$ represents halogen or $C_{1-4}$ haloalkyl, $X^{16}$ and $X^{17}$ each independently represent halogen, $C_{1-4}$ alkyl, $C_{1-4}$ haloalkyl, $C_{1-4}$ haloalkoxy, $C_{1-4}$ haloalkyl-S—, $C_{1-4}$ haloalkyl-S(O)— or $C_{1-4}$ haloalkyl-S(O)$_2$— and J is as defined above);

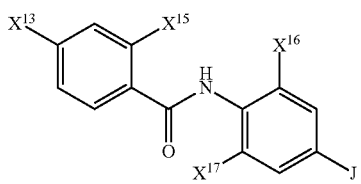
(V-2)

(wherein $X^{15}$ represents halogen, $C_{1-4}$ haloalkyl or a nitro group and $X^{13}$, $X^{16}$, $X^{17}$ and J are as defined above);

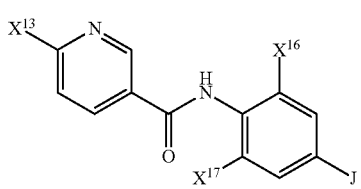
(V-3)

(wherein $X^{13}$, $X^{16}$, $X^{17}$ and J are as defined above);

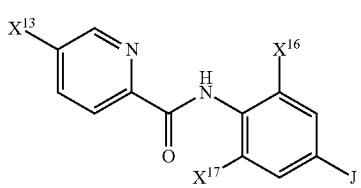
(V-4)

(wherein $X^{13}$, $X^{16}$, $X^{17}$ and J are as defined above); and

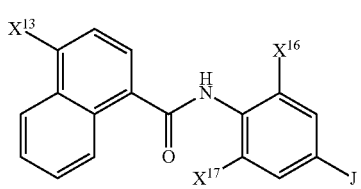
(V-5)

(wherein $X^{13}$, $X^{16}$, $X^{17}$ and J are as defined above).

Some of the compounds of Formula (IV) as starting materials for Preparation method (b) can be synthesized according to the methods disclosed in WO 2005/021488 and WO 2005/073165. Specifically, they can be synthesized by reacting the compounds of Formula (VI):

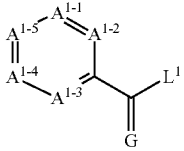
(VI)

(wherein $A^{1-1}$, $A^{1-2}$, $A^{1-3}$, $A^{1-4}$, $A^{1-5}$, G and $L^1$ each independently have the same meaning as defined above) with the compounds of Formula (III) described above according to Preparation method (a).

Specific preparation method of compound of Formula (IV) is shown in below:

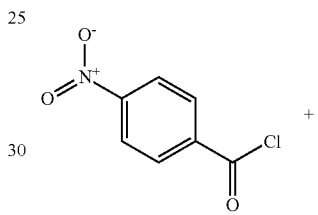

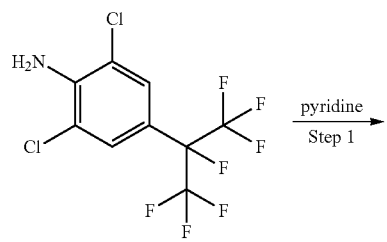

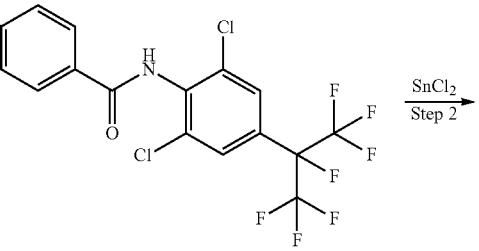

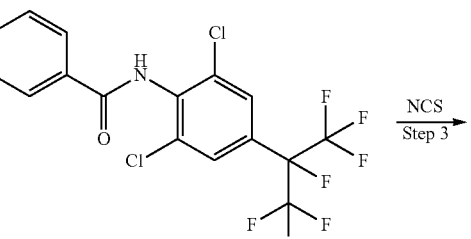

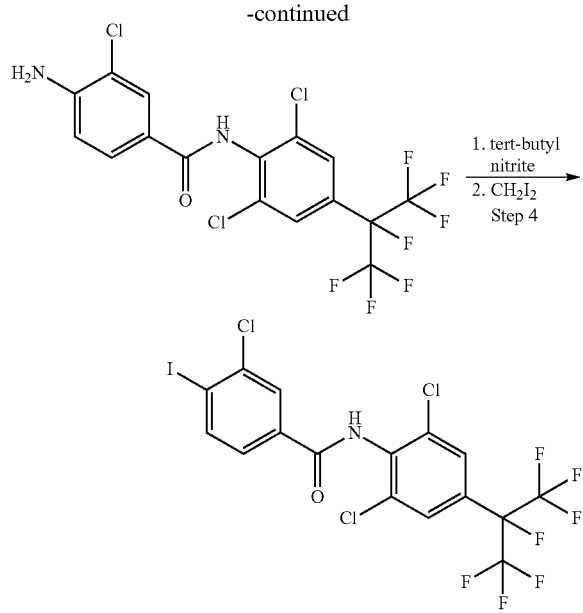

(wherein, Step 1 is done by following the metod descrived in Preparation method (a), Step 2 is done by following the method descrived in Scheme 1, step 1-1, Step 3 is clorination by using N-chlorosuccinimide (NCS) and Step 4 is done by following the method descrived in JP2008-505120A)

The reaction of Preparation method (b) can be carried out in the presence of an appropriate diluent, and examples thereof to be used are the same as the diluents described for Preparation method (a), and preferably dimethylformamide (DMF), dimethylacetamide (DMA), N-methylpyrrolidone or dimethyl sulfoxide (DMSO).

The reaction of Preparation method (b) can be carried out in the presence of an appropriate base, and examples thereof to be used are the same as the bases described for Preparation method (a), and preferably potassium carbonate.

The reaction of Preparation method (b) can be carried out by using a catalyst such as $Pd_2$ $(dba)_3$, $Pd_2$ $(dba)_3CHCl_3$, (dba=dibenzylideneacetone), Pd $(OAc)_2$, CuI, and $Cu_2O$ in the presence of an appropriate base, if necessary. Further, if necessary, phosphine type ligands such as 2,2'-bis(diphenylphosphino)-1,1'-binaphthalene (BINAP), 4,5-bis(diphenylphosphino)-9,9-dimethylxanthene (Xantphos) and tributylphosphine or amine type ligands such as 8-quinolinol, proline and N,N-dimethylglycine can be used.

Preparation method (b) can be carried out within a substantially wide temperature range. It may be generally carried out at a temperature between about −78° C. and about 200° C., preferably between about −10° C. and about 180° C. Said reaction is preferably carried out at normal pressure, although it may be carried out under elevated or reduced pressure. The reaction time is 0.1 to 72 hours, preferably 0.1 to 24 hours.

For carrying out Preparation method (b), for example, 1 mole of the compound of Formula (IV) can be reacted with 1 to 2 moles of the compound represented by W1-H, W2-H, W3-H, W4-H, W5-H, W6-H, W7-H, W8-H or W9-H in the presence of 1 to 3 moles of a base, for example potassium carbonate, in a diluent, for example dimethylformamide, thereby to obtain the compound of Formula (I) of the present invention. In addition, when the catalyst described above is used, for example, 1 mole of the compound of Formula (IV) can be reacted with 1 to 3 moles of the compound represented by W1-H, W2-H, W3-H, W4-H, W5-H, W6-H, W7-H, W8-H or W9-H in the presence of 1 to 3 moles of a base and a catalytic amount of CuI and proline in a diluent, for example dimethylsulfoxide, thereby to obtain the compound of Formula (I) of the present invention.

When $A^{1-1}$, $A^{1-2}$, $A^{1-3}$, $A^{1-4}$ or $A^{1-5}$, encompassed by the compounds of Formula (I) of the present invention obtained according to Preparation method (b), is C—$NO_2$, the nitro group can be easily converted to other substituents. Specific examples thereof are described in the following Scheme 1.

Scheme 1:

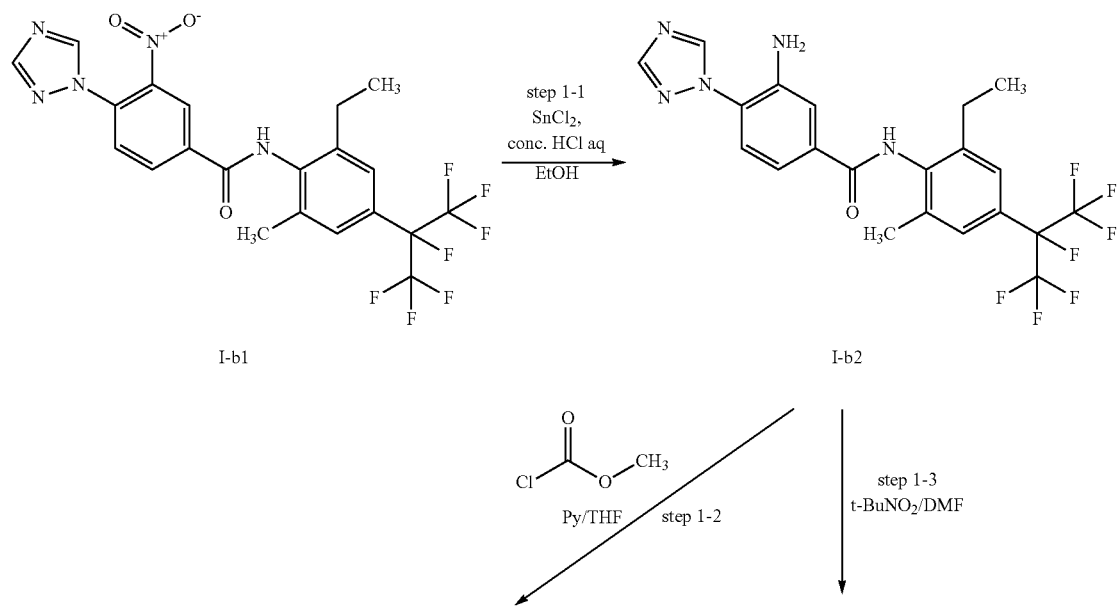

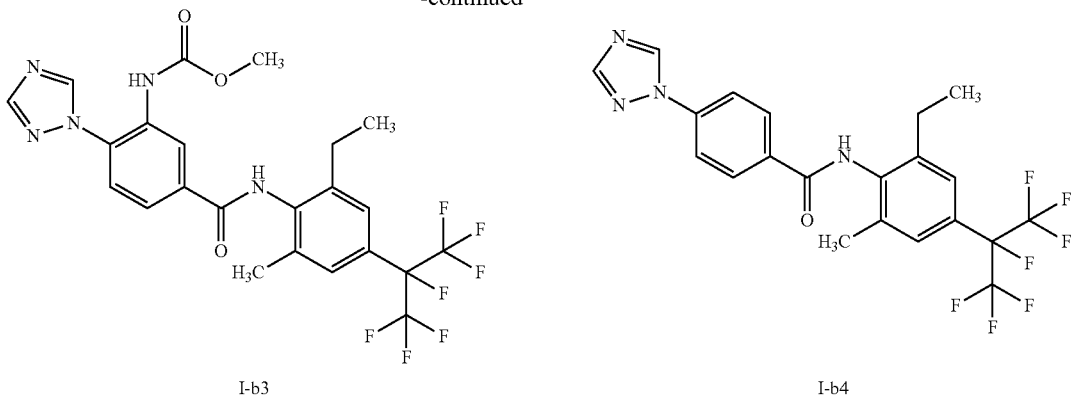

I-b3

I-b4

(In Scheme 1, conc. HCl aq indicates a concentrated hydrochloric acid aqueous solution, Py indicates pyridine, THF indicates tetrahydrofuran, t-Bu indicates tertiary butyl, and DMF indicates N,N-dimethylformamide. According to step 1-1, the nitro group is reduced to give the amino group. According to step 1-2, the acyl group is introduced to the amino group. According to step 1-3, the amino group can be converted to a diazonium salt through Sandmeyer reaction and then to hydrogen after removal of the diazonium salt.)

The compounds of Formula (I-c1) as starting materials for Preparation method (c), can be synthesized according to various methods. Representative examples thereof are shown in Schemes 2, 3, 3-1 and 4.

Scheme 2:

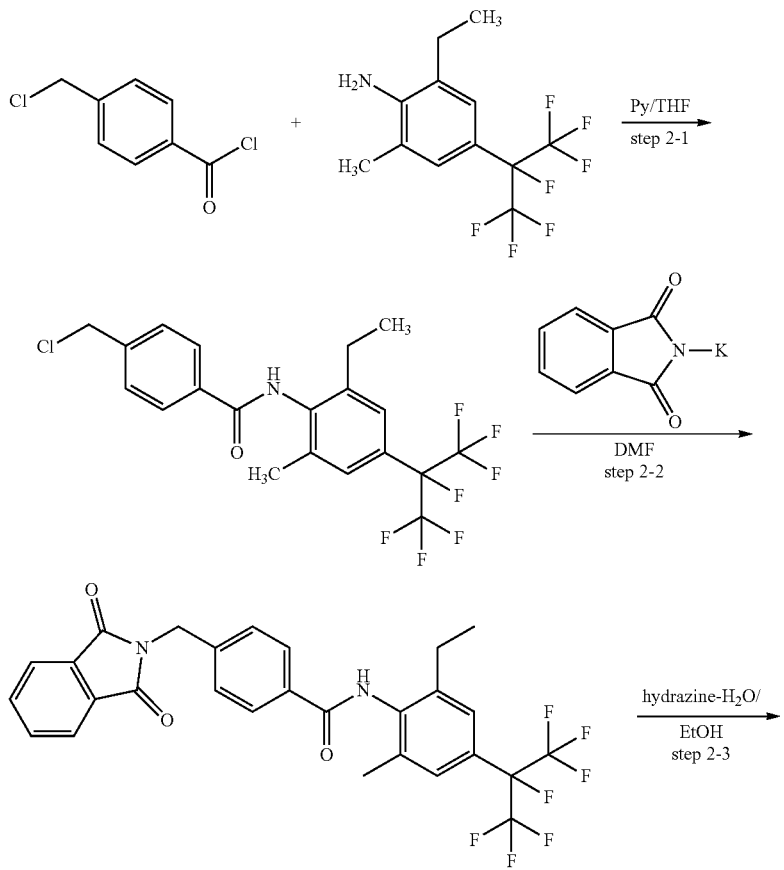

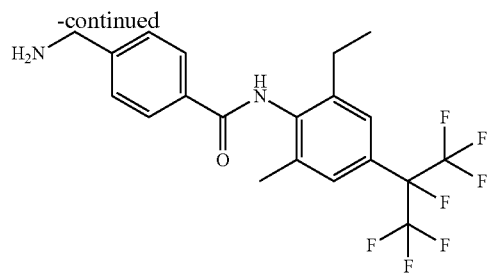

(In Scheme 2, hydrazine-$H_2O$ indicates a hydrazine hydrate, EtOH indicates ethanol and Py, THF and DMF are as defined above.)

According to Scheme 2, the benzyl halide derivative is obtained through an acid condensation reaction at step 2-1, which is then reacted with phthalimide potassium salt at step 2-2, and subsequently at step 2-3 the phthalimide residue is removed by hydrazine to give the benzylamino derivative. All the reactions defined above can be carried out according to general methods for synthesizing organic compounds.

Scheme 3:

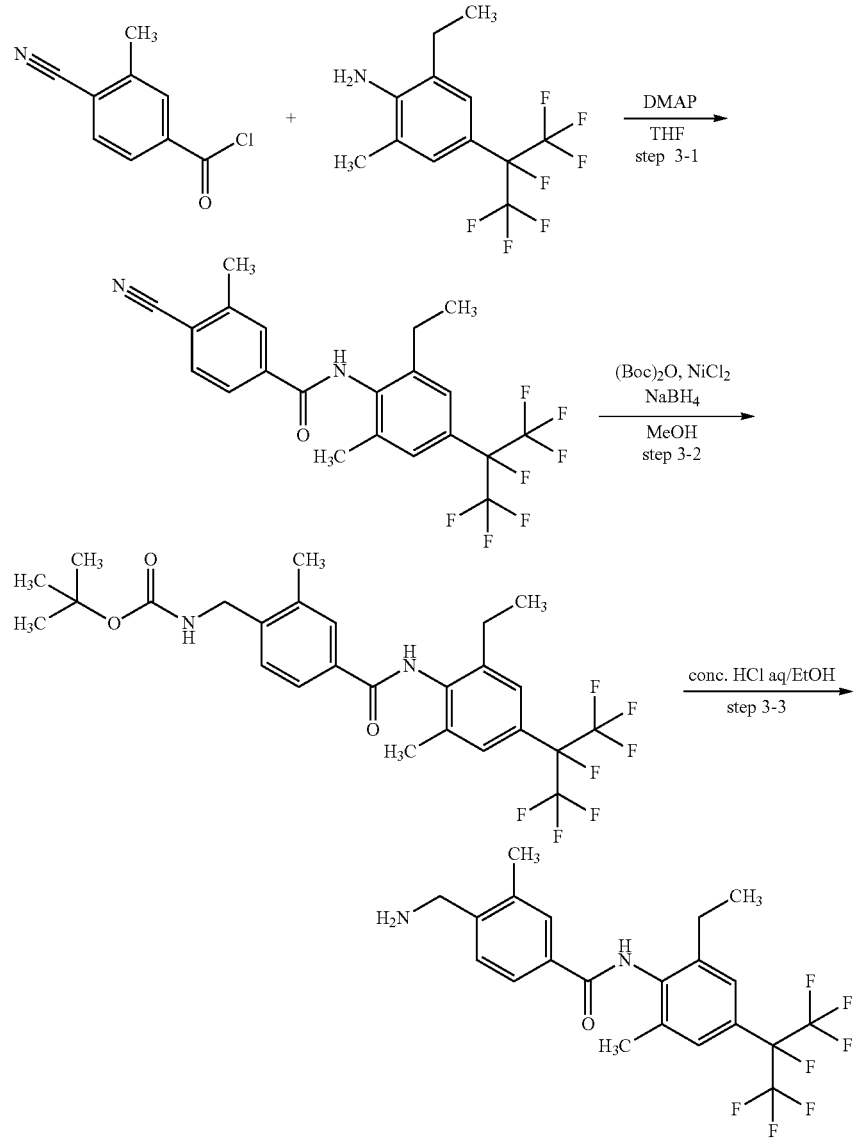

(In Scheme 3, DMAP indicates 4-dimethylaminopyridine, (Boc)₂O indicates di(t-butyl) bicarbonate, MeOH indicates methanol and conc. HCl aq and EtOH are as defined above.)

In accordance with the methods of step 3-2 and step 3-3 in Scheme 3 and 3, 1,4-(aminomethyl)-N-[2-ethyl-4-(1,1,1,2,3,3,3-heptafluoropropan-2-yl)-6-methylphenyl]-3-(1H-pyra- Scheme 3-1:

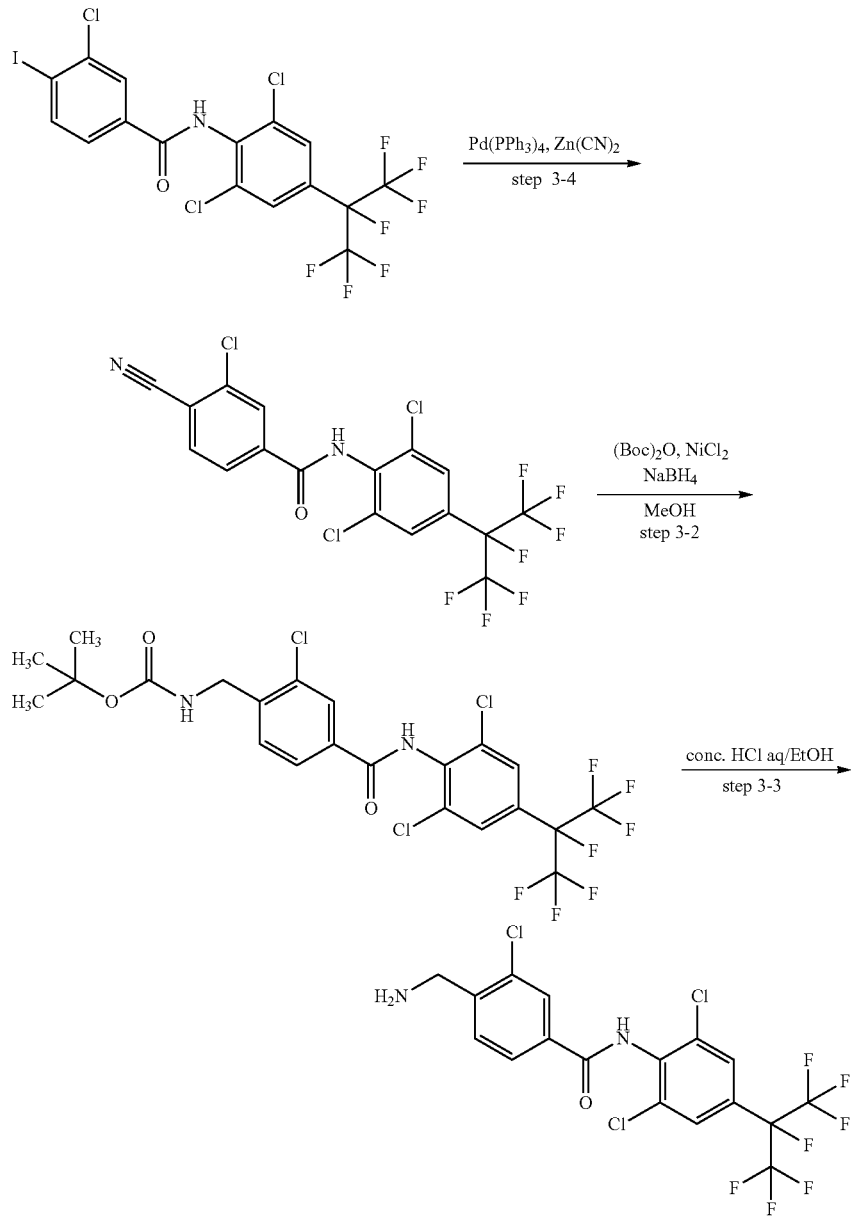

(In Scheme 3-1, PPh indicates triphenylphosphine, (Boc)₂O indicates di(t-butyl)bicarbonate, MeOH indicates methanol and conc. HCl aq and EtOH are as defined above.)

The reaction of step 3-2 in Scheme 3 and 3-1 can be carried out according to the method described in the literature (Tetrahedron Letters, 2000, 41, 3513-3516 or Tetrahedron, 2003, 59, 5417-5423).

The reaction of step 3-4 in Scheme 3-1 can be carried out according to the method described in the literature (Synthetic Communications, 1994, 887-890). Other methods can be carried out according to general methods for synthesizing organic compounds.

zol-1-yl)benzamide or 4-(aminomethyl)-N-[2-ethyl-4-(1,1,1,2,3,3,3-heptafluoropropan-2-yl)-6-methylphenyl]-3-(1H-1,2,4-triazolyl-1-yl)benzamide may be obtained by using 4-cyano-N-[2-ethyl-4-(1,1,1,2,3,3,3-heptafluoropropan-2-yl)-6-methylphenyl]-3-(1H-pyrazol-1-yl)benzamide or 4-cyano-N-[2-ethyl-4-(1,1,1,2,3,3,3-heptafluoro-propan-2-yl)-6-methylphenyl]-3-(1H-1,2,4-triazolyl-1-yl)benzamide, respectively, as a raw material. Further, 3-(aminomethyl)-N-[2-ethyl-4-(1,1,1,2,3,3,3-heptafluoropropan-2-yl)-6-methylphenyl]-4-(1H-1,2,4-triazol-1-yl)benzamide may be similarly obtained from 3-cyano-N-[2-ethyl-4-(1,1,1,2,3,3,3-heptafluoropropan-2-yl)-6-methyl-phenyl]-4-(1H-1,2,4-triazol-1-yl)benzamide.

Scheme 4:

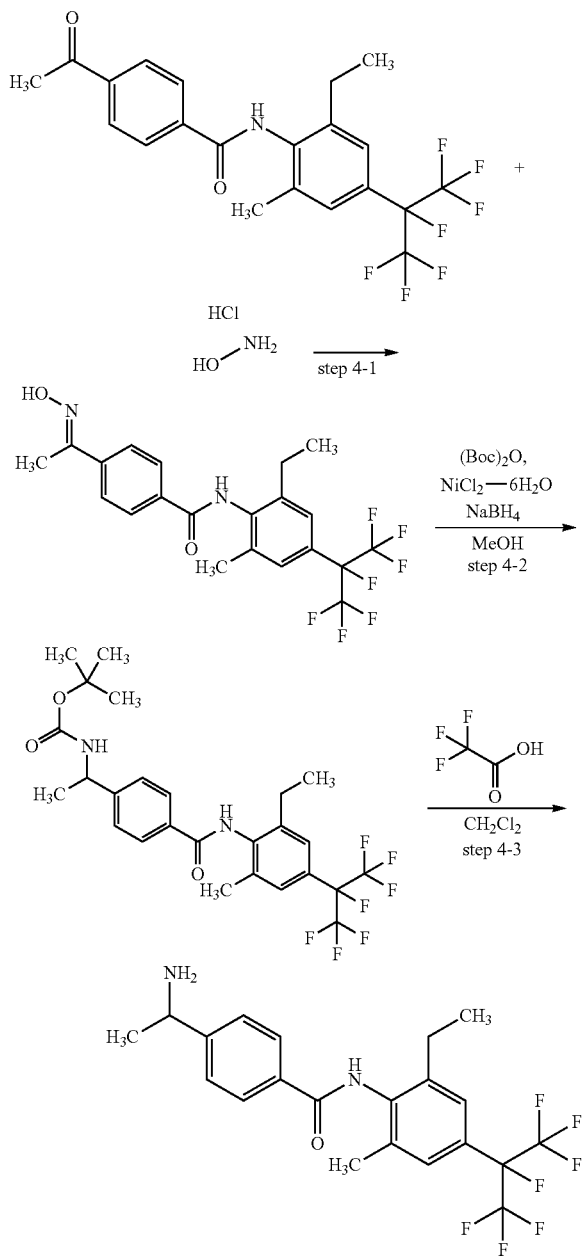

(In Scheme 4, (Boc)₂O and MeOH are as defined above.)

The reaction of step 4-2 in Scheme 4 can be carried out in the same manner as step 3-2 in Scheme 3. Other methods can be carried out according to general methods for synthesizing organic compounds.

There are additional methods for synthesizing the compounds of Formula (I-c1) as starting materials for Preparation method (c), and examples include a method in which hexamethylenetetramine is reacted with the benzyl halide derivative of Scheme 2 followed by hydrolysis under an acidic condition to give the benzylamino derivative (Delepine amine synthesis, reference literatures: Bull. Soc. Chim. Fr. 1895, 13, S 352, J. Org. Chem. 1993, 58, 270, J. Org. Chem. 1990, 55, 1796, Org. React. 1954, 8, 197.), a method in which a benzyl alcohol derivative or the benzyl halide derivative is converted into a benzyl azide derivative followed by its reduction to give the benzylamino derivative (reference literatures: Chemical Review, 1988, 88, 297, J. Org. Chem., 1993, 58, 5886) or a method in which the benzyl halide derivative is converted to a benzylnitro derivative via Kornblum nitration followed by reduction to give the benzylamino derivative (reference literatures: Organic Synthesis Collective Volume, 1963, 4, 724, Organic Reactions, 1962, 12, 101), etc.

Representative examples of the compounds of Formula (I-c1) as starting materials for Preparation method (c) are as follows:

4-(aminomethyl)-N-[4-(1,1,1,2,3,3,3-heptafluoropropan-2-yl)-2,6-dimethyl-phenyl]benzamide,
4-(aminomethyl)-2-fluoro-N-[4-(1,1,1,2,3,3,3-heptafluoropropan-2-yl)-2,6-dimethylphenyl]benzamide,
4-(aminomethyl)-N-[2-ethyl-4-(1,1,1,2,3,3,3-heptafluoropropan-2-yl)-6-methylphenyl]benzamide,
4-(aminomethyl)-N-[2-ethyl-4-(1,1,1,2,3,3,3-heptafluoropropan-2-yl)-6-methylphenyl]-2-fluoro-benzamide,
4-(aminomethyl)-N-[2-ethyl-4-(1,1,1,2,3,3,3-heptafluoropropan-2-yl)-6-methylphenyl]-2,3-difluorobenz-amide,
4-(aminomethyl)-N-[2-ethyl-4-(1,1,1,2,3,3,3-heptafluoropropan-2-yl)-6-methylphenyl]-2,5-difluorobenz-amide,
4-(aminomethyl)-2-chloro-N-[2-ethyl-4-(1,1,1,2,3,3,3-heptafluoropropan-2-yl)-6-methylphenyl] benzamide,
4-(aminomethyl)-N-[2-ethyl-4-(1,1,1,2,3,3,3-heptafluoropropan-2-yl)-6-methylphenyl]-3-fluoro-benzamide,
4-(aminomethyl)-3-chloro-N-[2-ethyl-4-(1,1,1,2,3,3,3-heptafluoropropan-2-yl)-6-methylphenyl] benzamide,
4-(aminomethyl)-3-bromo-N-[2-ethyl-4-(1,1,1,2,3,3,3-heptafluoropropan-2-yl)-6-methylphenyl] benzamide,
4-(aminomethyl)-N-[2-ethyl-4-(1,1,1,2,3,3,3-heptafluoropropan-2-yl)-6-methylphenyl]-3-methyl benzamide,
4-(aminomethyl)-N-[2-ethyl-4-(1,1,1,2,3,3,3-heptafluoropropan-2-yl)-6-methylphenyl]-3-(trifluoro-methyl)benz amide,
4-(aminomethyl)-N-[2-ethyl-4-(1,1,1,2,3,3,3-heptafluoropropan-2-yl)-6-methylphenyl]-3-nitro-benzamide,
4-(aminomethyl)-N-[2,6-dibromo-4-(1,1,1,2,3,3,3-heptafluoropropan-2-yl)-phenyl]benzamide,
4-(aminomethyl)-N-[2,6-dimethyl-4-(1,1,1,2,3,3,4,4,4-nonafluorobutan-2-yl)-phenyl]benzamide,
4-(aminomethyl)-3-chloro-N-[2,6-dimethyl-4-(1,1,1,2,3,3,4,4,4-nonafluoro-butan-2-yl)phenyl]-benzamide,
4-(aminomethyl)-N-[2-ethyl-6-methyl-4-(1,1,1,2,3,3,4,4,4-nonafluorobutan-2-yl)phenyl]benzamide,
4-(aminomethyl)-N-[2-ethyl-6-methyl-4-(1,1,1,2,3,3,4,4,4-nonafluorobutan-2-yl)phenyl]-3-fluoro-benzamide,
4-(aminomethyl)-3-bromo-N-[2-ethyl-6-methyl-4-(1,1,1,2,3,3,4,4,4-nona-fluorobutan-2-yl)phenyl]benz-amide,
4-(aminomethyl)-N-[2,6-dibromo-4-(1,1,1,2,3,3,4,4,4-nonafluorobutan-2-yl)-phenyl]benzamide,
4-(aminomethyl)-3-chloro-N-[2-ethyl-6-methyl-4-(undecafluorocyclohexyl)-phenyl]benzamide,
4-(aminomethyl)-N-[2-ethyl-4-(1,1,1,2,3,3,3-heptafluoropropan-2-yl)-6-methylphenyl]-1-naphthamide,
4-(aminomethyl)-N-[2-ethyl-6-methyl-4-(1,1,1,2,3,3,4,4,4-nonafluorobutan-2-yl)phenyl]-1-naphthamide,
4-(aminomethyl)-N-[2-ethyl-6-methyl-4-(undecafluorocyclohexyl)phenyl]-1-naphthamide,
5-(aminomethyl)-N-[2-ethyl-4-(1,1,1,2,3,3,3-heptafluoropropan-2-yl)-6-methylphenyl]pyridine-2-carboxamide,
5-(aminomethyl)-N-[2-ethyl-6-methyl-4-(1,1,1,2,3,3,4,4,4-nonafluorobutan-2-yl)phenyl]pyridine-2-carboxamide,
5-(aminomethyl)-N-[2-ethyl-6-methyl-4-(undecafluorocyclohexyl)phenyl]-pyridine-2-carboxamide, 6-(aminomethyl)-N-[2-ethyl-4-(1,1,1,2,3,3,3-heptafluoropropan-2-yl)-6-methylphenyl]nicotinamide,
6-(aminomethyl)-N-[2-ethyl-6-methyl-4-(1,1,1,2,3,3,4,4,4-nonafluorobutan-2-yl)phenyl]nicotinamide,
6-(aminomethyl)-N-[2-ethyl-6-methyl-4-(undecafluorocyclohexyl)phenyl]-nicotinamide,
4-(1-aminoethyl)-N-[2-ethyl-4-(1,1,1,2,3,3,3-heptafluoropropan-2-yl)-6-methylphenyl]benzamide,
4-(1-aminoethyl)-N-[2-ethyl-6-methyl-4-(1,1,1,2,3,3,4,4,4-nonafluorobutan-2-yl)phenyl]benzamide,
4-(1-aminoethyl)-N-[2-ethyl-6-methyl-4-(undecafluorocyclohexyl)phenyl]-benzamide, and the like.

Specific examples of novel intermediates shown in Schemes 2 to 3 are as follows:
4-(chloromethyl)-N-[4-(1,1,1,2,3,3,3-heptafluoropropan-2-yl)-2,6-dimethyl-phenyl]benzamide,
4-(chloromethyl)-N-[2-ethyl-4-(1,1,1,2,3,3,3-heptafluoropropan-2-yl)-6-methylphenyl]benzamide,
3-chloro-4-(chloromethyl)-N-[2-ethyl-4-(1,1,1,2,3,3,3-heptafluoropropan-2-yl)-6-methylphenyl]-benzamide,
3-bromo-4-(chloromethyl)-N-[2-ethyl-4-(1,1,1,2,3,3,3-heptafluoropropan-2-yl)-6-methylphenyl]-benzamide,
4-(chloromethyl)-N-[2-ethyl-6-methyl-4-(1,1,1,2,3,3,4,4,4-nonafluorobutan-2-yl)phenyl]benzamide,
4-(chloromethyl)-N-[2-ethyl-6-methyl-4-(1,1,1,2,3,3,4,4,4-nonafluorobutan-2-yl)phenyl]-3-fluoro-benzamide,
3-chloro-4-(chloromethyl)-N-[2-ethyl-6-methyl-4-(1,1,1,2,3,3,4,4,4-nona-fluorobutan-2-yl)phenyl]benz-amide,
4-(chloromethyl)-N-[2-ethyl-4-(1,1,1,2,3,3,3-heptafluoropropan-2-yl)-6-methylphenyl]-1-naphthamide,
4-[(1,3-dioxo-1,3-dihydro-2H-isoindol-2-yl)methyl]-N-[4-(1,1,1,2,3,3,3-hepta-fluoropropan-2-yl)-2,6-dimethyl phenyl]benzamide,
4-[(1,3-dioxo-1,3-dihydro-2H-isoindol-2-yl)methyl]-N-[2-ethyl-4-(1,1,1,2,3,3,3-heptafluoropropan-2-yl)-6methylphenyl]benzamide,
3-chloro-4-[(1,3-dioxo-1,3-dihydro-2H-isoindol-2-yl)methyl]-N-[2-ethyl-4-(1,1,1,2,3,3,3-hepta-fluoropropan-2-yl)-6-methylphenyl]benzamide,
3-bromo-4-[[(1,3-dioxo-1,3-dihydro-2H-isoindol-2-yl)methyl]-N-[2-ethyl-4-(1,1,1,2,3,3,3-hepta-fluoropropan-2-yl)-6-methylphenyl]benzamide,
4-[(1,3-dioxo-1,3-dihydro-2H-isoindol-2-yl)methyl]-N-[2-ethyl-4-(1,1,1,2,3,3,3-heptafluoropropan-2-yl)-6methylphenyl]-3-nitrobenzamide,
4-[(1,3-dioxo-1,3-dihydro-2H-isoindol-2-yl)methyl]-N-[2-ethyl-6-methyl-4-(1,1,1,2,3,3,4,4,4-nona-fluorobutan-2-yl)phenyl]benzamide,
4-[(1,3-dioxo-1,3-dihydro-2H-isoindol-2-yl)methyl]-N-[2-ethyl-6-methyl-4-(1,1,1,2,3,3,4,4,4-nona-fluorobutan-2-yl)phenyl]-3-fluorobenzamide,
3-chloro-4-[(1,3-dioxo-1,3-dihydro-2H-isoindol-2-yl)methyl]-N-[2-ethyl-6-methyl-4-(1,1,1,2,3,3,4, 4,4-nona fluorobutan-2-yl)phenyl]benzamide,
4-[(1,3-dioxo-1,3-dihydro-2H-isoindol-2-yl)methyl]-N-[2-ethyl-4-(1,1,1,2,3,3,3-heptafluoropropan-2-yl)-6methylphenyl]-1-naphthamide,
4-cyano-2-fluoro-N-[4-(1,1,1,2,3,3,3-heptafluoropropan-2-yl)-2,6-dimethyl-phenyl]benzamide,
4-cyano-N-[2-ethyl-4-(1,1,1,2,3,3,3-heptafluoropropan-2-yl)-6-methylphenyl]-benzamide,
4-cyano-N-[2-ethyl-4-(1,1,1,2,3,3,3-heptafluoropropan-2-yl)-6-methylphenyl]-2-fluorobenzamide,
2-chloro-4-cyano-N-[2-ethyl-4-(1,1,1,2,3,3,3-heptafluoropropan-2-yl)-6-methylphenyl]benzamide,
4-cyano-N-[2-ethyl-4-(1,1,1,2,3,3,3-heptafluoropropan-2-yl)-6-methylphenyl]-3-methylbenzamide,
4-cyano-N-[2-ethyl-4-(1,1,1,3,3,3-hexafluoro-2-hydroxypropan-2-yl)-6-methylphenyl]benzamide,
2-{4-[(4-cyanobenzoyl)amino]-3-ethyl-5-methylphenyl}1,1,1,3,3,3-hexa-fluoropropan-2-yl-methanesulfonate,
5-cyano-N-[2-ethyl-4-(1,1,1,2,3,3,3-heptafluoropropan-2-yl)-6-methyl-phenyl]pyridine-2carboxamide,
6-cyano-N-[2-ethyl-4-(1,1,1,2,3,3,3-heptafluoropropan-2-yl)-6-methylphenyl]-nicotinamide, and the like.

The novel intermediates are shown with Formulae (VII-1) to (VII-6):

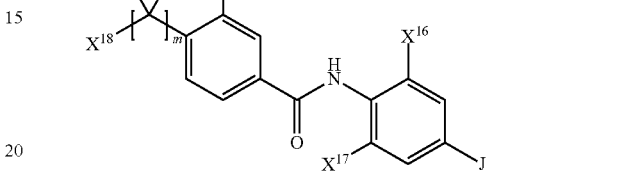

(VII-1)

wherein $X^{18}$ represents halogen, hydroxy, azide or 1,3-dioxo-1,3-dihydro-2H-isoindol-2-yl, $X^{19}$ represents hydrogen, halogen or $C_{1-4}$ alkyl; and $X^9$, $X^{10}$, $X^{16}$, $X^{17}$, J and m are as defined above;

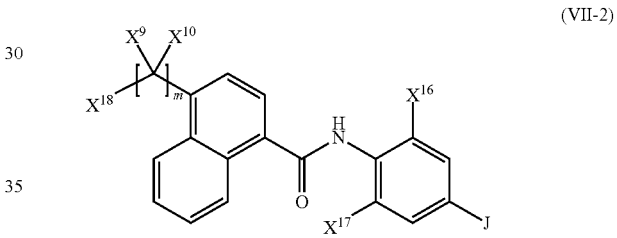

(VII-2)

wherein $X^1$, $X^9$, $X^{10}$, $X^{16}$, $X^{17}$, J and m are as defined above;

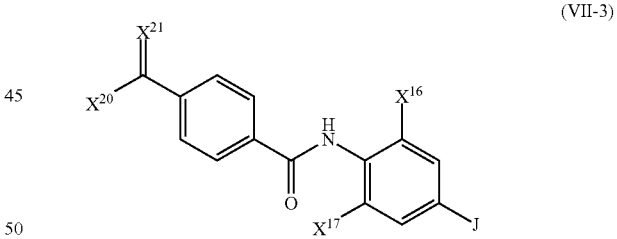

(VII-3)

wherein $X^{20}$ represents hydrogen or $C_{1-4}$ alkyl, $X^{21}$ represents an oxygen or N—$X^{22}$, $X^{22}$ represents hydroxy, $C_{1-4}$ alkyl or $C_{1-4}$ alkoxy, and $X^{16}$, $X^{17}$ and J are as defined above;

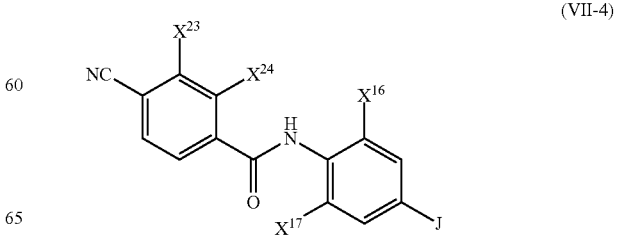

(VII-4)

wherein $X^{23}$ represents hydrogen or $C_{1-4}$ alkyl, $X^{24}$ represents hydrogen or halogen and $X^{16}$, $X^{17}$ and J are as defined above;

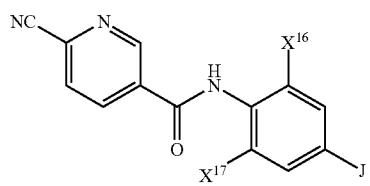

(VII-5)

wherein $X^{16}$, $X^{17}$ and J are as defined above; and

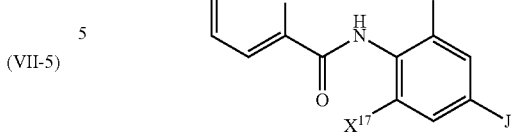

(VII-6)

wherein $X^{16}$, $X^{17}$ and J are as defined above.

Preparation method (c) can be carried out according to general methods for synthesizing organic compounds. In addition, a diluent, a base and the like are the same as those described for Preparation method (a).

With respect to Preparation method (d), an exemplary synthetic method including its starting materials is shown in Scheme 5.

Scheme 5

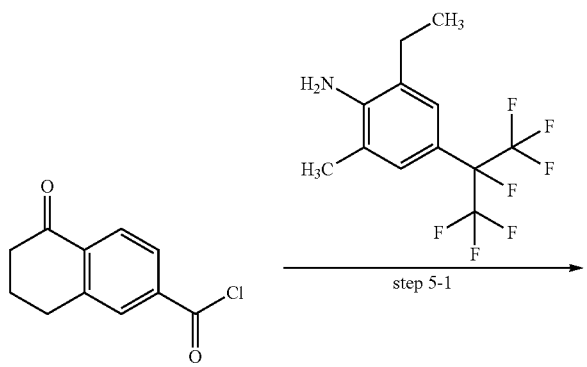

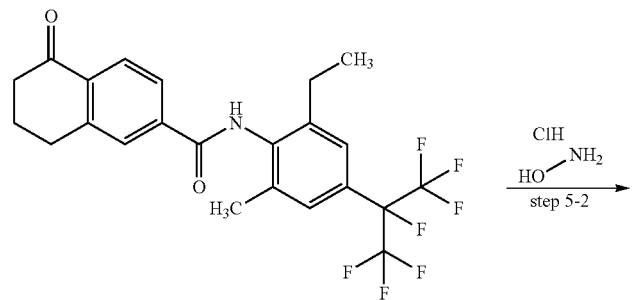

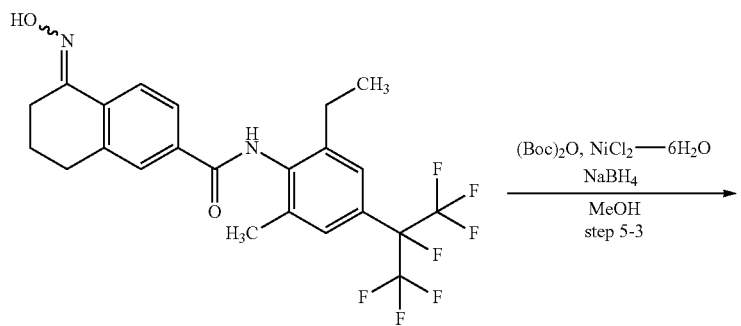

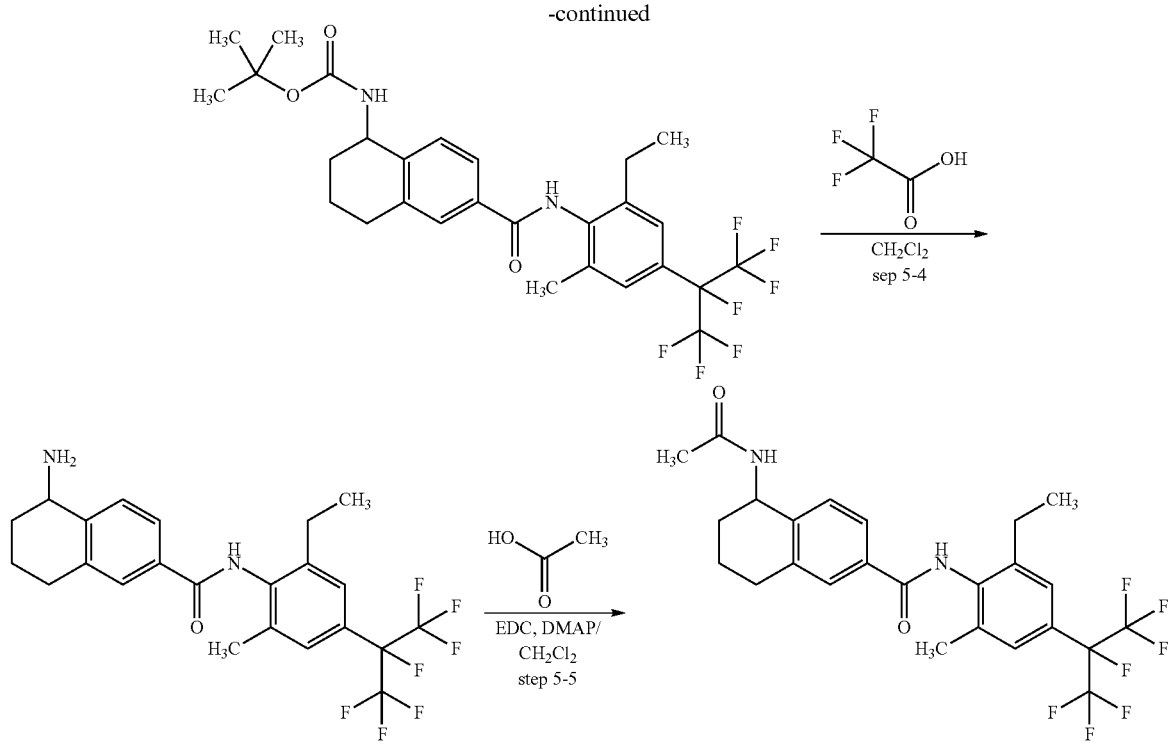

In Scheme 5, corresponding acid chloride and aniline are condensed during step 5-1 to give the anilide, which is subsequently reacted with hydroxylamine during step 5-2 to give the hydroxyimino compound, and although the subsequent step 5-3 is a reductive amination, it can be carried out in the same manner as in step 4-2 described above, and after deprotection during step 5-4, step 5-5 which corresponds to Preparation method (d) is carried out. Preparation method (d) can be carried out in the same manner as in Preparation method (c).]

Representative examples of novel intermediates in Scheme 5 are as follows: N-[2-ethyl-4-(1,1,1,2,3,3,3-heptafluoropropan-2-yl)-6-methylphenyl]-5-oxo-5,6,7,8-tetrahydronaphthalene-2-carboxamide, N-[2-ethyl-4-(1,1,1,2,3,3,3-heptafluoropropan-2-yl)-6methylphenyl]-5-(hydroxyimino)-5,6,7,8-tetrahydronaph-thalene-2-carboxamide, and the like.

The novel intermediates described above are summarized in Formula (VIII):

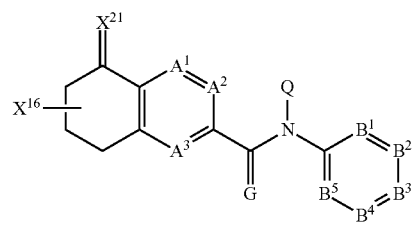

wherein $A^1$ to $A^3$, $B^1$ to $B^5$, G, Q, $X^{16}$ and $X^{21}$ are as defined above.

With respect to Preparation method (e), an exemplary synthetic method including its starting materials is shown in Scheme 6.

Scheme 6:

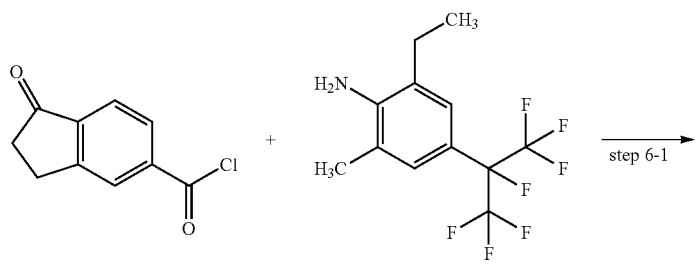

-continued

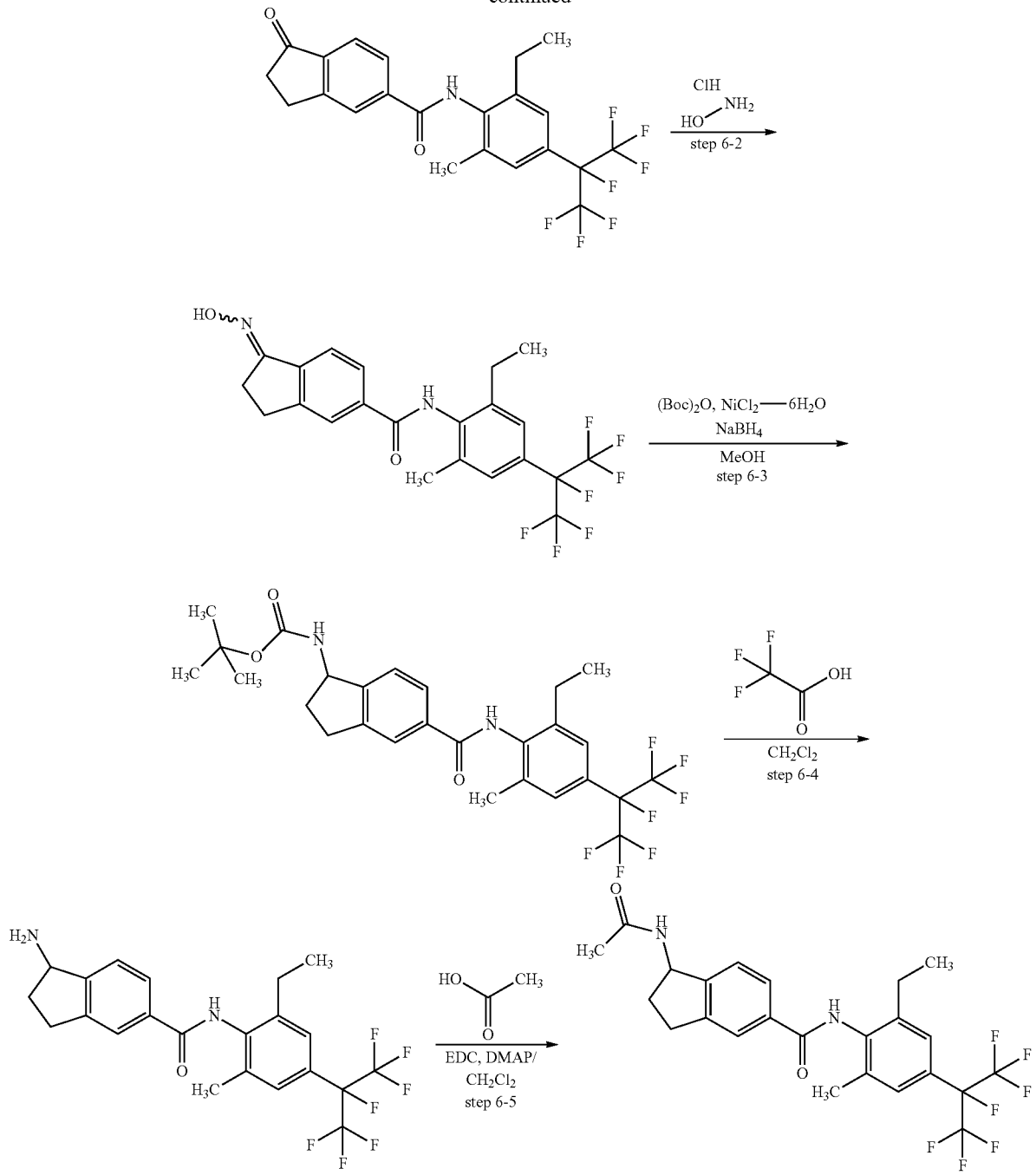

Each step in Scheme 6 can be carried out in the same manner as each step in Scheme 5.

Representative examples of novel intermediates in Scheme 6 are as follows:

N-[2-ethyl-4-(1,1,1,2,3,3,3-heptafluoropropan-2-yl)-6-methylphenyl]-1-oxoindane-5-carboxamide, N-[2ethyl-4-(1,1,1,2,3,3,3-heptafluoropropan-2-yl)-6-methylphenyl]-1-(hydroxyimino)indane-5-carboxamide, and the like.

The novel intermediates defined above are summarized in Formula (IX):

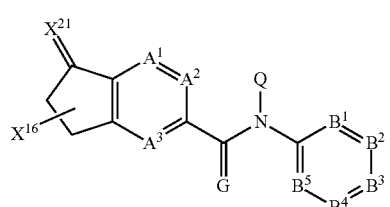

(IX)

wherein $A^1$ to $A^3$, $B^1$ to $B^5$, G, Q, $X^{16}$ and $X^{21}$ are as defined above.

The compounds of Formula (r-3) as starting materials for Preparation method (f) are publicly known and representative examples thereof include methyl iodide, ethyl iodide, benzyl bromide, dimethyl sulfate, diethyl sulfate, and the like.

The reaction of Preparation method (f) can be carried out in the presence of an appropriate diluent, and examples thereof to be used are the same as the diluents described for Preparation method (a), and preferably DMF.

The reaction of Preparation method (f) can be carried out in the presence of an appropriate base, and examples thereof to be used are the same as the bases described for Preparation method (a), and preferably sodium hydride.

The temperature range, pressure and time for the reaction of Preparation method (f) are the same as those described for Preparation method (a).

For carrying out Preparation method (f), for example, 1 mole of the compound of Formula (I-f1) can be reacted with 1 to 3 moles of the compound of Formula (r-3), for example methyl iodide, in the presence of an appropriate base, for example sodium hydride, in an appropriate diluent, for example DMF, thereby to obtain the compound of Formula (I) of the present invention.

The compounds of Formula (I-g1) as starting materials for Preparation method (g), are encompassed by the compounds of Formula (I) of the present invention and their representative examples are as follows:

N-[4-(1,1,1,2,3,3,3-heptafluoropropan-2-yl)-2,6-dimethylphenyl]-4-(1H-1,2,4-triazol-1-yl)benzamide,
N-[2-ethyl-4-(1,1,1,2,3,3,3-heptafluoropropan-2-yl)-6-methylphenyl]-4-(1H-1,2,4-triazol-1-yl)-benzamide, and the like.

Examples of the sulfurizing agents to be used in Preparation method (g) are phosphorous pentasulfide, Lawesson reagent and the like.

The reaction of Preparation method (g) can be carried out in the presence of an appropriate diluent, and examples thereof to be used are the same as the diluents described for Preparation method (a), and preferably toluene.

The reaction of Preparation method (g) can be carried out with the reaction temperature, pressure and time that are the same as those for Preparation method (a).

For carrying out Preparation method (g), for example, 1 mole of the compound of Formula (I-g1) can be reacted with 0.5 mole to 3 moles of Lawesson reagent in an appropriate diluent, for example toluene, thereby to obtain the compound of Formula (I).

The compounds of Formula (I) of the present invention exhibit a potent pesticidal effect. Therefore, the compounds of Formula (I) of the present invention can be used as pesticides. The active compounds of Formula (I) of the present invention also exhibit suitable controlling effect against noxious pests without phytotoxicity to cultivated crop plants. In addition, the compounds of the present invention can be used for controlling a wide variety of pests, such as harmful sucking insects, chewing insects and other plant parasitic pests, stored grain pests, hygienic pests etc., and can be applied for the disinfection and destruction of them.

Such harmful insects may be illustrated by examples as follows:

As an insect,
beetles (Coleopteran), such as adzuki bean beetle (*Callosobruchus Chinensis*), maize weevil (*Sitophilus zeamais*), red flour beetle (*Tribolium Castaneum*), large twenty-eight-spotted lady bird (*Epilachna vigintioctomaculata*), barley wireworm (*Agriotes ogurae fuscicollis*), soy bean beetle (*Anomala rufocuprea*), Colorado potato beetle (*Leptinotarsa decemlineata*), corn root worm (*Diabrotica* spp.), Japanese pine sawyer beetle (*Monochamus alternatus endai*), rice water weevil (*Lissorhoptrus oryzophilus*), powder-post beetle (Lyctus bruneus);

lepidopteran pests, such as gypsy moth (*Lymantria dispar*), Lackey moth (*Malacosoma neustria*), small white (*Pieris rapae crucivora*), cotton leafworm (*Spodoptera litura*), cabbage moth (*Mamestra brassicae*), rice stem borer (*Chilo suppressalis*), European corn borer (*Ostrinia nubilalis*), dried currant moth (*Cadra cautella*), chyanokokakumonhamaki (*Adoxophyes honmai*), codling moth (*Cydia pomonella*), Turnip Moth (*Agrotis segetum*), Wax Moth (*Galleria mellonella*), Diamondback moth (*Plutella xylostella*), tobacco budworm moth (*Heliothis virescens*), citrus leaf miner (*Phyllocnistis citrella*);

hemipterous pests, such as green rice leafhopper (*Nephotettix cincticeps*), brown planthopper (*Nilaparvata lugens*), comstock mealybug (*Pseudococcus comstocki*), arrowheat scale (*Unaspis yanonensis*), Momoaka-aburamusi (*Myzus persicas*), green apple aphid (*Aphis pomi*), cotton aphid (*Aphis gossypii*), turnip aphid (*Lipaphis erysimi*), Nashi-gunbai (*Stephanitis nashi*), Nezara (*Nezara* spp.), greenhouse whitefly (*Trialeurodes vaporariorum*), Pshylla (*Pshylla* spp.);

thysanoptera pests, such as palm thrips (*Thrips palmi*), western flower thrips (*Franklinella occidentalis*);

orthopteran pests, such as mole cricket (*Gryllotalpa Africana*), migratory locust (*Locusta migratoria*);

blattarian pests, such as German cockroach (*Blatella germanica*), American cockroach (*Periplaneta americana*), yamato white ant (*Reticulitermes speratus*), Formosan subterranean termite (*Coptotermes formosanus*);

dipterous pests, such as housefly (*Musca domestica*), yellow fever mosquito (*Aedes aegypti*), Seedcorn maggot (*Delia platura*), Aka-ie-ka (*Culex pipiens pallens*), Sina-hamadara-ka (*Anopheles sinensis*), kodaka-aka-ie-ka (*Culex tritaeniorhynchus*), serpentine leafininer (*Liriomyza trifolii*) and the like.

Further, as mites, Carmine spider mite (*Tetranychus cinnabarinus*), two-spotted spider mite (*Tetrahychus urticae*), Citrus red mite (*Panonychus citri*), Pink citrus rust mite (*Aculops pelekassi*), Tarsonemus (*Tarsonemus* spp.) and the like can be mentioned.

In addition, as nematodes, sweet potato root-knot nematode (*Meloidogyne incognita*), pine wood nematode (*Bursaphelenchus xylophilus*), rice white-tip nematode (*Aphelenchoides besseyi*), soybean cyst nematode (*Heterodera glycines*), meadow nematode (*Pratylenchus* spp.) and the like can be mentioned.

In veterinary medicine field, i.e., veterinary science, the active compounds of the present invention can be effectively used against various harmful animal parasites, particularly, endoparasites and ectoparasites. The term "endoparasites" include in particular worms (tapeworm, eelworm, trematode and the like) and *plasmodium* (coccidium and the like). The term "ectoparasites" include in general and preferably an arthropod, in particular insects (fly (a fly which can sting and suck), larva of parasitic fly, sucking lice, crab lice, bird lice, flea and the like) or acaroid mites (ticks and the like, for example, hard tick and soft tick) or mites (itch mite, chigger mite, bird mite and the like).

These parasites are as follows:
from Anoplurida, for example, *Haematopinus* spp., *Linognathus* spp., *Pediculus* spp., *Phtirus* spp., *Solenopotes* spp.; particularly, for representative examples, *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis,*

Pediculus humanus capitis, Pediculus humanus corporis, Phylloera vastatrix, Phthirus pubis, Solenopotes capillatus;

from Mallophagida, Amblycerina, and Ischnocerina, for example, Trimenopon spp., Menopon spp., Trinoton spp., Bovicola spp., Werneckiella spp., Lepikentron spp., Damalina spp., Trichodectes spp., Felicola spp.; particularly, for representative examples, Bovicola bovis, Bovicola ovis, Bovicola limbata, Damalina bovis, Trichodectes canis, Felicola subrostratus, Bovicola caprae, Lepikentron ovis, Werneckiella equi;

from Diptera, Nematocerina, and Brachycerina, for example, Aedes spp., Anopheles ssp., Culex spp., Simulium spp., Eusimulium spp., Phlebotomus spp., Lutzomyia spp., Culicoides spp., Chrysops spp., Odagmia spp., Wilhelmia spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp., Melophagus spp., Rhinoestrus spp., Tipula spp.; particularly, for representative examples, Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus interrnis, Gasterophilus nasalis, Gasterophilus nigricornis, Gasterophilus pecorum, Braula coeca;

from Siphonapterida, for example, Pulex spp., Ctenocephalides spp., Tunga spp., Xenopsylla spp., Ceratophyllus spp.; particularly, for representative examples, Ctenocephalides canis, Ctenocephalides felis, Pulex irritans, Tunga penetrans, Xenopsylla cheopis;

from Heteropterida, for example, Cimex spp., Triatoma spp., Rhodnius spp., Panstrongylus spp.;

from Blattarida, for example, Blatta orientalis, Periplaneta americana, Blattela germanica, Supella spp. (for example, Suppella longipalpa);

from Acari(Acarina), Metastigmata, and Mesostigmata, for example, Argas spp., Ornithodorus spp., Otobius spp., Ixodes spp., Amblyomma spp., Rhipicephalus (Boophilus) spp., Dermacentor spp., Haemophysalis spp., Hyalomma spp., Dermanyssus spp., Rhipicephalus spp. (original genus of heteroxenous mites), Ornithonyssus spp., Pneumonyssus spp., Raillietia spp., Pneumonyssus spp., Sternostoma spp., Varroa spp., Acarapis spp.); particularly, for representative examples, Argas persicus, Argas reflexus, Ornithodorus moubata, Otobius megnini, Rhipicephalus(Boophilus) microplus, Rhipicephalus(Boophilus) decoloratus, Rhipicephalus (Boophilus) annulatus, Rhipicephalus(Boophilus) calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsconi;

from Actinedida(Prostigmata), and Acaridida(Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp., Laminosioptes spp.; particularly, Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleli, Neoschonegastia xerothermobia, Trombicula akamushi, Otodectes cynotis, Notoedres cati, Sarcoptis canis, Sarcoptes bovis, Sarcoptes ovis, Sarcoptes rupicaprae(=S. caprae), Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi.

The active compounds of the present invention are also useful for controlling an arthropod, a worm and a plasmodium which attacks an animal. Examples of the animal include an agricultural animals such as a cow, a sheep, a goat, a horse, a pig, a donkey, a camel, a buffalo, a rabbit, a chicken, a turkey, a duck, a goose, a nursery fish, a honey bee, etc. In addition, a pet which is also called as a companion animal, for example, a dog, a cat, a caged bird, an aquarium fish, and an animal for experimental testing (e.g., a hamster, a guinea pig, a rat, a mouse and the like) is also included.

With control of the arthropod, worm and/or plasmodium by using the active compounds of the present invention, death ratio of a host animal can be reduced and productivity (for meat, milk, wool, leather, egg, and honey) and health of the animal can be improved. As a result, it is intended to achieve economically more favorable and simple animal breeding.

For example, it is preferable that introduction of blood from a parasite to a host is ether prevented or inhibited (if possible). Parasite control can be useful for preventing infection which is caused by inflammatory pathogens.

The term "control" that is used in the present specification regarding a veterinary medicine field means that the active compounds are effective for reducing the occurrence ratio of each parasite in an animal infected with it to an innoxious level. More specifically, the term "to control" means that the active compounds of the present invention are effective for destroying parasites, inhibiting growth or propagation thereof.

In the present invention, substances having pesticidal effects against harmful pests including all of such pests are referred to as pesticides.

When used as pesticides, the active compounds of the present invention can be prepared in a form of a common preparation. Such preparation form may includes, for example, liquids, emulsions, wettable powders, granulated wettable powders, suspensions, powders, foams, pastes, tablets, granules, aerosols, natural or synthetic agents impregnated with the active compounds, microcapsules, coating agents for seeds, formulations equipped with a combustion device (the combustion device can be a smoke or fog cartridge, a can or a coil, etc.) and ULV (cold mist, warm mist), and the like.

These formulations can be produced by known methods per se. For example, they can be prepared by mixing the active compounds with extenders, namely, liquid diluents or carriers; liquefied gas diluents or carriers; solid diluents or carriers and, optionally, with surfactants, namely, emulsifiers and/or dispersants and/or foam formers and the like.

In case of using water as an extender, for example, organic solvents can be used as auxiliary solvents.

The liquid diluents or carriers may include, for example, aromatic hydrocarbons (e.g. xylene, toluene, alkylnaphthalene etc.), chlorinated aromatic or chlorinated aliphatic hydrocarbons (e.g. chlorobenzenes, ethylene chlorides, methylene chlorides etc.), aliphatic hydrocarbons (e.g. cyclohexanes or paraffins (e.g. mineral oil fractions)), alcohols (e.g. butanol, glycol and ethers or esters thereof, etc.), ketones (e.g. acetone, methylethylketone, methylisobutylketone, cyclohexanone etc.), strong polar solvents (e.g. dimethylformamide, dimethylsulfoxide etc.), water and the like.

The liquefied gas diluent or carrier may include those present as gas at atmospheric pressure and temperature, for example, bulan, propane, nitrogen gas, carbon dioxide, and aerosol propellant such as halogenated hydrocarbons.

Examples of the solid diluents may include ground natural minerals (for example, kaolins, clay, talc, chalk, quartz, attapulgite, montmorillonite or diatomaceous earth, etc.) and ground synthetic minerals (for example, highly dispersed silicic acid, alumina and silicate, etc.) and the like.

Examples of the solid carriers for granules may include crushed and fractionated rocks (for example, calcite, marble, pumice, sepiolite and dolomite, etc.), synthetic granules of inorganic or organic powders, and fine granules of organic materials (for example, sawdust, coconut shells, maize cobs and tobacco stalks, etc.) and the like.

Examples of the emulsifiers and/or foam formers may include nonionic and anionic emulsifiers [for example, polyoxyethylene fatty acid esters, polyoxyethylene fatty acid alcohol ethers (for example, alkylaryl polyglycol ether), alkyl sulfonates, alkyl sulfates and aryl sulfonates] and albumin hydrolysates and the like.

The dispersants include lignin sulfite waste liquor and methylcellulose.

Binders may also be used in formulations (powders, granules and emulsion). Examples of the binders may include carboxymethyl cellulose, natural or synthetic polymers (for example, gum arabic, polyvinyl alcohol and polyvinyl acetate, etc.).

Colorants may also be used. Examples of the colorants may include inorganic pigments (for example, iron oxide, titanium oxide and Prussian blue, etc.), organic dyes such as Alizarin dyes, azo dyes or metal phthalocyanine dyes, and further, trace elements such as salts of iron, manganese, boron, copper, cobalt, molybdenum or zinc.

The formulation may include the above active component in an amount of 0.1 to 95 wt %, preferably 0.5 to 90 wt %.

The active compounds of Formula (I) of the present invention can be provided as a mixture with other active compounds such as a pesticide, a poison bait, a sterilizing agent, an acaricidal agent, a nematocide, a fungicide, a growth regulating agent, a herbicide, and the like in a form of commercially useful formulation or an application form prepared from formulation thereof. The pesticide may include, for example, an organic phosphorous agent, carbamate agent, carboxylate agent, chlorinated hydrocarbon agent, and pesticidal substance produced by microorganisms, etc.

Further, the active compounds of Formula (I) of the present invention can be provided as a mixture with a synergist. Such formulation and application form may include those that are commercially useful. The synergist is not necessarily active by itself. Rather, it is the compound which enhances the activity of the active compounds.

The amount of the active compounds of Formula (I) of the present invention that is included in a commercially useful form may vary over a broad range.

The concentration of the active compounds of Formula (I) of the present invention for actual use can be, for example, between 0.0000001 and 100% by weight, preferably between 0.00001 and 1% by weight.

The compounds of Formula (I) of the present invention can be used according to any common method that is appropriate for an application form.

The active compounds of the present invention have stability that is effective for alkaline substances present in lime materials when the compounds are used against hygienic pests and storage pests. In addition, it exhibits excellent residual effectiveness in woods and soils.

Generally, when the active compounds of the present invention are used for the treatment of animals, they can be directly applied to the animal. Preferably, the compounds are applied in a form of pharmaceutical composition which may include a vehicle, an auxiliary agent, or both, that are known in the field and pharmaceutically acceptable.

For a veterinary medicine field and animal breeding, the active compounds can be applied (administered) according to various known ways, for example; intraintestinal administration with a tablet, a capsule, a drink, a drinkable medicine, granules, paste, and bolus administration, feed-through method, suppository; non-intraintestinal administration based on skin application such as injection (intramuscular, subcutaneous, intravenous, intraperitoneal, etc.), embedding, intranasal application including bathing or immersion, spray, pouring, dropping, washing and scattering, and by using a molding article containing the active compounds such as a necklace, an earmark, a tag, a leg brace, a net, a marking device and the like. The active compounds of the present invention can be formulated into an appropriate formulation form that can be applied with a shampoo, aerosol, a non-pressurized spray, for example a pump spray and a vaporizer spray, etc.

When used for livestock, fouls, pets and the like, the active compounds of the present invention can be used as a formulation which includes them in an amount of 1 to 80 wt % (for example, powders, wettable powders (WP), emulsion, emulsifiable concentrate (EC), fluid, homogeneous solution and suspension concentrate (SC)), and Formulation can be applied as it is or after dilution (for example, dilution of 100 to 10,000 times), or as a chemical shower as an alternative method.

When used in a veterinary medicine field, the active compounds of the present invention can be used in combination with other appropriate synergistic agent or other active compounds, for example an acaricide, an insecticide, a parasiticide, an anti *plasmodium* agent, etc.

The active compounds of the present invention have low toxicity and can be safely used for warm-blooded animals.

Herein below, the present invention is described in greater detail with reference to the following examples. However, it is evident that the present invention is not limited thereto alone.

EXAMPLES

Synthetic Example 1

Synthesis of N-[2,6-d]bromo-4-(1,1,1,2,3,3,3-heptafluoropropan-2-yl)phenyl]-4-(1H-1,2,4-triazol-1-yl)benzamide (Compound No. 1-78).

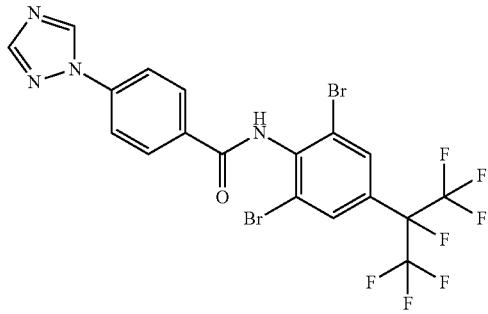 [SMILES: O=C(Nc1c(Br)cc(C(F)(C(F)(F)F)C(F)(F)F)cc1Br)c1ccc(-n2cncn2)cc1]

Step 1-1: Synthesis of 4-(1H-1,2,4-triazol-1-yl)benzoyl Chloride

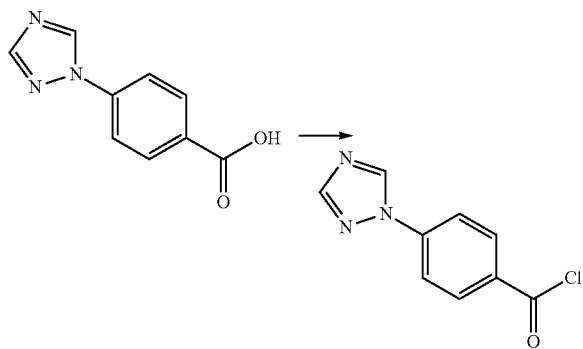

4-(1H-1,2,4-triazol-1-yObenzoic acid (0.90 g) was suspended in toluene. To the suspension, thionyl chloride (5.7 g) and an catalytic amount of N,N-dimethylformamide (2 to 3 drops) were added and the mixture was refluxed under heating for 4 hours. After adjusting the reaction solution to room temperature, the solvent was distilled off under reduced pressure to obtain 4-(1H-1,2,4-triazol-1-yl)-benzoyl chloride as a crude product (0.95 g). Without further purification, the crude product was used for the next reaction.

Step 1-2: Synthesis of N-[2,6-dibromo-4-(1,1,1,2,3,3,3-heptafluoropropan-2-yl)-phenyl]-4-(1H-1,2,4-triazol-1-yl)benzamide (Compound No. 1-78)

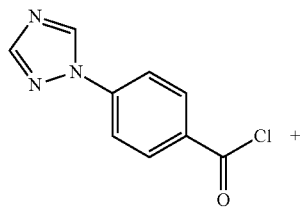

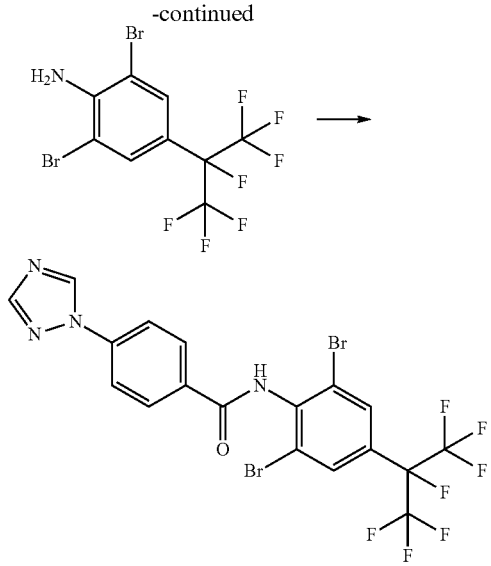

2,6-Dibromo-4-(1,1,1,2,3,3,3-heptafluoropropan-2-yl) aniline (0.45 g) was dissolved in pyridine (5 ml). To the solution, the crude product of 4-(1H-1,2,4-triazol-1-yl)benzoyl chloride (0.45 g) was added and the mixture was refluxed under heating for 1.5 hours. After cooling to room temperature, the reaction solution was diluted with water and extracted twice with ethyl acetate. The organic phases were combined, washed with 2N hydrochloric acid and dried over magnesium sulfate. After filtering off the drying agent, the solvent was distilled off under reduced pressure to obtain a residue, which were then dissolved in tetrahydrofuran (20 ml), added with a 2N sodium hydroxide solution (5 ml) and stirred under heating at 50° C. for 2 hours. After cooling to room temperature, the reaction solution was diluted with water and extracted twice with ethyl acetate. The organic phases were combined, washed with water and dried over magnesium sulfate. After filtering off the drying agent, the solvent was distilled off under reduced pressure to obtain a crude product. The crude product was purified by column chromatography to obtain N-[2,6-d]bromo-4-(1,1,1,2,3,3,3-heptafluoropropan-2-yl)phenyl]-4-(1H-1,2,4-triazol-1-yl) benzamide (0.18 g, yield 28%).

$^1$H-NMR (CDCl$_3$): see the Table below.

Synthetic Example 2

Synthesis of N-[2-ethyl-4-(1,1,1,2,3,3,3-heptafluoropropan-2-yl)-6-methyl-phenyl]-3-nitro-4-(1H-1,2,4-triazol-1-yl)benzamide (Compound No. 1-39).

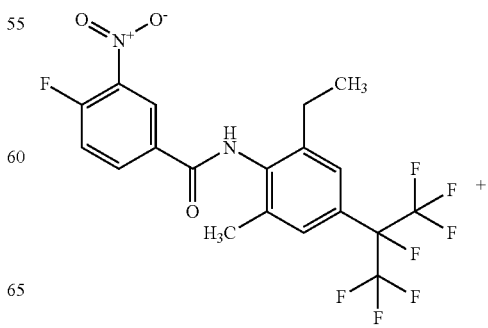

-continued

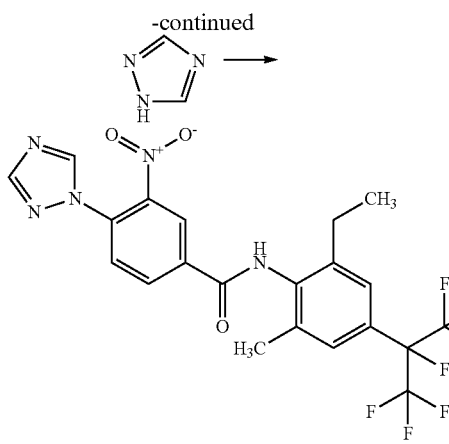

N-[2-Ethyl-4-(1,1,1,2,3,3,3-heptafluoropropan-2-yl)-6-methylphenyl]-4-fluoro-3-nitrobenzamide (1.5 g, see WO 2005/073165) and 1H-1,2,4-triazole (0.24 g) were dissolved in N,N-dimethylformamide (15 ml). To the solution, potassium carbonate (0.88 g) was added and the mixture was stirred under heating at 70° C. for 3 hours. After cooling to room temperature, the reaction solution was diluted with water and extracted twice with ethyl acetate. The organic phases were combined, washed with water and dried over magnesium sulfate. After filtering off the drying agent, the solvent was distilled off under reduced pressure to obtain a crude product. The resulting crude product was purified by column chromatography to obtain N-[2ethyl-4-(1,1,1,2,3,3,3-heptafluoropropan-2-yl)-6-methylphenyl]-3-nitro-4-(1H-1,2,4-triazol-1-yl)benzamide (1.4 g, yield 80%).

$^1$H-NMR (CDCl$_3$): see the Table below.

Synthetic Example 3

Synthesis of 3-amino-N-[2-ethyl-4-(1,1,1,2,3,3,3-heptafluoropropan-2-yl)-6-methylphenyl]-4-(1H-1,2,4-triazol-1-yl)benzamide (Compound No. 1-38).

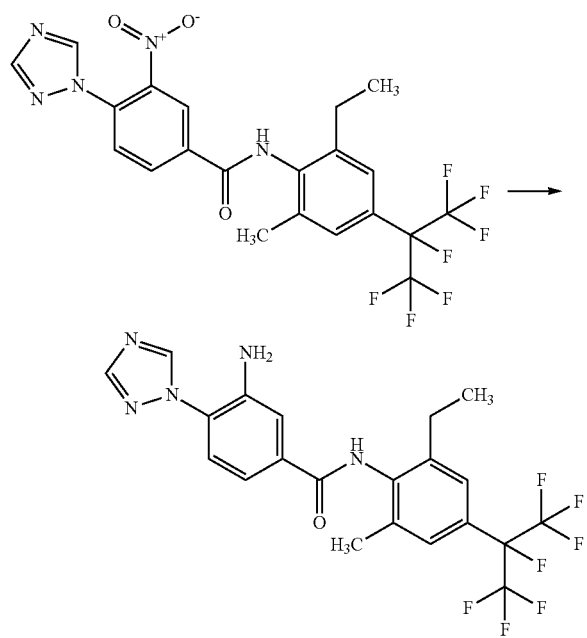

N-[2-Ethyl-4-(1,1,1,2,3,3,3-heptafluoropropan-2-yl)-6-methylphenyl]-3-nitro-4-(1H-1,2,4-triazol-1-yl)benzamide (1.3 g) was dissolved in ethanol (20 ml). To the solution, tin (II) chloride dihydrate (1.4 g) and conc. hydrochloric acid (1 ml) were added and the mixture was stirred under heating at 60° C. for 4 hours. The reaction solution was neutralized with potassium carbonate while it is vigorously stirred with addition of ethyl acetate and water. The resulting precipitates were filtered using Celite, the aqueous phase was separated from the organic phase and the aqueous phase was extracted with ethyl acetate. The organic phases were combined, washed with brine and dried over magnesium sulfate. After filtering off the drying agent, the solvent was distilled off under reduced pressure to obtain a crude product. The crude product was purified by column chromatography to obtain 3-amino-N-[2-ethyl-4-(1,1,1,2,3,3,3-heptafluoropropan-2-yl)-6-methylphenyl]-4-(1H-1,2,4-triazol-1-yl)benzamide (1.0 g, yield 97%).

$^1$H-NMR (CDCl$_3$): see the Table below.

Synthetic Example 4

Synthesis of Methyl[5-{[2-ethyl-4-(1,1,1,2,3,3,3-heptafluoropropan-2-yl)-6methylphenyl]carbamoyl}-2-(1H-1,2,4-triazol-1-yl)phenyl]carbamate (Compound No. 1-47).

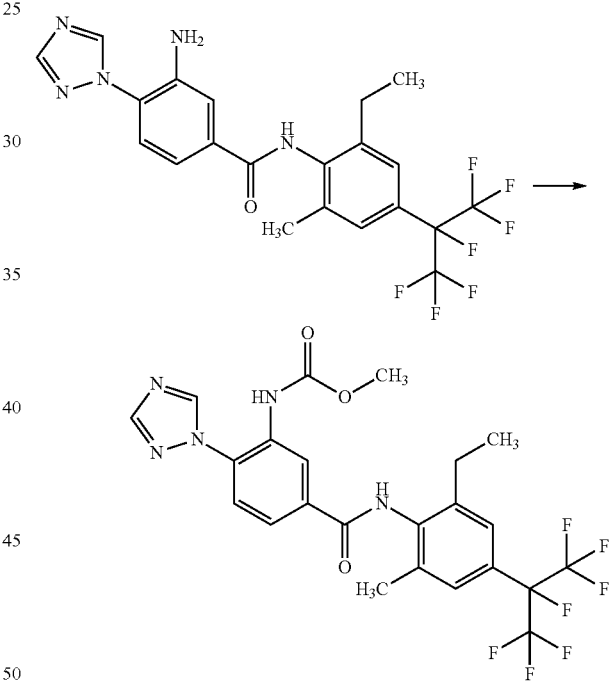

3-Amino-N-[2-ethyl-4-(1,1,1,2,3,3,3-heptafluoropropan-2-yl)-6-methyl-phenyl]-4-(1H-1,2,4-triazol-1-yl)benzamide (0.2 g) and pyridine (0.05 g) were dissolved in tetrahydrofuran (5 ml). To the solution, ethyl chlorocarbonate (0.04 g) was added under ice cooling. After adjusting to room temperature, the mixture was stirred for 1 hr. The reaction mixture was diluted with water and extracted twice with ethyl acetate. The organic phases were combined, washed with water and dried over magnesium sulfate. After filtering off the drying agent, the solvent was distilled off under reduced pressure to obtain a crude product. The crude product was purified by column chromatography to obtain methyl[5-{[2-ethyl-4-(1,1,1,2,3,3,3-heptafluoro-propan-2-yl)-6-methylphenyl]carbamoyl}-2-(1H-1,2,4-triazol-1-yl)phenyl]carbamate (0.14 g, yield 58%).

$^1$H-NMR (CDCl$_3$): see the Table below.

Synthetic Example 5

Synthesis of N-[2-ethyl-4-(1,1,1,2,3,3,3-heptafluoropropan-2-yl)-6-methylphenyl]-4-(1H-1,2,4-triazol-1-yl)benzamide (Compound No. 1-31).

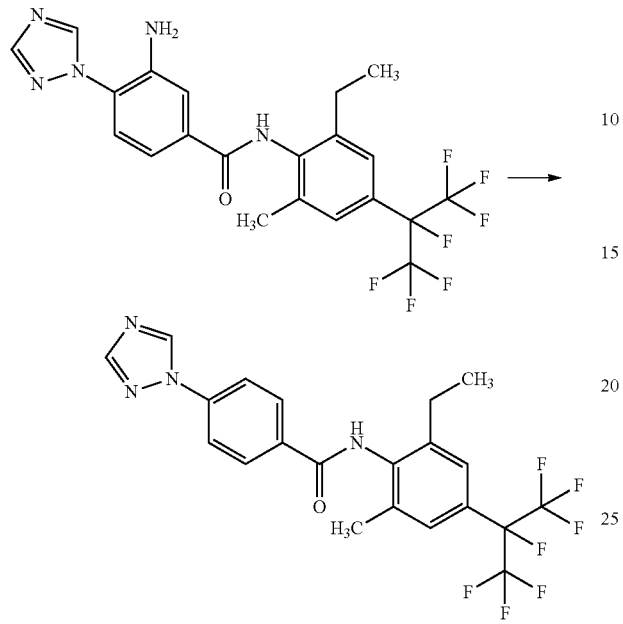

N,N-dimethylformamide (3 ml) was heated to 65° C. and added with tert-butyl nitrite (0.15 g). To the solution, an N,N-dimethylformamide solution (2 ml) in which 3-amino-N-[2-ethyl-4-(1,1,1,2,3, 3,3-heptafluoropropan-2-yl)-6-methylphenyl]-4-(1H-1,2,4-triazol-1-yl) benzamide (0.5 g) has been dissolved was slowly added dropwise, while maintaining the temperature of 65° C. After confirming that no more gas is generated, the mixture was adjusted to room temperature and added with a mixture including 2N hydrochloric acid and a small amount of ice. The mixture was diluted with water and extracted twice with ethyl acetate. The organic phases were combined, washed with 2N hydrochloric acid, and dried over magnesium sulfate. After filtering off the drying agent, the solvent was distilled off under reduced pressure to obtain a crude product. The crude product was purified by column chromatography to obtain N-[2-ethyl-4-(1,1,1,2,3,3,3-heptafluoropropan-2-yl)-6-methylphenyl]-4-(1H-1,2,4-triazol-1-yl)benzamide (0.31 g, yield 61%).

$^1$H-NMR (CDCl$_3$): see the Table below.

Synthetic Example 6

Synthesis of 4-(acetamidomethyl)-N-[2-ethyl-4-(1,1,1,2,3,3,3-heptafluoro-propan-2-yl)-6-methylphenyl]benzamide (Compound No. 5-28).

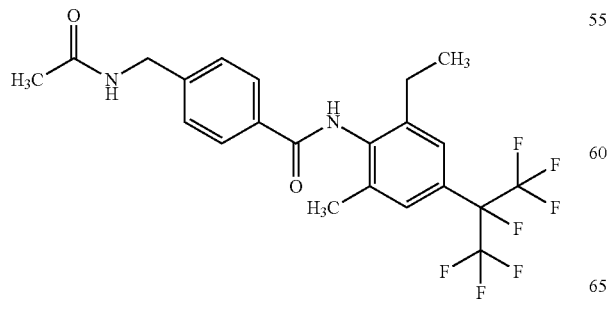

Step 6-1: Synthesis of 4-(chloromethyl)-N-[2-ethyl-4-(1,1,1,2,3,3,3-hepta-fluoropropan-2-yl)-6-methylphenyl]benzamide (Compound No. F-3)

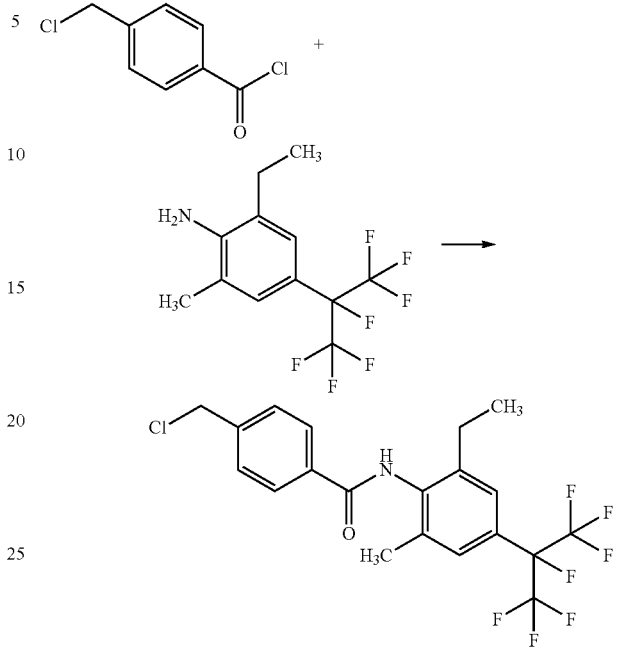

2-Ethyl-4-(1,1,1,2,3,3,3-heptafluoropropan-2-yl)-6-methylaniline (0.50 g) and pyridine (0.20 g) were dissolved in tetrahydrofuran (10 ml). To the solution, 4-(chloromethyl)benzoyl chloride (0.33 g) and 4-dimethylaminopyridine (0.02 g) were added and the mixture was refluxed under heating for 3 hours. After adjusting to room temperature, the reaction solution was diluted with water and extracted twice with ethyl acetate. The organic phases were combined, washed with 2N hydrochloric acid and dried over Mg(SO$_4$). After filtering off the drying agent, the solvent was distilled off under reduced pressure to obtain a crude product. The crude product was washed with hexane to obtain 4-(chloro methyl)-N-[2-ethyl-4-(1,1,1,2,3,3,3-heptafluoro-propan-2-yl)-6-methylphenyl]benzamide (0.62 g, yield 74%).

$^1$H-NMR (CDCl$_3$): see the Table below.

Step 6-2: Synthesis of 4-[(1,3-dioxo-1,3-dihydro-2H-isoindol-2-yl)methyl]-N-[2-ethyl-4-(1,1,1,2,3,3,3-hepta-fluoropropan-2-yl)-6-methylphenyl]benzamide (Compound No. F-4)

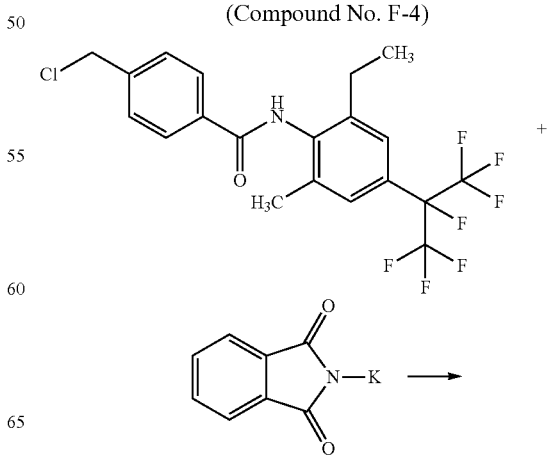

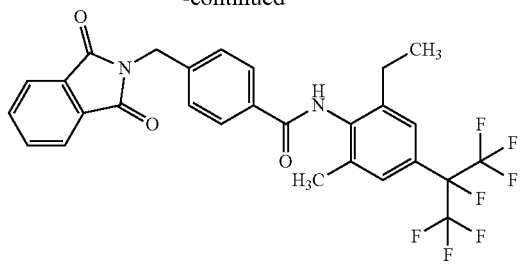

4-(Chloromethyl)-N-[2-ethyl-4-(1,1,1,2,3,3,3-heptafluoropropan-2-yl)-6-methylphenyl]benz amide (1.2 g) was dissolved in N,N-dimethylformamide (15 ml). To the solution, potassium phthalimide (0.95 g) and potassium iodide (0.09 g) were added and the mixture was stirred under heating at 60° C. for 2 hours. After adjusting to room temperature, the reaction solution was diluted with water and extracted twice with ethyl acetate. The organic phases were combined, washed with water and dried over magnesium sulfate. After filtering off the drying agent, the solvent was distilled off under reduced pressure to obtain a crude product. The crude product was washed with tert-butyl methyl ether to obtain 4-[(1,3-dioxo-1,3-dihydro-2H-isoindol-2-yl)-methyl]-N-[2-ethyl-4-(1,1,1,2,3,3,3-hepta-fluoropropan-2-yl)-6-methylphenyl]-benzamide (0.85 g, yield 56%).

$^1$H-NMR (CDCl$_3$): see the Table below.

Step 6-3: Synthesis of 4-(aminomethyl)-N-[2-ethyl-4-(1,1,1,2,3,3,3-hepta-fluoropropan-2-yl)-6methylphenyl]benzamide (Compound No. 5-27)

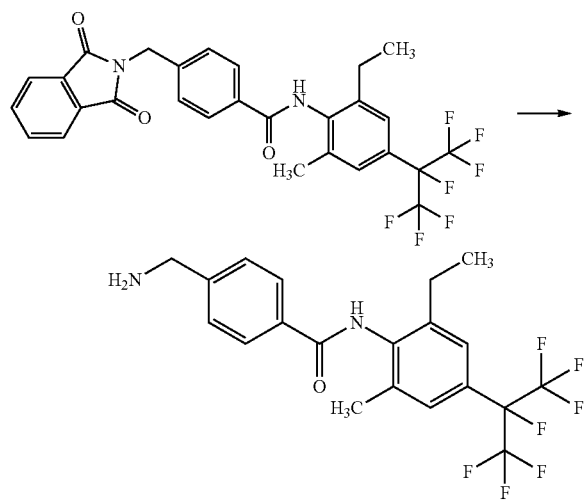

4-[(1,3-Dioxo-1,3-dihydro-2H-isoindol-2-yl)methyl]-N-[2-ethyl-4-(1,1,1,2,3,3,3-heptafluoro propan-2-yl)-6-methylphenyl]benzamide (0.80 g) was dissolved in ethanol (20 ml). To the solution, hydrazine monohydrate (0.28 g) was added and the mixture was stirred under heating at 60° C. for 4 hours. After adjusting to room temperature, the reaction solution was diluted with water and extracted twice with ethyl acetate. The organic phases were combined, washed with a saturated sodium bicarbonate solution and dried over magnesium sulfate. After filtering off the drying agent, the solvent was distilled off under reduced pressure to obtain 4-(aminomethyl)-N-[2-ethyl-4-(1,1,1,2,3,3,3-heptafluoropropan-2-yl)-6-methylphenyl] benzamide as a crude product (0.63 g). Without further purification, the crude product was used for the next reaction.

$^1$H-NMR (CDCl$_3$): see the Table below.

Step 6-4: Synthesis of 4-(acetamidomethyl)-N-[2-ethyl-4-(1,1,1,2,3,3,3-hepta-fluoropropan-2-yl)-6-methylphenyl]benzamide (Compound No. 5-28)

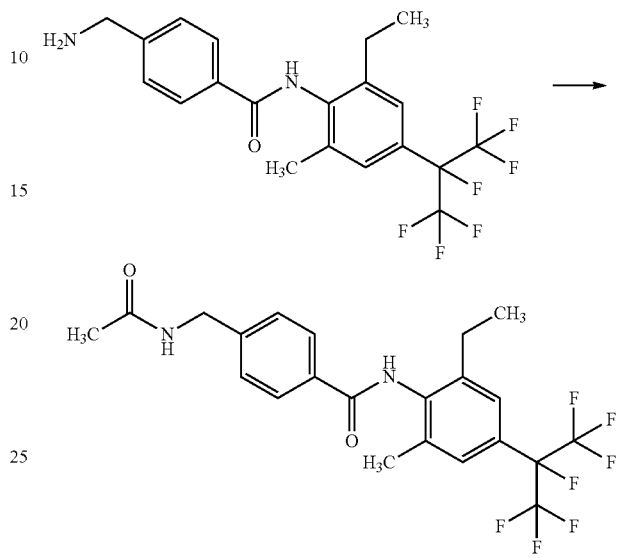

The crude product of 4-(aminomethyl)-N-[2-ethyl-4-(1,1,1,2,3,3,3-heptafluoro-propan-2-yl)-6-methylphenyl]benzamide (0.30 g) was dissolved in tetrahydrofuran (5 ml). To the solution, acetic anhydride (0.07 g) was added and the mixture was stirred at room temperature for 2 hours. The reaction solution was diluted with water and extracted twice with ethyl acetate. The organic phases were combined, washed with 2N hydrochloric acid and dried over magnesium sulfate. After filtering off the drying agent, the solvent was distilled off under reduced pressure to obtain a crude product. The crude product was separated and purified by column chromatography to obtain 4-(acetamidomethyl)-N-[2-ethyl-4-(1,1,1,2,3,3,3-heptafluoropropan-2-yl)-6-methyl-phenyl]benzamide (0.27 g, yield 77%).

$^1$H-NMR (CDCl$_3$): see the Table below.

Synthetic Example 7

Synthesis of N-[2-ethyl-4-(1,1,1,2,3,3,3-heptafluoropropan-2-yl)-6-methyl-phenyl]-3-{[(3,3,3-trifluoropropanoyl)amino]methyl}benzamide (Compound No. 5-102).

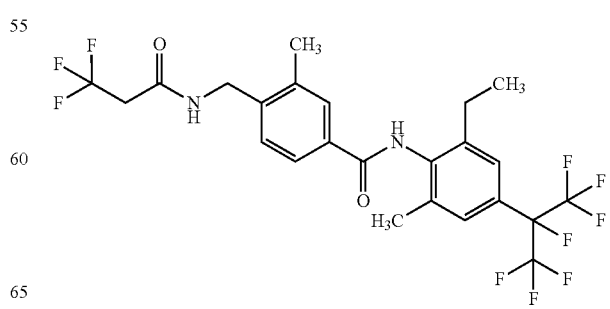

Step 7-1: Synthesis of 4-cyano-3-methylbenzoic Acid

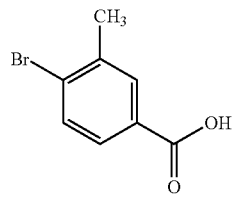 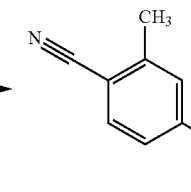

4-Bromo-3-methylbenzoic acid (3.0 g) was dissolved in N,N-dimethylformamide (20 ml). The resulting solution was subjected to deaeration three times under argon atmosphere (i.e., the reaction solution was de-pressurized to 20 mmHg, and then brought back to atmospheric pressure under argon atmosphere). To the solution, zinc cyanide (1.6 g) and tetrakis (triphenylphosphine) palladium (0) (1.6 g) were added and the mixture was stirred under heating at 90° C. for 6 hours under argon atmosphere. After adjusting to room temperature, precipitates were filtered off. The filtrate was diluted with water, added with lithium hydroxide monohydrate (2.9 g) and washed twice with tert-butyl methyl ether. The aqueous phase was acidified with 2N hydrochloric acid and extracted twice with ethyl acetate. The organic phases were combined, washed with brine and dried over magnesium sulfate. After filtering off the drying agent, the solvent was distilled off under reduced pressure to obtain 4-cyano-3methylbenzoic acid as a crude product (1.9 g). Without further purification, the crude product was used for the next reaction.

Step 7-2: Synthesis of 4-cyano-3-methylbenzoyl Chloride

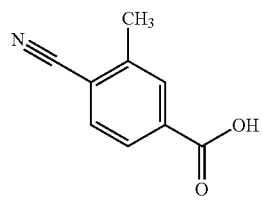

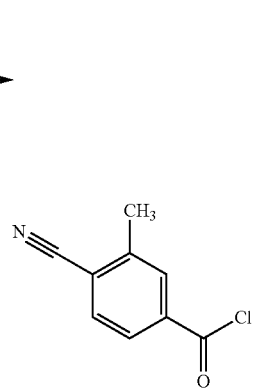

The crude product of 4-cyano-3-methylbenzoic acid (1.0 g) was suspended in dichloromethane. To the mixture, oxalyl chloride (1.2 g) and an catalytic amount of N,N-dimethylformamide (2 to 3 drops) were added under ice cooling. After adjusting to room temperature, the reaction solution was stirred for three hours. The solvent was distilled off under reduced pressure to obtain 4-cyano-3-methylbenzoyl chloride as a crude product (1.0 g).

Step 7-3: Synthesis of 4-cyano-N[2-ethyl-4-(1,1,1,2,3,3,3-heptafluoropropan-2-yl)-6-methylphenyl]-3-methylbenzamide (Compound No. I-5)

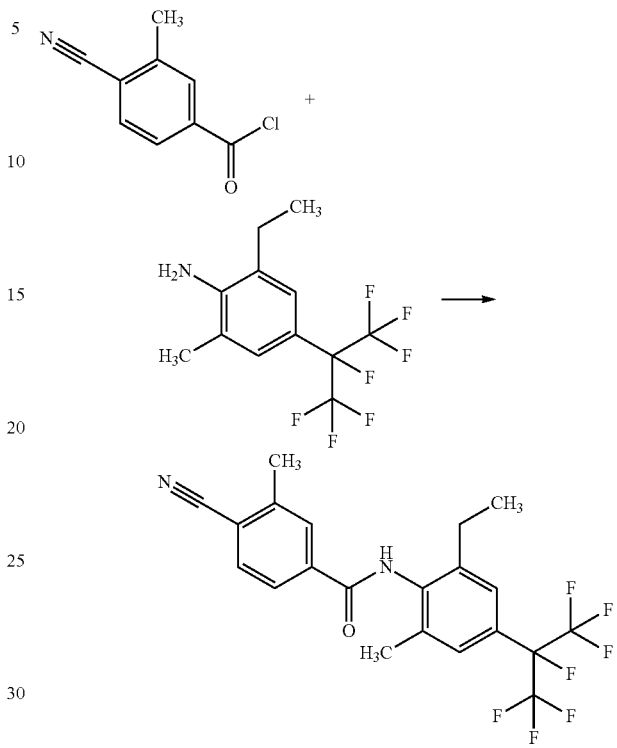

2-Ethyl-4-(1,1,1,2,3,3,3-heptafluoropropan-2-yl)-6-methylaniline (1.7 g) and pyridine (0.88 g) were dissolved in tetrahydrofuran (30 ml). To the solution, the crude product of 4-cyano-3-methylbenzoyl chloride (1.0 g) and 4-dimethylaminopyridine (0.03 g) were added and the mixture was stirred under heating at 50° C. for 2 hours. After adjusting to room temperature, the reaction solution was diluted with water and extracted twice with ethyl acetate. The organic phases were combined, washed with 2N hydrochloric acid and dried over magnesium sulfate. After filtering off the drying agent, the solvent was distilled off under reduced pressure to obtain a crude product. The crude product was washed with a mixed solvent of hexane and ethyl acetate (ethyl acetate 10%) to obtain 4-cyano-N-[2-ethyl-4-(1,1,1,2,3,3,3-heptafluoropropan-2-yl)-6-methylphenyl]-3-methylbenzamide (2.1 g, yield 83%).

$^1$H-NMR (CDCl$_3$): see the Table below.

Step 7-4: Synthesis of Tert-butyl (4-{[2-ethyl-4-(1,1,1,2,3,3,3-heptafluoro-propan-2-yl)-6-methylphenyl]carbamoyl}-2-methylbenzyl)carbamate (Compound No. 5-104)

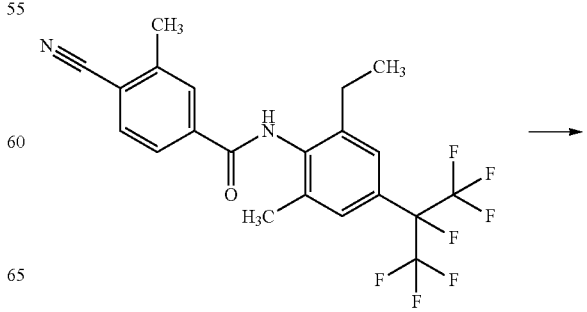

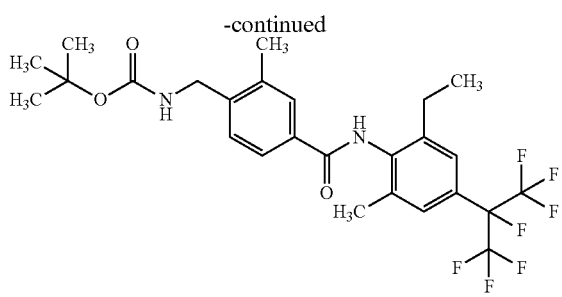

4-Cyano-N-[2-ethyl-4-(1,1,1,2,3,3,3-heptafluoropropan-2-yl)-6-methylphenyl]-3-methylbenz amide (2.0 g) was dissolved in methanol (50 ml). To the solution, di-tert-butyl bicarbonate (2.0 g) and nickel (II) chloride hexahydrate (0.53 g) were added and dissolved therein. To the reaction solution, NaBH$_4$ (0.80 g) was slowly added under ice cooling. Upon the completion of the reaction, diethylenetriamine (4.9 ml) was added, and then stirred for 30 minutes while adjusting the mixture to room temperature. The mixture was diluted with ethyl acetate and water and vigorously stirred for 5 minutes. The organic phase was separated and the aqueous phase was extracted with ethyl acetate. The organic phases were combined, washed with a saturated sodium bicarbonate aqueous solution and dried over magnesium sulfate. After filtering off the drying agent, the solvent was distilled off under reduced pressure to obtain a crude product. The crude product was purified by column chromatography to obtain tert-butyl (4-{[2-ethyl-4-(1,1,1,2,3,3,3-heptafluoro-propan-2-yl)-6-methylphenyl]carbamoyl}-2-methylbenzyl)carbamate (1.8 g, yield 72%).

$^1$H-NMR (CDCl$_3$): see the Table below.

Step 7-5: Synthesis of 4-(aminomethyl)-N-[2-ethyl-4-(1,1,1,2,3,3,3-hepta-fluoropropan-2-yl)-6methylphenyl]-3-methylbenzamide (Compound No. 5-98).

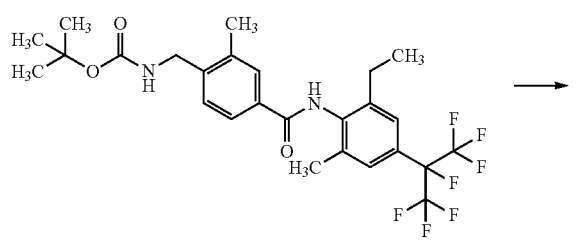

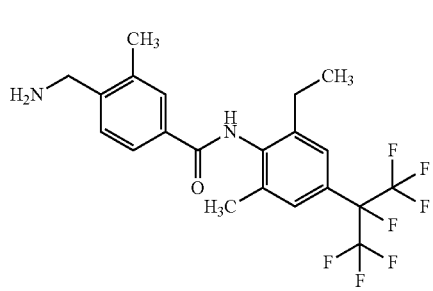

Tert-Butyl (4-{[2-ethyl-4-(1,1,1,2,3,3,3-heptafluoropropan-2-yl)-6-methylphenyl]-carbamoyl}-2-methylbenzyl) carbamate (1.7 g) was dissolved in ethanol (30 ml). To the solution, conc. hydrochloric acid (3 ml) was added and the mixture was stirred under heating at 60° C. for 4 hours. After adjusting to room temperature, the reaction solution was diluted with ethyl acetate and water and neutralized with sodium hydrocarbonate under vigorous stirring. The organic phase was separated and the aqueous phase was extracted with ethyl acetate. The organic phases were combined, washed with water and dried over magnesium sulfate. After filtering off the drying agent, the solvent was distilled off under reduced pressure to obtain 4-(aminomethyl)-N-[2-ethyl-4-(1,1,1,2,3,3,3-heptafluoropropan-2-yl)-6-methylphenyl]-3-methyl benzamide as a crude product (0.81 g). Without further purification, the crude product was used for the next reaction.

$^1$H-NMR (CDCl$_3$): see the Table below.

Step 7-6: Synthesis of N-[2-ethyl-4(1,1,1,2,3,3,3-heptafluoropropan-2-yl)-6-methylphenyl]-3-{[(3,3,3-trifluoropropanoyl)amino]methyl}benzamide (Compound No. 5-102)

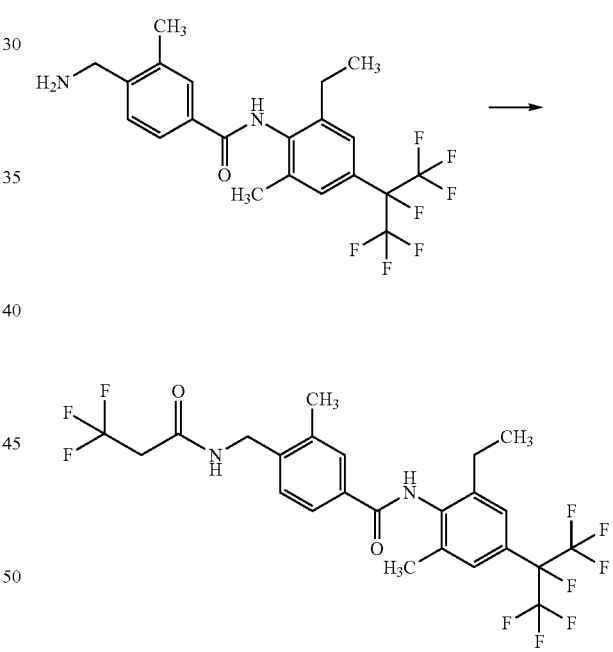

To a methylene chloride solution (2 ml) of the crude product of 4-(aminomethyl)-N-[2-ethyl-4-(1,1,1,2,3,3,3-heptafluoropropan-2-yl)-6-methylphenyl]-3-methylbenzamide (150 mg) and 3,3,3-trifluoropropionic acid (50 mg), 1-ethyl-3-(3-dimethyl-aminopropyl)carbodiimide hydrochloride (93 mg) was added under stirring at room temperature. The mixture was further stirred for 3 hours. The reaction solution was separated and purified by column chromatography to obtain N-[2-ethyl-4-(1,1,1,2,3,3,3-heptafluoropropan-2-yl)-6-methylphenyl]-3-{[(3,3,3-trifluoropropanoyl)amino]methyl}benzamide (155 mg, yield 85%).

$^1$H-NMR (CDCl$_3$): see the Table below.

Synthetic Example 8

Synthesis of 4-(1-acetamidoethyl)-N-[2-ethyl-4-(1,1,1,2,3,3,3-heptafluoro propan-2-yl)-6-methylphenyl]benzamide (Compound No. 9-2)

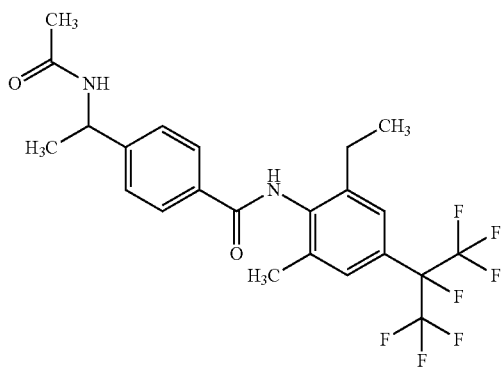 [SMILES: CCc1cc(C(F)(C(F)(F)F)C(F)(F)F)cc(C)c1NC(=O)c1ccc(C(C)NC(C)=O)cc1]

Step 8-1: Synthesis of 4-acetyl-N-[2-ethyl-4-(1,1,1,2,3,3,3-heptafluoro-propan-2-yl)-6-methylphenyl]benzamide (Compound No. H-1)

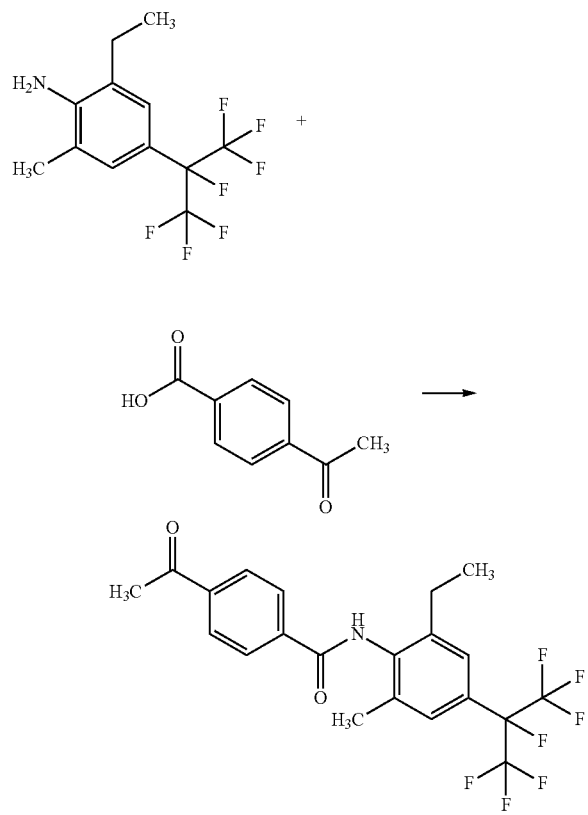

4-Acetylbenzoic acid (3.5 g) was suspended in methylene chloride (30 ml). To the suspension, oxalyl chloride (1.5 g) and a small amount of N,N-dimethylformamide (2 to 3 drops) were added and the mixture was stirred at room temperature for 2 hours. After the reflux under heating for 30 minutes, the solvent and oxalyl chloride were distilled off under reduced pressure. To the residue, 2-ethyl-4-(1,1,1,2,3,3,3-heptafluoropropan-2-yl)-6-methylaniline (1.5 g) dissolved in pyridine (30 ml) was added and the reaction solution was stirred at 140° C. for 4 hours. After adjusting to the room temperature, the reaction solution was added with a 1N hydrochloric acid aqueous solution and extracted twice with ethyl acetate. The organic phases were combined, washed with a 1N hydrochloric acid solution and water in turns and dried over anhydrous magnesium sulfate. After filtering off the drying agent, the solvent was distilled off under reduced pressure. The residue was purified by column chromatography to obtain 4-acetyl-N-[2-ethyl-4-(1,1,1,2,3,3,3-heptafluoropropan-2-yl)-6-methylphenyl] benzamide (2.4 g, yield 47%).

$^1$H-NMR (CDCl$_3$): see the Table below.

Step 8-2: Synthesis of N-[2-ethyl-4-(1,1,1,2,3,3,3-heptafluoropropan-2-yl)-6-methylphenyl]-4-[N-hydroxyethaneimidoyl]benzamide (Compound No. H-2)

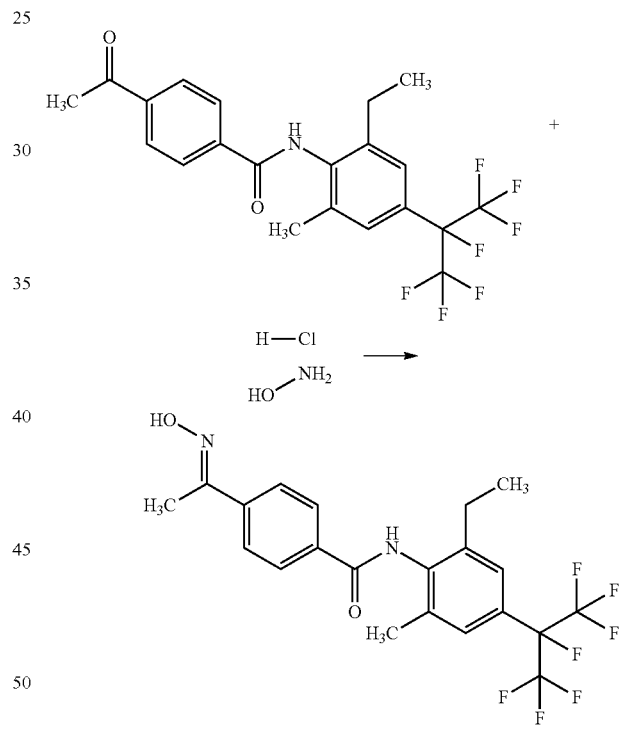

4-Acetyl-N-[2-ethyl-4-(1,1,1,2,3,3,3-heptafluoropropan-2-yl)-6-methylphenyl]-benzamide (2.2 g) was dissolved in ethanol (15 ml) and water (15 ml). To the solution, sodium acetate (0.6 g) and hydroxylamine hydrochloride (0.30 g) were added and the mixture was refluxed under heating for 4 hours. The reaction solution was extracted twice with ethyl acetate. The organic phases were combined, washed with water and dried over anhydrous magnesium sulfate. After filtering off the drying agent, the solvent was distilled off under reduced pressure to obtain N-[2-ethyl-4-(1,1,1,2,3,3,3-heptafluoropropan-2-yl)-6-methylphenyl]-4-[N-hydroxyethaneimidoyl]benzamide (2.1 g, yield 96%).

$^1$H-NMR (CDCl$_3$): see the Table below.

Step 8-3: Synthesis of tert-butyl [1-(4-{[2-ethyl-4-(1,1,1,2,3,3,3-heptafluoro propan-2-yl)-6-methylphenyl]carbamoyl}-phenyl)ethyl]carbamate (Compound No. 9-7)

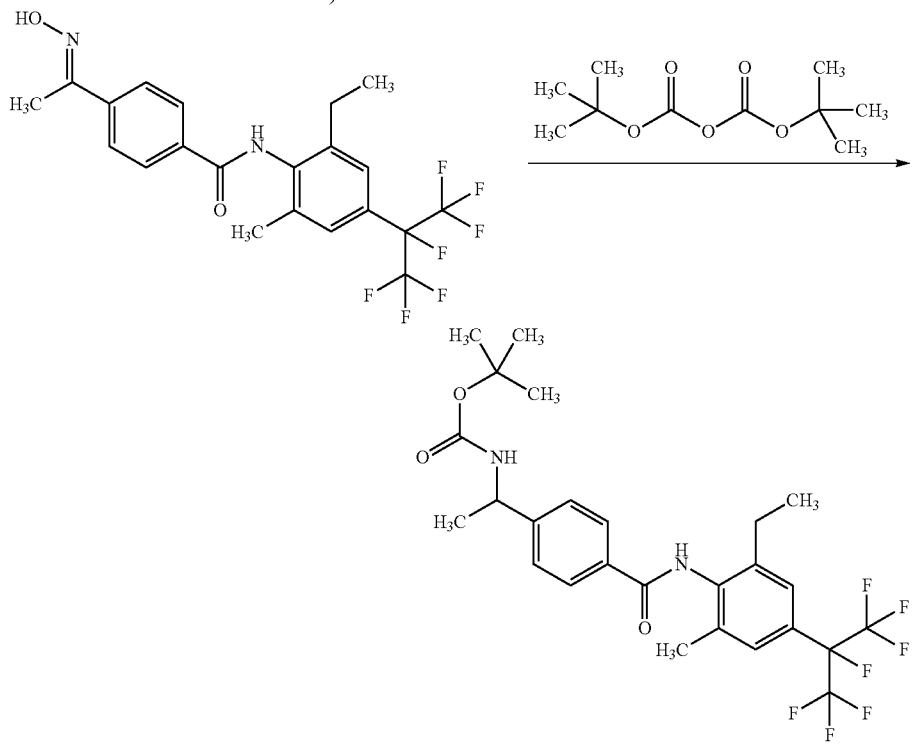

N-[2-Ethyl-4-(1,1,1,2,3,3,3-heptafluoropropan-2-yl)-6-methylphenyl]-4-[N-hydroxy-ethaneimidoyl]benzamide (2.1 g) was dissolved in methanol (25 ml) and 1,4-dioxane (5 ml). To the solution, di-tert-butyl bicarbonate (1.8 g) and nickel (II) chloride hexahydrate (0.49 g) were added. The resulting solution was cooled to 4° C., and sodium borohydride (0.62 g) was added in small portions. The mixture was stirred at 4° C. for 2 hours. Then, diethylenetriamine (1.1 g) was added and stirred for 30 minutes, and then diluted the solution with water followed by extraction twice with ethyl acetate. The organic phases were combined, washed with a saturated sodium bicarbonate aqueous solution and water in turns and dried over anhydrous magnesium sulfate. After filtering off the drying agent, the solvent was distilled off under reduced pressure. The residue was purified by column chromatography to obtain tert-butyl [1-(4-{[2-ethyl-4-(1,1,1,2,3,3,3-heptafluoropropan-2-yl)-6-methylphenyl]carbamoyl}-phenyl)ethyl]carbamate (1.7 g, yield 62%).

$^1$H-NMR (CDCl$_3$): see the Table below.

Step 8-4: Synthesis of 4-(1-aminoethyl)-N-[2-ethyl-4-(1,1,1,2,3,3,3-hepta-fluoropropan-2-yl)-6-methylphenyl]benzamide (Compound No. 9-1)

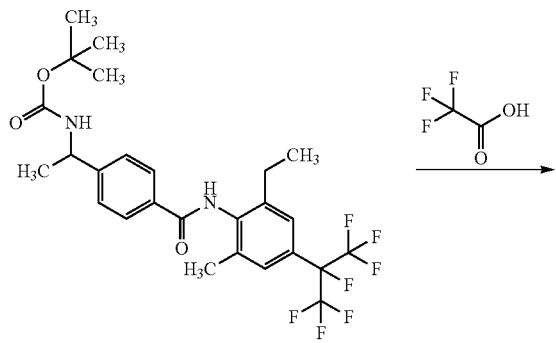

-continued

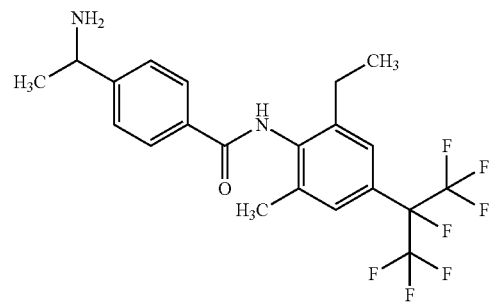

Tert-Butyl [1-(4-{[2-ethyl-4-(1,1,1,2,3,3,3-heptafluoropropan-2-yl)-6-methylphenyl]carbamoyl}phenyl)ethyl]carbamate (1.7 g) was dissolved in methylene chloride (20 ml). To the solution, trifluoroacetic acid (1.5 g) was added and the mixture was stirred at room temperature for 3 hours. The solvent was distilled off under reduced pressure and the residue was neutralized by adding water and potassium carbonate followed by extraction twice with ethyl acetate. The organic phases were combined, washed with a saturated sodium bicarbonate aqueous solution and water in turns and dried over anhydrous magnesium sulfate. After filtering off the drying agent, the solvent was distilled off under reduced pressure to obtain 4-(1-aminoethyl)-N-[2-ethyl-4-(1,1,1,2,3,3,3-heptafluoropropan-2-yl)-6-methylphenyl]benzamide as a crude product (1.8 g).

$^1$H-NMR (CDCl$_3$): see the Table below.

Step 8-5: Synthesis of 4-(1-acetamidoethyl)-N-[2-ethyl-4-(1,1,1,2,3,3,3-hepta-fluoropropan-2-yl)-6-methylphenyl]benzamide (Compound No. 9-2)

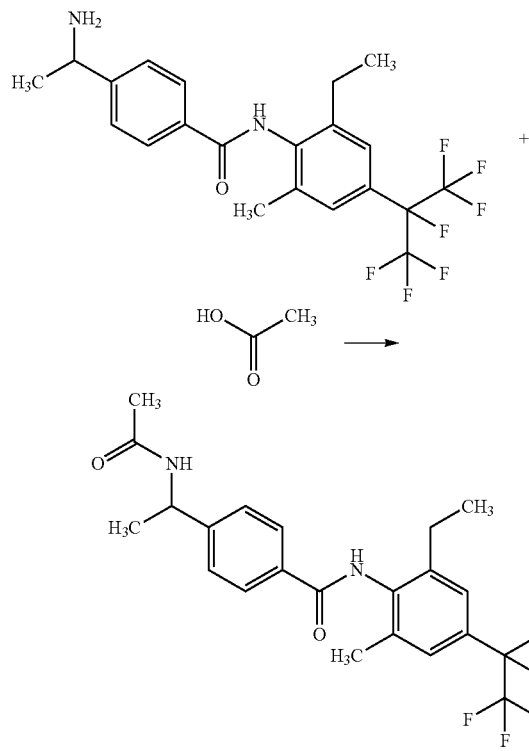

4-(1-Aminoethyl)-N-[2-ethyl-4-(1,1,1,2,3,3,3-heptafluoropropan-2-yl)-6-methylphenyl]benz amide (0.4 g) was dissolved in methylene chloride (15 ml). To the solution, acetic acid (0.06 g), 1-ethyl-3-(3-dimethylaminopropyl)carbodiimide hydrochloride (0.26 g) and an catalytic amount of dimethylaminopyridine were added and the mixture was stirred at room temperature for 3 hours. The solvent was distilled off under reduced pressure and the residue was added with water followed by extraction twice with ethyl acetate. The organic phases were combined, washed with water and dried over anhydrous magnesium sulfate. After filtering off the drying agent, the solvent was distilled off under reduced pressure. The residue was purified by column chromatography to obtain 4-(1-acetamidoethyl)-N-[2-ethyl-4-(1,1,1,2,3,3,3-heptafluoro propan-2-yl)-6-methylphenyl]benzamide (0.35 g, yield 95%).
$^1$H-NMR (CDCl$_3$): see the Table below.

Synthetic Example 9

Synthesis of 1-acetamide-N-[2-ethyl-4-(1,1,1,2,3,3,3-heptafluoropropan-2-yl)-6-methylphenyl]indane-5-carboxamide (Compound No. 10-2).

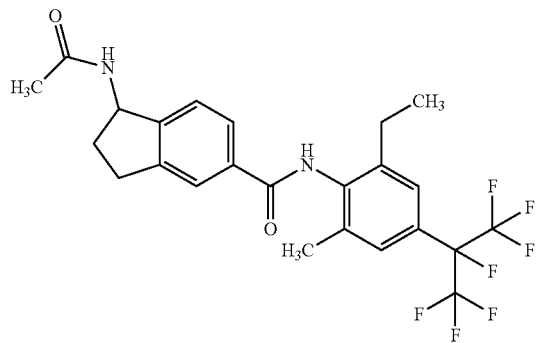 [SMILES: CCc1cc(C(F)(C(F)(F)F)C(F)(F)F)cc(C)c1NC(=O)c1ccc2c(c1)CCC2NC(C)=O]

Step 9-1: Synthesis of N-[2-ethyl-4-(1,1,1,2,3,3,3-heptafluoropropan-2-yl)-6-methylphenyl]-1xoindane-carboxamide (Compound No. L-1).

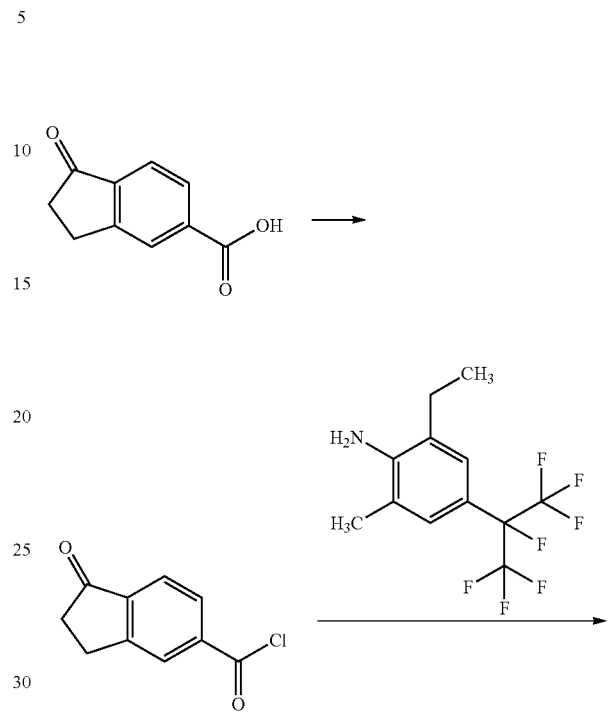

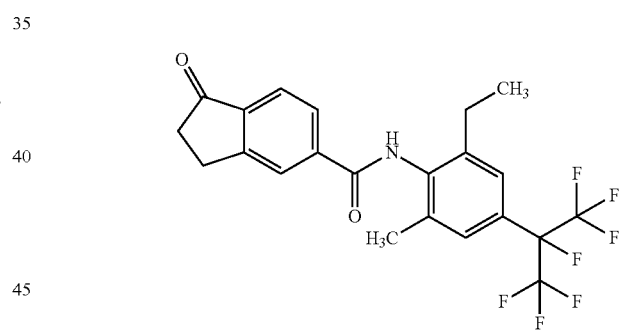

1-Oxoindane-5-carboxylic acid (3.0 g) was suspended in methylene chloride (30 ml), and oxalyl chloride (1.8 g) and a small amount of N,N-dimethylformamide (2 to 3 drops) were added thereto, and then stirred at room temperature for 2 hours. Thereafter, the solvent and oxalyl chloride were distilled off under reduced pressure. Pyridine (1.6 g) and 2-ethyl-4-(1,1,1,2,3,3,3-heptafluoropropan-2-yl)-6-methylaniline (1.6 g) dissolved in methylene chloride (30 ml) were added to the residue, and the mixture was stirred at room temperature overnight. The reaction solution was concentrated under reduced pressure and the residue was purified by column chromatography to obtain N-[2-ethyl-4-(1,1,1,2,3,3,3-heptafluoropropan-2-yl)-6-methylphenyl]-1-oxoindane-5-carboxamide (2.4 g, yield 53%).
$^1$H-NMR (CDCl$_3$): see the Table below.

Step 9-2: Synthesis of N-[2-ethyl-4-(1,1,1,2,3,3,3-heptafluoropropan-2-yl)-6methylphenyl]-1-(hydroxyimino)indane-5-carboxamide (Compound No. L-2).

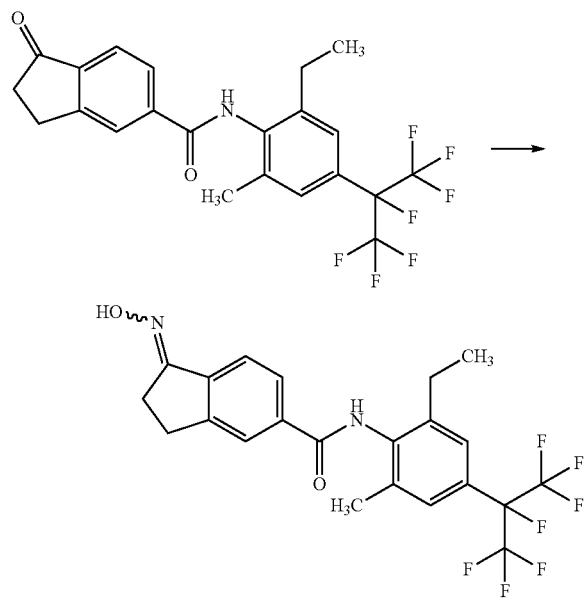

N-[2-Ethyl-4-(1,1,1,2,3,3,3-heptafluoropropan-2-yl)-6-methylphenyl]-1-oxoindane-5-carboxamide (2.4 g) was dissolved in ethanol (40 ml), and sodium acetate (0.85 g) and hydroxylamine hydrochloride (0.43 g) were added thereto, and then stirred and heated at reflux temperature for 2 hours. The reaction solution was brought back to room temperature and diluted with water. The resulting crystals were collected by filtration and dried to obtain N-[2-ethyl-4-(1,1,1,2,3,3,3-heptafluoropropan-2-yl)-6-methylphenyl]-1-(hydroxyimino) indane-5-carboxamide (2.3 g, yield 91%).

$^1$H-NMR (CDCl$_3$): see the Table below.

Step 9-3: Synthesis of tert-butyl 5-{[2-ethyl-4-(1,1,1,2,3,3,3-heptafluoropropan-2-yl)-6-methylphenyl]carbamoyl}-2,3-dihydro-1H-inden-1-yl)carbamate (Compound No. 10-7).

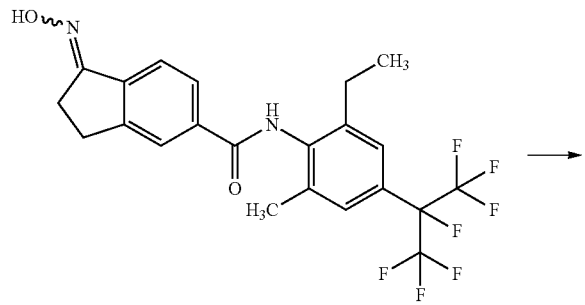

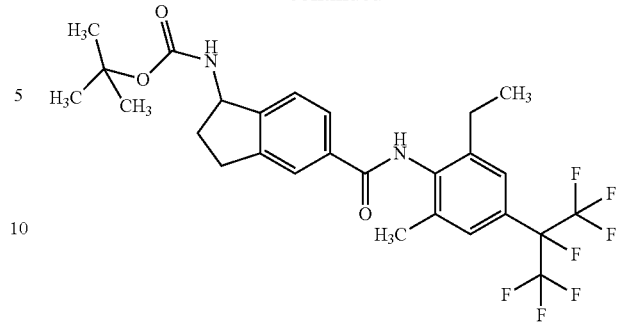

N-[2-Ethyl-4-(1,1,1,2,3,3,3-heptafluoropropan-2-yl)-6-methylphenyl]-1-(hydroxyimino)indane-5carboxamide (2.3 g) was dissolved in methanol (40 ml) and 1,4-dioxane (20 ml), and di-tert-butyl bicarbonate (2.1 g) and nickel (II) chloride hexahydrate (0.56 g) were added thereto. The solution was cooled to 4° C., small portions of sodium borohydride (0.45 g) were added thereto, and then stirred at 4° C. for 2 hours. To the mixture, diethylenetriamine (1.2 g) was added and stirred for 30 min. The solution was diluted with water and extracted twice with ethyl acetate. The organic phases were combined, washed with a saturated sodium bicarbonate aqueous solution and water, and then dried over anhydrous magnesium sulfate. The drying agent was removed by filtration, and the solvent was distilled off under reduced pressure. The residue was purified by column chromatography to obtain tert-butyl 5-{[2-ethyl-4-(1,1,1,2,3,3,3-heptafluoropropan-2-yl)-6-methylphenyl]carbamoyl}-2,3-dihydro-1H-inden-1-yl)carbamate (2.3 g, yield 87%).

$^1$H-NMR (CDCl$_3$): see the Table below.

Step 9-4: Synthesis of 1-amino-N-[2-ethyl-4-(1,1,1,2,3,3,3-heptafluoropropan-2-yl)-6-methylphenyl]indane-5-carboxamide

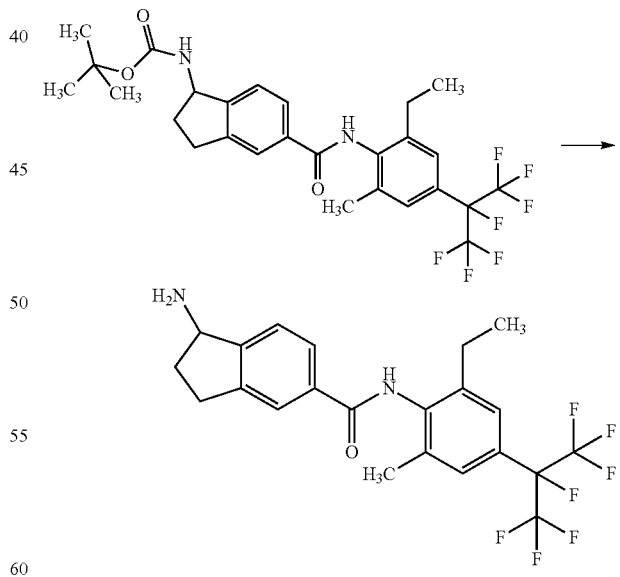

Tert-butyl (5-{[2-ethyl-4-(1,1,1,2,3,3,3-heptafluoropropan-2-yl)-6-methylphenyl]-carbamoyl}-2,3-dihydro-1H-inden-1-yl)carbamate (1.3 g) was dissolved in methylene chloride (15 ml), trifluoroacetic acid (1.5 ml) was added thereto and then stirred at room temperature for 3 hours. The solvent was distilled off under reduced pressure. Water and potassium carbonate were added to neutralize the residue and extracted twice with ethyl acetate. The organic phases were combined, washed with a saturated sodium bicarbonate aqueous solution and water sequentially, and then dried over anhydrous magnesium sulfate. The drying agent was removed by filtration, and the solvent was distilled off under reduced pressure to obtain 1-amino-N-[2-ethyl-4-(1,1,1,2,3,3,3-heptafluoropropan-2-yl)-6-methylphenyl]indane-5-carboxamide as a crude product (0.84 g). The crude product was used for the next step without further purification.

Step 9-5: Synthesis of 1-acetamide-N-[2-ethyl-4-(1,1,1,2,3,3,3-heptafluoro propan-2-yl)-6-methylphenyl]indane-5-carboxamide (Compound No. 10-2).

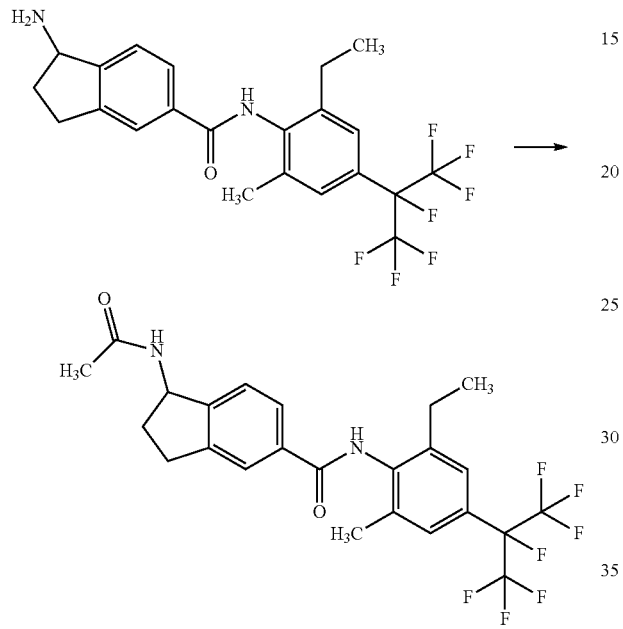

The crude product of 1-amino-N-[2-ethyl-4-(1,1,1,2,3,3,3-heptafluoro propan-2-yl)-6-methylphenyl]indane-5-carboxamide (0.12 g) was dissolved in methylene chloride (2 ml). Acetic anhydride (0.04 ml) was added to the solution and stirred at room temperature for 2 hours. The reaction solution was separated and purified by column chromatography to obtain 1-acetamide-N-[2-ethyl-4-(1,1,1,2,3,3,3-heptafluoropropan-2-yl)-6-methylphenyl]indane-5-carboxamide (0.07 g, yield 52%).
$^1$H-NMR (CDCl$_3$): see the Table below.

Synthetic Example 10

Synthesis of 4-(acetamidemethyl)-3-chloro-N-[2,6-dichloro-4-(1,1,1,2,3,3,3-heptafluoropropan-2-yl)phenyl]benzamide (Compound No. 5-229).

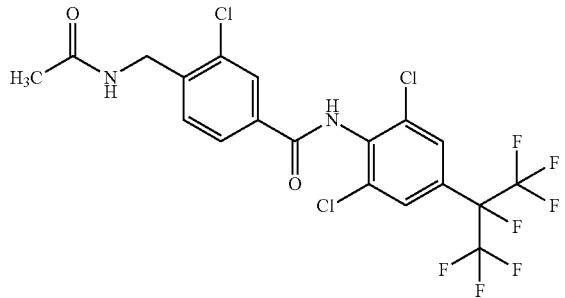 [SMILES: CC(=O)NCc1ccc(C(=O)Nc2c(Cl)cc(C(F)(C(F)(F)F)C(F)(F)F)cc2Cl)cc1Cl]

Step 10-1: Synthesis of N-[2,6-dichloro-4-(1,1,1,2,3,3,3-heptafluoropropan-2-yl)phenyl]-4-nitrobenzamide (Compound No. N-1).

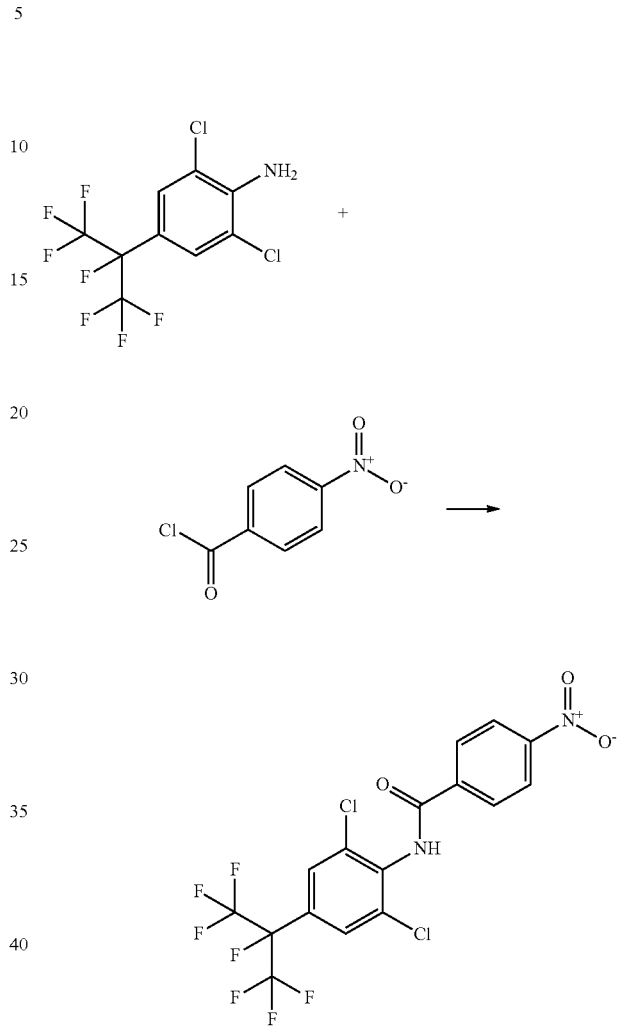

4-Nitrobenzoyl chloride (4.55 g) was dissolved in a pyridine (30 ml) solution of 2,6-dichloro-4-(1,1,1,2,3,3,3-heptafluoropropan-2-yl)aniline (2.7 g). The solution was refluxed under heating for 3 hours. After cooling to room temperature, the solution was diluted with water and extracted twice with ethyl acetate. The organic phases were combined and dried over magnesium sulfate. The drying agent was removed by filtration, and the solvent was distilled off under reduced pressure. The residue was dissolved in tetrahydrofuran (30 ml), and an aqueous solution (5 ml) containing sodium hydroxide (2.0 g) was added, and then stirred at room temperature for 4 hours. The reaction solution was extracted twice with ethyl acetate. The organic phases were combined, washed with 1 N hydrochloric acid and water, and dried over anhydrous magnesium sulfate. The drying agent (i.e., anhydrous magnesium sulfate) was removed by filtration, and the solvent was distilled off under reduced pressure. The residue was purified by column chromatography to obtain N-[2,6-dichloro-4-(1,1,1,2,3,3,3-heptafluoropropan-2-yl)phenyl]-4-nitrobenzamide (3.27 g, yield 83.4%).
$^1$H-NMR (CDCl$_3$) δ: 7.68 (2H, d), 7.80 (1H, s), 8.13 (2H, d), 8.39 (2H, d).

Step 10-2: Synthesis of 4-amino-N-[2,6-dichloro-4-(1,1,1,2,3,3,3-heptafluoro-propan-2-yl)phenyl]benzamide (Compound No. O-1).

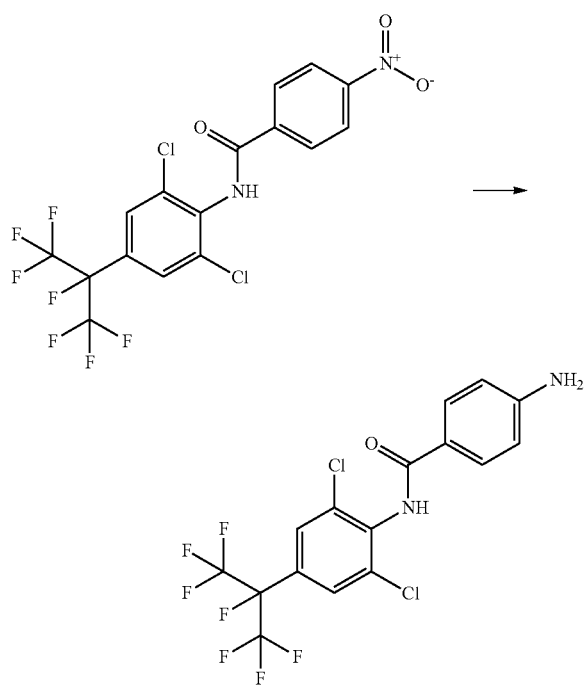

N-[2,6-Dichloro-4-(1,1,1,2,3,3,3-heptafluoropropan-2-yl)phenyl]-4-nitro-benzamide (3.2 g) and nickel (II) chloride hexahydrate (3.33 g) were dissolved in methanol (30 ml). To the reaction solution, NaBH$_4$ (0.80 g) was added slowly under ice cooling, and the mixture was stirred for 1 hour while increasing the temperature to room temperature. Aqueous ammonia (about 5 ml) was added to the reaction solution under stirring, and then diluted with ethyl acetate and water. The organic phase was separated and the aqueous layer was extracted with ethyl acetate. The organic phases were combined, and then dried over magnesium sulfate. The drying agent was removed by filtration, and the solvent was distilled off under reduced pressure to obtain a crude product, which was then separated and purified by column chromatography to give 4-amino-N-[2,6-dichloro-4-(1,1,1,2,3,3,3-heptafluoropropan-2-yl)phenyl]-benzamide (2.89 g, yield 96%).

$^1$H-NMR (CDCl$_3$) δ: 6.72 (2H, d), 7.56 (1H, s), 7.63 (2H, s), 7.78 (2H, d).

Step 10-3: Synthesis of 4-amino-3-chloro-N-[2,6-dichloro-4-(1,1,1,2,3,3,3-heptafluoropropan-2-yl)phenyl]benzamide (Compound No. O-4).

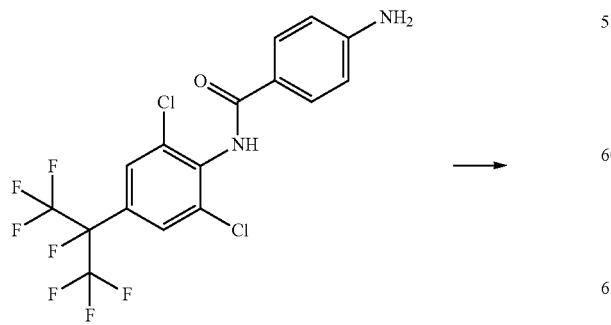

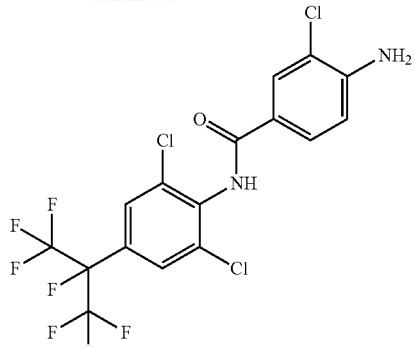

To the toluene (30 ml) solution in which 4-amino-N-[2,6-dichloro-4-(1,1,1,2,3,3,3-heptafluoro propan-2-yl)phenyl] benzamide (2.80 g) is dissolved, N-chlorosuccinimide (0.87 g) was added. The reaction solution was stirred for 6 hours at 80° C. under heating. The solution was cooled to room temperature, diluted with water and extracted twice with ethyl acetate. The organic phases were combined, and then dried over magnesium sulfate. The drying agent was removed by filtration, and the solvent was distilled off under reduced pressure to obtain a crude product, which was then separated and purified by column chromatography to give 4-amino-3-chloro-N-[2,6-dichloro-4-(1,1,1,2,3,3,3-heptafluoropropan-2-yl)phenyl] benzamide (2.03 g, yield 67.3%).

$^1$H-NMR (CDCl$_3$) δ: 4.53 (2H, s), 6.82 (1H, d), 7.52 (1H, s), 7.64 (2H, s), 7.68 (1H, dd), 7.90 (1H, d).

Step 10-4: Synthesis of 3-chloro-N-[2,6-dichloro-4-(1,1,1,2,3,3,3-heptafluoro propan-2-yl)phenyl]-4-iodobenzamide (compound No. A-7).

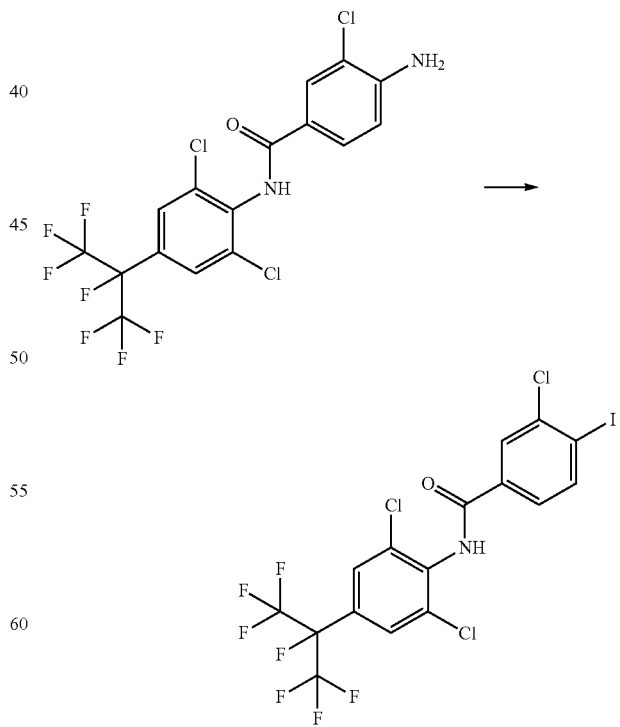

To the acetonitrile (20 ml) solution in which 4-amino-3-chloro-N-[2,6-di-chloro-4-(1,1,1,2,3,3,3-heptafluoropropan-2-yl)phenyl]benzamide (1.95 g) and diiodomethane (1.30 ml) are dissolved, an acetonitrile solution (5 ml) containing t-butyl nitrite (1.05 ml) was added dropwise. The solution was stirred for 1 hour at room temperature and then stirred further for 1 hour at 60° C. under heating. The reaction mixture was cooled, diluted with ethyl acetate, and washed twice with water and twice with an aqueous solution of sodium bisulfite. The organic phase was dried over magnesium sulfate. The drying agent was removed by filtration, and the solvent was distilled off under reduced pressure to obtain a crude product, which was then separated and purified by column chromatography to give 3-chloro-N-[2,6-dichloro-4-(1,1,1,2,3,3,3-heptafluoropropan-2-yl)phenyl]-4-iodobenzamide (1.65 g, yield 68.8%).

¹H-NMR (CDCl₃) δ: 7.49 (1H, dd), 7.60 (1H, s), 7.67 (2H, s), 8.00 (1H, d), 8.04 (1H, d).

Step 10-5: Synthesis of 3-chloro-4-cyano-N-[2,6-dichloro-4-(1,1,1,2,3,3,3-heptafluoropropan-2-yl)phenyl]benzamide (Compound No. 1-38).

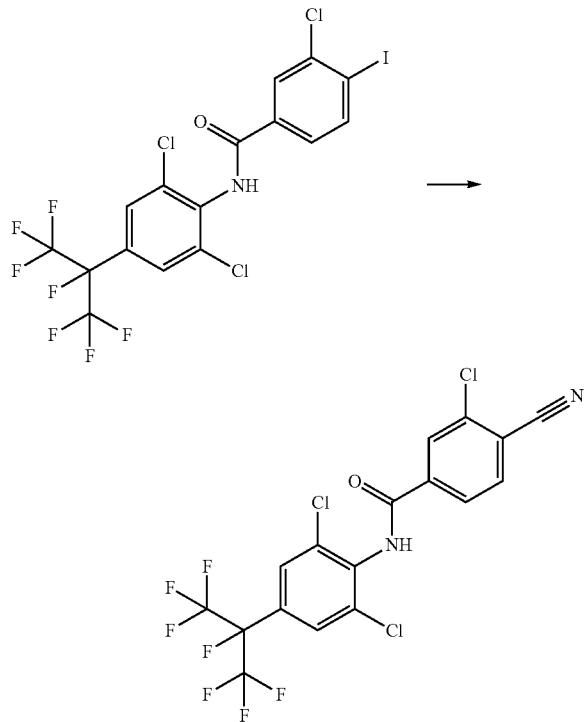

3-Chloro-N-[2,6-dichloro-4-(1,1,1,2,3,3,3-heptafluoropropan-2-yl)phenyl]-4-iodobenzamide (1.59 g) was dissolved in N,N-dimethylformamide (20 ml). The resulting solution was deaerated under argon atmosphere, and then zinc cyanide (0.38 g) and tetrakis(triphenyl phosphine) palladium (0) (0.37 g) were added thereto. The mixture was heated and stirred for 7 hours at 80° C. under argon atmosphere. The reaction mixture was cooled, diluted with ethyl acetate, and then washed twice with water. The organic phase was dried over magnesium sulfate. The drying agent was removed by filtration, and the solvent was distilled off under reduced pressure to obtain a crude product, which was then purified by column chromatography to give 3-chloro-4-cyano-N-[2,6-dichloro-4-(1,1,1,2,3,3,3-heptafluoropropan-2-yl)-phenyl]-benzamide (0.90 g, yield 68.2%).

¹H-NMR (CDCl₃) δ: 7.69 (2H, s), 7.72 (1H, s), 7.85 (1H, d), 7.93 (1H, dd), 8.09 (1H, d).

Step 10-6: Synthesis of tert-butyl (2-chloro-4-{[2,6-dichloro-4-(1,1,1,2,3,3,3heptafluoro propan-2-yl)phenyl]carbamoyl} benzyl)carbamate (Compound No. 5-317).

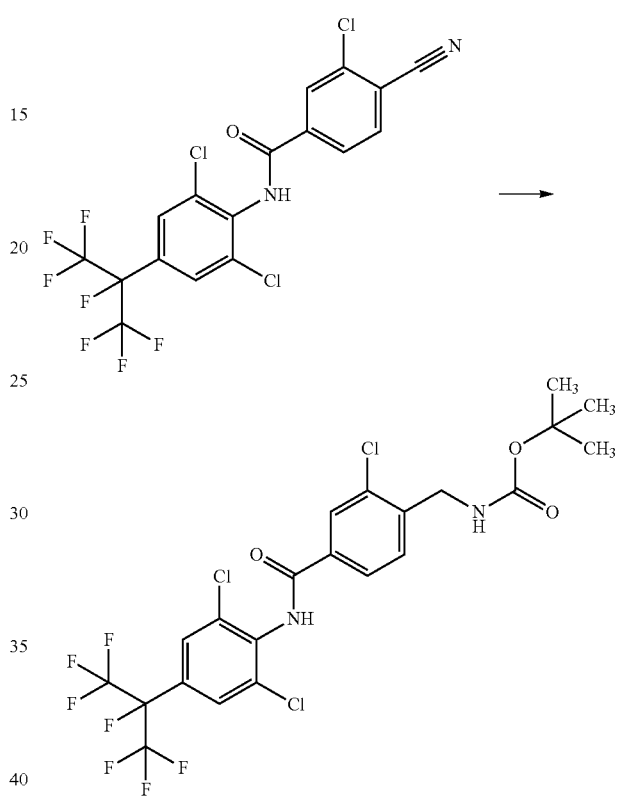

3-Chloro-4-cyano-N-[2,6-dichloro-4-(1,1,1,2,3,3,3-heptafluoropropan-2-yl)-phenyl]benzamide (0.85 g) was dissolved in methanol (50 ml). To the solution, di-tert-butyl bicarbonate (0.75 g) and nickel (II) chloride hexahydrate (0.41 g) were dissolved. To this reaction solution, NaBH₄ (0.62 g) was added in small portions under stirring and ice cooling conditions. After stirring for 2 hours, diethylenetriamine (3.7 ml) was added to the reaction solution, and then further stirred for 30 min while increasing the temperature to room temperature. The mixture was diluted with ethyl acetate and water, and then vigorously stirred for 5 min. The organic phase was separated and the aqueous layer was extracted with ethyl acetate. The organic phases were combined, washed with a saturated sodium bicarbonate aqueous solution, and then dried over magnesium sulfate. The drying agent was removed by filtration, and the solvent was distilled off under reduced pressure to obtain a crude product, which was then purified by column chromatography to give tert-butyl (2-chloro-4-{[2,6-dichloro-4-(1,1,1,2,3,3,3-heptafluoropropan-2-yl)phenyl]carbamoyl}benzyl) carbamate (0.95 g, yield 92.3%).

¹H-NMR (CDCl₃) δ: 1.46 (9H, s), 4.47 (2H, d), 5.09 (1H, s), 7.55 (1H, d), 7.63 (1H, s), 7.67 (2H, s), 7.82 (1H, dd), 7.96 (1H, d).

Step 10-7: Synthesis of 4-(aminomethyl)-3-chloro-N-[2,6-dichloro-4-(1,1,1,2,3,3,3-heptafluoropropan-2-yl)phenyl]benzamide (Compound No. 5-228).

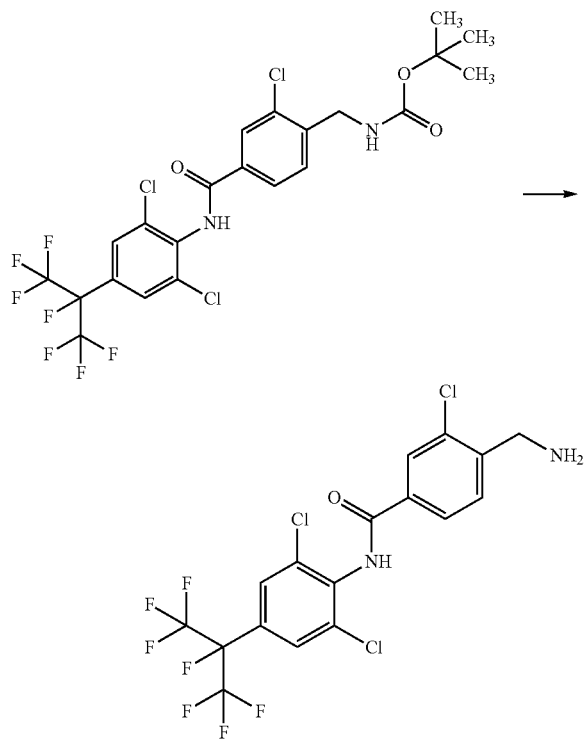

Tert-butyl (2-chloro-4-{[2,6-dichloro-4-(1,1,1,2,3,3,3-heptafluoropropan-2-yl)-phenyl]carbamoyl}benzyl)carbamate (0.85 g) was dissolved in methylene chloride (15 ml). Trifluoroacetic acid (2 ml) was added to the solution, and the mixture was stirred at room temperature for 16 hours. The solvent was distilled off under reduced pressure. The residue was dissolved in methylene chloride (15 ml), and an aqueous solution of potassium carbonate was added to the solution under stirring. The organic phase was separated and the aqueous layer was extracted with methylene chloride and dried over magnesium sulfate. The drying agent was removed by filtration, and the solvent was distilled off under reduced pressure to obtain a crude product (0.65 g) of 4-(aminomethyl)-3-chloro-N-[2,6-dichloro-4-(1,1,1,2,3,3,3heptafluoropropan-2-yl)-phenyl]benzamide. The crude product was used for the next step without further purification.

$^1$H-NMR: see the Table below.

Step 10-8: Synthesis of 4-(acetamidemethyl)-3-chloro-N-[2,6-dichloro-4-(1,1,1,2,3,3,3-heptafluoropropan-2-yl)phenyl]benzamide (Compound No. 5-229).

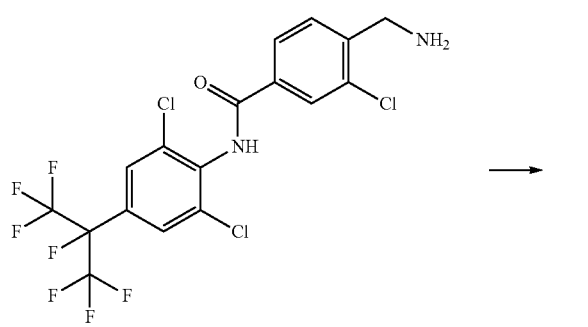

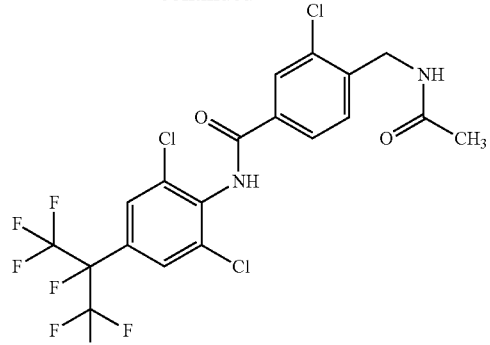

The crude product of 4-(aminomethyl)-3-chloro-N-[2,6-dichloro-4-(1,1,1,2,3,3,3-heptafluoropropan-2-yl)phenyl]benzamide (0.15 g) was dissolved in methylene chloride (2 ml). Acetic anhydride (0.05 ml) was added to the solution and stirred for 2 hours at room temperature. The reaction solution was separated and purified by column chromatography to obtain 4-(acetamidemethyl)-3-chloro-N-[2,6-dichloro-4-(1,1,1,2,3,3,3-heptafluoropropan-2-yl)phenyl]benzamide (0.13 g).

$^1$H-NMR: see the Table below.

Synthetic Example 11

Synthesis of 3-chloro-N-[2,6-dichloro-4-(1,1,1,2,3,3,3-heptafluoropropan-2-yl)phenyl]-4-[(propionylamino)methyl]benzamide (Compound No. 5-230).

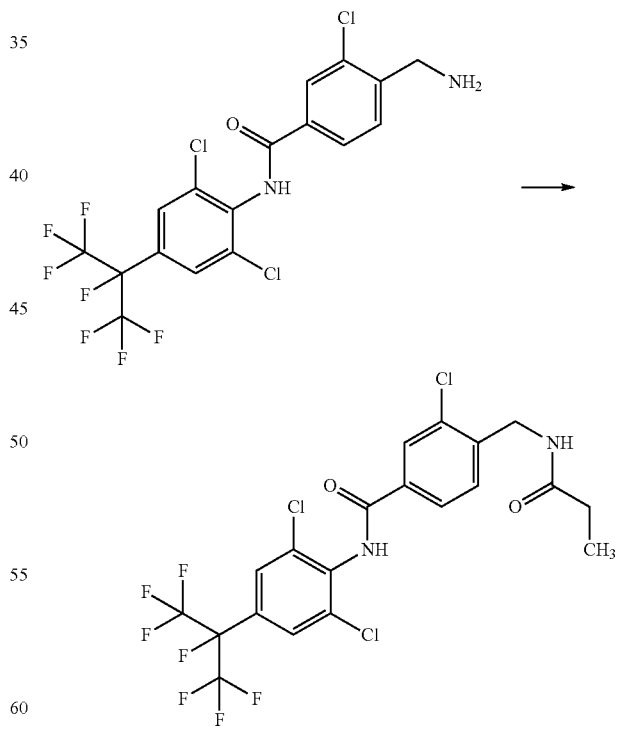

To the methylene chloride solution (2 ml) of the crude product of 4-(aminomethyl)-3-chloro-N-[2,6-dichloro-4-(1,1,1,2,3,3,3-heptafluoropropan-2-yl)-phenyl]benzamide (150 mg), which had been obtained from Step 10-7 of Synthetic example 10, and propionic acid (23 mg), 1-ethyl-3-(3-dimethylaminopropyl)-carbodiimide hydrochloride (93 mg) was added at room temperature under stirring. The mixture was then stirred for 3 hours. The reaction solution was separated and purified by column chromatography to obtain 3-chloro-N-[2,6-dichloro-4-(1,1,1,2,3,3,3-heptafluoropropan-2-yl)phenyl]-4-[(propionylamino)methyl]benzamide (150 mg).

¹H-NMR: see the Table below.

Synthetic Example 12

Synthesis of 3-(acetamidemethyl)-N-[2-ethyl-4-(1,1,1,2,3,3,3-heptafluoro propan-2-yl)-6-methylphenyl]-4-(1H-1,2,4-triazol-1-yl)benzamide (Compound No. 12-3).

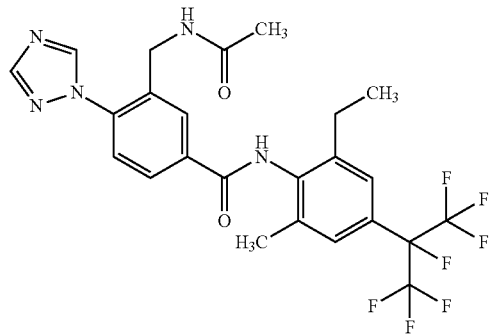 [SMILES: CCc1cc(C(F)(C(F)(F)F)C(F)(F)F)cc(C)c1NC(=O)c1ccc(-n2cncn2)c(CNC(C)=O)c1]

Step 12-1: Synthesis of 3-cyano-N[2-ethyl-4-(1,1,1,2,3,3,3-heptafluoro propan-2-yl)-6-methylphenyl]-4-fluorobenzamide

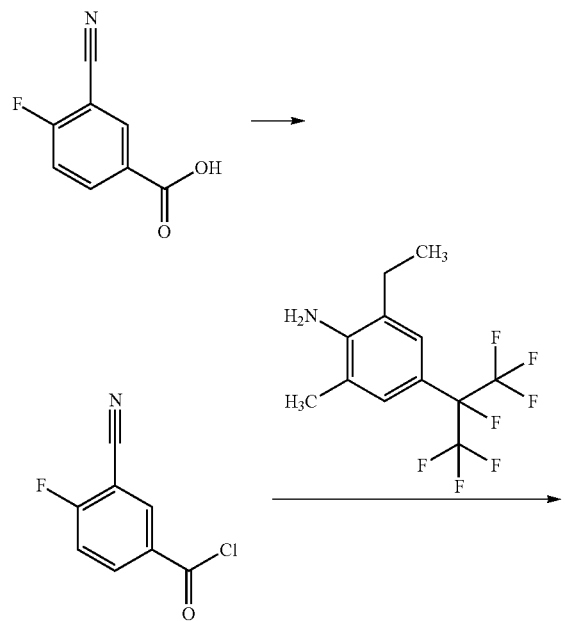

-continued

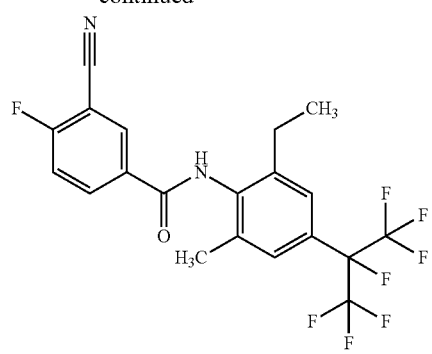

3-Cyano-4-fluorobenzoic acid (1.0 g) was suspended in toluene (20 ml), thionyl chloride (0.79 g) and a small amount of N,N-dimethylformamide (2 to 3 drops) were added thereto, and the mixture was heated and stirred for 6 hours at reflux temperature. After cooling to room temperature, the solvent and excess thionyl chloride were distilled off under reduced pressure. The residue was dissolved in tetrahydrofuran (10 ml). The solution was added dropwise at room temperature to tetrahydrofuran (15 ml) in which 2-ethyl-4-(1,1,1,2,3,3,3-heptafluoropropan-2-yl)-6-methylaniline (1.7 g) and pyridine (0.91 g) are dissolved, and the mixture was stirred overnight. The reaction solution was diluted with water and extracted twice with ethyl acetate. The organic phases were combined, washed with water and 2 N hydrochloric acid, and then dried over anhydrous sodium sulfate. The drying agent was removed by filtration, and the solvent was distilled off under reduced pressure to obtain a crude product, which was then purified by column chromatography to give 3-cyano-N-[2-ethyl-4-(1,1,1,2,3,3,3-heptafluoropropan-2-yl)-6-methylphenyl]-4fluorobenzamide (1.7 g, yield 65%).

¹H-NMR (CDCl₃) δ: 1.21 (3H, t), 2.31 (3H, s), 2.66 (2H, q), 7.35-7.40 (3H, m), 7.53 (1H, s), 8.17-8.25 (2H, m).

Step 12-2: Synthesis of 3-cyano-N-[2-ethyl-4-(1,1,1,2,3,3,3-heptafluoro propan-2-yl)-6-methylphenyl]-4-(1H-1,2,4-triazol-1-yl)benzamide (Compound No. 1-49).

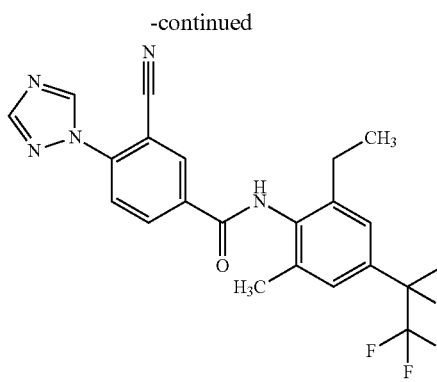

According to the method of Synthetic example 2, the title compound was obtained from 3-cyano-N-[2-ethyl-4-(1,1,1,2,3,3,3-heptafluoropropan-2-yl)-6-methylphenyl]-4fluorobenzamide which had been obtained in Step 12-1.

$^1$H-NMR: see the Table below.

Step 12-3: Synthesis of tert-butyl[5-{[2-ethyl-4-(1,1,1,2,3,3,3-heptafluoropropan-2-yl)-6-methylphenyl]carbamoyl}-2-(1H-1,2,4-triazol-1-yl)benzyl]carbamate (Compound No. 12-1).

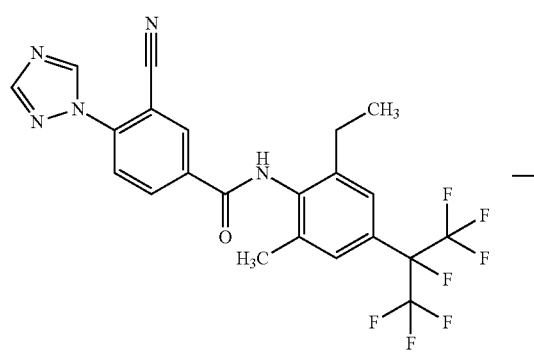

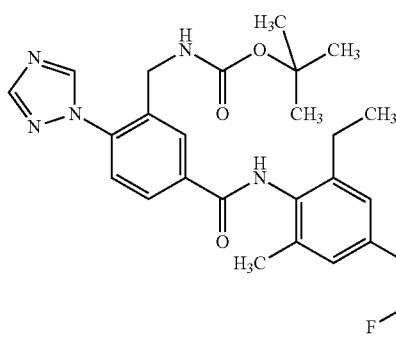

According to the method of Step 7-4 of Synthetic example 7, the title compound was obtained from 3-cyano-N-[2-ethyl-4-(1,1,1,2,3,3,3-heptafluo-ropropan-2-yl)-6methylphenyl]-4-(1H-1,2,4-triazol-1-yl)benzamide which had been obtained in Step 12-2.

$^1$H-NMR: see the Table below.

Step 12-4: Synthesis of 3-(aminomethyl)-N-[2-ethyl-4-(1,1,1,2,3,3,3-heptafluoro-propan-2-yl)-6-methylphenyl]-4-(1H-1,2,4-triazol-1-yl)benzamide (Compound No. 12-2).

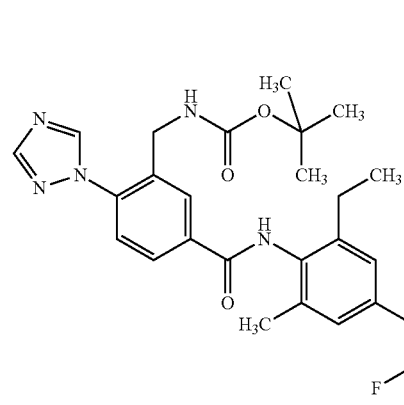

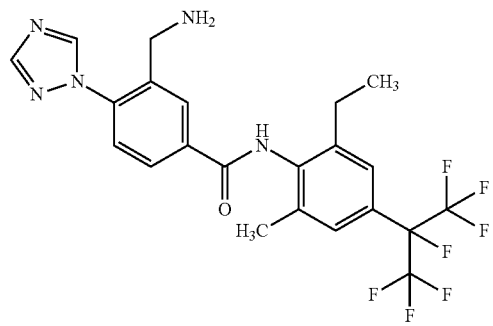

According to the method of Step 7-5 of Synthetic example 7, the title compound was obtained from tert-butyl [5-{[2-ethyl-4-(1,1,1,2,3,3,3-heptafluoropropan-2-yl)-6-methylphenyl]carbamoyl}-2-(1H-1,2,4-triazol-1-yl)benzyl]carbamate which had been obtained in Step 12-3.

$^1$H-NMR: see the Table below.

Step 12-5: Synthesis of 3-(acetamidemethyl)-N-[2-ethyl-4-(1,1,1,2,3,3,3-heptafluoro-propan-2-yl)-6-methylphenyl]-4-(1H-1,2,4-triazol-1-yl)benzamide (Compound No. 12-3).

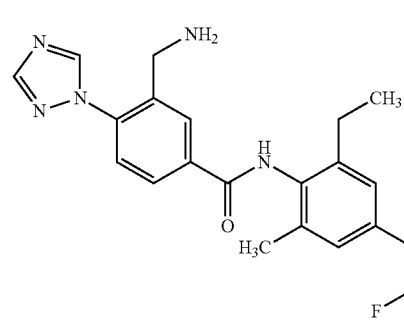

-continued

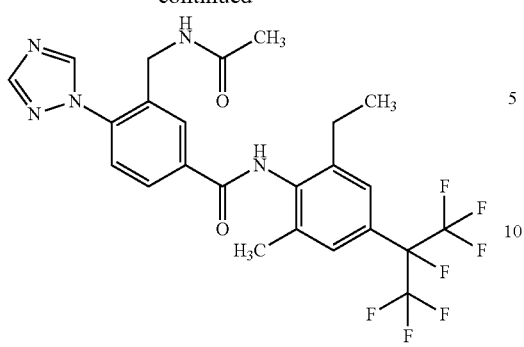

According to the method of Step 6-4 of Synthetic example 6, the title compound was obtained from 3-(aminomethyl)-N-[2-ethyl-4-(1,1,1,2,3,3,3-heptafluoropropan-2-yl)-6methylphenyl]-4-(1H-1,2,4-triazol-1-yl)benzamide which had been obtained in Step 12-4.

$^1$H-NMR: see the Table below.

Synthetic Example 13

Synthesis of N-[2-ethyl-4-(1,1,1,2,3,3,3-heptafluoropropan-2-yl)-6-methyl-phenyl]-4-[(propionylamino)methyl]-3-(1H-pyrazol-1-yl)benzamide (Compound No. 13-1).

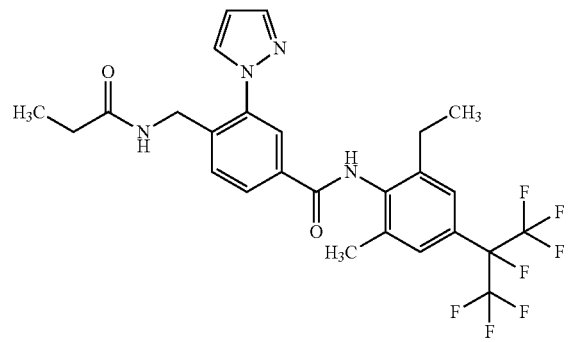 [SMILES: CCC(=O)NCc1ccc(C(=O)Nc2c(C)cc(C(F)(C(F)(F)F)C(F)(F)F)cc2CC)cc1-n1cccn1]

Step 13-1: Synthesis of Methyl 4-cyano-3-(1H-pyrazol-1-yl)benzoate

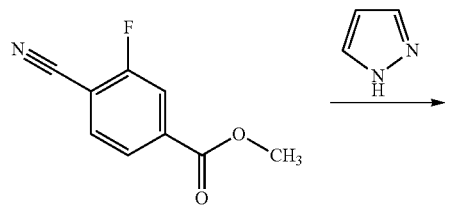

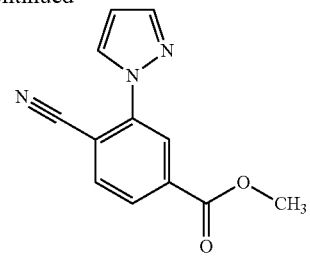

Methyl 4-cyano-3-fluorobenzoate (0.30 g) and 1H-pyrazole (0.14 g) were dissolved in N,N-dimethylformamide (10 ml). To the reaction solution, sodium hydride (0.10 g) was added under ice cooling while stirring the mixture, and the mixture was stirred for 30 min. After increasing the temperature to room temperature, the solution was further stirred for 2 hours. The reaction solution was diluted with water and extracted twice with ethyl acetate. The organic phases were combined, washed with water, and then dried over anhydrous sodium sulfate. The drying agent was removed by filtration, and the solvent was distilled off under reduced pressure to obtain a crude product, which was then purified by column chromatography to give methyl 4-cyano-3-(1H-pyrazol-1-yl)benzoate (0.28 g, yield 73%).

$^1$H-NMR (CDCl$_3$) δ: 3.99 (3H, s), 6.58 (1H, dd), 7.85-7.88 (2H, m), 8.06 (1H, dd), 8.18 (1H, dd), 8.43 (1H, d).

Step 13-2: Synthesis of 4-cyano-3-(1H-pyrazol-1-yl)benzoic Acid

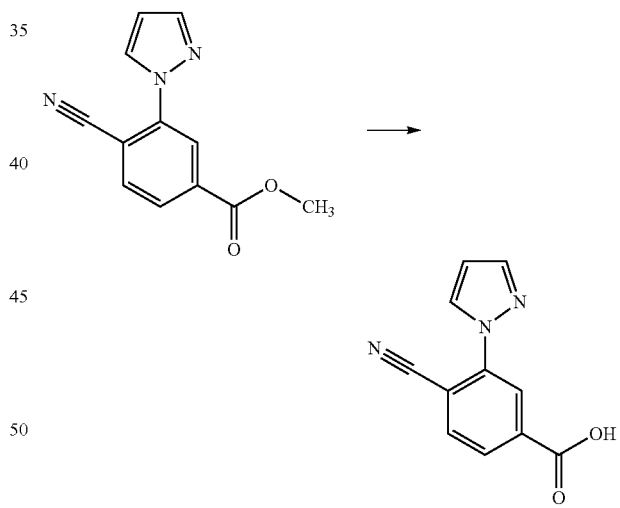

Methyl 4-cyano-3-(1H-pyrazol-1-yl)benzoate (0.27 g) was dissolved in tetrahydrofuran (10 ml). To the solution, a solution in which lithium hydroxide monohydrate (0.10 g) is dissolved in water (10 ml) was added at room temperature. The reaction mixture was stirred for 2 hours. The reaction solution was acidified with 2 N hydrochloric acid, and then extracted twice with ethyl acetate. The organic phases were combined, washed with water, and then dried over anhydrous sodium sulfate. The drying agent was removed by filtration, and the solvent was distilled off under reduced pressure to obtain a crude product of 4-cyano-3-(1H-pyrazol-1-yl)benzoic acid (0.23 g). The crude product was used for the next step without further purification.

¹H-NMR (DMSO-d₆) δ: 6.66 (1H, dd), 7.91 (1H, s), 8.02 (1H, d), 8.14 (1H, d), 8.22 (1H, s), 8.54 (1H, d).

Step 13-3: Synthesis of 4-cyano-N-[2-ethyl-4-(1,1,1,2,3,3,3-heptafluoropropan-2-yl)-6-methylphenyl]-3-(1H-pyrazol-1-yl)benzamide (Compound No. 14-1).

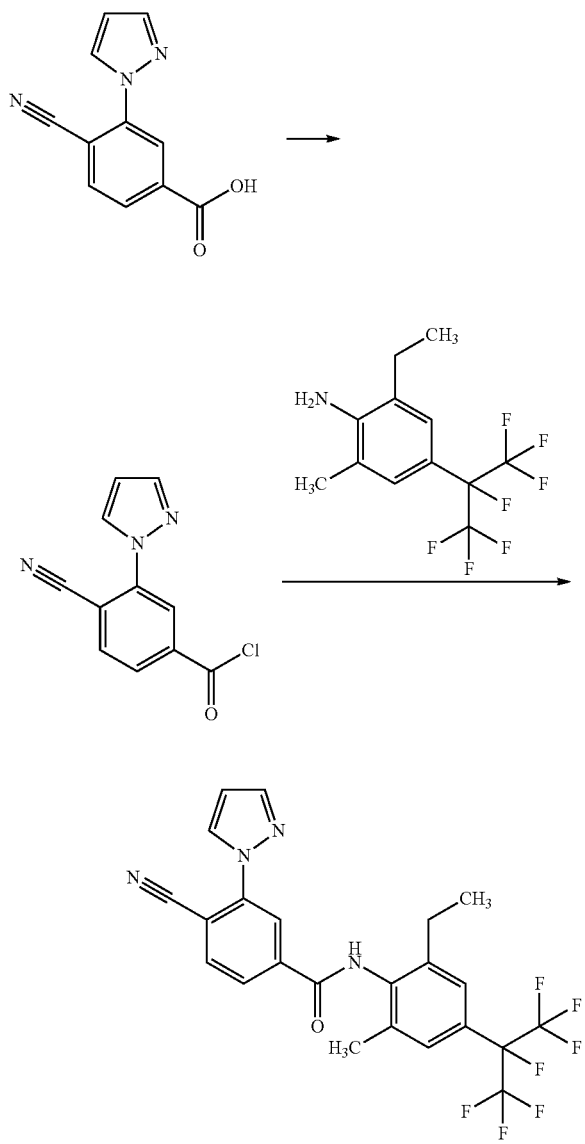

The crude product of 4-cyano-3-(1H-pyrazol-1-yl)benzoic acid (0.23 g) was suspended in toluene (10 ml), thionyl chloride (0.64 g) and a small amount of N,N-dimethylformamide (2 to 3 drops) were added thereto, and the mixture was heated and stirred for 6 hours at reflux temperature. After cooling to room temperature, the solvent and excess thionyl chloride were distilled off under reduced pressure. To the residue, 4-dimethylaminopyridine (7 mg), pyridine (0.18 g) and 2-ethyl-4-(1,1,1,2,3,3,3-heptafluoro propan-2-yl)-6-methylaniline (0.34 g) dissolved in tetrahydrofuran (15 ml) were added, and the mixture was stirred at room temperature for 3 hours. The mixture was further heated and stirred for 3 hours at reflux temperature. After cooling to room temperature, the reaction solution was diluted with water and extracted twice with ethyl acetate. The organic phases were combined, washed with water and a saturated sodium bicarbonate aqueous solution sequentially, and then dried over anhydrous sodium sulfate. The drying agent was removed by filtration, and the solvent was distilled off under reduced pressure to obtain a crude product, which was then purified by column chromatography to give 4-cyano-N-[2-ethyl-4-(1,1,1,2,3,3,3-heptafluoro-propan-2-yl)-6-methylphenyl]-3-(1H-pyrazol-1-yl)benzamide (0.13 g, yield 23%).

¹H-NMR: see the Table below.

Step 13-4: Synthesis of N-[2-ethyl-4-(1,1,1,2,3,3,3-heptafluoropropan-2-yl)-6-methylphenyl]-4-[(propionylamino)methyl]-3-(1H-pyrazol-1-yl)benzamide (Compound No. 13-1).

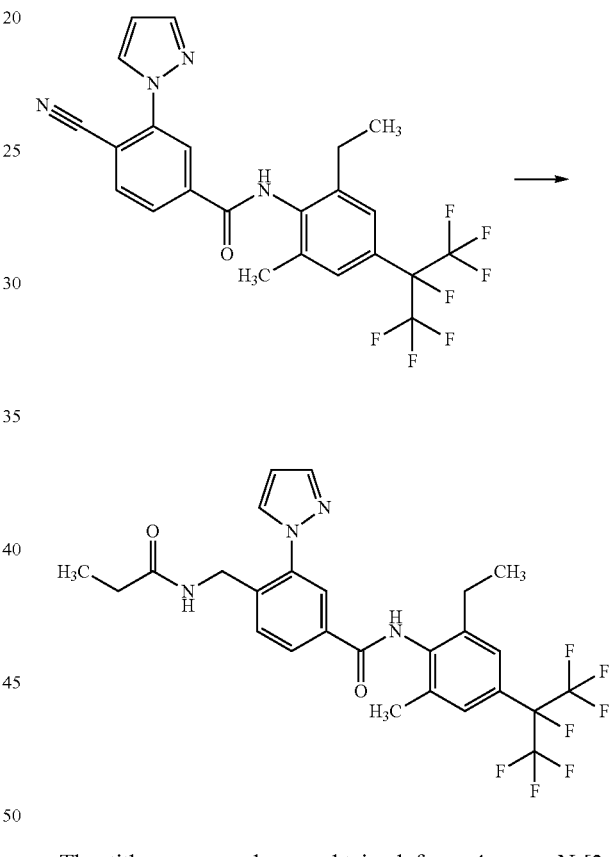

The title compound was obtained from 4-cyano-N-[2-ethyl-4-(1,1,1,2,3,3,3-heptafluoro-propan-2-yl)-6-methylphenyl]-3-(1H-pyrazol-1-yl)benzamide which had been obtained in Step 13-3 according to the method of Step 7-4 of Synthetic example 7 by using propionic anhydride instead of di-tert-butyl bicarbonate.

¹H-NMR (CDCl₃): see the Table below.

The compounds of Formula (I) of the present invention and intermediates thereof, that are obtained by the same methods as those of the above Synthetic examples or obtained in accordance with the methods described in detail above as well as their physical properties are set forth in Tables 1 to 14, Tables A to M and NMR Table below. The compounds obtained in the above Synthetic examples are also described in the corresponding tables.

TABLE 1

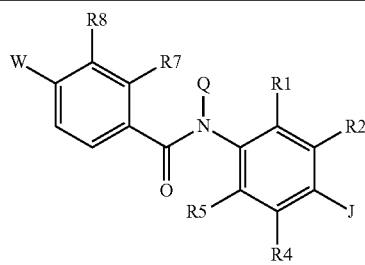

| Exa | R1 | R2 | J | R4 | R5 | Q | R7 | R8 | W |
|---|---|---|---|---|---|---|---|---|---|
| 1-1 | $CH_3$ | H | 1,1,1,2,3,3,3-heptafluoropropan-2-yl | H | $CH_3$ | H | H | H | 1H-pyrazol-1-yl |
| 1-2 | $CH_3$ | H | 1,1,1,2,3,3,3-heptafluoropropan-2-yl | H | $CH_3$ | H | H | H | 4-chloro-1H-pyrazol-1-yl |
| 1-3 | $CH_3$ | H | 1,1,1,2,3,3,3-heptafluoropropan-2-yl | H | $CH_3$ | H | H | H | 1H-1,2,4-triazol-1-yl |
| 1-4 | $CH_3$ | H | 1,1,1,2,3,3,3-heptafluoropropan-2-yl | H | $CH_3$ | $CH_3$ | H | H | 1H-1,2,4-triazol-1-yl |
| 1-5 | $CH_3$ | H | 1,1,1,2,3,3,3-heptafluoropropan-2-yl | H | $CH_3$ | H | chloro | H | 1H-1,2,4-triazol-1-yl |
| 1-6 | $CH_3$ | H | 1,1,1,2,3,3,3-heptafluoropropan-2-yl | H | $CH_3$ | H | trifluoromethyl | H | 1H-124-triazol-1-yl |
| 1-7 | $CH_3$ | H | 1,1,1,2,3,3,3-heptafluoropropan-2-yl | H | $CH_3$ | H | nitro | H | 1H-1,2,4-triazol-1-yl |
| 1-8 | $CH_3$ | H | 1,1,1,2,3,3,3-heptafluoropropan-2-yl | H | $CH_3$ | H | H | chloro | 1H-1,2,4-triazol-1-yl |
| 1-9 | $CH_3$ | H | 1,1,1,2,3,3,3-heptafluoropropan-2-yl | H | $CH_3$ | H | H | bromo | 1H-1,2,4-triazol-1-yl |
| 1-10 | $CH_3$ | H | 1,1,1,2,3,3,3-heptafluoropropan-2-yl | H | $CH_3$ | H | H | trifluoromethyl | 1H-1,2,4-triazol-1-yl |
| 1-11 | $CH_3$ | H | 1,1,1,2,3,3,3-heptafluoropropan-2-yl | H | $CH_3$ | H | H | nitro | 1H-1,2,4-triazol-1-yl |
| 1-12 | $CH_3$ | H | 1,1,1,2,3,3,3-heptafluoropropan-2-yl | H | $CH_3$ | H | H | cyano | 1H-1,2,4-triazol-1-yl |
| 1-13 | $CH_3$ | H | 1,1,1,2,3,3,3-heptafluoropropan-2-yl | H | $CH_3$ | H | H | H | 5-(ethylsulfanyl)-1H-tetrazol-1-yl |
| 1-14 | $CH_3$ | H | 1,1,1,2,3,3,3-heptafluoropropan-2-yl | H | ethyl | H | H | nitro | 1H-pyrrol-1-yl |
| 1-15 | $CH_3$ | H | 1,1,1,2,3,3,3-heptafluoropropan-2-yl | H | ethyl | H | H | trifluoromethyl | 2-cyano-1H-pyrrol-1-yl |
| 1-16 | $CH_3$ | H | 1,1,1,2,3,3,3-heptafluoropropan-2-yl | H | ethyl | H | H | H | 1H-pyrazol-1-yl |
| 1-17 | $CH_3$ | H | 1,1,1,2,3,3,3-heptafluoropropan-2-yl | H | ethyl | H | H | nitro | 1H-pyrazol-1-yl |
| 1-18 | $CH_3$ | H | 1,1,1,2,3,3,3-heptafluoropropan-2-yl | H | ethyl | H | H | (phenylcarbonyl)amino | 1H-pyrazol-1-yl |
| 1-19 | $CH_3$ | H | 1,1,1,2,3,3,3-heptafluoropropan-2-yl | H | ethyl | H | H | [(2-fluorophenyl))carbonyl]amino | 1H-pyrazol-1-yl |
| 1-20 | $CH_3$ | H | 1,1,1,2,3,3,3-heptafluoropropan-2-yl | H | ethyl | H | H | [(2-chloropyridin-3-yl)carbonyl]amino | 1H-pyrazol-1-yl |
| 1-21 | $CH_3$ | H | 1,1,1,2,3,3,3-heptafluoropropan-2-yl | H | ethyl | H | H | H | 4-chloro-1H-pyrazol-1-yl |
| 1-22 | $CH_3$ | H | 1,1,1,2,3,3,3-heptafluoropropan-2-yl | H | ethyl | H | H | nitro | 4-(trifluoromethyl)-1H-pyrazol-1-yl |
| 1-23 | $CH_3$ | H | 1,1,1,2,3,3,3-heptafluoropropan-2-yl | H | ethyl | H | H | nitro | 4-nitro-1H-pyrazol-1-yl |
| 1-24 | $CH_3$ | H | 1,1,1,2,3,3,3-heptafluoropropan-2-yl | H | ethyl | H | H | nitro | 4-cyano-1H-pyrazol-1-yl |
| 1-25 | $CH_3$ | H | 1,1,1,2,3,3,3-heptafluoropropan-2-yl | H | ethyl | H | H | H | 1H-imidazol-1-yl |
| 1-26 | $CH_3$ | H | 1,1,1,2,3,3,3-heptafluoropropan-2-yl | H | ethyl | H | H | nitro | 1H-imidazol-1-yl |
| 1-27 | $CH_3$ | H | 1,1,1,2,3,3,3-heptafluoropropan-2-yl | H | ethyl | H | H | H | 1H-1,2,3-triazol-1-yl |
| 1-28 | $CH_3$ | H | 1,1,1,2,3,3,3-heptafluoropropan-2-yl | H | ethyl | H | H | nitro | 1H-1,2,3-triazol-1-yl |
| 1-29 | $CH_3$ | H | 1,1,1,2,3,3,3-heptafluoropropan-2-yl | H | ethyl | H | H | H | 2H-1,2,3-triazol-2-yl |
| 1-30 | $CH_3$ | H | 1,1,1,2,3,3,3-heptafluoropropan-2-yl | H | ethyl | H | H | nitro | 2H-1,2,3-triazol-2-yl |
| 1-31 | $CH_3$ | H | 1,1,1,2,3,3,3-heptafluoropropan-2-yl | H | ethyl | H | H | H | 1H-1,2,4-triazol-1-yl |
| 1-32 | $CH_3$ | H | 1,1,1,2,3,3,3-heptafluoropropan-2-yl | H | ethyl | H | H | $CH_3$ | 1H-1,2,4-triazol-1-yl |
| 1-33 | $CH_3$ | H | 1,1,1,2,3,3,3-heptafluoropropan-2-yl | H | ethyl | H | H | trifluoromethyl | 1H-1,2,4-triazol-1-yl |
| 1-34 | $CH_3$ | H | 1,1,1,2,3,3,3-heptafluoropropan-2-yl | H | ethyl | H | H | fluoro | 1H-1,2,4-triazol-1-yl |
| 1-35 | $CH_3$ | H | 1,1,1,2,3,3,3-heptafluoropropan-2-yl | H | ethyl | H | H | chloro | 1H-1,2,4-triazol-1-yl |
| 1-36 | $CH_3$ | H | 1,1,1,2,3,3,3-heptafluoropropan-2-yl | H | ethyl | H | H | bromo | 1H-1,2,4-triazol-1-yl |
| 1-37 | $CH_3$ | H | 1,1,1,2,3,3,3-heptafluoropropan-2-yl | H | ethyl | H | H | methoxy | 1H-1,2,4-triazol-1-yl |
| 1-38 | $CH_3$ | H | 1,1,1,2,3,3,3-heptafluoropropan-2-yl | H | ethyl | H | H | amino | 1H-1,2,4-triazol-1-yl |
| 1-39 | $CH_3$ | H | 1,1,1,2,3,3,3-heptafluoropropan-2-yl | H | ethyl | H | H | nitro | 1H-1,2,4-triazol-1-yl |
| 1-40 | $CH_3$ | H | 1,1,1,2,3,3,3-heptafluoropropan-2-yl | H | ethyl | H | H | propanoylamino | 1H-1,2,4-triazol-1-yl |
| 1-41 | $CH_3$ | H | 1,1,1,2,3,3,3-heptafluoropropan-2-yl | H | ethyl | H | H | (phenylcarbonyl)amino | 1H-1,2,4-triazol-1-yl |
| 1-42 | $CH_3$ | H | 1,1,1,2,3,3,3-heptafluoropropan-2-yl | H | ethyl | H | H | [(2-fluorophenyl)carbonyl]amino | 1H-1,2,4-triazol-1-yl |
| 1-43 | $CH_3$ | H | 1,1,1,2,3,3,3-heptafluoropropan-2-yl | H | ethyl | H | H | [(4-fluorophenyl)carbonyl]amino | 1H-1,2,4-triazol-1-yl |
| 1-44 | $CH_3$ | H | 1,1,1,2,3,3,3-heptafluoropropan-2-yl | H | ethyl | H | H | [(2,5-difluorophenyl)carbonyl]amino | 1H-1,2,4-triazol-1-yl |
| 1-45 | $CH_3$ | H | 1,1,1,2,3,3,3-heptafluoropropan-2-yl | H | ethyl | H | H | [(2-fluoropyridin-3-yl)carbonyl]amino | 1H-1,2,4-triazol-1-yl |
| 1-46 | $CH_3$ | H | 1,1,1,2,3,3,3-heptafluoropropan-2-yl | H | ethyl | H | H | [(2-chloropyridin-3-yl)carbonyl]amino | 1H-1,2,4-triazol-1-yl |
| 1-47 | $CH_3$ | H | 1,1,1,2,3,3,3-heptafluoropropan-2-yl | H | ethyl | H | H | (methoxycarbonyl)amino | 1H-1,2,4-triazol-1-yl |
| 1-48 | $CH_3$ | H | 1,1,1,2,3,3,3-heptafluoropropan-2-yl | H | ethyl | H | H | (methylsulfonyl)amino | 1H-1,2,4-triazol-1-yl |
| 1-49 | $CH_3$ | H | 1,1,1,2,3,3,3-heptafluoropropan-2-yl | H | ethyl | H | H | cyano | 1H-1,2,4-triazol-1-yl |
| 1-50 | $CH_3$ | H | 1,1,1,2,3,3,3-heptafluoropropan-2-yl | H | ethyl | H | H | H | 3-(trifluoromethyl)-1H-1,2,4-triazol-1-yl |

TABLE 1-continued

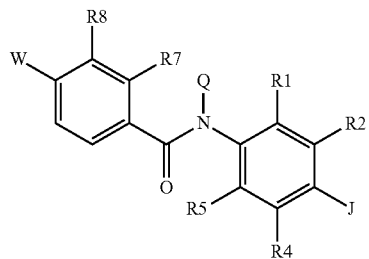

| Exa | R1 | R2 | J | R4 | R5 | Q | R7 | R8 | W |
|---|---|---|---|---|---|---|---|---|---|
| 1-51 | CH$_3$ | H | 1,1,1,2,3,3,3-heptafluoropropan-2-yl | H | ethyl | H | H | amino | 3-(trifluoromethyl)-1H-1,2,4-triazol-1-yl |
| 1-52 | CH$_3$ | H | 1,1,1,2,3,3,3-heptafluoropropan-2-yl | H | ethyl | H | H | nitro | 3-(trifluoromethyl)-1H-1,2,4-triazol-1-yl |
| 1-53 | CH$_3$ | H | 1,1,1,2,3,3,3-heptafluoropropan-2-yl | H | ethyl | H | H | nitro | 3-(methoxycarbonyl)-1H-1,2,4-triazol-1-yl |
| 1-54 | CH$_3$ | H | 1,1,1,2,3,3,3-heptafluoropropan-2-yl | H | ethyl | H | H | H | 3-carbamoyl-1H-1,2,4-triazol-1-yl |
| 1-55 | CH$_3$ | H | 1,1,1,2,3,3,3-heptafluoropropan-2-yl | H | ethyl | H | H | H | 1H-tetrazol-1-yl |
| 1-56 | CH$_3$ | H | 1,1,1,2,3,3,3-heptafluoropropan-2-yl | H | ethyl | H | fluoro | H | 1H-tetrazol-1-yl |
| 1-57 | CH$_3$ | H | 1,1,1,2,3,3,3-heptafluoropropan-2-yl | H | ethyl | H | H | nitro | 1H-tetrazol-1-yl |
| 1-58 | CH$_3$ | H | 1,1,1,2,3,3,3-heptafluoropropan-2-yl | H | ethyl | H | H | H | 2H-tetrazol-2-yl |
| 1-59 | CH$_3$ | H | 1,1,1,2,3,3,3-heptafluoropropan-2-yl | H | ethyl | H | H | nitro | 2H-tetrazol-2-yl |
| 1-60 | CH$_3$ | H | 1,1,1,2,3,3,3-heptafluoropropan-2-yl | H | ethyl | H | H | H | 5-(methylsulfanyl)-1H-tetrazol-1-yl |
| 1-61 | CH$_3$ | H | 1,1,1,2,3,3,3-heptafluoropropan-2-yl | H | ethyl | H | H | H | 1H-benzotriazol-1-yl |
| 1-62 | CH$_3$ | H | 1,1,1,2,3,3,3-heptafluoropropan-2-yl | H | ethyl | H | H | nitro | 1H-benzotriazol-1-yl |
| 1-63 | CH$_3$ | H | 1,1,1,2,3,3,3-heptafluoropropan-2-yl | H | ethyl | H | H | nitro | 2H-benzotriazol-2-yl |
| 1-64 | CH$_3$ | H | 1,1,1,2,3,3,3-heptafluoropropan-2-yl | H | propan-2-yl | H | H | H | 1H-1,2,4-triazol-1-yl |
| 1-65 | CH$_3$ | H | 1,1,1,2,3,3,3-heptafluoropropan-2-yl | H | propan-2-yl | H | H | amino | 1H-1,2,4-triazol-1-yl |
| 1-66 | CH$_3$ | H | 1,1,1,2,3,3,3-heptafluoropropan-2-yl | H | propan-2-yl | H | H | nitro | 1H-1,2,4-triazol-1-yl |
| 1-67 | CH$_3$ | H | 1,1,1,2,3,3,3-heptafluoropropan-2-yl | H | methoxymethyl | H | H | H | 1H-1,2,4-triazol-1-yl |
| 1-68 | CH$_3$ | H | 1,1,1,2,3,3,3-heptafluoropropan-2-yl | H | methoxymethyl | H | H | amino | 1H-1,2,4-triazol-1-yl |
| 1-69 | CH$_3$ | H | 1,1,1,2,3,3,3-heptafluoropropan-2-yl | H | methoxymethyl | H | H | nitro | 1H-1,2,4-triazol-1-yl |
| 1-70 | CH$_3$ | H | 1,1,1,2,3,3,3-heptafluoropropan-2-yl | H | methoxy | H | H | H | 1H-1,2,4-triazol-1-yl |
| 1-71 | CH$_3$ | H | 1,1,1,2,3,3,3-heptafluoropropan-2-yl | H | methoxy | H | H | amino | 1H-1,2,4-triazol-1-yl |
| 1-72 | CH$_3$ | H | 1,1,1,2,3,3,3-heptafluoropropan-2-yl | H | methoxy | H | H | nitro | 1H-1,2,4-triazol-1-yl |
| 1-73 | ethyl | H | 1,1,1,2,3,3,3-heptafluoropropan-2-yl | H | ethyl | H | H | H | 1H-1,2,4-triazol-1-yl |
| 1-74 | ethyl | H | 1,1,1,2,3,3,3-heptafluoropropan-2-yl | H | ethyl | H | H | chloro | 1H-1,2,4-triazol-1-yl |
| 1-75 | ethyl | H | 1,1,1,2,3,3,3-heptafluoropropan-2-yl | H | ethyl | H | H | bromo | 1H-1,2,4-triazol-1-yl |
| 1-76 | ethyl | H | 1,1,1,2,3,3,3-heptafluoropropan-2-yl | H | ethyl | H | H | amino | 1H-1,2,4-triazol-1-yl |
| 1-77 | ethyl | H | 1,1,1,2,3,3,3-heptafluoropropan-2-yl | H | ethyl | H | H | nitro | 1H-1,2,4-triazol-1-yl |
| 1-78 | bromo | H | 1,1,1,2,3,3,3-heptafluoropropan-2-yl | H | bromo | H | H | H | 1H-1,2,4-triazol-1-yl |
| 1-79 | bromo | H | 1,1,1,2,3,3,3-heptafluoropropan-2-yl | H | (trifluoromethyl)sulfanyl | H | H | H | 1H-1,2,4-triazol-1-yl |
| 1-80 | iodo | H | 1,1,1,2,3,3,3-heptafluoropropan-2-yl | H | iodo | H | H | H | 1H-1,2,4-triazol-1-yl |
| 1-81 | iodo | H | 1,1,1,2,3,3,3-heptafluoropropan-2-yl | H | iodo | H | H | nitro | 1H-1,2,4-triazol-1-yl |
| 1-82 | CH$_3$ | H | 2-chloro-1,1,1,3,3,3-hexafluoropropan-2-yl | H | ethyl | H | H | H | 1H-1,2,4-triazol-1-yl |
| 1-83 | CH$_3$ | H | 1,1,1,3,3,3-hexafluoro-2-hydroxypropan-2-yl | H | ethyl | H | H | H | 1H-1,2,4-triazol-1-yl |
| 1-84 | CH$_3$ | H | (2-ethoxy-1,1,1,3,3,3-hexafluoropropan-2-yl | H | ethyl | H | H | H | 1H-1,2,4-triazol-1-yl |
| 1-85 | CH$_3$ | H | 1,1,1,3,3,3-hexafluoro-2-[(methylsulfonyl)oxy]-propan-2-yl | H | ethyl | H | H | H | 1H-1,2,4-triazol-1-yl |
| 1-86 | CH$_3$ | H | 2-(4-chloro-1H-pyrazol-1-yl)-1,1,1,3,3,3-hexafluoropropan-2-yl | H | ethyl | H | H | H | 1H-tetrazol-1-yl |
| 1-87 | CH$_3$ | H | 1,1,1,3,3,3-hexafluoro-2-(1H-1,2,4-triazol-1-yl)-propan-2-yl | H | CH$_3$ | H | chloro | H | 1H-1,2,4-triazol-1-yl |
| 1-88 | CH$_3$ | H | 1,1,1,2,3,3,4,4,4-nonafluorobutan-2-yl | H | CH$_3$ | H | H | H | 1H-1,2,4-triazol-1-yl |
| 1-89 | CH$_3$ | H | 1,1,1,2,3,3,4,4,4-nonafluorobutan-2-yl | H | ethyl | H | H | H | 1H-1,2,4-triazol-1-yl |
| 1-90 | bromo | H | 1,1,1,2,3,3,4,4,4-nonafluorobutan-2-yl | H | bromo | H | H | H | 1H-1,2,4-triazol-1-yl |
| 1-91 | iodo | H | 1,1,1,2,3,3,4,4,4-nonafluorobutan-2-yl | H | iodo | H | H | H | 1H-1,2,4-triazol-1-yl |
| 1-92 | CH$_3$ | H | undecafluorocyclohexyl | H | CH$_3$ | H | H | H | 1H-1,2,4-triazol-1-yl |
| 1-93 | CH$_3$ | H | undecafluorocyclohexyl | H | ethyl | H | H | H | 1H-1,2,4-triazol-1-yl |
| 1-94 | bromo | H | undecafluorocyclohexyl | H | bromo | H | H | H | 1H-1,2,4-triazol-1-yl |

TABLE 1-continued

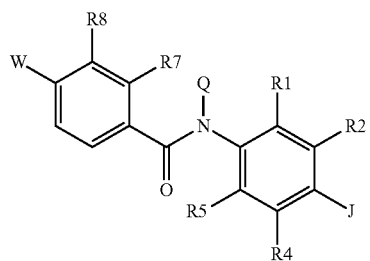

| Exa | R1 | R2 | J | R4 | R5 | Q | R7 | R8 | W |
|---|---|---|---|---|---|---|---|---|---|
| 1-95 | iodo | H | undecafluorocyclohexyl | H | iodo | H | H | H | 1H-1,2,4-triazol-1-yl |
| 1-96 | CH₃ | H | undecafluorocyclohexyl | H | ethyl | H | H | bromo | 1H-1,2,4-triazol-1-yl |
| 1-97 | bromo | H | trifluoromethoxy | H | bromo | H | H | H | 1H-1,2,4-triazol-1-yl |
| 1-98 | bromo | H | trifluoromethylsulfanyl | H | bromo | H | H | H | 1H-1,2,4-triazol-1-yl |
| 1-99 | CH₃ | H | (pentafluoroethyl)sulfanyl | H | ethyl | H | H | H | 1H-1,2,4-triazol-1-yl |
| 1-100 | CH₃ | H | (pentafluoroethyl)sulfanyl | H | ethyl | H | H | amino | 1H-1,2,4-triazol-1-yl |
| 1-101 | CH₃ | H | (pentafluoroethyl)sulfanyl | H | ethyl | H | H | nitro | 1H-1,2,4-triazol-1-yl |
| 1-102 | CH₃ | H | (pentafluoroethyl)sulfanyl | H | ethyl | H | H | propanoylamino | 1H-1,2,4-triazol-1-yl |
| 1-103 | CH₃ | H | (pentafluoroethyl)sulfanyl | H | ethyl | H | H | [(2-fluorophenyl))-carbonyl]amino | 1H-1,2,4-triazol-1-yl |
| 1-104 | CH₃ | H | (pentafluoroethyl)sulfanyl | H | ethyl | H | H | (methoxycarbonyl)-amino | 1H-1,2,4-triazol-1-yl |
| 1-105 | bromo | H | (pentafluoroethyl)sulfanyl | H | bromo | H | H | H | 1H-1,2,4-triazol-1-yl |
| 1-106 | bromo | H | (heptafluoropropyl)-sulfanyl | H | bromo | H | H | H | 1H-1,2,4-triazol-1-yl |
| 1-107 | bromo | H | (nonafluorobutyl)sulfanyl | H | bromo | H | H | H | 1H-1,2,4-triazol-1-yl |
| 1-108 | | | | | unused number | | | | |
| 1-109 | | | | | unused number | | | | |
| 1-110 | | | | | unused number | | | | |
| 1-111 | | | | | unused number | | | | |
| 1-112 | | | | | unused number | | | | |
| 1-113 | | | | | unused number | | | | |
| 1-114 | | | | | unused number | | | | |
| 1-115 | | | | | unused number | | | | |
| 1-116 | | | | | unused number | | | | |
| 1-117 | | | | | unused number | | | | |
| 1-118 | CH₃ | H | 1,1,1,2,3,3,4,4,4-nonafluorobutan-2-yl | H | CH₃ | H | H | cyano | 1H-1,2,4-triazol-1-yl |
| 1-119 | CH₃ | H | 1,1,1,2,3,3,4,4,4-nonafluorobutan-2-yl | H | ethyl | H | H | cyano | 1H-1,2,4-triazol-1-yl |
| 1-120 | CH₃ | H | 1-bromo-1,1,2,3,3,3-hexafluoropropan-2-yl | H | CH₃ | H | H | H | 1H-1,2,4-triazol-1-yl |
| 1-121 | CH₃ | H | 1-bromo-1,1,2,3,3,3-hexafluoropropan-2-yl | H | ethyl | H | H | H | 1H-1,2,4-triazol-1-yl |
| 1-122 | bromo | H | 1-bromo-1,1,2,3,3,3-hexafluoropropan-2-yl | H | bromo | H | H | H | 1H-1,2,4-triazol-1-yl |
| 1-123 | bromo | H | 1-bromo-1,1,2,3,3,3-hexafluoropropan-2-yl | H | difluoro-methoxy | H | H | H | 1H-1,2,4-triazol-1-yl |
| 1-124 | CH₃ | H | 1-bromo-1,1,2,3,3,3-hexafluoropropan-2-yl | H | CH₃ | H | H | cyano | 1H-1,2,4-triazol-1-yl |
| 1-125 | CH₃ | H | 1-bromo-1,1,2,3,3,3-hexafluoropropan-2-yl | H | ethyl | H | H | cyano | 1H-1,2,4-triazol-1-yl |
| 1-126 | bromo | H | 1,1,1,2,3,3,3-heptafluoropropan-2-yl | H | difluoro-methoxy | H | H | H | 1H-1,2,4-triazol-1-yl |
| 1-127 | bromo | H | 1,1,1,2,3,3,4,4,4-nonafluorobutan-2-yl | H | difluoro-methoxy | H | H | H | 1H-1,2,4-triazol-1-yl |
| 1-128 | bromo | H | 1,1,1,2,3,3,3-heptafluoropropan-2-yl | H | difluoro-methoxy | H | H | H | 1H-1,2,4-triazol-1-yl |
| 1-129 | CH | H | 1,1,1,2,3,3,3-heptafluoropropan-2-yl | H | difluoro-methoxy | H | H | H | 1H-1,2,4-triazol-1-yl |
| 1-130 | CH | H | 1,1,1,2,3,3,4,4,4-nonafluorobutan-2-yl | H | difluoro-methoxy | H | H | H | 1H-1,2,4-triazol-1yl |
| 1-131 | CH₃ | H | 1-bromo-1,1,2,3,3,3-hexafluoropropan-2-yl | H | difluoro-methoxy | H | H | H | 1H-1,2,4-triazol-1-yl |
| 1-132 | chloro | H | 1,1,1,2,3,3,3-heptafluoropropan-2-yl | H | difluoro-methoxy | H | H | H | 1H-1,2,4-triazol-1-yl |
| 1-133 | chloro | H | 1,1,1,2,3,3,4,4,4-nonafluorobutan-2-yl | H | difluoro-methoxy | H | H | H | 1H-1,2,4-triazol- -yl |
| 1-134 | chloro | H | 1-bromo-1,1,2,3,3,3-hexafluoropropan-2-yl | H | difluoro-methoxy | H | H | H | 1H-1,2,4-triazol-1-yl |

TABLE 2

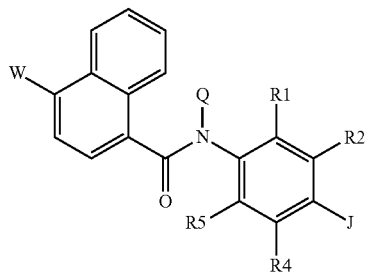

| Exa | R1 | R2 | J | R4 | R5 | Q | W |
|---|---|---|---|---|---|---|---|
| 2-1 | CH₃ | H | 1,1,1,2,3,3,3-heptafluoropropan-2-yl | H | CH₃ | H | 1H-1,2,4-triazol-1-yl |
| 2-2 | CH₃ | H | 1,1,1,2,3,3,3-heptafluoropropan-2-yl | H | ethyl | H | 1H-1,2,4-triazol-1-yl |
| 2-3 | bromo | H | 1,1,1,2,3,3,3-heptafluoropropan-2-yl | H | bromo | H | 1H-1,2,4-triazol-1-yl |
| 2-4 | CH₃ | H | 1,1,1,3,3,3-hexafluoro-2-(1H-1,2,4-triazol-1-yl)propan-2-yl | H | ethyl | H | 1H-1,2,4-triazol-1-yl |
| 2-5 | CH₃ | H | 1,1,1,2,3,3,4,4,4-nonafluorobutan-2-yl | H | CH₃ | H | 1H-1,2,4-triazol-1-yl |
| 2-6 | CH₃ | H | 1,1,1,2,3,3,4,4,4-nonafluorobutan-2-yl | H | ethyl | H | 1H-1,2,4-triazol-1-yl |
| 2-7 | bromo | H | 1,1,1,2,3,3,4,4,4-nonafluorobutan-2-yl | H | bromo | H | 1H-1,2,4-triazol-1-yl |
| 2-8 | iodo | H | 1,1,1,2,3,3,4,4,4-nonafluorobutan-2-yl | H | iodo | H | 1H-1,2,4-triazol-1-yl |
| 2-9 | CH₃ | H | undecafluorocyclohexyl | H | CH₃ | H | 1H-1,2,4-triazol-1-yl |
| 2-10 | CH₃ | H | undecafluorocyclohexyl | H | ethyl | H | 1H-1,2,4-triazol-1-yl |
| 2-11 | bromo | H | undecafluorocyclohexyl | H | bromo | H | 1H-1,2,4-triazol-1-yl |
| 2-12 | iodo | H | undecafluorocyclohexyl | H | iodo | H | 1H-1,2,4-triazol-1-yl |
| 2-13 | CH₃ | H | 1-bromo-1,1,2,3,3,3-hexafluoropropan-2-yl | H | CH₃ | H | 1H-1,2,4-triazol-1-yl |
| 2-14 | CH₃ | H | 1-bromo-1,1,2,3,3,3-hexafluoropropan-2-yl | H | ethyl | H | 1H-1,2,4-triazol-1-yl |
| 2-15 | bromo | H | 1-bromo-1,1,2,3,3,3-hexafluoropropan-2-yl | H | bromo | H | 1H-1,2,4-triazol-1-yl |
| 2-16 | bromo | H | 1-bromo-1,1,2,3,3,3-hexafluoropropan-2-yl | H | difluoromethoxy | H | 1H-1,2,4-triazol-1-yl |
| 2-17 | bromo | H | 1,1,1,2,3,3,3-heptafluoropropan-2-yl | H | difluoromethoxy | H | 1H-1,2,4-triazol-1-yl |
| 2-18 | bromo | H | 1,1,1,2,3,3,4,4,4-nonafluorobutan-2-yl | H | difluoromethoxy | H | 1H-1,2,4-triazol-1-yl |
| 2-19 | CH₃ | H | 1,1,1,2,3,3,3-heptafluoropropan-2-yl | H | difluoromethoxy | H | 1H-1,2,4-triazol-1-yl |
| 2-20 | CH₃ | H | 1,1,1,2,3,3,4,4,4-nonafluorobutan-2-yl | H | difluoromethoxy | H | 1H-1,2,4-triazol-1-yl |
| 2-21 | CH₃ | H | 1-bromo-1,1,2,3,3,3-hexafluoropropan-2-yl | H | difluoromethoxy | H | 1H-1,2,4-triazol-1-yl |
| 2-22 | chloro | H | 1,1,1,2,3,3,3-heptafluoropropan-2-yl | H | difluoromethoxy | H | 1H-1,2,4-triazol-1-yl |
| 2-23 | chloro | H | 1,1,1,2,3,3,4,4,4-nonafluorobutan-2-yl | H | difluoromethoxy | H | 1H-1,2,4-triazol-1-yl |
| 2-24 | chloro | H | 1-bromo-1,1,2,3,3,3-hexafluoropropan-2-yl | H | difluoromethoxy | H | 1H-1,2,4-triazol-1-yl |

TABLE 3

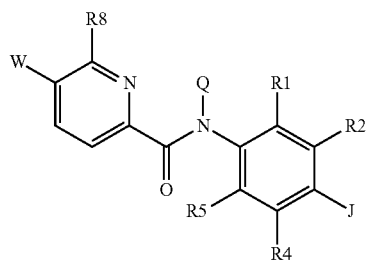

| Exa | R1 | R2 | J | R4 | R5 | Q | R8 | W |
|---|---|---|---|---|---|---|---|---|
| 3-1 | CH₃ | H | 1,1,1,2,3,3,3-heptafluoropropan-2-yl | H | CH₃ | H | H | 1H-1,2,4-triazol-1-yl |
| 3-2 | CH₃ | H | 1,1,1,2,3,3,3-heptafluoropropan-2-yl | H | ethyl | H | H | 1H-1,2,4-triazol-1-yl |
| 3-3 | bromo | H | 1,1,1,2,3,3,3-heptafluoropropan-2-yl | H | bromo | H | H | 1H-1,2,4-triazol-1-yl |
| 3-4 | CH₃ | H | 1,1,1,2,3,3,4,4,4-nonafluorobutan-2-yl | H | CH₃ | H | H | 1H-1,2,4-triazol-1-yl |
| 3-5 | CH₃ | H | 1,1,1,2,3,3,4,4,4-nonafluorobutan-2-yl | H | ethyl | H | H | 1H-1,2,4-triazol-1-yl |
| 3-6 | bromo | H | 1,1,1,2,3,3,4,4,4-nonafluorobutan-2-yl | H | bromo | H | H | 1H-1,2,4-triazol-1-yl |
| 3-7 | iodo | H | 1,1,1,2,3,3,4,4,4-nonafluorobutan-2-yl | H | iodo | H | H | 1H-1,2,4-triazol-1-yl |
| 3-8 | CH₃ | H | undecafluorocyclohexyl | H | CH₃ | H | H | 1H-1,2,4-triazol-1-yl |
| 3-9 | CH₃ | H | undecafluorocyclohexyl | H | ethyl | H | H | 1H-1,2,4-triazol-1-yl |
| 3-10 | bromo | H | undecafluorocyclohexyl | H | bromo | H | H | 1H-1,2,4-triazol-1-yl |
| 3-11 | iodo | H | undecafluorocyclohexyl | H | iodo | H | H | 1H-1,2,4-triazol-1-yl |
| 3-12 | CH₃ | H | 1-bromo-1,1,2,3,3,3-hexafluoropropan-2-yl | H | CH₃ | H | H | 1H-1,2,4-triazol-1-yl |
| 3-13 | CH₃ | H | 1-bromo-1,1,2,3,3,3-hexafluoropropan-2-yl | H | ethyl | H | H | 1H-1,2,4-triazol-1-yl |
| 3-14 | bromo | H | 1-bromo-1,1,2,3,3,3-hexafluoropropan-2-yl | H | bromo | H | H | 1H-1,2,4-triazol-1-yl |
| 3-15 | bromo | H | 1-bromo-1,1,2,3,3,3-hexafluoropropan-2-yl | H | difluoromethoxy | H | H | 1H-1,2,4-triazol-1-yl |
| 3-16 | bromo | H | 1,1,1,2,3,3,3-heptafluoropropan-2-yl | H | difluoromethoxy | H | H | 1H-1,2,4-triazol-1-yl |

TABLE 3-continued

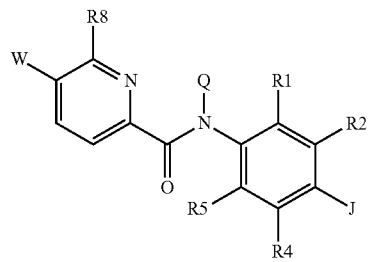

| Exa | R1 | R2 | J | R4 | R5 | Q | R8 | W |
|---|---|---|---|---|---|---|---|---|
| 3-17 | bromo | H | 1,1,1,2,3,3,4,4,4-nonafluorobutan-2-yl | H | difluoromethoxy | H | H | 1H-1,2,4-triazol-1-yl |
| 3-18 | CH₃ | H | 1,1,1,2,3,3,3-heptafluoropropan-2-yl | H | difluoromethoxy | H | H | 1H-1,2,4-triazol-1-yl |
| 3-19 | CH₃ | H | 1,1,1,2,3,3,4,4,4-nonafluorobutan-2-yl | H | difluoromethoxy | H | H | 1H-1,2,4-triazol-1-yl |
| 3-20 | CH₃ | H | 1-bromo-1,1,2,3,3,3-hexafluoropropan-2-yl | H | difluoromethoxy | H | H | 1H-1,2,4-triazol-1-yl |
| 3-21 | chloro | H | 1,1,1,2,3,3,3-heptafluoropropan-2-yl | H | difluoromethoxy | H | H | 1H-1,2,4-triazol-1-yl |
| 3-22 | chloro | H | 1,1,1,2,3,3,4,4,4-nonafluorobutan-2-yl | H | difluoromethoxy | H | H | 1H-1,2,4-triazol-1-yl |
| 3-23 | chloro | H | 1-bromo-1,1,2,3,3,3-hexafluoropropan-2-yl | H | difluoromethoxy | H | H | 1H-1,2,4-triazol-1-yl |

TABLE 4

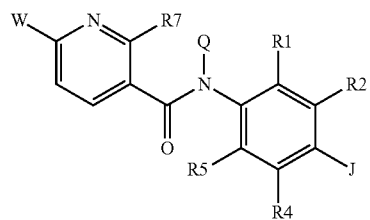

| Exa | R1 | R2 | J | R4 | R5 | Q | R7 | W |
|---|---|---|---|---|---|---|---|---|
| 4-1 | CH₃ | H | 1,1,1,2,3,3,3-heptafluoropropan-2-yl | H | CH₃ | H | H | 1H-1,2,4-triazol-1-yl |
| 4-2 | CH₃ | H | 1,1,1,2,3,3,3-heptafluoropropan-2-yl | H | ethyl | H | H | 1H-1,2,4-triazol-1-yl |
| 4-3 | bromo | H | 1,1,1,2,3,3,3-heptafluoropropan-2-yl | H | bromo | H | H | 1H-1,2,4-triazol-1-yl |
| 4-4 | CH₃ | H | 1,1,1,2,3,3,4,4,4-nonafluorobutan-2-yl | H | CH₃ | H | H | 1H-1,2,4-triazol-1-yl |
| 4-5 | CH₃ | H | 1,1,1,2,3,3,4,4,4-nonafluorobutan-2-yl | H | ethyl | H | H | 1H-1,2,4-triazol-1-yl |
| 4-6 | bromo | H | 1,1,1,2,3,3,4,4,4-nonafluorobutan-2-yl | H | bromo | H | H | 1H-1,2,4-triazol-1-yl |
| 4-7 | iodo | H | 1,1,1,2,3,3,4,4,4-nonafluorobutan-2-yl | H | iodo | H | H | 1H-1,2,4-triazol-1-yl |
| 4-8 | CH₃ | H | undecafluorocyclohexyl | H | CH₃ | H | H | 1H-1,2,4-triazol-1-yl |
| 4-9 | CH₃ | H | undecafluorocyclohexyl | H | ethyl | H | H | 1H-1,2,4-triazol-1-yl |
| 4-10 | bromo | H | undecafluorocyclohexyl | H | bromo | H | H | 1H-1,2,4-triazol-1-yl |
| 4-11 | iodo | H | undecafluorocyclohexyl | H | iodo | H | H | 1H-1,2,4-triazol-1-yl |
| 4-12 | CH₃ | H | 1-bromo-1,1,2,3,3,3-hexafluoropropan-2-yl | H | CH₃ | H | H | 1H-1,2,4-triazol-1-yl |
| 4-13 | CH₃ | H | 1-bromo-1,1,2,3,3,3-hexafluoropropan-2-yl | H | ethyl | H | H | 1H-1,2,4-triazol-1-yl |
| 4-14 | bromo | H | 1-bromo-1,1,2,3,3,3-hexafluoropropan-2-yl | H | bromo | H | H | 1H-1,2,4-triazol-1-yl |
| 4-15 | bromo | H | 1-bromo-1,1,2,3,3,3-hexafluoropropan-2-yl | H | difluoromethoxy | H | H | 1H-1,2,4-triazol-1-yl |
| 4-16 | bromo | H | 1,1,1,2,3,3,3-heptafluoropropan-2-yl | H | difluoromethoxy | H | H | 1H-1,2,4-triazol-1-yl |
| 4-17 | bromo | H | 1,1,1,2,3,3,4,4,4-nonafluorobutan-2-yl | H | difluoromethoxy | H | H | 1H-1,2,4-triazol-1-yl |
| 4-18 | CH₃ | H | 1,1,1,2,3,3,3-heptafluoropropan-2-yl | H | difluoromethoxy | H | H | 1H-1,2,4-triazol-1-yl |
| 4-19 | CH₃ | H | 1,1,1,2,3,3,4,4,4-nonafluorobutan-2-yl | H | difluoromethoxy | H | H | 1H-1,2,4-triazol-1-yl |
| 4-20 | CH₃ | H | 1-bromo-1,1,2,3,3,3-hexafluoropropan-2-yl | H | difluoromethoxy | H | H | 1H-1,2,4-triazol-1-yl |
| 4-21 | chloro | H | 1,1,1,2,3,3,3-heptafluoropropan-2-yl | H | difluoromethoxy | H | H | 1H-1,2,4-triazol-1-yl |
| 4-22 | chloro | H | 1,1,1,2,3,3,4,4,4-nonafluorobutan-2-yl | H | difluoromethoxy | H | H | 1H-1,2,4-triazol-1-yl |
| 4-23 | chloro | H | 1-bromo-1,1,2,3,3,3-hexafluoropropan-2-yl | H | difluoromethoxy | H | H | 1H-1,2,4-triazol-1-yl |

TABLE 5

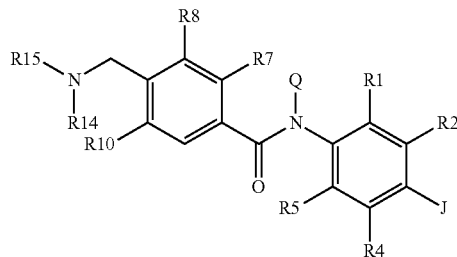

| Exa | R1 | R2 | J | R4 | R5 | Q | R7 | R8 | R10 | R14 | R15 |
|---|---|---|---|---|---|---|---|---|---|---|---|
| 5-1 | CH₃ | H | 1,1,1,2,3,3,3-heptafluoropropan-2-yl | H | CH₃ | H | H | H | H | H | H |
| 5-2 | CH₃ | H | 1,1,1,2,3,3,3-heptafluoropropan-2-yl | H | CH₃ | H | H | H | H | H | acetyl |
| 5-3 | CH₃ | H | 1,1,1,2,3,3,3-heptafluoropropan-2-yl | H | CH₃ | H | H | H | H | H | propanoyl |
| 5-4 | CH₃ | H | 1,1,1,2,3,3,3-heptafluoropropan-2-yl | H | CH₃ | H | H | H | H | H | 2-methylpropanoyl |
| 5-5 | CH₃ | H | 1,1,1,2,3,3,3-heptafluoropropan-2-yl | H | CH₃ | H | H | H | H | H | chloroacetyl |
| 5-6 | CH₃ | H | 1,1,1,2,3,3,3-heptafluoropropan-2-yl | H | CH₃ | H | H | H | H | H | difluoroacetyl |
| 5-7 | CH₃ | H | 1,1,1,2,3,3,3-heptafluoropropan-2-yl | H | CH₃ | H | H | H | H | H | 3,3,3-trifluoro-propanoyl |
| 5-8 | CH₃ | H | 1,1,1,2,3,3,3-heptafluoropropan-2-yl | H | CH₃ | H | H | H | H | H | cyclopropylacetyl |
| 5-9 | CH₃ | H | 1,1,1,2,3,3,3-heptafluoropropan-2-yl | H | CH₃ | H | H | H | H | H | cyclobutylcarbonyl |
| 5-10 | CH₃ | H | 1,1,1,2,3,3,3-heptafluoropropan-2-yl | H | CH₃ | H | H | H | H | H | cyclopentylcarbonyl |
| 5-11 | CH₃ | H | 1,1,1,2,3,3,3-heptafluoropropan-2-yl | H | CH₃ | H | H | H | H | H | cyclohexylcarbonyl |
| 5-12 | CH₃ | H | 1,1,1,2,3,3,3-heptafluoropropan-2-yl | H | CH₃ | H | H | H | H | H | (2E)-but-2-enoyl |
| 5-13 | CH₃ | H | 1,1,1,2,3,3,3-heptafluoropropan-2-yl | H | CH₃ | H | H | H | H | H | (2E)-2-methylbut-2-enoyl |
| 5-14 | CH₃ | H | 1,1,1,2,3,3,3-heptafluoropropan-2-yl | H | CH₃ | H | H | H | H | H | methoxyacetyl |
| 5-15 | CH₃ | H | 1,1,1,2,3,3,3-heptafluoropropan-2-yl | H | CH₃ | H | H | H | H | H | 3-methoxy-propanoyl |
| 5-16 | CH₃ | H | 1,1,1,2,3,3,3-heptafluoropropan-2-yl | H | CH₃ | H | H | H | H | H | 3-methoxybutanoyl |
| 5-17 | CH₃ | H | 1,1,1,2,3,3,3-heptafluoropropan-2-yl | H | CH₃ | H | H | H | H | H | 1H-1,2,4-triazol-1-ylacetyl |
| 5-18 | CH₃ | H | 1,1,1,2,3,3,3-heptafluoropropan-2-yl | H | CH₃ | H | H | H | H | H | (4-fluorophenyl)-acetyl |
| 5-19 | CH₃ | H | 1,1,1,2,3,3,3-heptafluoropropan-2-yl | H | CH₃ | H | H | H | H | H | (2-fluoropyridin-3-yl)carbonyl |
| 5-20 | CH₃ | H | 1,1,1,2,3,3,3-heptafluoropropan-2-yl | H | CH₃ | H | fluoro | H | H | H | H |
| 5-21 | CH₃ | H | 1,1,1,2,3,3,3-heptafluoropropan-2-yl | H | CH₃ | H | fluoro | H | H | H | acetyl |
| 5-22 | CH₃ | H | 1,1,1,2,3,3,3-heptafluoropropan-2-yl | H | CH₃ | H | fluoro | H | H | H | propanoyl |
| 5-23 | CH₃ | H | 1,1,1,2,3,3,3-heptafluoropropan-2-yl | H | CH₃ | H | fluoro | H | H | H | cyclopropylcarbonyl |
| 5-24 | CH₃ | H | 1,1,1,2,3,3,3-heptafluoropropan-2-yl | H | CH₃ | H | fluoro | H | H | H | cyclopropylacetyl |
| 5-25 | CH₃ | H | 1,1,1,2,3,3,3-heptafluoropropan-2-yl | H | CH₃ | H | fluoro | H | H | H | 3,3,3-trifluoro-propanoyl |
| 5-26 | CH₃ | H | 1,1,1,2,3,3,3-heptafluoropropan-2-yl | H | CH₃ | H | fluoro | H | H | H | tert-butoxy carbonyl |
| 5-27 | CH₃ | H | 1,1,1,2,3,3,3-heptafluoropropan-2-yl | H | ethyl | H | H | H | H | H | H |
| 5-28 | CH₃ | H | 1,1,1,2,3,3,3-heptafluoropropan-2-yl | H | ethyl | H | H | H | H | H | acetyl |
| 5-29 | CH₃ | H | 1,1,1,2,3,3,3-heptafluoropropan-2-yl | H | ethyl | H | H | H | H | H | propanoyl |
| 5-30 | CH₃ | H | 1,1,1,2,3,3,3-heptafluoropropan-2-yl | H | ethyl | H | H | H | H | H | cyclopropylcarbonyl |
| 5-31 | CH₃ | H | 1,1,1,2,3,3,3-heptafluoropropan-2-yl | H | ethyl | H | H | H | H | H | cyclopropylacetyl |
| 5-32 | CH₃ | H | 1,1,1,2,3,3,3-heptafluoropropan-2-yl | H | ethyl | H | H | H | H | H | 3,3,3-trifluoro-propanoyl |

TABLE 5-continued

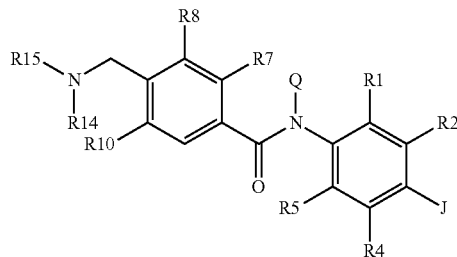

| Exa | R1 | R2 | J | R4 | R5 | Q | R7 | R8 | R10 | R14 | R15 |
|---|---|---|---|---|---|---|---|---|---|---|---|
| 5-33 | CH₃ | H | 1,1,1,2,3,3,3-heptafluoropropan-2-yl | H | ethyl | H | H | H | H | H | (methylsulfanyl)acetyl |
| 5-34 | CH₃ | H | 1,1,1,2,3,3,3-heptafluoropropan-2-yl | H | ethyl | H | H | H | H | H | (2-fluorophenyl)carbonyl |
| 5-35 | CH₃ | H | 1,1,1,2,3,3,3-heptafluoropropan-2-yl | H | ethyl | H | H | H | H | H | (3-fluorophenyl)carbonyl |
| 5-36 | CH₃ | H | 1,1,1,2,3,3,3-heptafluoropropan-2-yl | H | ethyl | H | H | H | H | H | (4-fluorophenyl)carbonyl |
| 5-37 | CH₃ | H | 1,1,1,2,3,3,3-heptafluoropropan-2-yl | H | ethyl | H | H | H | H | H | (2-chlorophenyl)carbonyl |
| 5-38 | CH₃ | H | 1,1,1,2,3,3,3-heptafluoropropan-2-yl | H | ethyl | H | H | H | H | H | (3-chlorophenyl)carbonyl |
| 5-39 | CH₃ | H | 1,1,1,2,3,3,3-heptafluoropropan-2-yl | H | ethyl | H | H | H | H | H | (4-chlorophenyl)carbonyl |
| 5-40 | CH₃ | H | 1,1,1,2,3,3,3-heptafluoropropan-2-yl | H | ethyl | H | H | H | H | H | (2-fluoropyridin-3-yl)carbonyl |
| 5-41 | CH₃ | H | 1,1,1,2,3,3,3-heptafluoropropan-2-yl | H | ethyl | H | H | H | H | H | (2-chloropyridin-3-yl)carbonyl |
| 5-42 | CH₃ | H | 1,1,1,2,3,3,3-heptafluoropropan-2-yl | H | ethyl | H | H | H | H | H | (2,2,2-trichloroethoxy)carbonyl |
| 5-43 | CH₃ | H | 1,1,1,2,3,3,3-heptafluoropropan-2-yl | H | ethyl | H | fluoro | H | H | H | H |
| 5-44 | CH₃ | H | 1,1,1,2,3,3,3-heptafluoropropan-2-yl | H | ethyl | H | fluoro | H | H | H | acetyl |
| 5-45 | CH₃ | H | 1,1,1,2,3,3,3-heptafluoropropan-2-yl | H | ethyl | H | fluoro | H | H | H | propanoyl |
| 5-46 | CH₃ | H | 1,1,1,2,3,3,3-heptafluoropropan-2-yl | H | ethyl | H | fluoro | H | H | H | cyclopropylacetyl |
| 5-47 | CH₃ | H | 1,1,1,2,3,3,3-heptafluoropropan-2-yl | H | ethyl | H | fluoro | H | H | H | 3,3,3-trifluoropropanoyl |
| 5-48 | CH₃ | H | 1,1,1,2,3,3,3-heptafluoropropan-2-yl | H | ethyl | H | fluoro | H | H | H | (2-fluoropyridin-3-yl)carbonyl |
| 5-49 | CH₃ | H | 1,1,1,2,3,3,3-heptafluoropropan-2-yl | H | ethyl | H | fluoro | H | H | H | tert-butoxycarbonyl |
| 5-50 | CH₃ | H | 1,1,1,2,3,3,3-heptafluoropropan-2-yl | H | ethyl | H | fluoro | fluoro | H | H | H |
| 5-51 | CH₃ | H | 1,1,1,2,3,3,3-heptafluoropropan-2-yl | H | ethyl | H | fluoro | fluoro | H | H | acetyl |
| 5-52 | CH₃ | H | 1,1,1,2,3,3,3-heptafluoropropan-2-yl | H | ethyl | H | fluoro | fluoro | H | H | propanoyl |
| 5-53 | CH₃ | H | 1,1,1,2,3,3,3-heptafluoropropan-2-yl | H | ethyl | H | fluoro | fluoro | H | H | cyclopropylcarbonyl |
| 5-54 | CH₃ | H | 1,1,1,2,3,3,3-heptafluoropropan-2-yl | H | ethyl | H | fluoro | fluoro | H | H | cyclopropylacetyl |
| 5-55 | CH₃ | H | 1,1,1,2,3,3,3-heptafluoropropan-2-yl | H | ethyl | H | fluoro | fluoro | H | H | 3,3,3-trifluoropropanoyl |
| 5-56 | CH₃ | H | 1,1,1,2,3,3,3-heptafluoropropan-2-yl | H | ethyl | H | fluoro | fluoro | H | H | tert-butoxycarbonyl |
| 5-57 | CH₃ | H | 1,1,1,2,3,3,3-heptafluoropropan-2-yl | H | ethyl | H | fluoro | H | fluoro | H | H |
| 5-58 | CH₃ | H | 1,1,1,2,3,3,3-heptafluoropropan-2-yl | H | ethyl | H | fluoro | H | fluoro | H | acetyl |
| 5-59 | CH₃ | H | 1,1,1,2,3,3,3-heptafluoropropan-2-yl | H | ethyl | H | fluoro | H | fluoro | H | propanoyl |
| 5-60 | CH₃ | H | 1,1,1,2,3,3,3-heptafluoropropan-2-yl | H | ethyl | H | fluoro | H | fluoro | H | cyclopropylcarbonyl |
| 5-61 | CH₃ | H | 1,1,1,2,3,3,3-heptafluoropropan-2-yl | H | ethyl | H | fluoro | H | fluoro | H | cyclopropylacetyl |
| 5-62 | CH₃ | H | 1,1,1,2,3,3,3-heptafluoropropan-2-yl | H | ethyl | H | fluoro | H | fluoro | H | 3,3,3-trifluoropropanoyl |
| 5-63 | CH₃ | H | 1,1,1,2,3,3,3-heptafluoropropan-2-yl | H | ethyl | H | fluoro | H | fluoro | H | tert-butoxycarbonyl |
| 5-64 | CH₃ | H | 1,1,1,2,3,3,3-heptafluoropropan-2-yl | H | ethyl | H | chloro | H | H | H | H |

TABLE 5-continued

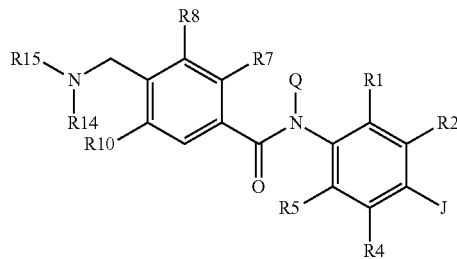

| Exa | R1 | R2 | J | R4 | R5 | Q | R7 | R8 | R10 | R14 | R15 |
|---|---|---|---|---|---|---|---|---|---|---|---|
| 5-65 | CH$_3$ | H | 1,1,1,2,3,3,3-heptafluoropropan-2-yl | H | ethyl | H | chloro | H | H | H | acetyl |
| 5-66 | CH$_3$ | H | 1,1,1,2,3,3,3-heptafluoropropan-2-yl | H | ethyl | H | chloro | H | H | H | propanoyl |
| 5-67 | CH$_3$ | H | 1,1,1,2,3,3,3-heptafluoropropan-2-yl | H | ethyl | H | chloro | H | H | H | cyclopropylacetyl |
| 5-68 | CH$_3$ | H | 1,1,1,2,3,3,3-heptafluoropropan-2-yl | H | ethyl | H | chloro | H | H | H | 3,3,3-trifluoro-propanoyl |
| 5-69 | CH$_3$ | H | 1,1,1,2,3,3,3-heptafluoropropan-2-yl | H | ethyl | H | chloro | H | H | H | tert-butoxycarbonyl |
| 5-70 | CH$_3$ | H | 1,1,1,2,3,3,3-heptafluoropropan-2-yl | H | ethyl | H | H | fluoro | H | H | H |
| 5-71 | CH$_3$ | H | 1,1,1,2,3,3,3-heptafluoropropan-2-yl | H | ethyl | H | H | fluoro | H | H | acetyl |
| 5-72 | CH$_3$ | H | 1,1,1,2,3,3,3-heptafluoropropan-2-yl | H | ethyl | H | H | fluoro | H | H | propanoyl |
| 5-73 | CH$_3$ | H | 1,1,1,2,3,3,3-heptafluoropropan-2-yl | H | ethyl | H | H | fluoro | H | H | cyclopropylcarbonyl |
| 5-74 | CH$_3$ | H | 1,1,1,2,3,3,3-heptafluoropropan-2-yl | H | ethyl | H | H | fluoro | H | H | cyclopropylacetyl |
| 5-75 | CH$_3$ | H | 1,1,1,2,3,3,3-heptafluoropropan-2-yl | H | ethyl | H | H | fluoro | H | H | 3,3,3-trifluoro-propanoyl |
| 5-76 | CH$_3$ | H | 1,1,1,2,3,3,3-heptafluoropropan-2-yl | H | ethyl | H | H | chloro | H | H | H |
| 5-77 | CH$_3$ | H | 1,1,1,2,3,3,3-heptafluoropropan-2-yl | H | ethyl | H | H | chloro | H | H | acetyl |
| 5-78 | CH$_3$ | H | 1,1,1,2,3,3,3-heptafluoropropan-2-yl | H | ethyl | H | H | chloro | H | H | propanoyl |
| 5-79 | CH$_3$ | H | 1,1,1,2,3,3,3-heptafluoropropan-2-yl | H | ethyl | H | H | chloro | H | H | cyclopropylcarbonyl |
| 5-80 | CH$_3$ | H | 1,1,1,2,3,3,3-heptafluoropropan-2-yl | H | ethyl | H | H | chloro | H | H | cyclopropylacetyl |
| 5-81 | CH$_3$ | H | 1,1,1,2,3,3,3-heptafluoropropan-2-yl | H | ethyl | H | H | chloro | H | H | 3,3,3-trifluoro-propanoyl |
| 5-82 | CH$_3$ | H | 1,1,1,2,3,3,3-heptafluoropropan-2-yl | H | ethyl | H | H | chloro | H | H | (2-fluoropyridin-3-yl)carbonyl |
| 5-83 | CH$_3$ | H | 1,1,1,2,3,3,3-heptafluoropropan-2-yl | H | ethyl | H | H | bromo | H | H | H |
| 5-84 | CH$_3$ | H | 1,1,1,2,3,3,3-heptafluoropropan-2-yl | H | ethyl | H | H | bromo | H | H | formyl |
| 5-85 | CH$_3$ | H | 1,1,1,2,3,3,3-heptafluoropropan-2-yl | H | ethyl | H | H | bromo | H | H | acetyl |
| 5-86 | CH$_3$ | H | 1,1,1,2,3,3,3-heptafluoropropan-2-yl | H | ethyl | H | H | bromo | H | H | propanoyl |
| 5-87 | CH$_3$ | H | 1,1,1,2,3,3,3-heptafluoropropan-2-yl | H | ethyl | H | H | bromo | H | H | cyclopropylcarbonyl |
| 5-88 | CH$_3$ | H | 1,1,1,2,3,3,3-heptafluoropropan-2-yl | H | ethyl | H | H | bromo | H | H | cyclopropylacetyl |
| 5-89 | CH$_3$ | H | 1,1,1,2,3,3,3-heptafluoropropan-2-yl | H | ethyl | H | H | bromo | H | H | 3,3,3-trifluoro-propanoyl |
| 5-90 | CH$_3$ | H | 1,1,1,2,3,3,3-heptafluoropropan-2-yl | H | ethyl | H | H | bromo | H | H | (2E)-but-2-enoyl |
| 5-91 | CH$_3$ | H | 1,1,1,2,3,3,3-heptafluoropropan-2-yl | H | ethyl | H | H | bromo | H | H | methoxyacetyl |
| 5-92 | CH$_3$ | H | 1,1,1,2,3,3,3-heptafluoropropan-2-yl | H | ethyl | H | H | bromo | H | H | (4-fluorophenyl)-carbonyl |
| 5-93 | CH$_3$ | H | 1,1,1,2,3,3,3-heptafluoropropan-2-yl | H | ethyl | H | H | bromo | H | H | (2-fluoropyridin-3-yl)carbonyl |
| 5-94 | CH$_3$ | H | 1,1,1,2,3,3,3-heptafluoropropan-2-yl | H | ethyl | H | H | bromo | H | H | (2-chloropyridin-3-yl)carbonyl |
| 5-95 | CH$_3$ | H | 1,1,1,2,3,3,3-heptafluoropropan-2-yl | H | ethyl | H | H | bromo | H | H | ethylcarbamoyl |
| 5-96 | CH$_3$ | H | 1,1,1,2,3,3,3-heptafluoropropan-2-yl | H | ethyl | H | H | bromo | H | H | methylsulfonyl |

TABLE 5-continued

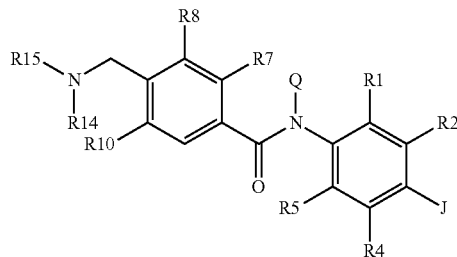

| Exa | R1 | R2 | J | R4 | R5 | Q | R7 | R8 | R10 | R14 | R15 |
|---|---|---|---|---|---|---|---|---|---|---|---|
| 5-97 | CH$_3$ | H | 1,1,1,2,3,3,3-heptafluoropropan-2-yl | H | ethyl | H | H | bromo | H | H | dimethylsulfamoyl |
| 5-98 | CH$_3$ | H | 1,1,1,2,3,3,3-heptafluoropropan-2-yl | H | ethyl | H | H | CH$_3$ | H | H | H |
| 5-99 | CH$_3$ | H | 1,1,1,2,3,3,3-heptafluoropropan-2-yl | H | ethyl | H | H | CH$_3$ | H | H | acetyl |
| 5-100 | CH$_3$ | H | 1,1,1,2,3,3,3-heptafluoropropan-2-yl | H | ethyl | H | H | CH$_3$ | H | H | propanoyl |
| 5-101 | CH$_3$ | H | 1,1,1,2,3,3,3-heptafluoropropan-2-yl | H | ethyl | H | H | CH$_3$ | H | H | cyclopropylacetyl |
| 5-102 | CH$_3$ | H | 1,1,1,2,3,3,3-heptafluoropropan-2-yl | H | ethyl | H | H | CH$_3$ | H | H | 3,3,3-trifluoro-propanoyl |
| 5-103 | CH$_3$ | H | 1,1,1,2,3,3,3-heptafluoropropan-2-yl | H | ethyl | H | H | CH$_3$ | H | H | (2-fluoropyridin-3-yl)carbonyl |
| 5-104 | CH$_3$ | H | 1,1,1,2,3,3,3-heptafluoropropan-2-yl | H | ethyl | H | H | CH$_3$ | H | H | tert-butoxycarbonyl |
| 5-105 | CH$_3$ | H | 1,1,1,2,3,3,3-heptafluoropropan-2-yl | H | ethyl | H | H | trifluoro-methyl | H | H | H |
| 5-106 | CH$_3$ | H | 1,1,1,2,3,3,3-heptafluoropropan-2-yl | H | ethyl | H | H | trifluoro-methyl | H | H | acetyl |
| 5-107 | CH$_3$ | H | 1,1,1,2,3,3,3-heptafluoropropan-2-yl | H | ethyl | H | H | trifluoro-methyl | H | H | propanoyl |
| 5-108 | CH$_3$ | H | 1,1,1,2,3,3,3-heptafluoropropan-2-yl | H | ethyl | H | H | trifluoro-methyl | H | H | cyclopropylcarbonyl |
| 5-109 | CH$_3$ | H | 1,1,1,2,3,3,3-heptafluoropropan-2-yl | H | ethyl | H | H | trifluoro-methyl | H | H | cyclopropylacetyl |
| 5-110 | CH$_3$ | H | 1,1,1,2,3,3,3-heptafluoropropan-2-yl | H | ethyl | H | H | trifluoro-methyl | H | H | 3,3,3-trifluoro-propanoyl |
| 5-111 | CH$_3$ | H | 1,1,1,2,3,3,3-heptafluoropropan-2-yl | H | ethyl | H | H | trifluoro-methyl | H | H | (4-fluorophenyl)-carbonyl |
| 5-112 | CH$_3$ | H | 1,1,1,2,3,3,3-heptafluoropropan-2-yl | H | ethyl | H | H | trifluoro-methyl | H | H | (2-fluoropyridin-3-yl)carbonyl |
| 5-113 | CH$_3$ | H | 1,1,1,2,3,3,3-heptafluoropropan-2-yl | H | ethyl | H | H | nitoro | H | H | H |
| 5-114 | CH$_3$ | H | 1,1,1,2,3,3,3-heptafluoropropan-2-yl | H | ethyl | H | H | nitoro | H | H | acetyl |
| 5-115 | CH$_3$ | H | 1,1,1,2,3,3,3-heptafluoropropan-2-yl | H | ethyl | H | H | nitoro | H | H | propanoyl |
| 5-116 | CH$_3$ | H | 1,1,1,2,3,3,3-heptafluoropropan-2-yl | H | ethyl | H | H | nitoro | H | H | cyclopropylcarbonyl |
| 5-117 | CH$_3$ | H | 1,1,1,2,3,3,3-heptafluoropropan-2-yl | H | ethyl | H | H | nitoro | H | H | cyclopropylacetyl |
| 5-118 | CH$_3$ | H | 1,1,1,2,3,3,3-heptafluoropropan-2-yl | H | ethyl | H | H | nitoro | H | H | 3,3,3-trifluoropropanoyl |
| 5-119 | bromo | H | 1,1,1,2,3,3,3-heptafluoropropan-2-yl | H | bromo | H | H | H | H | H | H |
| 5-120 | bromo | H | 1,1,1,2,3,3,3-heptafluoropropan-2-yl | H | bromo | H | H | H | H | H | acetyl |
| 5-121 | bromo | H | 1,1,1,2,3,3,3-heptafluoropropan-2-yl | H | bromo | H | H | H | H | H | propanoyl |
| 5-122 | bromo | H | 1,1,1,2,3,3,3-heptafluoropropan-2-yl | H | bromo | H | H | H | H | H | cyclopropylcarbonyl |
| 5-123 | bromo | H | 1,1,1,2,3,3,3-heptafluoropropan-2-yl | H | bromo | H | H | H | H | H | cyclopropylacetyl |
| 5-124 | bromo | H | 1,1,1,2,3,3,3-heptafluoropropan-2-yl | H | bromo | H | H | H | H | H | 3,3,3-trifluoro-propanoyl |
| 5-125 | CH$_3$ | H | 1,1,1,2,3,3,4,4,4-nonafluorobutan-2-yl | H | CH$_3$ | H | H | H | H | H | H |
| 5-126 | CH$_3$ | H | 1,1,1,2,3,3,4,4,4-nonafluorobutan-2-yl | H | CH$_3$ | H | H | H | H | H | acetyl |
| 5-127 | CH$_3$ | H | 1,1,1,2,3,3,4,4,4-nonafluorobutan-2-yl | H | CH$_3$ | H | H | H | H | H | propanoyl |
| 5-128 | CH$_3$ | H | 1,1,1,2,3,3,4,4,4-nonafluorobutan-2-yl | H | CH$_3$ | H | H | H | H | H | cyclopropylcarbonyl |

TABLE 5-continued

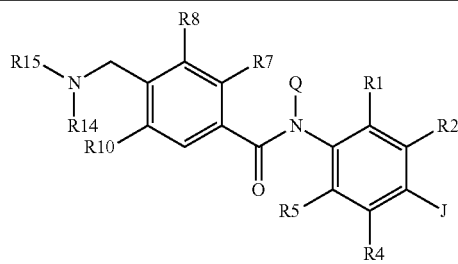

| Exa | R1 | R2 | J | R4 | R5 | Q | R7 | R8 | R10 | R14 | R15 |
|---|---|---|---|---|---|---|---|---|---|---|---|
| 5-129 | $CH_3$ | H | 1,1,1,2,3,3,4,4,4-nonafluorobutan-2-yl | H | $CH_3$ | H | H | H | H | H | cyclopropylacetyl |
| 5-130 | $CH_3$ | H | 1,1,1,2,3,3,4,4,4-nonafluorobutan-2-yl | H | $CH_3$ | H | H | H | H | H | 3,3,3-trifluoropropanoyl |
| 5-131 | $CH_3$ | H | 1,1,1,2,3,3,4,4,4-nonafluorobutan-2-yl | H | $CH_3$ | H | H | chloro | H | H | H |
| 5-132 | $CH_3$ | H | 1,1,1,2,3,3,4,4,4-nonafluorobutan-2-yl | H | $CH_3$ | H | H | chloro | H | H | acetyl |
| 5-133 | $CH_3$ | H | 1,1,1,2,3,3,4,4,4-nonafluorobutan-2-yl | H | $CH_3$ | H | H | chloro | H | H | propanoyl |
| 5-134 | $CH_3$ | H | 1,1,1,2,3,3,4,4,4-nonafluorobutan-2-yl | H | $CH_3$ | H | H | chloro | H | H | cyclopropylcarbonyl |
| 5-135 | $CH_3$ | H | 1,1,1,2,3,3,4,4,4-nonafluorobutan-2-yl | H | $CH_3$ | H | H | chloro | H | H | cyclopropylacetyl |
| 5-136 | $CH_3$ | H | 1,1,1,2,3,3,4,4,4-nonafluorobutan-2-yl | H | $CH_3$ | H | H | chloro | H | H | 3,3,3-trifluoropropanoyl |
| 5-137 | $CH_3$ | H | 1,1,1,2,3,3,4,4,4-nonafluorobutan-2-yl | H | ethyl | H | H | H | H | H | H |
| 5-138 | $CH_3$ | H | 1,1,1,2,3,3,4,4,4-nonafluorobutan-2-yl | H | ethyl | H | H | H | H | H | acetyl |
| 5-139 | $CH_3$ | H | 1,1,1,2,3,3,4,4,4-nonafluorobutan-2-yl | H | ethyl | H | H | H | H | H | propanoyl |
| 5-140 | $CH_3$ | H | 1,1,1,2,3,3,4,4,4-nonafluorobutan-2-yl | H | ethyl | H | H | H | H | H | cyclopropylcarbonyl |
| 5-141 | $CH_3$ | H | 1,1,1,2,3,3,4,4,4-nonafluorobutan-2-yl | H | ethyl | H | H | H | H | H | cyclopropylacetyl |
| 5-142 | $CH_3$ | H | 1,1,1,2,3,3,4,4,4-nonafluorobutan-2-yl | H | ethyl | H | H | H | H | H | 3,3,3-trifluoropropanoyl |
| 5-143 | $CH_3$ | H | 1,1,1,2,3,3,4,4,4-nonafluorobutan-2-yl | H | ethyl | H | H | fluoro | H | H | H |
| 5-144 | $CH_3$ | H | 1,1,1,2,3,3,4,4,4-nonafluorobutan-2-yl | H | ethyl | H | H | fluoro | H | H | acetyl |
| 5-145 | $CH_3$ | H | 1,1,1,2,3,3,4,4,4-nonafluorobutan-2-yl | H | ethyl | H | H | fluoro | H | H | propanoyl |
| 5-146 | $CH_3$ | H | 1,1,1,2,3,3,4,4,4-nonafluorobutan-2-yl | H | ethyl | H | H | fluoro | H | H | cyclopropylcarbonyl |
| 5-147 | $CH_3$ | H | 1,1,1,2,3,3,4,4,4-nonafluorobutan-2-yl | H | ethyl | H | H | fluoro | H | H | cyclopropylacetyl |
| 5-148 | $CH_3$ | H | 1,1,1,2,3,3,4,4,4-nonafluorobutan-2-yl | H | ethyl | H | H | fluoro | H | H | 3,3,3-trifluoropropanoyl |
| 5-149 | $CH_3$ | H | 1,1,1,2,3,3,4,4,4-nonafluorobutan-2-yl | H | ethyl | H | H | chloro | H | H | H |
| 5-150 | $CH_3$ | H | 1,1,1,2,3,3,4,4,4-nonafluorobutan-2-yl | H | ethyl | H | H | chloro | H | H | acetyl |
| 5-151 | $CH_3$ | H | 1,1,1,2,3,3,4,4,4-nonafluorobutan-2-yl | H | ethyl | H | H | chloro | H | H | propanoyl |
| 5-152 | $CH_3$ | H | 1,1,1,2,3,3,4,4,4-nonafluorobutan-2-yl | H | ethyl | H | H | chloro | H | H | cyclopropylcarbonyl |
| 5-153 | $CH_3$ | H | 1,1,1,2,3,3,4,4,4-nonafluorobutan-2-yl | H | ethyl | H | H | chloro | H | H | cyclopropylacetyl |
| 5-154 | $CH_3$ | H | 1,1,1,2,3,3,4,4,4-nonafluorobutan-2-yl | H | ethyl | H | H | chloro | H | H | 3,3,3-trifluoropropanoyl |
| 5-155 | $CH_3$ | H | 1,1,1,2,3,3,4,4,4-nonafluorobutan-2-yl | H | ethyl | H | H | chloro | H | H | (2-fluoropyridin-3-yl)carbonyl |
| 5-156 | $CH_3$ | H | 1,1,1,2,3,3,4,4,4-nonafluorobutan-2-yl | H | ethyl | H | H | bromo | H | H | H |
| 5-157 | $CH_3$ | H | 1,1,1,2,3,3,4,4,4-nonafluorobutan-2-yl | H | ethyl | H | H | bromo | H | H | acetyl |
| 5-158 | $CH_3$ | H | 1,1,1,2,3,3,4,4,4-nonafluorobutan-2-yl | H | ethyl | H | H | bromo | H | H | propanoyl |
| 5-159 | $CH_3$ | H | 1,1,1,2,3,3,4,4,4-nonafluorobutan-2-yl | H | ethyl | H | H | bromo | H | H | cyclopropylcarbonyl |
| 5-160 | $CH_3$ | H | 1,1,1,2,3,3,4,4,4-nonafluorobutan-2-yl | H | ethyl | H | H | bromo | H | H | cyclopropylacetyl |

TABLE 5-continued

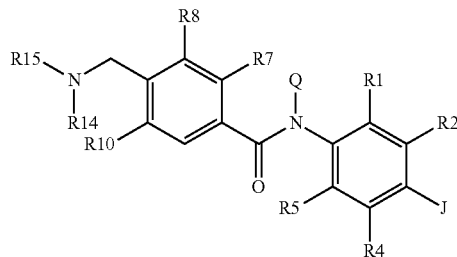

| Exa | R1 | R2 | J | R4 | R5 | Q | R7 | R8 | R10 | R14 | R15 |
|---|---|---|---|---|---|---|---|---|---|---|---|
| 5-161 | CH₃ | H | 1,1,1,2,3,3,4,4,4-nonafluorobutan-2-yl | H | ethyl | H | H | bromo | H | H | 3,3,3-trifluoropropanoyl |
| 5-162 | bromo | H | 1,1,1,2,3,3,4,4,4-nonafluorobutan-2-yl | H | bromo | H | H | H | H | H | H |
| 5-163 | bromo | H | 1,1,1,2,3,3,4,4,4-nonafluorobutan-2-yl | H | bromo | H | H | H | H | H | acetyl |
| 5-164 | bromo | H | 1,1,1,2,3,3,4,4,4-nonafluorobutan-2-yl | H | bromo | H | H | H | H | H | propanoyl |
| 5-165 | bromo | H | 1,1,1,2,3,3,4,4,4-nonafluorobutan-2-yl | H | bromo | H | H | H | H | H | cyclopropylcarbonyl |
| 5-166 | bromo | H | 1,1,1,2,3,3,4,4,4-nonafluorobutan-2-yl | H | bromo | H | H | H | H | H | cyclopropylacetyl |
| 5-167 | bromo | H | 1,1,1,2,3,3,4,4,4-nonafluorobutan-2-yl | H | bromo | H | H | H | H | H | 3,3,3-trifluoropropanoyl |
| 5-168 | CH₃ | H | undecafluorocyclohexyl | H | ethyl | H | H | chloro | H | H | H |
| 5-169 | CH₃ | H | undecafluorocyclohexyl | H | ethyl | H | H | chloro | H | H | acetyl |
| 5-170 | CH₃ | H | undecafluorocyclohexyl | H | ethyl | H | H | chloro | H | H | propanoyl |
| 5-171 | CH₃ | H | undecafluorocyclohexyl | H | ethyl | H | H | chloro | H | H | cyclopropylcarbonyl |
| 5-172 | CH₃ | H | undecafluorocyclohexyl | H | ethyl | H | H | chloro | H | H | cyclopropylacetyl |
| 5-173 | CH₃ | H | undecafluorocyclohexyl | H | ethyl | H | H | chloro | H | H | 3,3,3-trifluoropropanoyl |
| 5-174 | CH₃ | H | 1,1,1,2,3,3,4,4,4-nonafluorobutan-2-yl | H | ethyl | H | H | fluoro | H | H | (2-fluoropyridin-3-yl)carbonyl |
| 5-175 | CH₃ | H | 1,1,1,2,3,3,4,4,4-nonafluorobutan-2-yl | H | ethyl | H | H | bromo | H | H | (2-chloropyridin-3-yl)carbonyl |
| 5-176 | CH₃ | H | 1,1,1,2,3,3,3-heptafluoropropan-2-yl | H | ethyl | H | H | bromo | H | H | (methylsulfanyl)acetyl |
| 5-177 | CH₃ | H | 1,1,1,2,3,3,3-heptafluoropropan-2-yl | H | ethyl | H | H | bromo | H | H | (methylsulfinyl)acetyl |
| 5-178 | CH₃ | H | 1,1,1,2,3,3,3-heptafluoropropan-2-yl | H | ethyl | H | H | bromo | H | H | (methylsulfonyl)acetyl |
| 5-179 | CH₃ | H | 1,1,1,2,3,3,3-nonafluorobutan-2-yl | H | ethyl | H | H | bromo | H | H | (methylsulfanyl)acetyl |
| 5-180 | CH₃ | H | 1,1,1,2,3,3,3-nonafluorobutan-2-yl | H | ethyl | H | H | bromo | H | H | (methylsulfinyl)acetyl |
| 5-181 | CH₃ | H | 1,1,1,2,3,3,3-nonafluorobutan-2-yl | H | ethyl | H | H | bromo | H | H | (methylsulfonyl)acetyl |
| 5-182 | CH₃ | H | 1,1,1,2,3,3,3-heptafluoropropan-2-yl | H | CH₃ | H | fluoro | H | H | H | (2-chloropyridin-3-yl)carbonyl |
| 5-183 | CH₃ | H | 1,1,1,2,3,3,3-heptafluoropropan-2-yl | H | ethyl | H | fluoro | H | fluoro | H | (2-chloropyridin-3-yl)carbonyl |
| 5-184 | CH₃ | H | 1,1,1,2,3,3,3-heptafluoropropan-2-yl | H | ethyl | H | H | H | H | CH₃ | H |
| 5-185 | CH₃ | H | 1,1,1,2,3,3,3-heptafluoropropan-2-yl | H | ethyl | H | H | H | H | CH₃ | acetyl |
| 5-186 | CH₃ | H | 1,1,1,2,3,3,3-heptafluoropropan-2-yl | H | ethyl | H | H | H | H | CH₃ | propanoyl |
| 5-187 | CH₃ | H | 1,1,1,2,3,3,3-heptafluoropropan-2-yl | H | ethyl | H | H | H | H | CH₃ | cyclopropylacetyl |
| 5-188 | CH₃ | H | 1,1,1,2,3,3,3-heptafluoropropan-2-yl | H | ethyl | H | H | H | H | CH₃ | 3,3,3-trifluoropropanoyl |
| 5-189 | CH₃ | H | 1,1,1,2,3,3,3-heptafluoropropan-2-yl | H | ethyl | H | H | H | H | CH₃ | (2-chloropyridin-3-yl)carbonyl |
| 5-190 | CH3 | H | 1,1,1,2,3,3,3-heptafluoropropan-2-yl | H | ethyl | H | H | iodo | H | H | acetyl |
| 5-191 | CH3 | H | 1,1,1,2,3,3,3-heptafluoropropan-2-yl | H | ethyl | H | H | iodo | H | H | propanoyl |
| 5-192 | CH3 | H | 1,1,1,2,3,3,3-heptafluoropropan-2-yl | H | ethyl | H | H | iodo | H | H | 3,3,3-trifluoropropanoyl |
| 5-193 | CH3 | H | 1,1,1,2,3,3,4,4,4-nonafluorobutan-2-yl | H | ethyl | H | H | iodo | H | H | H |
| 5-194 | CH3 | H | 1,1,1,2,3,3,4,4,4-nonafluorobutan-2-yl | H | ethyl | H | H | iodo | H | H | acetyl |
| 5-195 | CH3 | H | 1,1,1,2,3,3,4,4,4-nonafluorobutan-2-yl | H | ethyl | H | H | iodo | H | H | propanoyl |

TABLE 5-continued

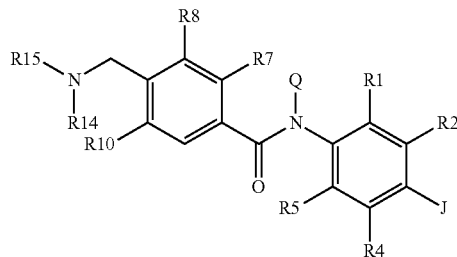

| Exa | R1 | R2 | J | R4 | R5 | Q | R7 | R8 | R10 | R14 | R15 |
|---|---|---|---|---|---|---|---|---|---|---|---|
| 5-196 | CH3 | H | 1,1,1,2,3,3,4,4,4-nonafluorobutan-2-yl | H | ethyl | H | H | iodo | H | H | cyclopropylcarbonyl |
| 5-197 | CH3 | H | 1,1,1,2,3,3,4,4,4-nonafluorobutan-2-yl | H | ethyl | H | H | iodo | H | H | cyclopropylacetyl |
| 5-198 | CH3 | H | 1,1,1,2,3,3,4,4,4-nonafluorobutan-2-yl | H | ethyl | H | H | iodo | H | H | 3,3,3-trifluoro-propanoyl |
| 5-199 | CH$_3$ | H | 1,1,1,2,3,3,4,4,4-heptafluoropropan-2-yl | H | ethyl | H | fluoro | fluoro | H | H | (2-chloropyridin-3-yl)carbonyl |
| 5-200 | CH$_3$ | H | 1,1,1,2,3,3,4,4,4-nonafluorobutan-2-yl | H | ethyl | H | fluoro | fluoro | H | H | H |
| 5-201 | CH$_3$ | H | 1,1,1,2,3,3,4,4,4-nonafluorobutan-2-yl | H | ethyl | H | fluoro | fluoro | H | H | acetyl |
| 5-202 | CH$_3$ | H | 1,1,1,2,3,3,4,4,4-nonafluorobutan-2-yl | H | ethyl | H | fluoro | fluoro | H | H | propanoyl |
| 5-203 | CH$_3$ | H | 1,1,1,2,3,3,4,4,4-nonafluorobutan-2-yl | H | ethyl | H | fluoro | fluoro | H | H | cyclopropylcarbonyl |
| 5-204 | CH$_3$ | H | 1,1,1,2,3,3,4,4,4-nonafluorobutan-2-yl | H | ethyl | H | fluoro | fluoro | H | H | cyclopropylacetyl |
| 5-205 | CH$_3$ | H | 1,1,1,2,3,3,4,4,4-nonafluorobutan-2-yl | H | ethyl | H | fluoro | fluoro | H | H | 3,3,3-trifluoro-propanoyl |
| 5-206 | CH$_3$ | H | 1,1,1,2,3,3,4,4,4-nonafluorobutan-2-yl | H | ethyl | H | fluoro | fluoro | H | H | (2-chloropyridin-3-yl)carbonyl |
| 5-207 | | | | | unused number | | | | | | |
| 5-208 | | | | | unused number | | | | | | |
| 5-209 | | | | | unused number | | | | | | |
| 5-210 | CH3 | H | 1,1,1,2,3,3,4,4,4-nonofluorobutan-2-yl | H | CH3 | H | H | bromo | H | H | H |
| 5-211 | CH$_3$ | H | 1,1,1,2,3,3,4,4,4-nonofluorobutan-2-yl | H | CH$_3$ | H | H | bromo | H | H | acetyl |
| 5-212 | CH$_3$ | H | 1,1,1,2,3,3,4,4,4-nonofluorobutan-2-yl | H | CH$_3$ | H | H | bromo | H | H | propanoyl |
| 5-213 | CH$_3$ | H | 1,1,1,2,3,3,4,4,4-nonofluorobutan-2-yl | H | CH$_3$ | H | fluoro | fluoro | H | H | 3,3,3-trifluoro-propanoyl |
| 5-214 | CH$_3$ | H | 1-bromo-1,1,2,3,3,3-hexafluoropropan-2-yl | H | CH$_3$ | H | H | chloro | H | H | H |
| 5-215 | CH$_3$ | H | 1-bromo-1,1,2,3,3,3-hexafluoropropan-2-yl | H | CH$_3$ | H | H | chloro | H | H | acetyl |
| 5-216 | CH$_3$ | H | 1-bromo-1,1,2,3,3,3-hexafluoropropan-2-yl | H | CH$_3$ | H | H | chloro | H | H | propanoyl |
| 5-217 | CH$_3$ | H | 1-bromo-1,1,2,3,3,3-hexafluoropropan-2-yl | H | CH$_3$ | H | H | chloro | H | H | 3,3,3-trifluoro-propanoyl |
| 5-218 | CH$_3$ | H | 1-bromo-1,1,2,3,3,3-hexafluoropropan-2-yl | H | ethyl | H | H | chloro | H | H | H |
| 5-219 | CH$_3$ | H | 1-bromo-1,1,2,3,3,3-hexafluoropropan-2-yl | H | ethyl | H | H | chloro | H | H | acetyl |
| 5-220 | CH$_3$ | H | 1-bromo-1,1,2,3,3,3-hexafluoropropan-2-yl | H | ethyl | H | H | chloro | H | H | propanoyl |
| 5-221 | CH$_3$ | H | 1-bromo-1,1,2,3,3,3-hexafluoropropan-2-yl | H | ethyl | H | H | chloro | H | H | 3,3,3-trifluoro-propanoyl |
| 5-222 | chloro | H | 1,1,1,2,3,3,3-heptafluoropropan-2-yl | H | chloro | H | H | H | H | H | H |
| 5-223 | chloro | H | 1,1,1,2,3,3,3-heptafluoropropan-2-yl | H | chloro | H | H | H | H | H | acetyl |
| 5-224 | chloro | H | 1,1,1,2,3,3,3-heptafluoropropan-2-yl | H | chloro | H | H | H | H | H | propanoyl |
| 5-225 | chloro | H | 1,1,1,2,3,3,3-heptafluoropropan-2-yl | H | chloro | H | H | H | H | H | cyclopropyl-acetyl |
| 5-226 | chloro | H | 1,1,1,2,3,3,3-heptafluoropropan-2-yl | H | chloro | H | H | H | H | H | 3,3,3-trifluoro-propanoyl |
| 5-227 | chloro | H | 1,1,1,2,3,3,3-heptafluoropropan-2-yl | H | chloro | H | H | H | H | H | tert-butoxy-carbonyl |
| 5-228 | chloro | H | 1,1,1,2,3,3,3-heptafluoropropan-2-yl | H | chloro | H | H | chloro | H | H | H |
| 5-229 | chloro | H | 1,1,1,2,3,3,3-heptafluoropropan-2-yl | H | chloro | H | H | chloro | H | H | acetyl |

TABLE 5-continued

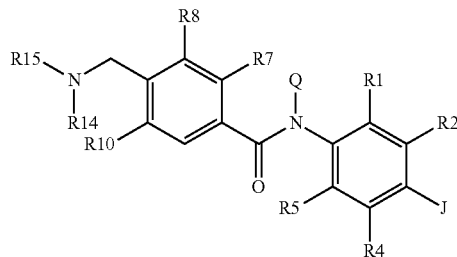

| Exa | R1 | R2 | J | R4 | R5 | Q | R7 | R8 | R10 | R14 | R15 |
|---|---|---|---|---|---|---|---|---|---|---|---|
| 5-230 | chloro | H | 1,1,1,2,3,3,3-heptafluoropropan-2-yl | H | chloro | H | H | chloro | H | H | propanoyl |
| 5-231 | chloro | H | 1,1,1,2,3,3,3-heptafluoropropan-2-yl | H | chloro | H | H | chloro | H | H | cyclopropyl-carbonyl |
| 5-232 | chloro | H | 1,1,1,2,3,3,3-heptafluoropropan-2-yl | H | chloro | H | H | chloro | H | H | 3,3,3-trifluoro-propanoyl |
| 5-233 | bromo | H | 1,1,1,2,3,3,3-heptafluoropropan-2-yl | H | bromo | H | H | chloro | H | H | H |
| 5-234 | bromo | H | 1,1,1,2,3,3,3-heptafluoropropan-2-yl | H | bromo | H | H | chloro | H | H | acetyl |
| 5-235 | bromo | H | 1,1,1,2,3,3,3-heptafluoropropan-2-yl | H | bromo | H | H | chloro | H | H | propanoyl |
| 5-236 | bromo | H | 1,1,1,2,3,3,3-heptafluoropropan-2-yl | H | bromo | H | H | chloro | H | H | 3,3,3-trifluoro-propanoyl |
| 5-237 | iodo | H | 1,1,1,2,3,3,3-heptafluoropropan-2-yl | H | iodo | H | H | chloro | H | H | H |
| 5-238 | iodo | H | 1,1,1,2,3,3,3-heptafluoropropan-2-yl | H | iodo | H | H | chloro | H | H | acetyl |
| 5-239 | iodo | H | 1,1,1,2,3,3,3-heptafluoropropan-2-yl | H | iodo | H | H | chloro | H | H | propanoyl |
| 5-240 | iodo | H | 1,1,1,2,3,3,3-heptafluoropropan-2-yl | H | iodo | H | H | chloro | H | H | 3,3,3-trifluoro-propanoyl |
| 5-241 | chloro | H | 1,1,1,2,3,3,4,4,4-nonafluorobutan-2-yl | H | chloro | H | H | chloro | H | H | H |
| 5-242 | chloro | H | 1,1,1,2,3,3,4,4,4-nonafluorobutan-2-yl | H | chloro | H | H | chloro | H | H | acetyl |
| 5-243 | chloro | H | 1,1,1,2,3,3,4,4,4-nonafluorobutan-2-yl | H | chloro | H | H | chloro | H | H | propanoyl |
| 5-244 | chloro | H | 1,1,1,2,3,3,4,4,4-nonafluorobutan-2-yl | H | chloro | H | H | chloro | H | H | 3,3,3-trifluoro-propanoyl |
| 5-245 | bromo | H | 1,1,1,2,3,3,4,4,4-nonafluorobutan-2-yl | H | bromo | H | H | chloro | H | H | H |
| 5-246 | bromo | H | 1,1,1,2,3,3,4,4,4-nonafluorobutan-2-yl | H | bromo | H | H | chloro | H | H | acetyl |
| 5-247 | bromo | H | 1,1,1,2,3,3,4,4,4-nonafluorobutan-2-yl | H | bromo | H | H | chloro | H | H | propanoyl |
| 5-248 | bromo | H | 1,1,1,2,3,3,4,4,4-nonafluorobutan-2-yl | H | bromo | H | H | chloro | H | H | 3,3,3-trifluoro-propanoyl |
| 5-249 | bromo | H | 1,1,1,2,3,3,4,4,4-nonafluorobutan-2-yl | H | difluoro-methoxy | H | H | chloro | H | H | H |
| 5-250 | bromo | H | 1,1,1,2,3,3,4,4,4-nonafluorobutan-2-yl | H | difluoro-methoxy | H | H | chloro | H | H | acetyl |
| 5-251 | bromo | H | 1,1,1,2,3,3,4,4,4-nonafluorobutan-2-yl | H | difluoro-methoxy | H | H | chloro | H | H | propanoyl |
| 5-252 | bromo | H | 1,1,1,2,3,3,4,4,4-nonafluorobutan-2-yl | H | difluoro-methoxy | H | H | chloro | H | H | 3,3,3-trifluoro-propanoyl |
| 5-253 | bromo | H | 1,1,1,2,3,3,4,4,4-nonafluorobutan-2-yl | H | trifluoro-methoxy | H | H | chloro | H | H | H |
| 5-254 | bromo | H | 1,1,1,2,3,3,4,4,4-nonafluorobutan-2-yl | H | trifluoro-methoxy | H | H | chloro | H | H | acetyl |
| 5-255 | bromo | H | 1,1,1,2,3,3,4,4,4-nonafluorobutan-2-yl | H | trifluoro-methoxy | H | H | chloro | H | H | propanoyl |
| 5-256 | bromo | H | 1,1,1,2,3,3,4,4,4-nonafluorobutan-2-yl | H | trifluoro-methoxy | H | H | chloro | H | H | 3,3,3-trifluoro-propanoyl |
| 5-257 | bromo | H | 1,1,1,2,3,3,4,4,4-nonafluorobutan-2-yl | H | (difluoromethyl)-sulfanyl | H | H | chloro | H | H | H |
| 5-258 | bromo | H | 1,1,1,2,3,3,4,4,4-nonafluorobutan-2-yl | H | (difluoromethyl)-sulfanyl | H | H | chloro | H | H | acetyl |
| 5-259 | bromo | H | 1,1,1,2,3,3,4,4,4-nonafluorobutan-2-yl | H | (difluoromethyl)-sulfanyl | H | H | chloro | H | H | propanoyl |
| 5-260 | bromo | H | 1,1,1,2,3,3,4,4,4-nonafluorobutan-2-yl | H | (difluoromethyl)-sulfanyl | H | H | chloro | H | H | 3,3,3-trifluoro-propanoyl |
| 5-261 | bromo | H | 1,1,1,2,3,3,4,4,4-nonafluorobutan-2-yl | H | (trifluoromethyl)-sulfanyl | H | H | chloro | H | H | H |

TABLE 5-continued

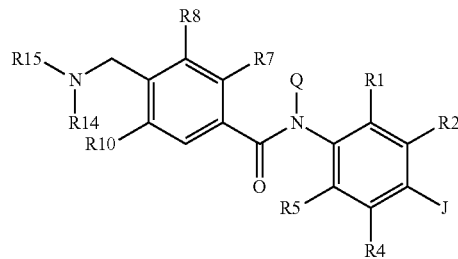

| Exa | R1 | R2 | J | R4 | R5 | Q | R7 | R8 | R10 | R14 | R15 |
|---|---|---|---|---|---|---|---|---|---|---|---|
| 5-262 | bromo | H | 1,1,1,2,3,3,4,4,4-nonafluorobutan-2-yl | H | (trifluoromethyl)-sulfanyl | H | H | chloro | H | H | acetyl |
| 5-263 | bromo | H | 1,1,1,2,3,3,4,4,4-nonafluorobutan-2-yl | H | (trifluoromethyl)-sulfanyl | H | H | chloro | H | H | propanoyl |
| 5-264 | bromo | H | 1,1,1,2,3,3,4,4,4-nonafluorobutan-2-yl | H | (trifluoromethyl)-sulfanyl | H | H | chloro | H | H | 3,3,3-trifluoro-propanoyl |
| 5-265 | iodo | H | 1,1,1,2,3,3,4,4,4-nonafluorobutan-2-yl | H | iodo | H | H | chloro | H | H | H |
| 5-266 | iodo | H | 1,1,1,2,3,3,4,4,4-nonafluorobutan-2-yl | H | iodo | H | H | chloro | H | H | acetyl |
| 5-267 | iodo | H | 1,1,1,2,3,3,4,4,4-nonafluorobutan-2-yl | H | iodo | H | H | chloro | H | H | propanoyl |
| 5-268 | iodo | H | 1,1,1,2,3,3,4,4,4-nonafluorobutan-2-yl | H | iodo | H | H | chloro | H | H | 3,3,3-trifluoro-propanoyl |
| 5-269 | chloro | H | 1-bromo-1,1,2,3,3,3-hexafluoropropan-2-yl | H | chloro | H | H | chloro | H | H | H |
| 5-270 | chloro | H | 1-bromo-1,1,2,3,3,3-hexafluoropropan-2-yl | H | chloro | H | H | chloro | H | H | acetyl |
| 5-271 | chloro | H | 1-bromo-1,1,2,3,3,3-hexafluoropropan-2-yl | H | chloro | H | H | chloro | H | H | propanoyl |
| 5-272 | chloro | H | 1-bromo-1,1,2,3,3,3-hexafluoropropan-2-yl | H | chloro | H | H | chloro | H | H | 3,3,3-trifluoro-propanoyl |
| 5-273 | bromo | H | 1-bromo-1,1,2,3,3,3-hexafluoropropan-2-yl | H | bromo | H | H | chloro | H | H | H |
| 5-274 | bromo | H | 1-bromo-1,1,2,3,3,3-hexafluoropropan-2-yl | H | bromo | H | H | chloro | H | H | acetyl |
| 5-275 | bromo | H | 1-bromo-1,1,2,3,3,3-hexafluoropropan-2-yl | H | bromo | H | H | chloro | H | H | propanoyl |
| 5-276 | bromo | H | 1-bromo-1,1,2,3,3,3-hexafluoropropan-2-yl | H | bromo | H | H | chloro | H | H | 3,3,3-trifluoro-propanoyl |
| 5-277 | iodo | H | 1-bromo-1,1,2,3,3,3-hexafluoropropan-2-yl | H | iodo | H | H | chloro | H | H | H |
| 5-278 | iodo | H | 1-bromo-1,1,2,3,3,3-hexafluoropropan-2-yl | H | iodo | H | H | chloro | H | H | acetyl |
| 5-279 | iodo | H | 1-bromo-1,1,2,3,3,3-hexafluoropropan-2-yl | H | iodo | H | H | chloro | H | H | propanoyl |
| 5-280 | iodo | H | 1-bromo-1,1,2,3,3,3-hexafluoropropan-2-yl | H | iodo | H | H | chloro | H | H | 3,3,3-trifluoro-propanoyl |
| 5-281 | bromo | H | pentafluoroethyl | H | difluoromethoxy | H | H | chloro | H | H | H |
| 5-282 | bromo | H | pentafluoroethyl | H | difluoromethoxy | H | H | chloro | H | H | acetyl |
| 5-283 | bromo | H | pentafluoroethyl | H | difluoromethoxy | H | H | chloro | H | H | propanoyl |
| 5-284 | bromo | H | pentafluoroethyl | H | difluoromethoxy | H | H | chloro | H | H | 3,3,3-trifluoro-propanoyl |
| 5-285 | bromo | H | 1,1,1,2,3,3,3-eptafluoropropan-2-yl | H | difluoromethoxy | H | H | chloro | H | H | H |
| 5-286 | bromo | H | 1,1,1,2,3,3,3-heptafluoropropan-2-yl | H | difluoromethoxy | H | H | chloro | H | H | acetyl |
| 5-287 | bromo | H | 1,1,1,2,3,3,3-heptafluoropropan-2-yl | H | difluoromethoxy | H | H | chloro | H | H | propanoyl |
| 5-288 | bromo | H | 1,1,1,2,3,3,3-heptafluoropropan-2-yl | H | difluoromethoxy | H | H | chloro | H | H | 3,3,3-trifluoro-propanoyl |
| 5-289 | bromo | H | 1-bromo-1,1,2,3,3,3-hexafluoropropan-2-yl | H | difluoromethoxy | H | H | chloro | H | H | H |
| 5-290 | bromo | H | 1-bromo-1,1,2,3,3,3-hexafluoropropan-2-yl | H | difluoromethoxy | H | H | chloro | H | H | acetyl |
| 5-291 | bromo | H | 1-bromo-1,1,2,3,3,3-hexafluoropropan-2-yl | H | difluoromethoxy | H | H | chloro | H | H | propanoyl |
| 5-292 | bromo | H | 1-bromo-1,1,2,3,3,3-hexafluoropropan-2-yl | H | difluoromethoxy | H | H | chloro | H | H | 3,3,3-trifluoro-propanoyl |
| 5-293 | CH3 | H | 1,1,1,2,3,3,3-heptafluoropropan-2-yl | H | difluoromethoxy | H | H | chloro | H | H | H |
| 5-294 | CH3 | H | 1,1,1,2,3,3,3-heptafluoropropan-2-yl | H | difluoromethoxy | H | H | chloro | H | H | acetyl |
| 5-295 | CH3 | H | 1,1,1,2,3,3,3-heptafluoropropan-2-yl | H | difluoromethoxy | H | H | chloro | H | H | propanoyl |

TABLE 5-continued

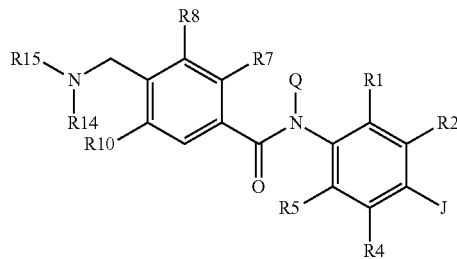

| Exa | R1 | R2 | J | R4 | R5 | Q | R7 | R8 | R10 | R14 | R15 |
|---|---|---|---|---|---|---|---|---|---|---|---|
| 5-296 | CH₃ | H | 1,1,1,2,3,3,3-heptafluoropropan-2-yl | H | difluoromethoxy | H | H | chloro | H | H | 3,3,3-trifluoro-propanoyl |
| 5-297 | CH₃ | H | 1,1,1,2,3,3,4,4,4-nonafluorobutan-2-yl | H | difluoromethoxy | H | H | chloro | H | H | H |
| 5-298 | CH₃ | H | 1,1,1,2,3,3,4,4,4-nonafluorobutan-2-yl | H | difluoromethoxy | H | H | chloro | H | H | acetyl |
| 5-299 | CH₃ | H | 1,1,1,2,3,3,4,4,4-nonafluorobutan-2-yl | H | difluoromethoxy | H | H | chloro | H | H | propanoyl |
| 5-300 | CH₃ | H | 1,1,1,2,3,3,4,4,4-nonafluorobutan-2-yl | H | difluoromethoxy | H | H | chloro | H | H | 3,3,3-trifluoro-propanoyl |
| 5-301 | CH₃ | H | 1-bromo-1,1,2,3,3,3-hexafluoropropan-2-yl | H | difluoromethoxy | H | H | chloro | H | H | H |
| 5-302 | CH₃ | H | 1-bromo-1,1,2,3,3,3-hexafluoropropan-2-yl | H | difluoromethoxy | H | H | chloro | H | H | acetyl |
| 5-303 | CH₃ | H | 1-bromo-1,1,2,3,3,3-hexafluoropropan-2-yl | H | difluoromethoxy | H | H | chloro | H | H | propanoyl |
| 5-304 | CH₃ | H | 1-bromo-1,1,2,3,3,3-hexafluoropropan-2-yl | H | difluoromethoxy | H | H | chloro | H | H | 3,3,3-trifluoro-propanoyl |
| 5-305 | chloro | H | 1,1,1,2,3,3,3-heptafluoropropan-2-yl | H | difluoromethoxy | H | H | chloro | H | H | H |
| 5-306 | chloro | H | 1,1,1,2,3,3,3-heptafluoropropan-2-yl | H | difluoromethoxy | H | H | chloro | H | H | acetyl |
| 5-307 | chloro | H | 1,1,1,2,3,3,3-heptafluoropropan-2-yl | H | difluoromethoxy | H | H | chloro | H | H | propanoyl |
| 5-308 | chloro | H | 1,1,1,2,3,3,3-heptafluoropropan-2-yl | H | difluoromethoxy | H | H | chloro | H | H | 3,3,3-trifluoro-propanoyl |
| 5-309 | chloro | H | 1,1,1,2,3,3,4,4,4-nonafluorobutan-2-yl | H | difluoromethoxy | H | H | chloro | H | H | H |
| 5-310 | chloro | H | 1,1,1,2,3,3,4,4,4-nonafluorobutan-2-yl | H | difluoromethoxy | H | H | chloro | H | H | acetyl |
| 5-311 | chloro | H | 1,1,1,2,3,3,4,4,4-nonafluorobutan-2-yl | H | difluoromethoxy | H | H | chloro | H | H | propanoyl |
| 5-312 | chloro | H | 1,1,1,2,3,3,4,4,4-nonafluorobutan-2-yl | H | difluoromethoxy | H | H | chloro | H | H | 3,3,3-trifluoro-propanoyl |
| 5-313 | chloro | H | 1-bromo-1,1,2,3,3,3-hexafluoropropan-2-yl | H | difluoromethoxy | H | H | chloro | H | H | H |
| 5-314 | chloro | H | 1-bromo-1,1,2,3,3,3-hexafluoropropan-2-yl | H | difluoromethoxy | H | H | chloro | H | H | acetyl |
| 5-315 | chloro | H | 1-bromo-1,1,2,3,3,3-hexafluoropropan-2-yl | H | difluoromethoxy | H | H | chloro | H | H | propanoyl |
| 5-316 | chloro | H | 1-bromo-1,1,2,3,3,3-hexafluoropropan-2-yl | H | difluoromethoxy | H | H | chloro | H | H | 3,3,3-trifluoro-propanoyl |
| 5-317 | chloro | H | 1,1,12,3,3,3-hepfluoropropan-2-yl | H | chloro | H | H | chloro | H | H | tert-butoxy carbonyl |
| 5-318 | CH₃ | H | 1-bromo-1,1,2,3,3,3-hexafluoropropan-2-yl | H | ethyl | H | H | chloro | H | H | Cyclopropyl carbonyl |
| 5-319 | CH₃ | H | 1-bromo-1,1,2,3,3,3-hexafluoropropan-2-yl | H | ethyl | H | H | chloro | H | H | cyclopropylacetyl |
| 5-320 | CH₃ | H | 1-bromo-1,1,2,3,3,3--fluoropropan-2-yl | H | ethyl | H | H | chloro | H | H | (methylsulfanyl)acetyl |
| 5-321 | chloro | H | 1,1,1,2,3,3,4,4,4-nonafluorobutan-2-yl | H | chloro | H | H | H | H | H | H |
| 5-322 | chloro | H | 1,1,1,2,3,3,4,4,4-nonafluorobutan-2-yl | H | chloro | H | H | H | H | H | acetyl |
| 5-323 | chloro | H | 1,1,1,2,3,3,4,4,4-nonafluorobutan-2-yl | H | chloro | H | H | H | H | H | propanoyl |
| 5-324 | chloro | H | 1,1,1,2,3,3,4,4,4-nonafluorobutan-2-yl | H | chloro | H | H | H | H | H | 3,3,3-trifluoro-propanoyl |
| 5-325 | chloro | H | 1,1,1,2,3,3,4,4,4-nonafluorobutan-2-yl | H | chloro | H | H | H | H | H | cyclopropylacetyl |
| 5-326 | chloro | H | 1,1,1,2,3,3,4,4,4-nonafluorobutan-2-yl | H | chloro | H | H | H | H | H | Cyclopropyl carbonyl |
| 5-327 | chloro | H | 1,1,1,2,3,3,4,4,4-nonafluorobutan-2-yl | H | chloro | H | H | H | H | H | (methylsulfanyl)acetyl |

TABLE 5-continued

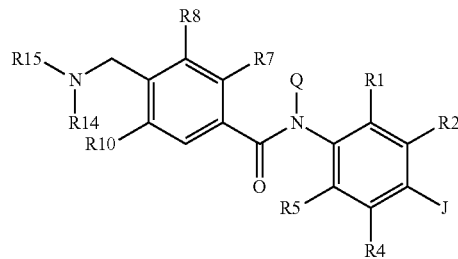

| Exa | R1 | R2 | J | R4 | R5 | Q | R7 | R8 | R10 | R14 | R15 |
|---|---|---|---|---|---|---|---|---|---|---|---|
| 5-328 | chloro | H | 1,1,1,2,3,3,4,4,4-nonafluorobutan-2-yl | H | chloro | H | H | H | H | H | tert-butoxy carbonyl |
| 5-329 | chloro | H | 1,1,1,2,3,3,4,4,4-nonafluorobutan-2-yl | H | chloro | H | H | chloro | H | H | tert-butoxy carbonyl |
| 5-330 | chloro | H | 1,1,1,2,3,3,4,4,4-nonafluorobutan-2-yl | H | chloro | H | H | chloro | H | H | cyclopropylacetyl |
| 5-331 | chloro | H | 1,1,1,2,3,3,4,4,4-nonafluorobutan-2-yl | H | chloro | H | H | chloro | H | H | (methylsulfanyl)acetyl |
| 5-332 | CH$_3$ | H | 1,1,1,2,3,3,3-heptafluoropropan-2-yl | H | chloro | H | H | H | H | H | H |
| 5-333 | CH$_3$ | H | 1,1,1,2,3,3,3-heptafluoropropan-2-yl | H | chloro | H | H | H | H | H | acetyl |
| 5-334 | CH$_3$ | H | 1,1,1,2,3,3,3-heptafluoropropan-2-yl | H | chloro | H | H | H | H | H | propanoyl |
| 5-335 | CH$_3$ | H | 1,1,1,2,3,3,3-heptafluoropropan-2-yl | H | chloro | H | H | H | H | H | 3,3,3-trifluoropropanoyl |
| 5-336 | CH$_3$ | H | 1,1,1,2,3,3,3-heptafluoropropan-2-yl | H | chloro | H | H | H | H | H | cyclopropylacetyl |
| 5-337 | CH$_3$ | H | 1,1,1,2,3,3,3-heptafluoropropan-2-yl | H | chloro | H | H | H | H | H | (methylsulfanyl)acetyl |
| 5-338 | CH$_3$ | H | 1,1,1,2,3,3,3-heptafluoropropan-2-yl | H | chloro | H | H | H | H | H | Cyclopropyl carbonyl |
| 5-339 | CH$_3$ | H | 1,1,1,2,3,3,3-heptafluoropropan-2-yl | H | chloro | H | H | H | H | H | tert-butoxy carbonyl |
| 5-340 | CH$_3$ | H | 1,1,1,2,3,3,3-heptafluoropropan-2-yl | H | difluoromethoxy | H | H | chloro | H | H | cyclopropylacetyl |
| 5-341 | CH$_3$ | H | 1,1,1,2,3,3,3-heptafluoropropan-2-yl | H | difluoromethoxy | H | H | chloro | H | H | Cyclopropyl carbonyl |
| 5-342 | CH$_3$ | H | 1,1,1,2,3,3,3-heptafluoropropan-2-yl | H | difluoromethoxy | H | H | chloro | H | H | tert-butoxy carbonyl |
| 5-343 | chloro | H | 1,1,1,2,3,3,3-heptafluoropropan-2-yl | H | chloro | H | H | CH$_3$ | H | H | H |
| 5-344 | chloro | H | 1,1,1,2,3,3,3-heptafluoropropan-2-yl | H | chloro | H | H | CH$_3$ | H | H | acetyl |
| 5-345 | chloro | H | 1,1,1,2,3,3,3-heptafluoropropan-2-yl | H | chloro | H | H | CH$_3$ | H | H | propanoyl |
| 5-346 | chloro | H | 1,1,1,2,3,3,3-heptafluoropropan-2-yl | H | chloro | H | H | CH$_3$ | H | H | 3,3,3-trifluoropropanoyl |
| 5-347 | chloro | H | 1,1,1,2,3,3,3-heptafluoropropan-2-yl | H | chloro | H | H | CH$_3$ | H | H | tert-butoxy carbonyl |
| 5-348 | chloro | H | 1,1,1,2,3,3,4,4,4-nonafluorobutan-2-yl | H | chloro | H | H | H | H | H | trifluoroacetyl |
| 5-349 | CH$_3$ | H | 1,1,1,2,3,3,3-heptafluoropropan-2-yl | H | ethyl | H | H | bromo | H | H | trifluoroacetyl |
| 5-350 | chloro | H | 1,1,1,2,3,3,3-heptafluoropropan-2-yl | H | (difluoromethyl)-sulfanyl | H | H | chloro | H | H | H |
| 5-351 | chloro | H | 1,1,1,2,3,3,3-heptafluoropropan-2-yl | H | (difluoromethyl)-sulfanyl | H | H | chloro | H | H | acetyl |
| 5-352 | chloro | H | 1,1,1,2,3,3,3-heptafluoropropan-2-yl | H | (difluoromethyl)-sulfanyl | H | H | chloro | H | H | propanoyl |
| 5-353 | chloro | H | 1,1,1,2,3,3,3-heptafluoropropan-2-yl | H | (difluoromethyl)-sulfanyl | H | H | chloro | H | H | 3,3,3-trifluoropropanoyl |
| 5-354 | chloro | H | 1,1,1,2,3,3,4,4,4-nonafluorobutan-2-yl | H | (difluoromethyl)-sulfanyl | H | H | chloro | H | H | H |
| 5-355 | chloro | H | 1,1,1,2,3,3,4,4,4-nonafluorobutan-2-yl | H | (difluoromethyl)-sulfanyl | H | H | chloro | H | H | acetyl |
| 5-356 | chloro | H | 1,1,1,2,3,3,4,4,4-nonafluorobutan-2-yl | H | (difluoromethyl)-sulfanyl | H | H | chloro | H | H | propanoyl |
| 5-357 | chloro | H | 1,1,1,2,3,3,4,4,4-nonafluorobutan-2-yl | H | (difluoromethyl)-sulfanyl | H | H | chloro | H | H | 3,3,3-trifluoropropanoyl |
| 5-358 | chloro | H | 1-bromo-1,1,2,3,3,3-hexafluoropropan-2-yl | H | (difluoromethyl)-sulfanyl | H | H | chloro | H | H | H |
| 5-359 | chloro | H | 1-bromo-1,1,2,3,3,3-hexafluoropropan-2-yl | H | (difluoromethyl)-sulfanyl | H | H | chloro | H | H | acetyl |

TABLE 5-continued

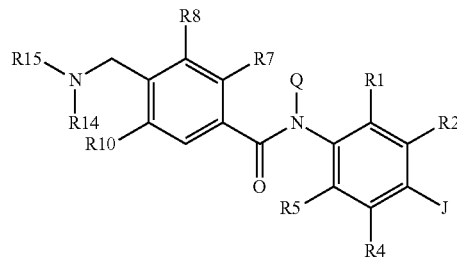

| Exa | R1 | R2 | J | R4 | R5 | Q | R7 | R8 | R10 | R14 | R15 |
|---|---|---|---|---|---|---|---|---|---|---|---|
| 5-360 | chloro | H | 1-bromo-1,1,2,3,3,3-hexafluoropropan-2-yl | H | (difluoromethyl)-sulfanyl | H | H | chloro | H | H | propanoyl |
| 5-361 | chloro | H | 1-bromo-1,1,2,3,3,3-hexafluoropropan-2-yl | H | (difluoromethyl)-sulfanyl | H | H | chloro | H | H | 3,3,3-trifluoro-propanoyl |
| 5-362 | bromo | H | 1,1,1,2,3,3,3-heptafluoropropan-2-yl | H | (difluoromethyl)-sulfanyl | H | H | chloro | H | H | H |
| 5-363 | bromo | H | 1,1,1,2,3,3,3-heptafluoropropan-2-yl | H | (difluoromethyl)-sulfanyl | H | H | chloro | H | H | acetyl |
| 5-364 | bromo | H | 1,1,1,2,3,3,3-heptafluoropropan-2-yl | H | (difluoromethyl)-sulfanyl | H | H | chloro | H | H | propanoyl |
| 5-365 | bromo | H | 1,1,1,2,3,3,3-heptafluoropropan-2-yl | H | (difluoromethyl)-sulfanyl | H | H | chloro | H | H | 3,3,3-trifluoro-propanoyl |
| 5-366 | bromo | H | 1-bromo-1,1,2,3,3,3-hexafluoropropan-2-yl | H | (difluoromethyl)-sulfanyl | H | H | chloro | H | H | H |
| 5-367 | bromo | H | 1-bromo-1,1,2,3,3,3-hexafluoropropan-2-yl | H | (difluoromethyl)-sulfanyl | H | H | chloro | H | H | acetyl |
| 5-368 | bromo | H | 1-bromo-1,1,2,3,3,3-hexafluoropropan-2-yl | H | (difluoromethyl)-sulfanyl | H | H | chloro | H | H | propanoyl |
| 5-369 | bromo | H | 1-bromo-1,1,2,3,3,3-hexafluoropropan-2-yl | H | (difluoromethyl)-sulfanyl | H | H | chloro | H | H | 3,3,3-trifluoro-propanoyl |
| 5-370 | chloro | H | 1,1,1,2,3,3,3-heptafluoropropan-2-yl | H | (trifluoromethyl)sulfanyl | H | H | chloro | H | H | H |
| 5-371 | chloro | H | 1,1,1,2,3,3,3-heptafluoropropan-2-yl | H | (trifluoromethyl)sulfanyl | H | H | chloro | H | H | acetyl |
| 5-372 | chloro | H | 1,1,1,2,3,3,3-heptafluoropropan-2-yl | H | (trifluoromethyl)sulfanyl | H | H | chloro | H | H | propanoyl |
| 5-373 | chloro | H | 1,1,1,2,3,3,3-heptafluoropropan-2-yl | H | (trifluoromethyl)sulfanyl | H | H | chloro | H | H | 3,3,3-trifluoro-propanoyl |
| 5-374 | chloro | H | 1,1,1,2,3,3,4,4,4-nonafluorobutan-2-yl | H | (trifluoromethyl)sulfanyl | H | H | chloro | H | H | H |
| 5-375 | chloro | H | 1,1,1,2,3,3,4,4,4-nonafluorobutan-2-yl | H | (trifluoromethyl)sulfanyl | H | H | chloro | H | H | acetyl |
| 5-376 | chloro | H | 1,1,1,2,3,3,4,4,4-nonafluorobutan-2-yl | H | (trifluoromethyl)sulfanyl | H | H | chloro | H | H | propanoyl |
| 5-377 | chloro | H | 1,1,1,2,3,3,4,4,4-nonafluorobutan-2-yl | H | (trifluoromethyl)sulfanyl | H | H | chloro | H | H | 3,3,3-trifluoro-propanoyl |
| 5-378 | chloro | H | 1-bromo-1,1,2,3,3,3-hexafluoropropan-2-yl | H | (trifluoromethyl)sulfanyl | H | H | chloro | H | H | H |
| 5-379 | chloro | H | 1-bromo-1,1,2,3,3,3-hexafluoropropan-2-yl | H | (trifluoromethyl)sulfanyl | H | H | chloro | H | H | acetyl |
| 5-380 | chloro | H | 1-bromo-1,1,2,3,3,3-hexafluoropropan-2-yl | H | (trifluoromethyl)sulfanyl | H | H | chloro | H | H | propanoyl |
| 5-381 | chloro | H | 1-bromo-1,1,2,3,3,3-hexafluoropropan-2-yl | H | (trifluoromethyl)sulfanyl | H | H | chloro | H | H | 3,3,3-trifluoro-propanoyl |
| 5-382 | bromo | H | 1,1,1,2,3,3,3-heptafluoropropan-2-yl | H | (trifluoromethyl)sulfanyl | H | H | chloro | H | H | H |
| 5-383 | bromo | H | 1,1,1,2,3,3,3-heptafluoropropan-2-yl | H | (trifluoromethyl)sulfanyl | H | H | chloro | H | H | acetyl |
| 5-384 | bromo | H | 1,1,1,2,3,3,3-heptafluoropropan-2-yl | H | (trifluoromethyl)sulfanyl | H | H | chloro | H | H | propanoyl |
| 5-385 | bromo | H | 1,1,1,2,3,3,3-heptafluoropropan-2-yl | H | (trifluoromethyl)sulfanyl | H | H | chloro | H | H | 3,3,3-trifluoro-propanoyl |
| 5-386 | bromo | H | 1-bromo-1,1,2,3,3,3-hexafluoropropan-2-yl | H | (trifluoromethyl)sulfanyl | H | H | chloro | H | H | H |
| 5-387 | bromo | H | 1-bromo-1,1,2,3,3,3-hexafluoropropan-2-yl | H | (trifluoromethyl)sulfanyl | H | H | chloro | H | H | acetyl |
| 5-388 | bromo | H | 1-bromo-1,1,2,3,3,3-hexafluoropropan-2-yl | H | (trifluoromethyl)sulfanyl | H | H | chloro | H | H | propanoyl |
| 5-389 | bromo | H | 1-bromo-1,1,2,3,3,3-hexafluoropropan-2-yl | H | (trifluoromethyl)sulfanyl | H | H | chloro | H | H | 3,3,3-trifluoro-propanoyl |
| 5-390 | chloro | H | 1,1,1,2,3,3,3-heptafluoropropan-2-yl | H | (trifluoromethyl)sulfinyl | H | H | chloro | H | H | acetyl |
| 5-391 | chloro | H | 1,1,1,2,3,3,3-heptafluoropropan-2-yl | H | (trifluoromethyl)sulfonyl | H | H | chloro | H | H | acetyl |

TABLE 5-continued

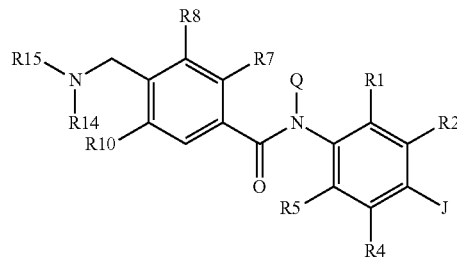

| Exa | R1 | R2 | J | R4 | R5 | Q | R7 | R8 | R10 | R14 | R15 |
|---|---|---|---|---|---|---|---|---|---|---|---|
| 5-392 | chloro | H | 1,1,1,2,3,3,3-heptafluoropropan-2-yl | H | difluoromethyl | H | H | chloro | H | H | H |
| 5-393 | chloro | H | 1,1,1,2,3,3,3-heptafluoropropan-2-yl | H | difluoromethyl | H | H | chloro | H | H | acetyl |
| 5-394 | chloro | H | 1,1,1,2,3,3,3-heptafluoropropan-2-yl | H | difluoromethyl | H | H | chloro | H | H | propanoyl |
| 5-395 | chloro | H | 1,1,1,2,3,3,3-heptafluoropropan-2-yl | H | difluoromethyl | H | H | chloro | H | H | 3,3,3-trifluoro-propanoyl |
| 5-396 | chloro | H | 1,1,1,2,3,3,4,4,4-nonafluorobutan-2-yl | H | difluoromethyl | H | H | chloro | H | H | H |
| 5-397 | chloro | H | 1,1,1,2,3,3,4,4,4-nonafluorobutan-2-yl | H | difluoromethyl | H | H | chloro | H | H | acetyl |
| 5-398 | chloro | H | 1,1,1,2,3,3,4,4,4-nonafluorobutan-2-yl | H | difluoromethyl | H | H | chloro | H | H | propanoyl |
| 5-399 | chloro | H | 1,1,1,2,3,3,4,4,4-nonafluorobutan-2-yl | H | difluoromethyl | H | H | chloro | H | H | 3,3,3-trifluoro-propanoyl |
| 5-400 | chloro | H | 1-bromo-1,1,2,3,3,3-hexafluoropropan-2-yl | H | difluoromethyl | H | H | chloro | H | H | H |
| 5-401 | chloro | H | 1-bromo-1,1,2,3,3,3-hexafluoropropan-2-yl | H | difluoromethyl | H | H | chloro | H | H | acetyl |
| 5-402 | chloro | H | 1-bromo-1,1,2,3,3,3-hexafluoropropan-2-yl | H | difluoromethyl | H | H | chloro | H | H | propanoyl |
| 5-403 | chloro | H | 1-bromo-1,1,2,3,3,3-hexafluoropropan-2-yl | H | difluoromethyl | H | H | chloro | H | H | 3,3,3-trifluoro-propanoyl |
| 5-404 | bromo | H | 1,1,1,2,3,3,3-heptafluoropropan-2-yl | H | difluoromethyl | H | H | chloro | H | H | H |
| 5-405 | bromo | H | 1,1,1,2,3,3,3-heptafluoropropan-2-yl | H | difluoromethyl | H | H | chloro | H | H | acetyl |
| 5-406 | bromo | H | 1,1,1,2,3,3,3-heptafluoropropan-2-yl | H | difluoromethyl | H | H | chloro | H | H | propanoyl |
| 5-407 | bromo | H | 1,1,1,2,3,3,3-heptafluoropropan-2-yl | H | difluoromethyl | H | H | chloro | H | H | 3,3,3-trifluoro-propanoyl |
| 5-408 | bromo | H | 1,1,1,2,3,3,4,4,4-nonafluorobutan-2-yl | H | difluoromethyl | H | H | chloro | H | H | H |
| 5-409 | bromo | H | 1,1,1,2,3,3,4,4,4-nonafluorobutan-2-yl | H | difluoromethyl | H | H | chloro | H | H | acetyl |
| 5-410 | bromo | H | 1,1,1,2,3,3,4,4,4-nonafluorobutan-2-yl | H | difluoromethyl | H | H | chloro | H | H | propanoyl |
| 5-411 | bromo | H | 1,1,1,2,3,3,4,4,4-nonafluorobutan-2-yl | H | difluoromethyl | H | H | chloro | H | H | 3,3,3-trifluoro-propanoyl |
| 5-412 | bromo | H | 1-bromo-1,1,2,3,3,3-hexafluoropropan-2-yl | H | difluoromethyl | H | H | chloro | H | H | H |
| 5-413 | bromo | H | 1-bromo-1,1,2,3,3,3-hexafluoropropan-2-yl | H | difluoromethyl | H | H | chloro | H | H | acetyl |
| 5-414 | bromo | H | 1-bromo-1,1,2,3,3,3-hexafluoropropan-2-yl | H | difluoromethyl | H | H | chloro | H | H | propanoyl |
| 5-415 | bromo | H | 1-bromo-1,1,2,3,3,3-hexafluoropropan-2-yl | H | difluoromethyl | H | H | chloro | H | H | 3,3,3-trifluoro-propanoyl |
| 5-416 | chloro | H | 1,1,1,2,3,3,3-heptafluoropropan-2-yl | H | trifluoromethyl | H | H | chloro | H | H | H |
| 5-417 | chloro | H | 1,1,1,2,3,3,3-heptafluoropropan-2-yl | H | trifluoromethyl | H | H | chloro | H | H | acetyl |
| 5-418 | chloro | H | 1,1,1,2,3,3,3-heptafluoropropan-2-yl | H | trifluoromethyl | H | H | chloro | H | H | propanoyl |
| 5-419 | chloro | H | 1,1,1,2,3,3,3-heptafluoropropan-2-yl | H | trifluoromethyl | H | H | chloro | H | H | 3,3,3-trifluoro-propanoyl |
| 5-420 | chloro | H | 1,1,1,2,3,3,4,4,4-nonafluorobutan-2-yl | H | trifluoromethyl | H | H | chloro | H | H | H |
| 5-421 | chloro | H | 1,1,1,2,3,3,4,4,4-nonafluorobutan-2-yl | H | trifluoromethyl | H | H | chloro | H | H | acetyl |
| 5-422 | chloro | H | 1,1,1,2,3,3,4,4,4-nonafluorobutan-2-yl | H | trifluoromethyl | H | H | chloro | H | H | propanoyl |
| 5-423 | chloro | H | 1,1,1,2,3,3,4,4,4-nonafluorobutan-2-yl | H | trifluoromethyl | H | H | chloro | H | H | 3,3,3-trifluoro-propanoyl |

TABLE 5-continued

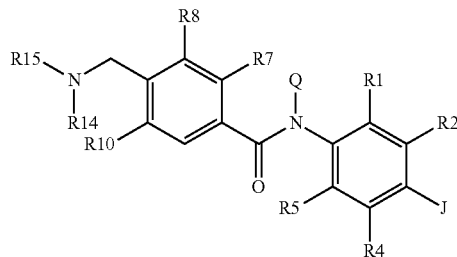

| Exa | R1 | R2 | J | R4 | R5 | Q | R7 | R8 | R10 | R14 | R15 |
|---|---|---|---|---|---|---|---|---|---|---|---|
| 5-424 | chloro | H | 1-bromo-1,1,2,3,3,3-hexafluoropropan-2-yl | H | trifluoromethyl | H | H | chloro | H | H | H |
| 5-425 | chloro | H | 1-bromo-1,1,2,3,3,3-hexafluoropropan-2-yl | H | trifluoromethyl | H | H | chloro | H | H | acetyl |
| 5-426 | chloro | H | 1-bromo-1,1,2,3,3,3-hexafluoropropan-2-yl | H | trifluoromethyl | H | H | chloro | H | H | propanoyl |
| 5-427 | chloro | H | 1-bromo-1,1,2,3,3,3-hexafluoropropan-2-yl | H | trifluoromethyl | H | H | chloro | H | H | 3,3,3-trifluoro-propanoyl |
| 5-428 | bromo | H | 1,1,1,2,3,3,3-heptafluoropropan-2-yl | H | trifluoromethyl | H | H | chloro | H | H | H |
| 5-429 | bromo | H | 1,1,1,2,3,3,3-heptafluoropropan-2-yl | H | trifluoromethyl | H | H | chloro | H | H | acetyl |
| 5-430 | bromo | H | 1,1,1,2,3,3,3-heptafluoropropan-2-yl | H | trifluoromethyl | H | H | chloro | H | H | propanoyl |
| 5-431 | bromo | H | 1,1,1,2,3,3,3-heptafluoropropan-2-yl | H | trifluoromethyl | H | H | chloro | H | H | 3,3,3-trifluoro-propanoyl |
| 5-432 | bromo | H | 1,1,1,2,3,3,4,4,4-nonafluorobutan-2-yl | H | trifluoromethyl | H | H | chloro | H | H | H |
| 5-433 | bromo | H | 1,1,1,2,3,3,4,4,4-nonafluorobutan-2-yl | H | trifluoromethyl | H | H | chloro | H | H | acetyl |
| 5-434 | bromo | H | 1,1,1,2,3,3,4,4,4-nonafluorobutan-2-yl | H | trifluoromethyl | H | H | chloro | H | H | propanoyl |
| 5-435 | bromo | H | 1,1,1,2,3,3,4,4,4-nonafluorobutan-2-yl | H | trifluoromethyl | H | H | chloro | H | H | 3,3,3-trifluoro-propanoyl |
| 5-436 | bromo | H | 1-bromo-1,1,2,3,3,3-hexafluoropropan-2-yl | H | trifluoromethyl | H | H | chloro | H | H | H |
| 5-437 | bromo | H | 1-bromo-1,1,2,3,3,3-hexafluoropropan-2-yl | H | trifluoromethyl | H | H | chloro | H | H | acetyl |
| 5-438 | bromo | H | 1-bromo-1,1,2,3,3,3-hexafluoropropan-2-yl | H | trifluoromethyl | H | H | chloro | H | H | propanoyl |
| 5-439 | bromo | H | 1-bromo-1,1,2,3,3,3-hexafluoropropan-2-yl | H | trifluoromethyl | H | H | chloro | H | H | 3,3,3-trifluoro-propanoyl |
| 5-440 | bromo | H | 1,1,1,2,3,3,3-heptafluoropropan-2-yl | H | bromo | H | H | H | H | H | tert-butoxy carbonyl |
| 5-441 | CH$_3$ | H | 1,1,1,2,3,3,3-heptafluoropropan-2-yl | H | ethyl | H | H | bromo | H | H | (2,2-difluorocyclo-propyl)carbonyl |
| 5-442 | CH$_3$ | H | 1,1,1,2,3,3,3-heptafluoropropan-2-yl | H | ethyl | H | H | bromo | H | H | cyanoacetyl |
| 5-443 | CH3 | H | 1,1,1,2,3,3,3-heptafluoropropan-2-yl | H | chloro | H | H | chloro | H | H | H |
| 5-444 | CH3 | H | 1,1,1,2,3,3,3-heptafluoropropan-2-yl | H | chloro | H | H | chloro | H | H | acetyl |
| 5-445 | CH3 | H | 1,1,1,2,3,3,3-heptafluoropropan-2-yl | H | chloro | H | H | chloro | H | H | propanoyl |
| 5-446 | CH3 | H | 1,1,1,2,3,3,3-heptafluoropropan-2-yl | H | chloro | H | H | chloro | H | H | 3,3,3-trifluoro-propanoyl |
| 5-447 | CH3 | H | 1,1,1,2,3,3,3-heptafluoropropan-2-yl | H | chloro | H | H | chloro | H | H | tert-butoxy carbonyl |
| 5-448 | chloro | H | 1,1,1,2,3,3,3-heptafluoropropan-2-yl | H | difluoromethoxy | H | H | chloro | H | H | tert-butoxy carbonyl |
| 5-449 | bromo | H | 1,1,1,2,3,3,3-heptafluoropropan-2-yl | H | difluoromethoxy | H | H | chloro | H | H | tert-butoxy carbonyl |
| 5-450 | chloro | H | 1,1,1,2,3,3,3-heptafluoropropan-2-yl | H | difluoromethoxy | H | H | chloro | H | H | cyclopropylacetyl |
| 5-451 | bromo | H | 1,1,1,2,3,3,3-heptafluoropropan-2-yl | H | bromo | H | H | chloro | H | H | tert-butoxy carbonyl |
| 5-452 | chloro | H | 1,1,1,2,3,3,4,4,4-nonafluorobutan-2-yl | H | difluoromethoxy | H | H | H | H | H | 3,3,3-trifluoro-propanoyl |
| 5-453 | chloro | H | 1,1,1,2,3,3,4,4,4-nonafluorobutan-2-yl | H | difluoromethoxy | H | H | H | H | H | tert-butoxy carbonyl |
| 5-454 | chloro | H | 1,1,1,2,3,3,4,4,4-nonafluorobutan-2-yl | H | difluoromethoxy | H | H | chloro | H | H | Cyclopropyl carbonyl |
| 5-455 | chloro | H | 1,1,1,2,3,3,4,4,4-nonafluorobutan-2-yl | H | difluoromethoxy | H | H | chloro | H | H | cyclopropylacetyl |

TABLE 5-continued

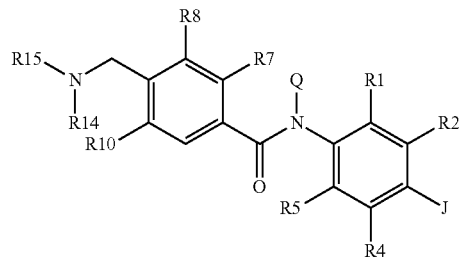

| Exa | R1 | R2 | J | R4 | R5 | Q | R7 | R8 | R10 | R14 | R15 |
|---|---|---|---|---|---|---|---|---|---|---|---|
| 5-456 | chloro | H | 1,1,1,2,3,3,4,4,4-nonafluorobutan-2-yl | H | difluoromethoxy | H | H | chloro | H | H | tert-butoxycarbonyl |

TABLE 6

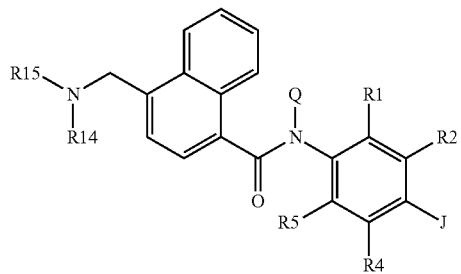

| Exa | R1 | R2 | J | R4 | R5 | Q | R14 | R15 |
|---|---|---|---|---|---|---|---|---|
| 6-1 | CH₃ | H | 1,1,1,2,3,3,3-heptafluoropropan-2-yl | H | ethyl | H | H | H |
| 6-2 | CH₃ | H | 1,1,1,2,3,3,3-heptafluoropropan-2-yl | H | ethyl | H | H | acetyl |
| 6-3 | CH₃ | H | 1,1,1,2,3,3,3-heptafluoropropan-2-yl | H | ethyl | H | H | propanoyl |
| 6-4 | CH₃ | H | 1,1,1,2,3,3,3-heptafluoropropan-2-yl | H | ethyl | H | H | cyclopropylcarbonyl |
| 6-5 | CH₃ | H | 1,1,1,2,3,3,3-heptafluoropropan-2-yl | H | ethyl | H | H | cyclopropylacetyl |
| 6-6 | CH₃ | H | 1,1,1,2,3,3,3-heptafluoropropan-2-yl | H | ethyl | H | H | 3,3,3-trifluoropropanoyl |
| 6-7 | CH₃ | H | 1,1,1,2,3,3,3-heptafluoropropan-2-yl | H | ethyl | H | H | (2-fluoropyridin-3-yl)carbonyl |
| 6-8 | CH₃ | H | 1,1,1,2,3,3,4,4,4-nonafluorobutan-2-yl | H | ethyl | H | H | H |
| 6-9 | CH₃ | H | 1,1,1,2,3,3,4,4,4-nonafluorobutan-2-yl | H | ethyl | H | H | acetyl |
| 6-10 | CH₃ | H | 1,1,1,2,3,3,4,4,4-nonafluorobutan-2-yl | H | ethyl | H | H | propanoyl |
| 6-11 | CH₃ | H | 1,1,1,2,3,3,4,4,4-nonafluorobutan-2-yl | H | ethyl | H | H | cyclopropylcarbonyl |
| 6-12 | CH₃ | H | 1,1,1,2,3,3,4,4,4-nonafluorobutan-2-yl | H | ethyl | H | H | cyclopropylacetyl |
| 6-13 | CH₃ | H | 1,1,1,2,3,3,4,4,4-nonafluorobutan-2-yl | H | ethyl | H | H | 3,3,3-trifluoropropanoyl |
| 6-14 | CH₃ | H | undecafluorocyclohexyl | H | ethyl | H | H | H |
| 6-15 | CH₃ | H | undecafluorocyclohexyl | H | ethyl | H | H | acetyl |
| 6-16 | CH₃ | H | undecafluorocyclohexyl | H | ethyl | H | H | propanoyl |
| 6-17 | CH₃ | H | undecafluorocyclohexyl | H | ethyl | H | H | cyclopropylcarbonyl |
| 6-18 | CH₃ | H | undecafluorocyclohexyl | H | ethyl | H | H | cyclopropylacetyl |
| 6-19 | CH₃ | H | undecafluorocyclohexyl | H | ethyl | H | H | 3,3,3-trifluoropropanoyl |
| 6-20 | CH₃ | H | 1-bromo-1,1,2,3,3,3-hexafluoropropan-2-yl | H | CH₃ | H | H | H |
| 6-21 | CH₃ | H | 1-bromo-1,1,2,3,3,3-hexafluoropropan-2-yl | H | CH₃ | H | H | acetyl |
| 6-22 | CH₃ | H | 1-bromo-1,1,2,3,3,3-hexafluoropropan-2-yl | H | CH₃ | H | H | propanoyl |
| 6-23 | CH₃ | H | 1-bromo-1,1,2,3,3,3-hexafluoropropan-2-yl | H | CH₃ | H | H | 3,3,3-trifluoropropanoyl |
| 6-24 | CH₃ | H | 1-bromo-1,1,2,3,3,3-hexafluoropropan-2-yl | H | ethyl | H | H | H |
| 6-25 | CH₃ | H | 1-bromo-1,1,2,3,3,3-hexafluoropropan-2-yl | H | ethyl | H | H | acetyl |
| 6-26 | CH₃ | H | 1-bromo-1,1,2,3,3,3-hexafluoropropan-2-yl | H | ethyl | H | H | propanoyl |
| 6-27 | CH₃ | H | 1-bromo-1,1,2,3,3,3-hexafluoropropan-2-yl | H | ethyl | H | H | 3,3,3-trifluoropropanoyl |
| 6-28 | bromo | H | 1-bromo-1,1,2,3,3,3-hexafluoropropan-2-yl | H | bromo | H | H | H |
| 6-29 | bromo | H | 1-bromo-1,1,2,3,3,3-hexafluoropropan-2-yl | H | bromo | H | H | acetyl |
| 6-30 | bromo | H | 1-bromo-1,1,2,3,3,3-hexafluoropropan-2-yl | H | bromo | H | H | propanoyl |
| 6-31 | bromo | H | 1-bromo-1,1,2,3,3,3-hexafluoropropan-2-yl | H | bromo | H | H | 3,3,3-trifluoropropanoyl |
| 6-32 | bromo | H | 1-bromo-1,1,2,3,3,3-hexafluoropropan-2-yl | H | difluoromethoxy | H | H | H |
| 6-33 | bromo | H | 1-bromo-1,1,2,3,3,3-hexafluoropropan-2-yl | H | difluoromethoxy | H | H | acetyl |
| 6-34 | bromo | H | 1-bromo-1,1,2,3,3,3-hexafluoropropan-2-yl | H | difluoromethoxy | H | H | propanoyl |
| 6-35 | bromo | H | 1-bromo-1,1,2,3,3,3-hexafluoropropan-2-yl | H | difluoromethoxy | H | H | 3,3,3-trifluoropropanoyl |
| 6-36 | bromo | H | 1,1,1,2,3,3,3-heptafluoropropan-2-yl | H | bromo | H | H | H |
| 6-37 | bromo | H | 1,1,1,2,3,3,3-heptafluoropropan-2-yl | H | bromo | H | H | acetyl |
| 6-38 | bromo | H | 1,1,1,2,3,3,3-heptafluoropropan-2-yl | H | bromo | H | H | propanoyl |
| 6-39 | bromo | H | 1,1,1,2,3,3,3-heptafluoropropan-2-yl | H | bromo | H | H | 3,3,3-trifluoropropanoyl |
| 6-40 | bromo | H | 1,1,1,2,3,3,3-heptafluoropropan-2-yl | H | difluoromethoxy | H | H | H |
| 6-41 | bromo | H | 1,1,1,2,3,3,3-heptafluoropropan-2-yl | H | difluoromethoxy | H | H | acetyl |
| 6-42 | bromo | H | 1,1,1,2,3,3,3-heptafluoropropan-2-yl | H | difluoromethoxy | H | H | propanoyl |

TABLE 6-continued

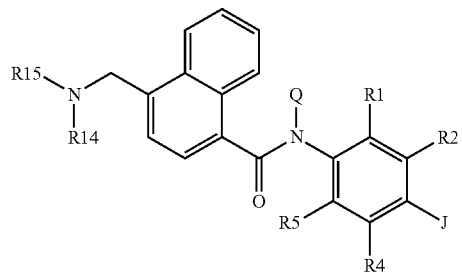

| Exa | R1 | R2 | J | R4 | R5 | Q | R14 | R15 |
|---|---|---|---|---|---|---|---|---|
| 6-43 | bromo | H | 1,1,1,2,3,3,3-heptafluoropropan-2-yl | H | difluoromethoxy | H | H | 3,3,3-trifluoropropanoyl |
| 6-44 | bromo | H | 1,1,1,2,3,3,4,4,4-nonafluorobutan-2-yl | H | bromo | H | H | H |
| 6-45 | bromo | H | 1,1,1,2,3,3,4,4,4-nonafluorobutan-2-yl | H | bromo | H | H | acetyl |
| 6-46 | bromo | H | 1,1,1,2,3,3,4,4,4-nonafluorobutan-2-yl | H | bromo | H | H | propanoyl |
| 6-47 | bromo | H | 1,1,1,2,3,3,4,4,4-nonafluorobutan-2-yl | H | bromo | H | H | 3,3,3-trifluoropropanoyl |
| 6-48 | bromo | H | 1,1,1,2,3,3,4,4,4-nonafluorobutan-2-yl | H | difluoromethoxy | H | H | H |
| 6-49 | bromo | H | 1,1,1,2,3,3,4,4,4-nonafluorobutan-2-yl | H | difluoromethoxy | H | H | acetyl |
| 6-50 | bromo | H | 1,1,1,2,3,3,4,4,4-nonafluorobutan-2-yl | H | difluoromethoxy | H | H | propanoyl |
| 6-51 | bromo | H | 1,1,1,2,3,3,4,4,4-nonafluorobutan-2-yl | H | difluoromethoxy | H | H | 3,3,3-trifluoropropanoyl |
| 6-52 | CH$_3$ | H | 1,1,1,2,3,3,3-heptafluoropropan-2-yl | H | difluoromethoxy | H | H | H |
| 6-53 | CH$_3$ | H | 1,1,1,2,3,3,3-heptafluoropropan-2-yl | H | difluoromethoxy | H | H | acetyl |
| 6-54 | CH$_3$ | H | 1,1,1,2,3,3,3-heptafluoropropan-2-yl | H | difluoromethoxy | H | H | propanoyl |
| 6-55 | CH$_3$ | H | 1,1,1,2,3,3,3-heptafluoropropan-2-yl | H | difluoromethoxy | H | H | 3,3,3-trifluoropropanoyl |
| 6-56 | CH$_3$ | H | 1,1,1,2,3,3,4,4,4-nonafluorobutan-2-yl | H | difluoromethoxy | H | H | H |
| 6-57 | CH$_3$ | H | 1,1,1,2,3,3,4,4,4-nonafluorobutan-2-yl | H | difluoromethoxy | H | H | acetyl |
| 6-58 | CH$_3$ | H | 1,1,1,2,3,3,4,4,4-nonafluorobutan-2-yl | H | difluoromethoxy | H | H | propanoyl |
| 6-59 | CH$_3$ | H | 1,1,1,2,3,3,4,4,4-nonafluorobutan-2-yl | H | difluoromethoxy | H | H | 3,3,3-trifluoropropanoyl |
| 6-60 | CH$_3$ | H | 1-bromo-1,1,2,3,3,3-hexafluoropropan-2-yl | H | difluoromethoxy | H | H | H |
| 6-61 | CH$_3$ | H | 1-bromo-1,1,2,3,3,3-hexafluoropropan-2-yl | H | difluoromethoxy | H | H | acetyl |
| 6-62 | CH$_3$ | H | 1-bromo-1,1,2,3,3,3-hexafluoropropan-2-yl | H | difluoromethoxy | H | H | propanoyl |
| 6-63 | CH$_3$ | H | 1-bromo-1,1,2,3,3,3-hexafluoropropan-2-yl | H | difluoromethoxy | H | H | 3,3,3-trifluoropropanoyl |
| 6-64 | chloro | H | 1,1,1,2,3,3,3-heptafluoropropan-2-yl | H | difluoromethoxy | H | H | H |
| 6-65 | chloro | H | 1,1,1,2,3,3,3-heptafluoropropan-2-yl | H | difluoromethoxy | H | H | acetyl |
| 6-66 | chloro | H | 1,1,1,2,3,3,3-heptafluoropropan-2-yl | H | difluoromethoxy | H | H | propanoyl |
| 6-67 | chloro | H | 1,1,1,2,3,3,3-heptafluoropropan-2-yl | H | difluoromethoxy | H | H | 3,3,3-trifluoropropanoyl |
| 6-68 | chloro | H | 1,1,1,2,3,3,4,4,4-nonafluorobutan-2-yl | H | difluoromethoxy | H | H | H |
| 6-69 | chloro | H | 1,1,1,2,3,3,4,4,4-nonafluorobutan-2-yl | H | difluoromethoxy | H | H | acetyl |
| 6-70 | chloro | H | 1,1,1,2,3,3,4,4,4-nonafluorobutan-2-yl | H | difluoromethoxy | H | H | propanoyl |
| 6-71 | chloro | H | 1,1,1,2,3,3,4,4,4-nonafluorobutan-2-yl | H | difluoromethoxy | H | H | 3,3,3-trifluoropropanoyl |
| 6-72 | chloro | H | 1-bromo-1,1,2,3,3,3-hexafluoropropan-2-yl | H | difluoromethoxy | H | H | H |
| 6-73 | chloro | H | 1-bromo-1,1,2,3,3,3-hexafluoropropan-2-yl | H | difluoromethoxy | H | H | acetyl |
| 6-74 | chloro | H | 1-bromo-1,1,2,3,3,3-hexafluoropropan-2-yl | H | difluoromethoxy | H | H | propanoyl |
| 6-75 | chloro | H | 1-bromo-1,1,2,3,3,3-hexafluoropropan-2-yl | H | difluoromethoxy | H | H | 3,3,3-trifluoropropanoyl |

TABLE 7

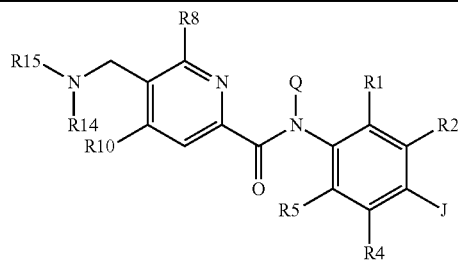

| Exa | R1 | R2 | J | R4 | R5 | Q | R8 | R10 | R14 | R15 |
|---|---|---|---|---|---|---|---|---|---|---|
| 7-1 | CH$_3$ | H | 1,1,1,2,3,3,3-heptafluoropropan-2-yl | H | ethyl | H | H | H | H | H |
| 7-2 | CH$_3$ | H | 1,1,1,2,3,3,3-heptafluoropropan-2-yl | H | ethyl | H | H | H | H | acetyl |
| 7-3 | CH$_3$ | H | 1,1,1,2,3,3,3-heptafluoropropan-2-yl | H | ethyl | H | H | H | H | propanoyl |
| 7-4 | CH$_3$ | H | 1,1,1,2,3,3,3-heptafluoropropan-2-yl | H | ethyl | H | H | H | H | cyclopropylcarbonyl |
| 7-5 | CH$_3$ | H | 1,1,1,2,3,3,3-heptafluoropropan-2-yl | H | ethyl | H | H | H | H | cyclopropylacetyl |
| 7-6 | CH$_3$ | H | 1,1,1,2,3,3,3-heptafluoropropan-2-yl | H | ethyl | H | H | H | H | 3,3,3-trifluoropropanoyl |
| 7-7 | CH$_3$ | H | 1,1,1,2,3,3,4,4,4-nonafluorobutan-2-yl | H | ethyl | H | H | H | H | H |
| 7-8 | CH$_3$ | H | 1,1,1,2,3,3,4,4,4-nonafluorobutan-2-yl | H | ethyl | H | H | H | H | acetyl |
| 7-9 | CH$_3$ | H | 1,1,1,2,3,3,4,4,4-nonafluorobutan-2-yl | H | ethyl | H | H | H | H | propanoyl |
| 7-10 | CH$_3$ | H | 1,1,1,2,3,3,4,4,4-nonafluorobutan-2-yl | H | ethyl | H | H | H | H | cyclopropylcarbonyl |
| 7-11 | CH$_3$ | H | 1,1,1,2,3,3,4,4,4-nonafluorobutan-2-yl | H | ethyl | H | H | H | H | cyclopropylacetyl |

TABLE 7-continued

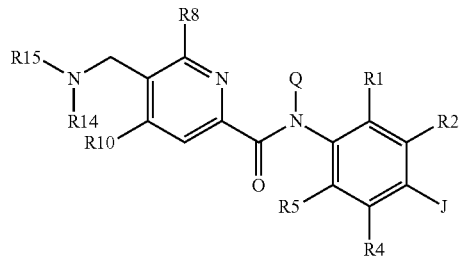

| Exa | R1 | R2 | J | R4 | R5 | Q | R8 | R10 | R14 | R15 |
|---|---|---|---|---|---|---|---|---|---|---|
| 7-12 | CH₃ | H | 1,1,1,2,3,3,4,4,4-nonafluorobutan-2-yl | H | ethyl | H | H | H | H | 3,3,3-trifluoropropanoyl |
| 7-13 | CH₃ | H | undecafluorocyclohexyl | H | ethyl | H | H | H | H | H |
| 7-14 | CH₃ | H | undecafluorocyclohexyl | H | ethyl | H | H | H | H | acetyl |
| 7-15 | CH₃ | H | undecafluorocyclohexyl | H | ethyl | H | H | H | H | propanoyl |
| 7-16 | CH₃ | H | undecafluorocyclohexyl | H | ethyl | H | H | H | H | cyclopropylcarbonyl |
| 7-17 | CH₃ | H | undecafluorocyclohexyl | H | ethyl | H | H | H | H | cyclopropylacetyl |
| 7-18 | CH₃ | H | undecafluorocyclohexyl | H | ethyl | H | H | H | H | 3,3,3-trifluoropropanoyl |
| 7-19 | CH₃ | H | 1,1,1,2,3,3,3-heptafluoropropan-2-yl | H | ethyl | H | H | H | H | tert-butoxycarbonyl |
| 7-20 | CH₃ | H | 1-bromo-1,1,2,3,3,3-hexafluoropropan-2-yl | H | CH₃ | H | H | H | H | H |
| 7-21 | CH₃ | H | 1-bromo-1,1,2,3,3,3-hexafluoropropan-2-yl | H | CH₃ | H | H | H | H | acetyl |
| 7-22 | CH₃ | H | 1-bromo-1,1,2,3,3,3-hexafluoropropan-2-yl | H | CH₃ | H | H | H | H | propanoyl |
| 7-23 | CH₃ | H | 1-bromo-1,1,2,3,3,3-hexafluoropropan-2-yl | H | CH₃ | H | H | H | H | 3,3,3-trifluoropropanoyl |
| 7-24 | CH₃ | H | 1-bromo-1,1,2,3,3,3-hexafluoropropan-2-yl | H | ethyl | H | H | H | H | H |
| 7-25 | CH₃ | H | 1-bromo-1,1,2,3,3,3-hexafluoropropan-2-yl | H | ethyl | H | H | H | H | acetyl |
| 7-26 | CH₃ | H | 1-bromo-1,1,2,3,3,3-hexafluoropropan-2-yl | H | ethyl | H | H | H | H | propanoyl |
| 7-27 | CH₃ | H | 1-bromo-1,1,2,3,3,3-hexafluoropropan-2-yl | H | ethyl | H | H | H | H | 3,3,3-trifluoropropanoyl |
| 7-28 | chloro | H | 1-bromo-1,1,2,3,3,3-hexafluoropropan-2-yl | H | chloro | H | H | H | H | H |
| 7-29 | chloro | H | 1-bromo-1,1,2,3,3,3-hexafluoropropan-2-yl | H | chloro | H | H | H | H | acetyl |
| 7-30 | chloro | H | 1-bromo-1,1,2,3,3,3-hexafluoropropan-2-yl | H | chloro | H | H | H | H | propanoyl |
| 7-31 | chloro | H | 1-bromo-1,1,2,3,3,3-hexafluoropropan-2-yl | H | chloro | H | H | H | H | 3,3,3-trifluoropropanoyl |
| 7-32 | bromo | H | 1-bromo-1,1,2,3,3,3-hexafluoropropan-2-yl | H | bromo | H | H | H | H | H |
| 7-33 | bromo | H | 1-bromo-1,1,2,3,3,3-hexafluoropropan-2-yl | H | bromo | H | H | H | H | acetyl |
| 7-34 | bromo | H | 1-bromo-1,1,2,3,3,3-hexafluoropropan-2-yl | H | bromo | H | H | H | H | propanoyl |
| 7-35 | bromo | H | 1-bromo-1,1,2,3,3,3-hexafluoropropan-2-yl | H | bromo | H | H | H | H | 3,3,3-trifluoropropanoyl |
| 7-36 | bromo | H | 1-bromo-1,1,2,3,3,3-hexafluoropropan-2-yl | H | difluoromethoxy | H | H | H | H | H |
| 7-37 | bromo | H | 1-bromo-1,1,2,3,3,3-hexafluoropropan-2-yl | H | difluoromethoxy | H | H | H | H | acetyl |
| 7-38 | bromo | H | 1-bromo-1,1,2,3,3,3-hexafluoropropan-2-yl | H | difluoromethoxy | H | H | H | H | propanoyl |
| 7-39 | bromo | H | 1-bromo-1,1,2,3,3,3-hexafluoropropan-2-yl | H | difluoromethoxy | H | H | H | H | 3,3,3-trifluoropropanoyl |
| 7-40 | chloro | H | 1,1,1,2,3,3,3-heptafluoropropan-2-yl | H | chloro | H | H | H | H | H |
| 7-41 | chloro | H | 1,1,1,2,3,3,3-heptafluoropropan-2-yl | H | chloro | H | H | H | H | acetyl |
| 7-42 | chloro | H | 1,1,1,2,3,3,3-heptafluoropropan-2-yl | H | chloro | H | H | H | H | propanoyl |
| 7-43 | chloro | H | 1,1,1,2,3,3,3-heptafluoropropan-2-yl | H | chloro | H | H | H | H | 3,3,3-trifluoropropanoyl |
| 7-44 | bromo | H | 1,1,1,2,3,3,3-heptafluoropropan-2-yl | H | bromo | H | H | H | H | H |
| 7-45 | bromo | H | 1,1,1,2,3,3,3-heptafluoropropan-2-yl | H | bromo | H | H | H | H | acetyl |
| 7-46 | bromo | H | 1,1,1,2,3,3,3-heptafluoropropan-2-yl | H | bromo | H | H | H | H | propanoyl |
| 7-47 | bromo | H | 1,1,1,2,3,3,3-heptafluoropropan-2-yl | H | bromo | H | H | H | H | 3,3,3-trifluoropropanoyl |
| 7-48 | bromo | H | 1,1,1,2,3,3,3-heptafluoropropan-2-yl | H | difluoromethoxy | H | H | H | H | H |
| 7-49 | bromo | H | 1,1,1,2,3,3,3-heptafluoropropan-2-yl | H | difluoromethoxy | H | H | H | H | acetyl |
| 7-50 | bromo | H | 1,1,1,2,3,3,3-heptafluoropropan-2-yl | H | difluoromethoxy | H | H | H | H | propanoyl |
| 7-51 | bromo | H | 1,1,1,2,3,3,3-heptafluoropropan-2-yl | H | difluoromethoxy | H | H | H | H | 3,3,3-trifluoropropanoyl |
| 7-52 | chloro | H | 1,1,1,2,3,3,4,4,4-nonafluorobutan-2-yl | H | chloro | H | H | H | H | H |
| 7-53 | chloro | H | 1,1,1,2,3,3,4,4,4-nonafluorobutan-2-yl | H | chloro | H | H | H | H | acetyl |
| 7-54 | chloro | H | 1,1,1,2,3,3,4,4,4-nonafluorobutan-2-yl | H | chloro | H | H | H | H | propanoyl |
| 7-55 | chloro | H | 1,1,1,2,3,3,4,4,4-nonafluorobutan-2-yl | H | chloro | H | H | H | H | 3,3,3-trifluoropropanoyl |
| 7-56 | bromo | H | 1,1,1,2,3,3,4,4,4-nonafluorobutan-2-yl | H | bromo | H | H | H | H | H |

TABLE 7-continued

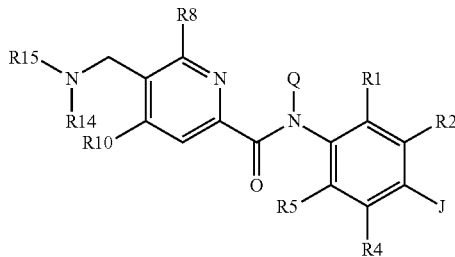

| Exa | R1 | R2 | J | R4 | R5 | Q | R8 | R10 | R14 | R15 |
|---|---|---|---|---|---|---|---|---|---|---|
| 7-57 | bromo | H | 1,1,1,2,3,3,4,4,4-nonafluorobutan-2-yl | H | bromo | H | H | H | H | acetyl |
| 7-58 | bromo | H | 1,1,1,2,3,3,4,4,4-nonafluorobutan-2-yl | H | bromo | H | H | H | H | propanoyl |
| 7-59 | bromo | H | 1,1,1,2,3,3,4,4,4-nonafluorobutan-2-yl | H | bromo | H | H | H | H | 3,3,3-trifluoropropanoyl |
| 7-60 | bromo | H | 1,1,1,2,3,3,4,4,4-nonafluorobutan-2-yl | H | difluoromethoxy | H | H | H | H | H |
| 7-61 | bromo | H | 1,1,1,2,3,3,4,4,4-nonafluorobutan-2-yl | H | difluoromethoxy | H | H | H | H | acetyl |
| 7-62 | bromo | H | 1,1,1,2,3,3,4,4,4-nonafluorobutan-2-yl | H | difluoromethoxy | H | H | H | H | propanoyl |
| 7-63 | bromo | H | 1,1,1,2,3,3,4,4,4-nonafluorobutan-2-yl | H | difluoromethoxy | H | H | H | H | 3,3,3-trifluoropropanoyl |
| 7-64 | CH₃ | H | 1,1,1,2,3,3,3-heptafluoropropan-2-yl | H | difluoromethoxy | H | H | H | H | H |
| 7-65 | CH₃ | H | 1,1,1,2,3,3,3-heptafluoropropan-2-yl | H | difluoromethoxy | H | H | H | H | acetyl |
| 7-66 | CH₃ | H | 1,1,1,2,3,3,3-heptafluoropropan-2-yl | H | difluoromethoxy | H | H | H | H | propanoyl |
| 7-67 | CH₃ | H | 1,1,1,2,3,3,3-heptafluoropropan-2-yl | H | difluoromethoxy | H | H | H | H | 3,3,3-trifluoropropanoyl |
| 7-68 | CH₃ | H | 1,1,1,2,3,3,4,4,4-nonafluorobutan-2-yl | H | difluoromethoxy | H | H | H | H | H |
| 7-69 | CH₃ | H | 1,1,1,2,3,3,4,4,4-nonafluorobutan-2-yl | H | difluoromethoxy | H | H | H | H | acetyl |
| 7-70 | CH₃ | H | 1,1,1,2,3,3,4,4,4-nonafluorobutan-2-yl | H | difluoromethoxy | H | H | H | H | propanoyl |
| 7-71 | CH₃ | H | 1,1,1,2,3,3,4,4,4-nonafluorobutan-2-yl | H | difluoromethoxy | H | H | H | H | 3,3,3-trifluoropropanoyl |
| 7-72 | CH₃ | H | 1-bromo-1,1,2,3,3,3-hexafluoropropan-2-yl | H | difluoromethoxy | H | H | H | H | H |
| 7-73 | CH₃ | H | 1-bromo-1,1,2,3,3,3-hexafluoropropan-2-yl | H | difluoromethoxy | H | H | H | H | acetyl |
| 7-74 | CH₃ | H | 1-bromo-1,1,2,3,3,3-hexafluoropropan-2-yl | H | difluoromethoxy | H | H | H | H | propanoyl |
| 7-75 | CH₃ | H | 1-bromo-1,1,2,3,3,3-hexafluoropropan-2-yl | H | difluoromethoxy | H | H | H | H | 3,3,3-trifluoropropanoyl |
| 7-76 | CH₃ | H | 1,1,1,2,3,3,3-heptafluoropropan-2-yl | H | CH₃ | H | chloro | H | H | H |
| 7-77 | CH₃ | H | 1,1,1,2,3,3,3-heptafluoropropan-2-yl | H | CH₃ | H | chloro | H | H | acetyl |
| 7-78 | CH₃ | H | 1,1,1,2,3,3,3-heptafluoropropan-2-yl | H | CH₃ | H | chloro | H | H | propanoyl |
| 7-79 | CH₃ | H | 1,1,1,2,3,3,3-heptafluoropropan-2-yl | H | CH₃ | H | chloro | H | H | 3,3,3-trifluoropropanoyl |
| 7-80 | CH₃ | H | 1,1,1,2,3,3,3-heptafluoropropan-2-yl | H | ethyl | H | chloro | H | H | H |
| 7-81 | CH₃ | H | 1,1,1,2,3,3,3-heptafluoropropan-2-yl | H | ethyl | H | chloro | H | H | acetyl |
| 7-82 | CH₃ | H | 1,1,1,2,3,3,3-heptafluoropropan-2-yl | H | ethyl | H | chloro | H | H | propanoyl |
| 7-83 | CH₃ | H | 1,1,1,2,3,3,3-heptafluoropropan-2-yl | H | ethyl | H | chloro | H | H | 3,3,3-trifluoropropanoyl |
| 7-84 | CH₃ | H | 1,1,1,2,3,3,4,4,4-nonafluorobutan-2-yl | H | CH₃ | H | chloro | H | H | H |
| 7-85 | CH₃ | H | 1,1,1,2,3,3,4,4,4-nonafluorobutan-2-yl | H | CH₃ | H | chloro | H | H | acetyl |
| 7-86 | CH₃ | H | 1,1,1,2,3,3,4,4,4-nonafluorobutan-2-yl | H | CH₃ | H | chloro | H | H | propanoyl |
| 7-87 | CH₃ | H | 1,1,1,2,3,3,4,4,4-nonafluorobutan-2-yl | H | CH₃ | H | chloro | H | H | 3,3,3-trifluoropropanoyl |
| 7-88 | CH₃ | H | 1,1,1,2,3,3,4,4,4-nonafluorobutan-2-yl | H | ethyl | H | chloro | H | H | H |
| 7-89 | CH₃ | H | 1,1,1,2,3,3,4,4,4-nonafluorobutan-2-yl | H | ethyl | H | chloro | H | H | acetyl |
| 7-90 | CH₃ | H | 1,1,1,2,3,3,4,4,4-nonafluorobutan-2-yl | H | ethyl | H | chloro | H | H | propanoyl |
| 7-91 | CH₃ | H | 1,1,1,2,3,3,4,4,4-nonafluorobutan-2-yl | H | ethyl | H | chloro | H | H | 3,3,3-trifluoropropanoyl |
| 7-92 | CH₃ | H | 1-bromo-1,1,2,3,3,3-hexafluoropropan-2-yl | H | CH₃ | H | chloro | H | H | H |
| 7-93 | CH₃ | H | 1-bromo-1,1,2,3,3,3-hexafluoropropan-2-yl | H | CH₃ | H | chloro | H | H | acetyl |
| 7-94 | CH₃ | H | 1-bromo-1,1,2,3,3,3-hexafluoropropan-2-yl | H | CH₃ | H | chloro | H | H | propanoyl |
| 7-95 | CH₃ | H | 1-bromo-1,1,2,3,3,3-hexafluoropropan-2-yl | H | CH₃ | H | chloro | H | H | 3,3,3-trifluoropropanoyl |
| 7-96 | CH₃ | H | 1-bromo-1,1,2,3,3,3-hexafluoropropan-2-yl | H | ethyl | H | chloro | H | H | H |
| 7-97 | CH₃ | H | 1-bromo-1,1,2,3,3,3-hexafluoropropan-2-yl | H | ethyl | H | chloro | H | H | acetyl |
| 7-98 | CH₃ | H | 1-bromo-1,1,2,3,3,3-hexafluoropropan-2-yl | H | ethyl | H | chloro | H | H | propanoyl |
| 7-99 | CH₃ | H | 1-bromo-1,1,2,3,3,3-hexafluoropropan-2-yl | H | ethyl | H | chloro | H | H | 3,3,3-trifluoropropanoyl |
| 7-100 | CH₃ | H | 1,1,1,2,3,3,3-heptafluoropropan-2-yl | H | CH₃ | H | H | chloro | H | H |
| 7-101 | CH₃ | H | 1,1,1,2,3,3,3-heptafluoropropan-2-yl | H | CH₃ | H | H | chloro | H | acetyl |
| 7-102 | CH₃ | H | 1,1,1,2,3,3,3-heptafluoropropan-2-yl | H | CH₃ | H | H | chloro | H | propanoyl |
| 7-103 | CH₃ | H | 1,1,1,2,3,3,3-heptafluoropropan-2-yl | H | CH₃ | H | H | chloro | H | 3,3,3-trifluoropropanoyl |
| 7-104 | CH₃ | H | 1,1,1,2,3,3,3-heptafluoropropan-2-yl | H | ethyl | H | H | chloro | H | H |
| 7-105 | CH₃ | H | 1,1,1,2,3,3,3-heptafluoropropan-2-yl | H | ethyl | H | H | chloro | H | acetyl |
| 7-106 | CH₃ | H | 1,1,1,2,3,3,3-heptafluoropropan-2-yl | H | ethyl | H | H | chloro | H | propanoyl |
| 7-107 | CH₃ | H | 1,1,1,2,3,3,3-heptafluoropropan-2-yl | H | ethyl | H | H | chloro | H | 3,3,3-trifluoropropanoyl |
| 7-108 | CH₃ | H | 1,1,1,2,3,3,4,4,4-nonafluorobutan-2-yl | H | CH₃ | H | H | chloro | H | H |
| 7-109 | CH₃ | H | 1,1,1,2,3,3,4,4,4-nonafluorobutan-2-yl | H | CH₃ | H | H | chloro | H | acetyl |

TABLE 7-continued

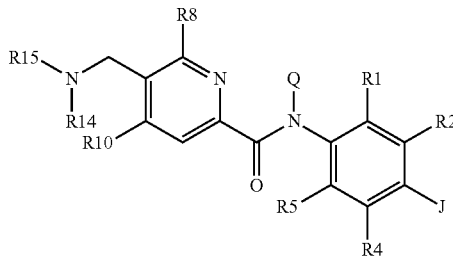

| Exa | R1 | R2 | J | R4 | R5 | Q | R8 | R10 | R14 | R15 |
|---|---|---|---|---|---|---|---|---|---|---|
| 7-110 | CH₃ | H | 1,1,1,2,3,3,4,4,4-nonafluorobutan-2-yl | H | CH₃ | H | H | chloro | H | propanoyl |
| 7-111 | CH₃ | H | 1,1,1,2,3,3,4,4,4-nonafluorobutan-2-yl | H | CH₃ | H | H | chloro | H | 3,3,3-trifluoropropanoyl |
| 7-112 | CH₃ | H | 1,1,1,2,3,3,4,4,4-nonafluorobutan-2-yl | H | ethyl | H | H | chloro | H | H |
| 7-113 | CH₃ | H | 1,1,1,2,3,3,4,4,4-nonafluorobutan-2-yl | H | ethyl | H | H | chloro | H | acetyl |
| 7-114 | CH₃ | H | 1,1,1,2,3,3,4,4,4-nonafluorobutan-2-yl | H | ethyl | H | H | chloro | H | propanoyl |
| 7-115 | CH₃ | H | 1,1,1,2,3,3,4,4,4-nonafluorobutan-2-yl | H | ethyl | H | H | chloro | H | 3,3,3-trifluoropropanoyl |
| 7-116 | CH₃ | H | 1-bromo-1,1,2,3,3,3-hexafluoropropan-2-yl | H | CH₃ | H | H | chloro | H | H |
| 7-117 | CH₃ | H | 1-bromo-1,1,2,3,3,3-hexafluoropropan-2-yl | H | CH₃ | H | H | chloro | H | acetyl |
| 7-118 | CH₃ | H | 1-bromo-1,1,2,3,3,3-hexafluoropropan-2-yl | H | CH₃ | H | H | chloro | H | propanoyl |
| 7-119 | CH₃ | H | 1-bromo-1,1,2,3,3,3-hexafluoropropan-1-2-yl | H | CH₃ | H | H | chloro | H | 3,3,3-trifluoropropanoyl |
| 7-120 | CH₃ | H | 1-bromo-1,1,2,3,3,3-hexafluoropropan-2-yl | H | ethyl | H | H | chloro | H | H |
| 7-121 | CH₃ | H | 1-bromo-1,1,2,3,3,3-hexafluoropropan-2-yl | H | ethyl | H | H | chloro | H | acetyl |
| 7-122 | CH₃ | H | 1-bromo-1,1,2,3,3,3-hexafluoropropan-2-yl | H | ethyl | H | H | chloro | H | propanoyl |
| 7-123 | CH₃ | H | 1-bromo-1,1,2,3,3,3-hexafluoropropan-2-yl | H | ethyl | H | H | chloro | H | 3,3,3-trifluoropropanoyl |
| 7-124 | chloro | H | 1,1,1,2,3,3,3-heptafluoropropan-2-yl | H | difluoromethoxy | H | H | H | H | H |
| 7-125 | chloro | H | 1,1,1,2,3,3,3-heptafluoropropan-2-yl | H | difluoromethoxy | H | H | H | H | acetyl |
| 7-126 | chloro | H | 1,1,1,2,3,3,3-heptafluoropropan-2-yl | H | difluoromethoxy | H | H | H | H | propanoyl |
| 7-127 | chloro | H | 1,1,1,2,3,3,3-heptafluoropropan-2-yl | H | difluoromethoxy | H | H | H | H | 3,3,3-trifluoropropanoyl |
| 7-128 | chloro | H | 1,1,1,2,3,3,4,4,4-nonafluorobutan-2-yl | H | difluoromethoxy | H | H | H | H | H |
| 7-129 | chloro | H | 1,1,1,2,3,3,4,4,4-nonafluorobutan-2-yl | H | difluoromethoxy | H | H | H | H | acetyl |
| 7-130 | chloro | H | 1,1,1,2,3,3,4,4,4-nonafluorobutan-2-yl | H | difluoromethoxy | H | H | H | H | propanoyl |
| 7-131 | chloro | H | 1,1,1,2,3,3,4,4,4-nonafluorobutan-2-yl | H | difluoro-methoxy | H | H | H | H | 3,3,3-trifluoropropanoyl |
| 7-132 | chloro | H | 1-bromo-1,1,2,3,3,3-hexafluoropropan-2-yl | H | difluoromethoxy | H | H | H | H | H |
| 7-133 | chloro | H | 1-bromo-1,1,2,3,3,3-hexafluoropropan-2-yl | H | difluoromethoxy | H | H | H | H | acetyl |
| 7-134 | chloro | H | 1-bromo-1,1,2,3,3,3-hexafluoropropan-2-yl | H | difluoromethoxy | H | H | H | H | propanoyl |
| 7-135 | chloro | H | 1-bromo-1,1,2,3,3,3-hexafluoropropan-2-yl | H | difluoromethoxy | H | H | H | H | 3,3,3-trifluoropropanoyl |

TABLE 8

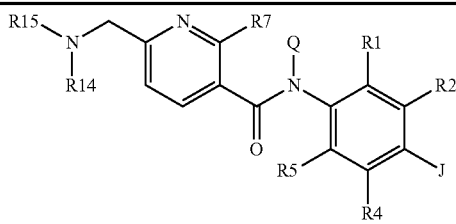

| Exa | R1 | R2 | J | R4 | R5 | Q | R7 | R14 | R15 |
|---|---|---|---|---|---|---|---|---|---|
| 8-1 | CH₃ | H | 1,1,1,2,3,3,3-heptafluoropropan-2-yl | H | ethyl | H | H | H | H |
| 8-2 | CH₃ | H | 1,1,1,2,3,3,3-heptafluoropropan-2-yl | H | ethyl | H | H | H | acetyl |
| 8-3 | CH₃ | H | 1,1,1,2,3,3,3-heptafluoropropan-2-yl | H | ethyl | H | H | H | propanoyl |
| 8-4 | CH₃ | H | 1,1,1,2,3,3,3-heptafluoropropan-2-yl | H | ethyl | H | H | H | cyclopropylcarbonyl |
| 8-5 | CH₃ | H | 1,1,1,2,3,3,3-heptafluoropropan-2-yl | H | ethyl | H | H | H | cyclopropylacetyl |
| 8-6 | CH₃ | H | 1,1,1,2,3,3,3-heptafluoropropan-2-yl | H | ethyl | H | H | H | 3,3,3-trifluoropropanoyl |
| 8-7 | CH₃ | H | 1,1,1,2,3,3,4,4,4-nonafluorobutan-2-yl | H | ethyl | H | H | H | H |
| 8-8 | CH₃ | H | 1,1,1,2,3,3,4,4,4-nonafluorobutan-2-yl | H | ethyl | H | H | H | acetyl |
| 8-9 | CH₃ | H | 1,1,1,2,3,3,4,4,4-nonafluorobutan-2-yl | H | ethyl | H | H | H | propanoyl |

TABLE 8-continued

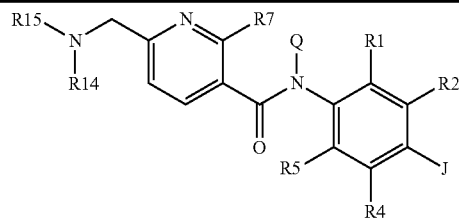

| Exa | R1 | R2 | J | R4 | R5 | Q | R7 | R14 | R15 |
|---|---|---|---|---|---|---|---|---|---|
| 8-10 | CH₃ | H | 1,1,1,2,3,3,4,4,4-nonafluorobutan-2-yl | H | ethyl | H | H | H | cyclopropylcarbonyl |
| 8-11 | CH₃ | H | 1,1,1,2,3,3,4,4,4-nonafluorobutan-2-yl | H | ethyl | H | H | H | cyclopropylacetyl |
| 8-12 | CH₃ | H | 1,1,1,2,3,3,4,4,4-nonafluorobutan-2-yl | H | ethyl | H | H | H | 3,3,3-trifluoropropanoyl |
| 8-13 | CH₃ | H | undecafluorocyclohexyl | H | ethyl | H | H | H | H |
| 8-14 | CH₃ | H | undecafluorocyclohexyl | H | ethyl | H | H | H | acetyl |
| 8-15 | CH₃ | H | undecafluorocyclohexyl | H | ethyl | H | H | H | propanoyl |
| 8-16 | CH₃ | H | undecafluorocyclohexyl | H | ethyl | H | H | H | cyclopropylcarbonyl |
| 8-17 | CH₃ | H | undecafluorocyclohexyl | H | ethyl | H | H | H | cyclopropylacetyl |
| 8-18 | CH₃ | H | undecafluorocyclohexyl | H | ethyl | H | H | H | 3,3,3-trifluoropropanoyl |
| 8-19 | CH₃ | H | 1,1,1,2,3,3,3-heptafluoropropan-2-yl | H | ethyl | H | H | H | tert-butoxycarbonyl |
| 8-20 | CH3 | H | 1-bromo-1,1,2,3,3,3-hexafluoropropan-2-yl | H | CH3 | H | H | H | H |
| 8-21 | CH3 | H | 1-bromo-1,1,2,3,3,3-hexafluoropropan-2-yl | H | CH3 | H | H | H | acetyl |
| 8-22 | CH3 | H | 1-bromo-1,1,2,3,3,3-hexafluoropropan-2-yl | H | CH3 | H | H | H | propanoyl |
| 8-23 | CH3 | H | 1-bromo-1,1,2,3,3,3-hexafluoropropan-2-yl | H | CH3 | H | H | H | 3,3,3-trifluoropropanoyl |
| 8-24 | CH3 | H | 1-bromo-1,1,2,3,3,3-hexafluoropropan-2-yl | H | ethyl | H | H | H | H |
| 8-25 | CH3 | H | 1-bromo-1,1,2,3,3,3-hexafluoropropan-2-yl | H | ethyl | H | H | H | acetyl |
| 8-26 | CH3 | H | 1-bromo-1,1,2,3,3,3-hexafluoropropan-2-yl | H | ethyl | H | H | H | propanoyl |
| 8-27 | CH₃ | H | 1-bromo-1,1,2,3,3,3-hexafluoropropan-2-yl | H | ethyl | H | H | H | 3,3,3-trifluoropropanoyl |
| 8-28 | bromo | H | 1-bromo-1,1,2,3,3,3-hexafluoropropan-2-yl | H | bromo | H | H | H | H |
| 8-29 | bromo | H | 1-bromo-1,1,2,3,3,3-hexafluoropropan-2-yl | H | bromo | H | H | H | acetyl |
| 8-30 | bromo | H | 1-bromo-1,1,2,3,3,3-hexafluoropropan-2-yl | H | bromo | H | H | H | propanoyl |
| 8-31 | bromo | H | 1-bromo-1,1,2,3,3,3-hexafluoropropan-2-yl | H | bromo | H | H | H | 3,3,3-trifluoropropanoyl |
| 8-32 | bromo | H | 1-bromo-1,1,2,3,3,3-hexafluoropropan-2-yl | H | difluoromethoxy | H | H | H | H |
| 8-33 | bromo | H | 1-bromo-1,1,2,3,3,3-hexafluoropropan-2-yl | H | difluoromethoxy | H | H | H | acetyl |
| 8-34 | bromo | H | 1-bromo-1,1,2,3,3,3-hexafluoropropan-2-yl | H | difluoromethoxy | H | H | H | propanoyl |
| 8-35 | bromo | H | 1-bromo-1,1,2,3,3,3-hexafluoropropan-2-yl | H | difluoromethoxy | H | H | H | 3,3,3-trifluoropropanoyl |
| 8-36 | bromo | H | 1,1,1,2,3,3,3-heptafluoropropan-2-yl | H | bromo | H | H | H | H |
| 8-37 | bromo | H | 1,1,1,2,3,3,3-heptafluoropropan-2-yl | H | bromo | H | H | H | acetyl |
| 8-38 | bromo | H | 1,1,1,2,3,3,3-heptafluoropropan-2-yl | H | bromo | H | H | H | propanoyl |
| 8-39 | bromo | H | 1,1,1,2,3,3,3-heptafluoropropan-2-yl | H | bromo | H | H | H | 3,3,3-trifluoropropanoyl |
| 8-40 | bromo | H | 1,1,1,2,3,3,3-heptafluoropropan-2-yl | H | difluoromethoxy | H | H | H | H |
| 8-41 | bromo | H | 1,1,1,2,3,3,3-heptafluoropropan-2-yl | H | difluoromethoxy | H | H | H | acetyl |
| 8-42 | bromo | H | 1,1,1,2,3,3,3-heptafluoropropan-2-yl | H | difluoromethoxy | H | H | H | propanoyl |
| 8-43 | bromo | H | 1,1,1,2,3,3,3-heptafluoropropan-2-yl | H | difluoromethoxy | H | H | H | 3,3,3-trifluoropropanoyl |
| 8-44 | bromo | H | 1,1,1,2,3,3,4,4,4-nonafluorobutan-2-yl | H | bromo | H | H | H | H |
| 8-45 | bromo | H | 1,1,1,2,3,3,4,4,4-nonafluorobutan-2-yl | H | bromo | H | H | H | acetyl |
| 8-46 | bromo | H | 1,1,1,2,3,3,4,4,4-nonafluorobutan-2-yl | H | bromo | H | H | H | propanoyl |
| 8-47 | bromo | H | 1,1,1,2,3,3,4,4,4-nonafluorobutan-2-yl | H | bromo | H | H | H | 3,3,3-trifluoropropanoyl |
| 8-48 | bromo | H | 1,1,1,2,3,3,4,4,4-nonafluorobutan-2-yl | H | difluoromethoxy | H | H | H | H |
| 8-49 | bromo | H | 1,1,1,2,3,3,4,4,4-nonafluorobutan-2-yl | H | difluoromethoxy | H | H | H | acetyl |
| 8-50 | bromo | H | 1,1,1,2,3,3,4,4,4-nonafluorobutan-2-yl | H | difluoromethoxy | H | H | H | propanoyl |
| 8-51 | bromo | H | 1,1,1,2,3,3,4,4,4-nonafluorobutan-2-yl | H | difluoromethoxy | H | H | H | 3,3,3-trifluoropropanoyl |
| 8-52 | CH₃ | H | 1,1,1,2,3,3,3-heptafluoropropan-2-yl | H | difluoromethoxy | H | H | H | H |
| 8-53 | CH₃ | H | 1,1,1,2,3,3,3-heptafluoropropan-2-yl | H | difluoromethoxy | H | H | H | acetyl |
| 8-54 | CH₃ | H | 1,1,1,2,3,3,3-heptafluoropropan-2-yl | H | difluoromethoxy | H | H | H | propanoyl |
| 8-55 | CH₃ | H | 1,1,1,2,3,3,3-heptafluoropropan-2-yl | H | difluoromethoxy | H | H | H | 3,3,3-trifluoropropanoyl |
| 8-56 | CH₃ | H | 1,1,1,2,3,3,4,4,4-nonafluorobutan-2-yl | H | difluoromethoxy | H | H | H | H |
| 8-57 | CH₃ | H | 1,1,1,2,3,3,4,4,4-nonafluorobutan-2-yl | H | difluoromethoxy | H | H | H | acetyl |
| 8-58 | CH₃ | H | 1,1,1,2,3,3,4,4,4-nonafluorobutan-2-yl | H | difluoromethoxy | H | H | H | propanoyl |
| 8-59 | CH₃ | H | 1,1,1,2,3,3,4,4,4-nonafluorobutan-2-yl | H | difluoromethoxy | H | H | H | 3,3,3-trifluoropropanoyl |
| 8-60 | CH₃ | H | 1-bromo-1,1,2,3,3,3-hexafluoropropan-2-yl | H | difluoromethoxy | H | H | H | H |
| 8-61 | CH₃ | H | 1-bromo-1,1,2,3,3,3-hexafluoropropan-2-yl | H | difluoromethoxy | H | H | H | acetyl |
| 8-62 | CH₃ | H | 1-bromo-1,1,2,3,3,3-hexafluoropropan-2-yl | H | difluoromethoxy | H | H | H | propanoyl |
| 8-63 | CH₃ | H | 1-bromo-1,1,2,3,3,3-hexafluoropropan-2-yl | H | difluoromethoxy | H | H | H | 3,3,3-trifluoropropanoyl |
| 8-64 | chloro | H | 1,1,1,2,3,3,3-heptafluoropropan-2-yl | H | difluoromethoxy | H | H | H | H |
| 8-65 | chloro | H | 1,1,1,2,3,3,3-heptafluoropropan-2-yl | H | difluoromethoxy | H | H | H | acetyl |
| 8-66 | chloro | H | 1,1,1,2,3,3,3-heptafluoropropan-2-yl | H | difluoromethoxy | H | H | H | propanoyl |
| 8-67 | chloro | H | 1,1,1,2,3,3,3-heptafluoropropan-2-yl | H | difluoromethoxy | H | H | H | 3,3,3-trifluoropropanoyl |
| 8-68 | chloro | H | 1,1,1,2,3,3,4,4,4-nonafluorobutan-2-yl | H | difluoromethoxy | H | H | H | H |
| 8-69 | chloro | H | 1,1,1,2,3,3,4,4,4-nonafluorobutan-2-yl | H | difluoromethoxy | H | H | H | acetyl |
| 8-70 | chloro | H | 1,1,1,2,3,3,4,4,4-nonafluorobutan-2-yl | H | difluoromethoxy | H | H | H | propanoyl |
| 8-71 | chloro | H | 1,1,1,2,3,3,4,4,4-nonafluorobutan-2-yl | H | difluoromethoxy | H | H | H | 3,3,3-trifluoropropanoyl |
| 8-72 | chloro | H | 1-bromo-1,1,2,3,3,3-hexafluoropropan-2-yl | H | difluoromethoxy | H | H | H | H |
| 8-73 | chloro | H | 1-bromo-1,1,2,3,3,3-hexafluoropropan-2-yl | H | difluoromethoxy | H | H | H | acetyl |
| 8-74 | chloro | H | 1-bromo-1,1,2,3,3,3-hexafluoropropan-2-yl | H | difluoromethoxy | H | H | H | propanoyl |
| 8-75 | chloro | H | 1-bromo-1,1,2,3,3,3-hexafluoropropan-2-yl | H | difluoromethoxy | H | H | H | 3,3,3-trifluoropropanoyl |

TABLE 9

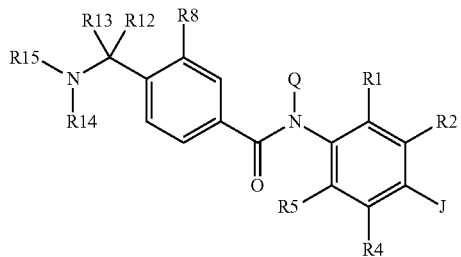

| Exa | R1 | R2 | J | R4 | R5 | Q | R8 | R12 | R13 | R14 | R15 |
|---|---|---|---|---|---|---|---|---|---|---|---|
| 9-1 | $CH_3$ | H | 1,1,1,2,3,3,3-heptafluoropropan-2-yl | H | ethyl | H | H | $CH_3$ | H | H | H |
| 9-2 | $CH_3$ | H | 1,1,1,2,3,3,3-heptafluoropropan-2-yl | H | ethyl | H | H | $CH_3$ | H | H | acetyl |
| 9-3 | $CH_3$ | H | 1,1,1,2,3,3,3-heptafluoropropan-2-yl | H | ethyl | H | H | $CH_3$ | H | H | propanoyl |
| 9-4 | $CH_3$ | H | 1,1,1,2,3,3,3-heptafluoropropan-2-yl | H | ethyl | H | H | $CH_3$ | H | H | cyclopropylcarbonyl |
| 9-5 | $CH_3$ | H | 1,1,1,2,3,3,3-heptafluoropropan-2-yl | H | ethyl | H | H | $CH_3$ | H | H | cyclopropylacetyl |
| 9-6 | $CH_3$ | H | 1,1,1,2,3,3,3-heptafluoropropan-2-yl | H | ethyl | H | H | $CH_3$ | H | H | 3,3,3-trifluoropropanoyl |
| 9-7 | $CH_3$ | H | 1,1,1,2,3,3,3-heptafluoropropan-2-yl | H | ethyl | H | H | $CH_3$ | H | H | tert-butoxycarbonyl |
| 9-8 | $CH_3$ | H | 1,1,1,2,3,3,4,4,4-nonafluorobutan-2-yl | H | ethyl | H | H | $CH_3$ | H | H | H |
| 9-9 | $CH_3$ | H | 1,1,1,2,3,3,4,4,4-nonafluorobutan-2-yl | H | ethyl | H | H | $CH_3$ | H | H | acetyl |
| 9-10 | $CH_3$ | H | 1,1,1,2,3,3,4,4,4-nonafluorobutan-2-yl | H | ethyl | H | H | $CH_3$ | H | H | propanoyl |
| 9-11 | $CH_3$ | H | 1,1,1,2,3,3,4,4,4-nonafluorobutan-2-yl | H | ethyl | H | H | $CH_3$ | H | H | cyclopropylcarbonyl |
| 9-12 | $CH_3$ | H | 1,1,1,2,3,3,4,4,4-nonafluorobutan-2-yl | H | ethyl | H | H | $CH_3$ | H | H | cyclopropylacetyl |
| 9-13 | $CH_3$ | H | 1,1,1,2,3,3,4,4,4-nonafluorobutan-2-yl | H | ethyl | H | H | $CH_3$ | H | H | 3,3,3-trifluoropropanoyl |
| 9-14 | $CH_3$ | H | 1,1,1,2,3,3,4,4,4-nonafluorobutan-2-yl | H | ethyl | H | H | $CH_3$ | H | H | tert-butoxycarbonyl |
| 9-15 | $CH_3$ | H | undecafluorocyclohexyl | H | ethyl | H | H | $CH_3$ | H | H | H |
| 9-16 | $CH_3$ | H | undecafluorocyclohexyl | H | ethyl | H | H | $CH_3$ | H | H | acetyl |
| 9-17 | $CH_3$ | H | undecafluorocyclohexyl | H | ethyl | H | H | $CH_3$ | H | H | propanoyl |
| 9-18 | $CH_3$ | H | undecafluorocyclohexyl | H | ethyl | H | H | $CH_3$ | H | H | cyclopropylcarbonyl |
| 9-19 | $CH_3$ | H | undecafluorocyclohexyl | H | ethyl | H | H | $CH_3$ | H | H | cyclopropylacetyl |
| 9-20 | $CH_3$ | H | undecafluorocyclohexyl | H | ethyl | H | H | $CH_3$ | H | H | 3,3,3-trifluoropropanoyl |
| 9-21 | $CH_3$ | H | undecafluorocyclohexyl | H | ethyl | H | H | $CH_3$ | H | H | tert-butoxycarbonyl |
| 9-22 | $CH_3$ | H | 1-bromo-1,1,2,3,3,3-hexafluoropropan-2-yl | H | $CH_3$ | H | H | $CH_3$ | H | H | H |
| 9-23 | $CH_3$ | H | 1-bromo-1,1,2,3,3,3-hexafluoropropan-2-yl | H | $CH_3$ | H | H | $CH_3$ | H | H | acetyl |
| 9-24 | $CH_3$ | H | 1-bromo-1,1,2,3,3,3-hexafluoropropan-2-yl | H | $CH_3$ | H | H | $CH_3$ | H | H | propanoyl |
| 9-25 | $CH_3$ | H | 1-bromo-1,1,2,3,3,3-hexafluoropropan-2-yl | H | $CH_3$ | H | H | $CH_3$ | H | H | 3,3,3-trifluoropropanoyl |
| 9-26 | $CH_3$ | H | 1-bromo-1,1,2,3,3,3-hexafluoropropan-2-yl | H | ethyl | H | H | $CH_3$ | H | H | H |
| 9-27 | $CH_3$ | H | 1-bromo-1,1,2,3,3,3-hexafluoropropan-2-yl | H | ethyl | H | H | $CH_3$ | H | H | acetyl |
| 9-28 | $CH_3$ | H | 1-bromo-1,1,2,3,3,3-hexafluoropropan-2-yl | H | ethyl | H | H | $CH_3$ | H | H | propanoyl |
| 9-29 | $CH_3$ | H | 1-bromo-1,1,2,3,3,3-hexafluoropropan-2-yl | H | ethyl | H | H | $CH_3$ | H | H | 3,3,3-trifluoropropanoyl |
| 9-30 | bromo | H | 1-bromo-1,1,2,3,3,3-hexafluoropropan-2-yl | H | bromo | H | H | $CH_3$ | H | H | H |
| 9-31 | bromo | H | 1-bromo-1,1,2,3,3,3-hexafluoropropan-2-yl | H | bromo | H | H | $CH_3$ | H | H | acetyl |
| 9-32 | bromo | H | 1-bromo-1,1,2,3,3,3-hexafluoropropan-2-yl | H | bromo | H | H | $CH_3$ | H | H | propanoyl |
| 9-33 | bromo | H | 1-bromo-1,1,2,3,3,3-hexafluoropropan-2-yl | H | bromo | H | H | $CH_3$ | H | H | 3,3,3-trifluoropropanoyl |
| 9-34 | bromo | H | 1-bromo-1,1,2,3,3,3-hexafluoropropan-2-yl | H | difluoromethoxy | H | H | $CH_3$ | H | H | H |
| 9-35 | bromo | H | 1-bromo-1,1,2,3,3,3-hexafluoropropan-2-yl | H | difluoromethoxy | H | H | $CH_3$ | H | H | acetyl |
| 9-36 | bromo | H | 1-bromo-1,1,2,3,3,3-hexafluoropropan-2-yl | H | difluoromethoxy | H | H | $CH_3$ | H | H | propanoyl |
| 9-37 | bromo | H | 1-bromo-1,1,2,3,3,3-hexafluoropropan-2-yl | H | difluoromethoxy | H | H | $CH_3$ | H | H | 3,3,3-trifluoropropanoyl |
| 9-38 | bromo | H | 1,1,1,2,3,3,3-heptafluoropropan-2-yl | H | bromo | H | H | $CH_3$ | H | H | H |
| 9-39 | bromo | H | 1,1,1,2,3,3,3-heptafluoropropan-2-yl | H | bromo | H | H | $CH_3$ | H | H | acetyl |
| 9-40 | bromo | H | 1,1,1,2,3,3,3-heptafluoropropan-2-yl | H | bromo | H | H | $CH_3$ | H | H | propanoyl |
| 9-41 | bromo | H | 1,1,1,2,3,3,3-heptafluoropropan-2-yl | H | bromo | H | H | $CH_3$ | H | H | 3,3,3-trifluoropropanoyl |
| 9-42 | bromo | H | 1,1,1,2,3,3,3-heptafluoropropan-2-yl | H | difluoromethoxy | H | H | $CH_3$ | H | H | H |
| 9-43 | bromo | H | 1,1,1,2,3,3,3-heptafluoropropan-2-yl | H | difluoromethoxy | H | H | $CH_3$ | H | H | acetyl |
| 9-44 | bromo | H | 1,1,1,2,3,3,3-heptafluoropropan-2-yl | H | difluoromethoxy | H | H | $CH_3$ | H | H | propanoyl |
| 9-45 | bromo | H | 1,1,1,2,3,3,3-heptafluoropropan-2-yl | H | difluoromethoxy | H | H | $CH_3$ | H | H | 3,3,3-trifluoropropanoyl |
| 9-46 | bromo | H | 1,1,1,2,3,3,4,4,4-nonafluorobutan-2-yl | H | bromo | H | H | $CH_3$ | H | H | H |
| 9-47 | bromo | H | 1,1,1,2,3,3,4,4,4-nonafluorobutan-2-yl | H | bromo | H | H | $CH_3$ | H | H | acetyl |
| 9-48 | bromo | H | 1,1,1,2,3,3,4,4,4-nonafluorobutan-2-yl | H | bromo | H | H | $CH_3$ | H | H | propanoyl |
| 9-49 | bromo | H | 1,1,1,2,3,3,4,4,4-nonafluorobutan-2-yl | H | bromo | H | H | $CH_3$ | H | H | 3,3,3-trifluoropropanoyl |
| 9-50 | bromo | H | 1,1,1,2,3,3,4,4,4-nonafluorobutan-2-yl | H | difluoromethoxy | H | H | $CH_3$ | H | H | H |
| 9-51 | bromo | H | 1,1,1,2,3,3,4,4,4-nonafluorobutan-2-yl | H | difluoromethoxy | H | H | $CH_3$ | H | H | acetyl |
| 9-52 | bromo | H | 1,1,1,2,3,3,4,4,4-nonafluorobutan-2-yl | H | difluoromethoxy | H | H | $CH_3$ | H | H | propanoyl |
| 9-53 | bromo | H | 1,1,1,2,3,3,4,4,4-nonafluorobutan-2-yl | H | difluoromethoxy | H | H | $CH_3$ | H | H | 3,3,3-trifluoropropanoyl |
| 9-54 | $CH_3$ | H | 1,1,1,2,3,3,3-heptafluoropropan-2-yl | H | difluoromethoxy | H | H | $CH_3$ | H | H | H |
| 9-55 | $CH_3$ | H | 1,1,1,2,3,3,3-heptafluoropropan-2-yl | H | difluoromethoxy | H | H | $CH_3$ | H | H | acetyl |
| 9-56 | $CH_3$ | H | 1,1,1,2,3,3,3-heptafluoropropan-2-yl | H | difluoromethoxy | H | H | $CH_3$ | H | H | propanoyl |
| 9-57 | $CH_3$ | H | 1,1,1,2,3,3,3-heptafluoropropan-2-yl | H | difluoromethoxy | H | H | $CH_3$ | H | H | 3,3,3-trifluoropropanoyl |
| 9-58 | $CH_3$ | H | 1,1,1,2,3,3,4,4,4-nonafluorobutan-2-yl | H | difluoromethoxy | H | H | $CH_3$ | H | H | H |
| 9-59 | $CH_3$ | H | 1,1,1,2,3,3,4,4,4-nonafluorobutan-2-yl | H | difluoromethoxy | H | H | $CH_3$ | H | H | acetyl |
| 9-60 | $CH_3$ | H | 1,1,1,2,3,3,4,4,4-nonafluorobutan-2-yl | H | difluoromethoxy | H | H | $CH_3$ | H | H | propanoyl |
| 9-61 | $CH_3$ | H | 1,1,1,2,3,3,4,4,4-nonafluorobutan-2-yl | H | difluoromethoxy | H | H | $CH_3$ | H | H | 3,3,3-trifluoropropanoyl |
| 9-62 | $CH_3$ | H | 1-bromo-1,1,2,3,3,3-hexafluoropropan-2-yl | H | difluoromethoxy | H | H | $CH_3$ | H | H | H |
| 9-63 | $CH_3$ | H | 1-bromo-1,1,2,3,3,3-hexafluoropropan-2-yl | H | difluoromethoxy | H | H | $CH_3$ | H | H | acetyl |
| 9-64 | $CH_3$ | H | 1-bromo-1,1,2,3,3,3-hexafluoropropan-2-yl | H | difluoromethoxy | H | H | $CH_3$ | H | H | propanoyl |
| 9-65 | $CH_3$ | H | 1-bromo-1,1,2,3,3,3-hexafluoropropan-2-yl | H | difluoromethoxy | H | H | $CH_3$ | H | H | 3,3,3-trifluoropropanoyl |

TABLE 9-continued

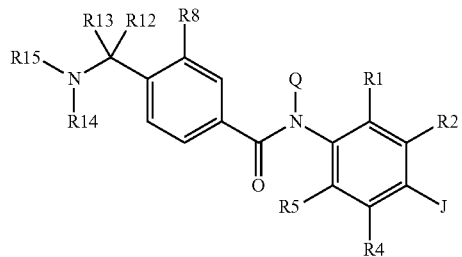

| Exa | R1 | R2 | J | R4 | R5 | Q | R8 | R12 | R13 | R14 | R15 |
|---|---|---|---|---|---|---|---|---|---|---|---|
| 9-66 | chloro | H | 1,1,1,2,3,3,3-heptafluoropropan-2-yl | H | difluoromethoxy | H | H | $CH_3$ | H | H | H |
| 9-67 | chloro | H | 1,1,1,2,3,3,3-heptafluoropropan-2-yl | H | difluoromethoxy | H | H | $CH_3$ | H | H | acetyl |
| 9-68 | chloro | H | 1,1,1,2,3,3,3-heptafluoropropan-2-yl | H | difluoromethoxy | H | H | $CH_3$ | H | H | propanoyl |
| 9-69 | chloro | H | 1,1,1,2,3,3,3-heptafluoropropan-2-yl | H | difluoromethoxy | H | H | $CH_3$ | H | H | 3,3,3-trifluoropropanoyl |
| 9-70 | chloro | H | 1,1,1,2,3,3,4,4,4-nonafluorobutan-2-yl | H | difluoromethoxy | H | H | $CH_3$ | H | H | H |
| 9-71 | chloro | H | 1,1,1,2,3,3,4,4,4-nonafluorobutan-2-yl | H | difluoromethoxy | H | H | $CH_3$ | H | H | acetyl |
| 9-72 | chloro | H | 1,1,1,2,3,3,4,4,4-nonafluorobutan-2-yl | H | difluoromethoxy | H | H | $CH_3$ | H | H | propanoyl |
| 9-73 | chloro | H | 1,1,1,2,3,3,4,4,4-nonafluorobutan-2-yl | H | difluoromethoxy | H | H | $CH_3$ | H | H | 3,3,3-trifluoropropanoyl |
| 9-74 | chloro | H | 1-bromo-1,1,2,3,3,3-hexafluoropropan-2-yl | H | difluoromethoxy | H | H | $CH_3$ | H | H | H |
| 9-75 | chloro | H | 1-bromo-1,1,2,3,3,3-hexafluoropropan-2-yl | H | difluoromethoxy | H | H | $CH_3$ | H | H | acetyl |
| 9-76 | chloro | H | 1-bromo-1,1,2,3,3,3-hexafluoropropan-2-yl | H | difluoromethoxy | H | H | $CH_3$ | H | H | propanoyl |
| 9-77 | chloro | H | 1-bromo-1,1,2,3,3,3-hexafluoropropan-2-yl | H | difluoromethoxy | H | H | $CH_3$ | H | H | 3,3,3-trifluoropropanoyl |

TABLE 10

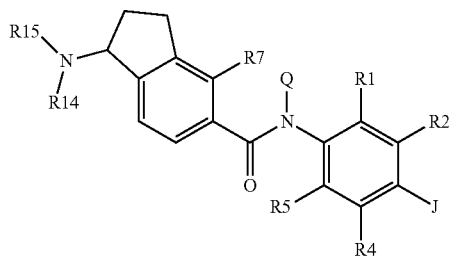

| Exa | R1 | R2 | J | R4 | R5 | Q | R7 | R14 | R15 |
|---|---|---|---|---|---|---|---|---|---|
| 10-1 | $CH_3$ | H | 1,1,1,2,3,3,3-heptafluoropropan-2-yl | H | ethyl | H | H | H | H |
| 10-2 | $CH_3$ | H | 1,1,1,2,3,3,3-heptafluoropropan-2-yl | H | ethyl | H | H | H | acetyl |
| 10-3 | $CH_3$ | H | 1,1,1,2,3,3,3-heptafluoropropan-2-yl | H | ethyl | H | H | H | propanoyl |
| 10-4 | $CH_3$ | H | 1,1,1,2,3,3,3-heptafluoropropan-2-yl | H | ethyl | H | H | H | cyclopropylcarbonyl |
| 10-5 | $CH_3$ | H | 1,1,1,2,3,3,3-heptafluoropropan-2-yl | H | ethyl | H | H | H | cyclopropylacetyl |
| 10-6 | $CH_3$ | H | 1,1,1,2,3,3,3-heptafluoropropan-2-yl | H | ethyl | H | H | H | 3,3,3-trifluoropropanoyl |
| 10-7 | $CH_3$ | H | 1,1,1,2,3,3,3-heptafluoropropan-2-yl | H | ethyl | H | H | H | tert-butoxycarbonyl |
| 10-8 | $CH_3$ | H | 1,1,1,2,3,3,4,4,4-nonafluorobutan-2-yl | H | ethyl | H | H | H | H |
| 10-9 | $CH_3$ | H | 1,1,1,2,3,3,4,4,4-nonafluorobutan-2-yl | H | ethyl | H | H | H | acetyl |
| 10-10 | $CH_3$ | H | 1,1,1,2,3,3,4,4,4-nonafluorobutan-2-yl | H | ethyl | H | H | H | propanoyl |
| 10-11 | $CH_3$ | H | 1,1,1,2,3,3,4,4,4-nonafluorobutan-2-yl | H | ethyl | H | H | H | cyclopropylcarbonyl |
| 10-12 | $CH_3$ | H | 1,1,1,2,3,3,4,4,4-nonafluorobutan-2-yl | H | ethyl | H | H | H | cyclopropylacetyl |
| 10-13 | $CH_3$ | H | 1,1,1,2,3,3,4,4,4-nonafluorobutan-2-yl | H | ethyl | H | H | H | 3,3,3-trifluoropropanoyl |
| 10-14 | $CH_3$ | H | undecafluorocyclohexyl | H | ethyl | H | H | H | tert-butoxycarbonyl |
| 10-15 | $CH_3$ | H | undecafluorocyclohexyl | H | ethyl | H | H | H | H |
| 10-16 | $CH_3$ | H | undecafluorocyclohexyl | H | ethyl | H | H | H | acetyl |
| 10-17 | $CH_3$ | H | undecafluorocyclohexyl | H | ethyl | H | H | H | propanoyl |
| 10-18 | $CH_3$ | H | undecafluorocyclohexyl | H | ethyl | H | H | H | cyclopropylcarbonyl |
| 10-19 | $CH_3$ | H | undecafluorocyclohexyl | H | ethyl | H | H | H | cyclopropylacetyl |
| 10-20 | $CH_3$ | H | undecafluorocyclohexyl | H | ethyl | H | H | H | 3,3,3-trifluoropropanoyl |
| 10-21 | $CH_3$ | H | undecafluorocyclohexyl | H | ethyl | H | H | H | tert-butoxycarbonyl |
| 10-22 | $CH_3$ | H | 1,1,1,2,3,3,3-heptafluoropropan-2-yl | H | ethyl | H | H | H | (methylsulfanyl)acetyl |
| 10-23 | $CH_3$ | H | 1-bromo-1,1,2,3,3,3-hexafluoropropan-2-yl | H | $CH_3$ | H | H | H | H |
| 10-24 | $CH_3$ | H | 1-bromo-1,1,2,3,3,3-hexafluoropropan-2-yl | H | $CH_3$ | H | H | H | acetyl |
| 10-25 | $CH_3$ | H | 1-bromo-1,1,2,3,3,3-hexafluoropropan-2-yl | H | $CH_3$ | H | H | H | propanoyl |
| 10-26 | $CH_3$ | H | 1-bromo-1,1,2,3,3,3-hexafluoropropan-2-yl | H | $CH_3$ | H | H | H | 3,3,3-trifluoropropanoyl |
| 10-27 | $CH_3$ | H | 1-bromo-1,1,2,3,3,3-hexafluoropropan-2-yl | H | ethyl | H | H | H | H |
| 10-28 | $CH_3$ | H | 1-bromo-1,1,2,3,3,3-hexafluoropropan-2-yl | H | ethyl | H | H | H | acetyl |
| 10-29 | $CH_3$ | H | 1-bromo-1,1,2,3,3,3-hexafluoropropan-2-yl | H | ethyl | H | H | H | propanoyl |
| 10-30 | $CH_3$ | H | 1-bromo-1,1,2,3,3,3-hexafluoropropan-2-yl | H | ethyl | H | H | H | 3,3,3-trifluoropropanoyl |
| 10-31 | bromo | H | 1-bromo-1,1,2,3,3,3-hexafluoropropan-2-yl | H | bromo | H | H | H | H |
| 10-32 | bromo | H | 1-bromo-1,1,2,3,3,3-hexafluoropropan-2-yl | H | bromo | H | H | H | acetyl |
| 10-33 | bromo | H | 1-bromo-1,1,2,3,3,3-hexafluoropropan-2-yl | H | bromo | H | H | H | propanoyl |

TABLE 10-continued

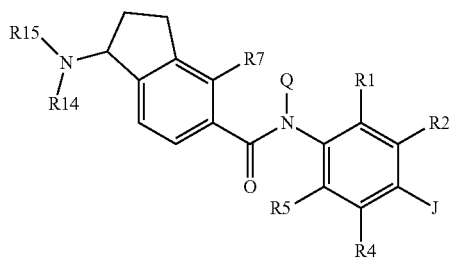

| Exa | R1 | R2 | J | R4 | R5 | Q | R7 | R14 | R15 |
|---|---|---|---|---|---|---|---|---|---|
| 10-34 | bromo | H | 1-bromo-1,1,2,3,3,3-hexafluoropropan-2-yl | H | bromo | H | H | H | 3,3,3-trifluoropropanoyl |
| 10-35 | bromo | H | 1-bromo-1,1,2,3,3,3-hexafluoropropan-2-yl | H | difluoromethoxy | H | H | H | H |
| 10-36 | bromo | H | 1-bromo-1,1,2,3,3,3-hexafluoropropan-2-yl | H | difluoromethoxy | H | H | H | acetyl |
| 10-37 | bromo | H | 1-bromo-1,1,2,3,3,3-hexafluoropropan-2-yl | H | difluoromethoxy | H | H | H | propanoyl |
| 10-38 | bromo | H | 1-bromo-1,1,2,3,3,3-hexafluoropropan-2-yl | H | difluoromethoxy | H | H | H | 3,3,3-trifluoropropanoyl |
| 10-39 | bromo | H | 1,1,1,2,3,3,3-heptafluoropropan-2-yl | H | bromo | H | H | H | H |
| 10-40 | bromo | H | 1,1,1,2,3,3,3-heptafluoropropan-2-yl | H | bromo | H | H | H | acetyl |
| 10-41 | bromo | H | 1,1,1,2,3,3,3-heptafluoropropan-2-yl | H | bromo | H | H | H | propanoyl |
| 10-42 | bromo | H | 1,1,1,2,3,3,3-heptafluoropropan-2-yl | H | bromo | H | H | H | 3,3,3-trifluoropropanoyl |
| 10-43 | bromo | H | 1,1,1,2,3,3,3-heptafluoropropan-2-yl | H | difluoromethoxy | H | H | H | H |
| 10-44 | bromo | H | 1,1,1,2,3,3,3-heptafluoropropan-2-yl | H | difluoromethoxy | H | H | H | acetyl |
| 10-45 | bromo | H | 1,1,1,2,3,3,3-heptafluoropropan-2-yl | H | difluoromethoxy | H | H | H | propanoyl |
| 10-46 | bromo | H | 1,1,1,2,3,3,3-heptafluoropropan-2-yl | H | difluoromethoxy | H | H | H | 3,3,3-trifluoropropanoyl |
| 10-47 | bromo | H | 1,1,1,2,3,3,4,4,4-nonafluorobutan-2-yl | H | bromo | H | H | H | H |
| 10-48 | bromo | H | 1,1,1,2,3,3,4,4,4-nonafluorobutan-2-yl | H | bromo | H | H | H | acetyl |
| 10-49 | bromo | H | 1,1,1,2,3,3,4,4,4-nonafluorobutan-2-yl | H | bromo | H | H | H | propanoyl |
| 10-50 | bromo | H | 1,1,1,2,3,3,4,4,4-nonafluorobutan-2-yl | H | bromo | H | H | H | 3,3,3-trifluoropropanoyl |
| 10-51 | bromo | H | 1,1,1,2,3,3,4,4,4-nonafluorobutan-2-yl | H | difluoromethoxy | H | H | H | H |
| 10-52 | bromo | H | 1,1,1,2,3,3,4,4,4-nonafluorobutan-2-yl | H | difluoromethoxy | H | H | H | acetyl |
| 10-53 | bromo | H | 1,1,1,2,3,3,4,4,4-nonafluorobutan-2-yl | H | difluoromethoxy | H | H | H | propanoyl |
| 10-54 | bromo | H | 1,1,1,2,3,3,4,4,4-nonafluorobutan-2-yl | H | difluoromethoxy | H | H | H | 3,3,3-trifluoropropanoyl |
| 10-55 | CH₃ | H | 1,1,1,2,3,3,3-heptafluoropropan-2-yl | H | difluoromethoxy | H | H | H | H |
| 10-56 | CH₃ | H | 1,1,1,2,3,3,3-heptafluoropropan-2-yl | H | difluoromethoxy | H | H | H | acetyl |
| 10-57 | CH₃ | H | 1,1,1,2,3,3,3-heptafluoropropan-2-yl | H | difluoromethoxy | H | H | H | propanoyl |
| 10-58 | CH₃ | H | 1,1,1,2,3,3,3-heptafluoropropan-2-yl | H | difluoromethoxy | H | H | H | 3,3,3-trifluoropropanoyl |
| 10-59 | CH₃ | H | 1,1,1,2,3,3,4,4,4-nonafluorobutan-2-yl | H | difluoromethoxy | H | H | H | H |
| 10-60 | CH₃ | H | 1,1,1,2,3,3,4,4,4-nonafluorobutan-2-yl | H | difluoromethoxy | H | H | H | acetyl |
| 10-61 | CH₃ | H | 1,1,1,2,3,3,4,4,4-nonafluorobutan-2-yl | H | difluoromethoxy | H | H | H | propanoyl |
| 10-62 | CH₃ | H | 1,1,1,2,3,3,4,4,4-nonafluorobutan-2-yl | H | difluoromethoxy | H | H | H | 3,3,3-trifluoropropanoyl |
| 10-63 | CH₃ | H | 1-bromo-1,1,2,3,3,3-hexafluoropropan-2-yl | H | difluoromethoxy | H | H | H | H |
| 10-64 | CH₃ | H | 1-bromo-1,1,2,3,3,3-hexafluoropropan-2-yl | H | difluoromethoxy | H | H | H | acetyl |
| 10-65 | CH₃ | H | 1-bromo-1,1,2,3,3,3-hexafluoropropan-2-yl | H | difluoromethoxy | H | H | H | propanoyl |
| 10-66 | CH₃ | H | 1-bromo-1,1,2,3,3,3-hexafluoropropan-2-yl | H | difluoromethoxy | H | H | H | 3,3,3-trifluoropropanoyl |
| 10-67 | chloro | H | 1,1,1,2,3,3,3-heptafluoropropan-2-yl | H | difluoromethoxy | H | H | H | H |
| 10-68 | chloro | H | 1,1,1,2,3,3,3-heptafluoropropan-2-yl | H | difluoromethoxy | H | H | H | acetyl |
| 10-69 | chloro | H | 1,1,1,2,3,3,3-heptafluoropropan-2-yl | H | difluoromethoxy | H | H | H | propanoyl |
| 10-70 | chloro | H | 1,1,1,2,3,3,3-heptafluoropropan-2-yl | H | difluoromethoxy | H | H | H | 3,3,3-trifluoropropanoyl |
| 10-71 | chloro | H | 1,1,1,2,3,3,4,4,4-nonafluorobutan-2-yl | H | difluoromethoxy | H | H | H | H |
| 10-72 | chloro | H | 1,1,1,2,3,3,4,4,4-nonafluorobutan-2-yl | H | difluoromethoxy | H | H | H | acetyl |
| 10-73 | chloro | H | 1,1,1,2,3,3,4,4,4-nonafluorobutan-2-yl | H | difluoromethoxy | H | H | H | propanoyl |
| 10-74 | chloro | H | 1,1,1,2,3,3,4,4,4-nonafluorobutan-2-yl | H | difluoromethoxy | H | H | H | 3,3,3-trifluoropropanoyl |
| 10-75 | chloro | H | 1-bromo-1,1,2,3,3,3-hexafluoropropan-2-yl | H | difluoromethoxy | H | H | H | H |
| 10-76 | chloro | H | 1-bromo-1,1,2,3,3,3-hexafluoropropan-2-yl | H | difluoromethoxy | H | H | H | acetyl |
| 10-77 | chloro | H | 1-bromo-1,1,2,3,3,3-hexafluoropropan-2-yl | H | difluoromethoxy | H | H | H | propanoyl |
| 10-78 | chloro | H | 1-bromo-1,1,2,3,3,3-hexafluoropropan-2-yl | H | difluoromethoxy | H | H | H | 3,3,3-trifluoropropanoyl |

TABLE 11

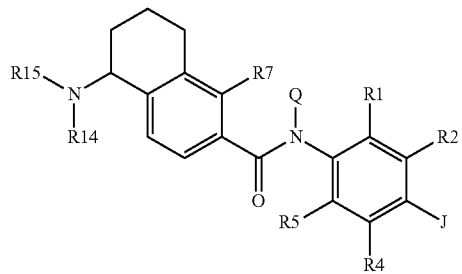

| Exa | R1 | R2 | J | R4 | R5 | Q | R7 | R14 | R15 |
|---|---|---|---|---|---|---|---|---|---|
| 11-1 | CH₃ | H | 1,1,1,2,3,3,3-heptafluoropropan-2-yl | H | ethyl | H | H | H | H |
| 11-2 | CH₃ | H | 1,1,1,2,3,3,3-heptafluoropropan-2-yl | H | ethyl | H | H | H | acetyl |
| 11-3 | CH₃ | H | 1,1,1,2,3,3,3-heptafluoropropan-2-yl | H | ethyl | H | H | H | propanoyl |
| 11-4 | CH₃ | H | 1,1,1,2,3,3,3-heptafluoropropan-2-yl | H | ethyl | H | H | H | cyclopropylcarbonyl |
| 11-5 | CH₃ | H | 1,1,1,2,3,3,3-heptafluoropropan-2-yl | H | ethyl | H | H | H | cyclopropylacetyl |
| 11-6 | CH₃ | H | 1,1,1,2,3,3,3-heptafluoropropan-2-yl | H | ethyl | H | H | H | 3,3,3-trifluoropropanoyl |
| 11-7 | CH₃ | H | 1,1,1,2,3,3,3-heptafluoropropan-2-yl | H | ethyl | H | H | H | tert-butoxycarbonyl |
| 11-8 | CH₃ | H | 1,1,1,2,3,3,4,4,4-nonafluorobutan-2-yl | H | ethyl | H | H | H | H |
| 11-9 | CH₃ | H | 1,1,1,2,3,3,4,4,4-nonafluorobutan-2-yl | H | ethyl | H | H | H | acetyl |
| 11-10 | CH₃ | H | 1,1,1,2,3,3,4,4,4-nonafluorobutan-2-yl | H | ethyl | H | H | H | propanoyl |
| 11-11 | CH₃ | H | 1,1,1,2,3,3,4,4,4-nonafluorobutan-2-yl | H | ethyl | H | H | H | cyclopropylcarbonyl |
| 11-12 | CH₃ | H | 1,1,1,2,3,3,4,4,4-nonafluorobutan-2-yl | H | ethyl | H | H | H | cyclopropylacetyl |
| 11-13 | CH₃ | H | 1,1,1,2,3,3,4,4,4-nonafluorobutan-2-yl | H | ethyl | H | H | H | 3,3,3-trifluoropropanoyl |
| 11-14 | CH₃ | H | 1,1,1,2,3,3,4,4,4-nonafluorobutan-2-yl | H | ethyl | H | H | H | tert-butoxycarbonyl |
| 11-15 | CH₃ | H | undecafluorocyclohexyl | H | ethyl | H | H | H | H |
| 11-16 | CH₃ | H | undecafluorocyclohexyl | H | ethyl | H | H | H | acetyl |
| 11-17 | CH₃ | H | undecafluorocyclohexyl | H | ethyl | H | H | H | propanoyl |
| 11-18 | CH₃ | H | undecafluorocyclohexyl | H | ethyl | H | H | H | cyclopropylcarbonyl |
| 11-19 | CH₃ | H | undecafluorocyclohexyl | H | ethyl | H | H | H | cyclopropylacetyl |
| 11-20 | CH₃ | H | undecafluorocyclohexyl | H | ethyl | H | H | H | 3,3,3-trifluoropropanoyl |
| 11-21 | CH₃ | H | undecafluorocyclohexyl | H | ethyl | H | H | H | tert-butoxycarbonyl |
| 11-22 | CH₃ | H | 1-bromo-1,1,2,3,3,3-hexafluoropropan-2-yl | H | CH₃ | H | H | H | H |
| 11-23 | CH₃ | H | 1-bromo-1,1,2,3,3,3-hexafluoropropan-2-yl | H | CH₃ | H | H | H | acetyl |
| 11-24 | CH₃ | H | 1-bromo-1,1,2,3,3,3-hexafluoropropan-2-yl | H | CH₃ | H | H | H | propanoyl |
| 11-25 | CH₃ | H | 1-bromo-1,1,2,3,3,3-hexafluoropropan-2-yl | H | CH₃ | H | H | H | 3,3,3-trifluoropropanoyl |
| 11-26 | CH₃ | H | 1-bromo-1,1,2,3,3,3-hexafluoropropan-2-yl | H | ethyl | H | H | H | H |
| 11-27 | CH₃ | H | 1-bromo-1,1,2,3,3,3-hexafluoropropan-2-yl | H | ethyl | H | H | H | acetyl |
| 11-28 | CH₃ | H | 1-bromo-1,1,2,3,3,3-hexafluoropropan-2-yl | H | ethyl | H | H | H | propanoyl |
| 11-29 | CH₃ | H | 1-bromo-1,1,2,3,3,3-hexafluoropropan-2-yl | H | ethyl | H | H | H | 3,3,3-trifluoropropanoyl |
| 11-30 | bromo | H | 1-bromo-1,1,2,3,3,3-hexafluoropropan-2-yl | H | bromo | H | H | H | H |
| 11-31 | bromo | H | 1-bromo-1,1,2,3,3,3-hexafluoropropan-2-yl | H | bromo | H | H | H | acetyl |
| 11-32 | bromo | H | 1-bromo-1,1,2,3,3,3-hexafluoropropan-2-yl | H | bromo | H | H | H | propanoyl |
| 11-33 | bromo | H | 1-bromo-1,1,2,3,3,3-hexafluoropropan-2-yl | H | bromo | H | H | H | 3,3,3-trifluoropropanoyl |
| 11-34 | bromo | H | 1-bromo-1,1,2,3,3,3-hexafluoropropan-2-yl | H | difluoromethoxy | H | H | H | H |
| 11-35 | bromo | H | 1-bromo-1,1,2,3,3,3-hexafluoropropan-2-yl | H | difluoromethoxy | H | H | H | acetyl |
| 11-36 | bromo | H | 1-bromo-1,1,2,3,3,3-hexafluoropropan-2-yl | H | difluoromethoxy | H | H | H | propanoyl |
| 11-37 | bromo | H | 1-bromo-1,1,2,3,3,3-hexafluoropropan-2-yl | H | difluoromethoxy | H | H | H | 3,3,3-trifluoropropanoyl |
| 11-38 | bromo | H | 1,1,1,2,3,3,3-heptafluoropropan-2-yl | H | bromo | H | H | H | H |
| 11-39 | bromo | H | 1,1,1,2,3,3,3-heptafluoropropan-2-yl | H | bromo | H | H | H | acetyl |
| 11-40 | bromo | H | 1,1,1,2,3,3,3-heptafluoropropan-2-yl | H | bromo | H | H | H | propanoyl |
| 11-41 | bromo | H | 1,1,1,2,3,3,3-heptafluoropropan-2-yl | H | bromo | H | H | H | 3,3,3-trifluoropropanoyl |
| 11-42 | bromo | H | 1,1,1,2,3,3,3-heptafluoropropan-2-yl | H | difluoromethoxy | H | H | H | H |
| 11-43 | bromo | H | 1,1,1,2,3,3,3-heptafluoropropan-2-yl | H | difluoromethoxy | H | H | H | acetyl |
| 11-44 | bromo | H | 1,1,1,2,3,3,3-heptafluoropropan-2-yl | H | difluoromethoxy | H | H | H | propanoyl |
| 11-45 | bromo | H | 1,1,1,2,3,3,3-heptafluoropropan-2-yl | H | difluoromethoxy | H | H | H | 3,3,3-trifluoropropanoyl |
| 11-46 | bromo | H | 1,1,1,2,3,3,4,4,4-nonafluorobutan-2-yl | H | bromo | H | H | H | H |
| 11-47 | bromo | H | 1,1,1,2,3,3,4,4,4-nonafluorobutan-2-yl | H | bromo | H | H | H | acetyl |
| 11-48 | bromo | H | 1,1,1,2,3,3,4,4,4-nonafluorobutan-2-yl | H | bromo | H | H | H | propanoyl |
| 11-49 | bromo | H | 1,1,1,2,3,3,4,4,4-nonafluorobutan-2-yl | H | bromo | H | H | H | 3,3,3-trifluoropropanoyl |
| 11-50 | bromo | H | 1,1,1,2,3,3,4,4,4-nonafluorobutan-2-yl | H | difluoromethoxy | H | H | H | H |
| 11-51 | bromo | H | 1,1,1,2,3,3,4,4,4-nonafluorobutan-2-yl | H | difluoromethoxy | H | H | H | acetyl |
| 11-52 | bromo | H | 1,1,1,2,3,3,4,4,4-nonafluorobutan-2-yl | H | difluoromethoxy | H | H | H | propanoyl |
| 11-53 | bromo | H | 1,1,1,2,3,3,4,4,4-nonafluorobutan-2-yl | H | difluoromethoxy | H | H | H | 3,3,3-trifluoropropanoyl |
| 11-54 | CH₃ | H | 1,1,1,2,3,3,3-heptafluoropropan-2-yl | H | difluoromethoxy | H | H | H | H |
| 11-55 | CH₃ | H | 1,1,1,2,3,3,3-heptafluoropropan-2-yl | H | difluoromethoxy | H | H | H | acetyl |
| 11-56 | CH₃ | H | 1,1,1,2,3,3,3-heptafluoropropan-2-yl | H | difluoromethoxy | H | H | H | propanoyl |
| 11-57 | CH₃ | H | 1,1,1,2,3,3,3-heptafluoropropan-2-yl | H | difluoromethoxy | H | H | H | 3,3,3-trifluoropropanoyl |
| 11-58 | CH₃ | H | 1,1,1,2,3,3,4,4,4-nonafluorobutan-2-yl | H | difluoromethoxy | H | H | H | H |
| 11-59 | CH₃ | H | 1,1,1,2,3,3,4,4,4-nonafluorobutan-2-yl | H | difluoromethoxy | H | H | H | acetyl |
| 11-60 | CH₃ | H | 1,1,1,2,3,3,4,4,4-nonafluorobutan-2-yl | H | difluoromethoxy | H | H | H | propanoyl |
| 11-61 | CH₃ | H | 1,1,1,2,3,3,4,4,4-nonafluorobutan-2-yl | H | difluoromethoxy | H | H | H | 3,3,3-trifluoropropanoyl |
| 11-62 | CH₃ | H | 1-bromo-1,1,2,3,3,3-hexafluoropropan-2-yl | H | difluoromethoxy | H | H | H | H |
| 11-63 | CH₃ | H | 1-bromo-1,1,2,3,3,3-hexafluoropropan-2-yl | H | difluoromethoxy | H | H | H | acetyl |
| 11-64 | CH₃ | H | 1-bromo-1,1,2,3,3,3-hexafluoropropan-2-yl | H | difluoromethoxy | H | H | H | propanoyl |

TABLE 11-continued

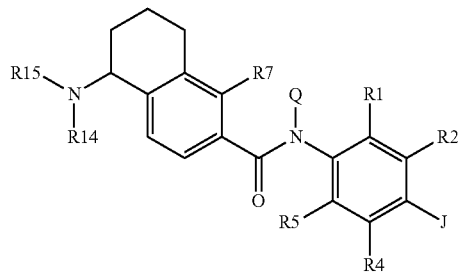

| Exa | R1 | R2 | J | R4 | R5 | Q | R7 | R14 | R15 |
|---|---|---|---|---|---|---|---|---|---|
| 11-65 | CH₃ | H | 1-bromo-1,1,2,3,3,3-hexafluoropropan-2-yl | H | difluoromethoxy | H | H | H | 3,3,3-trifluoropropanoyl |
| 11-66 | chloro | H | 1,1,1,2,3,3,3-heptafluoropropan-2-yl | H | difluoromethoxy | H | H | H | H |
| 11-67 | chloro | H | 1,1,1,2,3,3,3-heptafluoropropan-2-yl | H | difluoromethoxy | H | H | H | acetyl |
| 11-68 | chloro | H | 1,1,1,2,3,3,3-heptafluoropropan-2-yl | H | difluoromethoxy | H | H | H | propanoyl |
| 11-69 | chloro | H | 1,1,1,2,3,3,3-heptafluoropropan-2-yl | H | difluoromethoxy | H | H | H | 3,3,3-trifluoropropanoyl |
| 11-70 | chloro | H | 1,1,1,2,3,3,4,4,4-nonafluorobutan-2-yl | H | difluoromethoxy | H | H | H | H |
| 11-71 | chloro | H | 1,1,1,2,3,3,4,4,4-nonafluorobutan-2-yl | H | difluoromethoxy | H | H | H | acetyl |
| 11-72 | chloro | H | 1,1,1,2,3,3,4,4,4-nonafluorobutan-2-yl | H | difluoromethoxy | H | H | H | propanoyl |
| 11-73 | chloro | H | 1,1,1,2,3,3,4,4,4-nonafluorobutan-2-yl | H | difluoromethoxy | H | H | H | 3,3,3-trifluoropropanoyl |
| 11-74 | chloro | H | 1-bromo-1,1,2,3,3,3-hexafluoropropan-2-yl | H | difluoromethoxy | H | H | H | H |
| 11-75 | chloro | H | 1-bromo-1,1,2,3,3,3-hexafluoropropan-2-yl | H | difluoromethoxy | H | H | H | acetyl |
| 11-76 | chloro | H | 1-bromo-1,1,2,3,3,3-hexafluoropropan-2-yl | H | difluoromethoxy | H | H | H | propanoyl |
| 11-77 | chloro | H | 1-bromo-1,1,2,3,3,3-hexafluoropropan-2-yl | H | difluoromethoxy | H | H | H | 3,3,3-trifluoropropanoyl |

TABLE 12

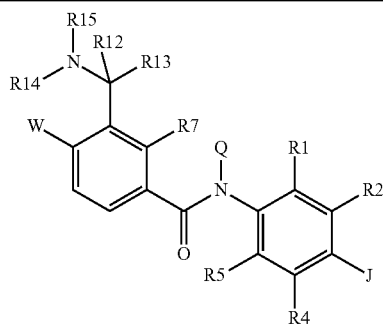

| Exa | R1 | R2 | J | R4 | R5 | Q | R7 | R12 | R13 | R14 | R15 | W |
|---|---|---|---|---|---|---|---|---|---|---|---|---|
| 12-1 | CH₃ | H | 1,1,1,2,3,3,3-heptafluoropropan-2-yl | H | ethyl | H | H | H | H | H | tert-butoxycarbonyl | 1H-1,2,4-triazol-1-yl |
| 12-2 | CH₃ | H | 1,1,1,2,3,3,3-heptafluoropropan-2-yl | H | ethyl | H | H | H | H | H | H | 1H-1,2,4-triazol-1-yl |
| 12-3 | CH₃ | H | 1,1,1,2,3,3,3-heptafluoropropan-2-yl | H | ethyl | H | H | H | H | H | acetyl | 1H-1,2,4-triazol-1-yl |
| 12-4 | CH₃ | H | 1,1,1,2,3,3,3-heptafluoropropan-2-yl | H | ethyl | H | H | H | H | H | propionyl | 1H-1,2,4-triazol-1-yl |
| 12-5 | CH₃ | H | 1,1,1,2,3,3,3-heptafluoropropan-2-yl | H | ethyl | H | H | H | H | H | methoxycarbonyl | 1H-1,2,4-triazol-1-yl |
| 12-6 | CH₃ | H | 1,1,1,2,3,3,4,4,4-nonafluorobutan-2-yl | H | ethyl | H | H | H | H | H | tert-butoxycarbonyl | 1H-1,2,4-triazol-1-yl |
| 12-7 | CH₃ | H | 1,1,1,2,3,3,4,4,4-nonafluorobutan-2-yl | H | ethyl | H | H | H | H | H | H | 1H-1,2,4-triazol-1-yl |
| 12-8 | CH₃ | H | 1,1,1,2,3,3,4,4,4-nonafluorobutan-2-yl | H | ethyl | H | H | H | H | H | acetyl | 1H-1,2,4-triazol-1-yl |
| 12-9 | CH₃ | H | 1,1,1,2,3,3,4,4,4-nonafluorobutan-2-yl | H | ethyl | H | H | H | H | H | propionyl | 1H-1,2,4-triazol-1-yl |
| 12-10 | CH₃ | H | 1,1,1,2,3,3,4,4,4-nonafluorobutan-2-yl | H | ethyl | H | H | H | H | H | methoxycarbonyl | 1H-1,2,4-triazol-1-yl |
| 12-11 | CH₃ | H | 1-bromo-1,1,2,3,3,3-hexafluoropropan-2-yl | H | ethyl | H | H | H | H | H | tert-butoxycarbonyl | 1H-1,2,4-triazol-1-yl |
| 12-12 | CH₃ | H | 1-bromo-1,1,2,3,3,3-hexafluoropropan-2-yl | H | ethyl | H | H | H | H | H | H | 1H-1,2,4-triazol-1-yl |
| 12-13 | CH₃ | H | 1-bromo-1,1,2,3,3,3-hexafluoropropan-2-yl | H | ethyl | H | H | H | H | H | acetyl | 1H-1,2,4-triazol-1-yl |

TABLE 12-continued

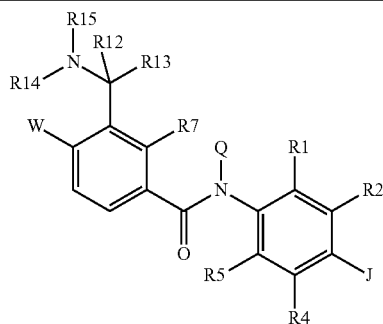

| Exa | R1 | R2 | J | R4 | R5 | Q | R7 | R12 | R13 | R14 | R15 | W |
|---|---|---|---|---|---|---|---|---|---|---|---|---|
| 12-14 | CH₃ | H | 1-bromo-1,1,2,3,3,3-hexafluoropropan-2-yl | H | ethyl | H | H | H | H | H | propionyl | 1H-1,2,4-triazol-1-yl |
| 12-15 | CH₃ | H | 1-bromo-1,1,2,3,3,3-hexafluoropropan-2-yl | H | ethyl | H | H | H | H | H | methoxycarbonyl | 1H-1,2,4-triazol-1-yl |

TABLE 13

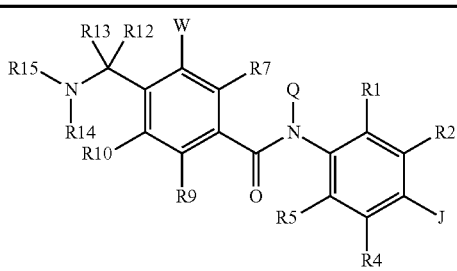

| Exa | R1 | R2 | J | R4 | R5 | Q | R7 | W | R9 | R10 | R12 | R13 | R14 | R15 |
|---|---|---|---|---|---|---|---|---|---|---|---|---|---|---|
| 13-1 | CH₃ | H | 1,1,1,2,3,3,3-heptafluoropropan-2-yl | H | ethyl | H | H | 1H-pyrazol-1-yl | H | H | H | H | H | propanoyl |
| 13-2 | CH₃ | H | 1,1,1,2,3,3,3-heptafluoropropan-2-yl | H | ethyl | H | H | 1H-1,2,4-triazol-1-yl | H | H | H | H | H | acetyl |
| 13-3 | CH₃ | H | 1,1,1,2,3,3,3-heptafluoropropan-2-yl | H | ethyl | H | H | 1H-1,2,4-triazol-1-yl | H | H | H | H | H | propanoyl |

TABLE 14

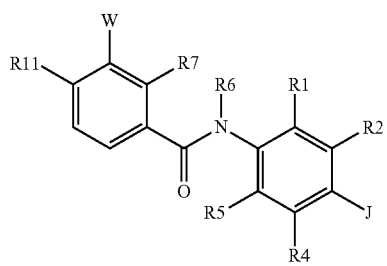

| Exa | R1 | R2 | J | R4 | R5 | Q | R7 | W | R11 |
|---|---|---|---|---|---|---|---|---|---|
| 14-1 | CH₃ | H | 1,1,1,2,3,3,3-heptafluoropropan-2-yl | H | ethyl | H | H | 1H-pyrazol-1-yl | cyano |
| 14-2 | CH₃ | H | 1,1,1,2,3,3,3-heptafluoropropan-2-yl | H | ethyl | H | H | 1H-1,2,4-triazol-1-yl | cyano |

TABLE A

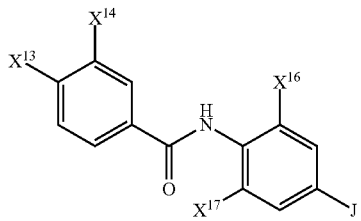

| Exa | $X^{16}$ | J | $X^{17}$ | $X^{14}$ | $X^{13}$ |
|---|---|---|---|---|---|
| A-1 | $CH_3$ | 1,1,1,2,3,3,3-heptafluoropropan-2-yl | $CH_3$ | trifluoromethyl | fluoro |
| A-2 | $CH_3$ | 1,1,1,2,3,3,3-heptafluoropropan-2-yl | ethyl | fluoro | fluoro |
| A-3 | $CH_3$ | 1,1,1,2,3,3,3-heptafluoropropan-2-yl | $CH_3$ | chloro | fluoro |
| A-4 | $CH_3$ | 1,1,1,2,3,3,3-heptafluoropropan-2-yl | ethyl | bromo | fluoro |
| A-5 | $CH_3$ | 1,1,1,2,3,3,3-heptafluoropropan-2-yl | ethyl | trifluoromethyl | fluoro |
| A-6 | chloro | 1,1,1,2,3,3,3-heptafluoropropan-2-yl | chloro | H | iodo |
| A-7 | chloro | 1,1,1,2,3,3,3-heptafluoropropan-2-yl | chloro | chloro | iodo |
| A-8 | bromo | 1,1,1,2,3,3,3-heptafluoropropan-2-yl | bromo | H | iodo |
| A-9 | chloro | 1,1,1,2,3,3,3-heptafluoropropan-2-yl | chloro | $CH_3$ | iodo |
| A-10 | chloro | 1,1,1,2,3,3,3,4,4,4-nonafluorobutan-2-yl | chloro | chloro | iodo |
| A-11 | $CH_3$ | 1,1,1,2,3,3,3-heptafluoropropan-2-yl | chloro | chloro | iodo |

TABLE B

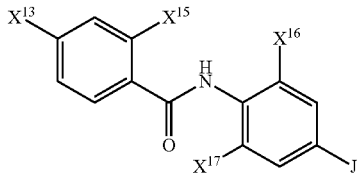

| Exa | $X^{16}$ | J | $X^{17}$ | $X^{15}$ | $X^{13}$ |
|---|---|---|---|---|---|
| B-1 | $CH_3$ | 1,1,1,2,3,3,3-heptafluoropropan-2-yl | $CH_3$ | chloro | fluoro |
| B-2 | $CH_3$ | 1,1,1,2,3,3,3-heptafluoropropan-2-yl | $CH_3$ | trifluoromethyl | fluoro |
| B-3 | $CH_3$ | 1,1,1,2,3,3,3-heptafluoropropan-2-yl | $CH_3$ | nitro | fluoro |

TABLE C

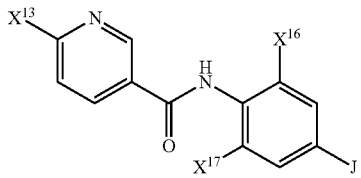

| Exa | $X^{16}$ | J | $X^{17}$ | $X^{13}$ |
|---|---|---|---|---|
| C-1 | $CH_3$ | 1,1,1,2,3,3,3-heptafluoropropan-2-yl | $CH_3$ | chloro |
| C-2 | $CH_3$ | 1,1,1,2,3,3,3-heptafluoropropan-2-yl | ethyl | chloro |
| C-3 | $CH_3$ | 1,1,1,2,3,3,4,4,4-nonafluorobutan-2-yl | ethyl | chloro |
| C-4 | $CH_3$ | 1-bromo-1,1,2,3,3,3-hexafluoropropan-2-yl | ethyl | chloro |

TABLE D

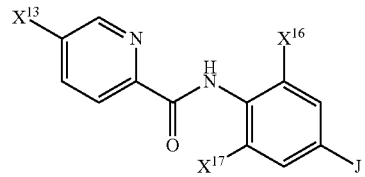

| Exa | $X^{16}$ | J | $X^{17}$ | $X^{13}$ |
|---|---|---|---|---|
| D-1 | $CH_3$ | 1,1,1,2,3,3,3-heptafluoropropan-2-yl | ethyl | bromo |
| D-2 | $CH_3$ | 1,1,1,2,3,3,4,4,4-nonafluorobutan-2-yl | $CH_3$ | bromo |
| D-3 | $CH_3$ | 1,1,1,2,3,3,4,4,4-nonafluorobutan-2-yl | ethyl | bromo |
| D-4 | $CH_3$ | 1-bromo-1,1,2,3,3,3-hexafluoropropan-2-yl | $CH_3$ | bromo |
| D-5 | $CH_3$ | 1-bromo-1,1,2,3,3,3-hexafluoropropan-2-yl | ethyl | bromo |

TABLE E

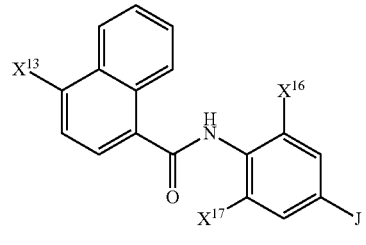

| Exa | $X^{16}$ | J | $X^{17}$ | $X^{13}$ |
|---|---|---|---|---|
| E-1 | $CH_3$ | 1,1,1,2,3,3,3-heptafluoropropan-2-yl | ethyl | fluoro |

TABLE F

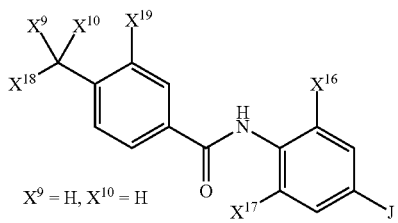

$X^9 = H, X^{10} = H$

| Exa | $X^{16}$ | J | $X^{17}$ | $X^{19}$ | $X^{18}$ |
|---|---|---|---|---|---|
| F-1 | CH₃ | 1,1,1,2,3,3,3-heptafluoropropan-2-yl | CH₃ | H | chloro |
| F-2 | CH₃ | 1,1,1,2,3,3,3-heptafluoropropan-2-yl | CH₃ | H | 1,3-dioxo-1,3-dihydro-2H-isoindol-2-yl |
| F-3 | CH₃ | 1,1,1,2,3,3,3-heptafluoropropan-2-yl | ethyl | H | chloro |
| F-4 | CH₃ | 1,1,1,2,3,3,3-heptafluoropropan-2-yl | ethyl | H | 1,3-dioxo-1,3-dihydro-2H-isoindol-2-yl |
| F-5 | CH₃ | 1,1,1,2,3,3,3-heptafluoropropan-2-yl | ethyl | chloro | chloro |
| F-6 | CH₃ | 1,1,1,2,3,3,3-heptafluoropropan-2-yl | ethyl | chloro | 1,3-dioxo-1,3-dihydro-2H-isoindol-2-yl |
| F-7 | CH₃ | 1,1,1,2,3,3,3-heptafluoropropan-2-yl | ethyl | bromo | chloro |
| F-8 | CH₃ | 1,1,1,2,3,3,3-heptafluoropropan-2-yl | ethyl | bromo | 1,3-dioxo-1,3-dihydro-2H-isoindol-2-yl |
| F-9 | CH₃ | 1,1,1,2,3,3,3-heptafluoropropan-2-yl | ethyl | nitro | 1,3-dioxo-1,3-dihydro-2H-isoindol-2-yl |
| F-10 | CH₃ | 1,1,1,2,3,3,4,4,4-nonafluorobutan-2-yl | ethyl | H | chloro |
| F-11 | CH₃ | 1,1,1,2,3,3,4,4,4-nonafluorobutan-2-yl | ethyl | H | 1,3-dioxo-1,3-dihydro-2H-isoindol-2-yl |
| F-12 | CH₃ | 1,1,1,2,3,3,4,4,4-nonafluorobutan-2-yl | ethyl | fluoro | chloro |
| F-13 | CH₃ | 1,1,1,2,3,3,4,4,4-nonafluorobutan-2-yl | ethyl | fluoro | 1,3-dioxo-1,3-dihydro-2H-isoindol-2-yl |
| F-14 | CH₃ | 1,1,1,2,3,3,4,4,4-nonafluorobutan-2-yl | ethyl | chloro | chloro |
| F-15 | CH₃ | 1,1,1,2,3,3,4,4,4-nonafluorobutan-2-yl | ethyl | chloro | 1,3-dioxo-1,3-dihydro-2H-isoindol-2-yl |
| F-16 | CH₃ | 1,1,1,2,3,3,4,4,4-nonafluorobutan-2-yl | ethyl | bromo | 1,3-dioxo-1,3-dihydro-2H-isoindol-2-yl |
| F-17 | CH₃ | 1,1,1,2,3,3,3-heptafluoropropan-2-yl | ethyl | iodo | 1,3-dioxo-1,3-dihydro-2H-isoindol-2-yl |
| F-18 | CH₃ | 1-bromo-1,1,2,3,3,3-hexafluoropropan-2-yl | ethyl | chloro | chloro |
| F-19 | CH₃ | 1-bromo-1,1,2,3,3,3-hexafluoropropan-2-yl | ethyl | chloro | 1,3-dioxo-1,3-dihydro-2H-isoindol-2-yl |

TABLE G

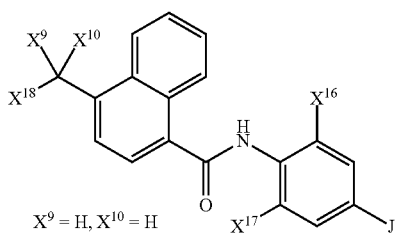

$X^9 = H, X^{10} = H$

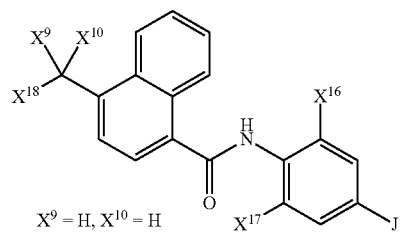

$X^9 = H, X^{10} = H$

| Exa | $X^{16}$ | J | $X^{17}$ | $X^{18}$ |
|---|---|---|---|---|
| G-1 | CH₃ | 1,1,1,2,3,3,3-heptafluoropropan-2-yl | ethyl | chloro |
| G-2 | CH₃ | 1,1,1,2,3,3,3-heptafluoropropan-2-yl | ethyl | 1,3-dioxo-1,3-dihydro-2H-isoindol-2-yl |
| G-3 | CH₃ | 1,1,1,2,3,3,4,4,4-nonafluorobutan-2-yl | ethyl | chloro |
| G-4 | CH₃ | 1,1,1,2,3,3,4,4,4-nonafluorobutan-2-yl | ethyl | 1,3-dioxo-1,3-dihydro-2H-isoindol-2-yl |
| G-5 | CH₃ | 1-bromo-1,1,2,3,3,3-hexafluoropropan-2-yl | ethyl | chloro |
| G-6 | CH₃ | 1-bromo-1,1,2,3,3,3-hexafluoropropan-2-yl | ethyl | 1,3-dioxo-1,3-dihydro-2H-isoindol-2-yl |

TABLE H

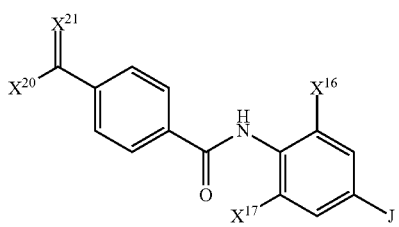

| Exa | $X^{16}$ | J | $X^{17}$ | $X^{20}$ | $X^{21}$ |
|---|---|---|---|---|---|
| H-1 | $CH_3$ | 1,1,1,2,3,3,3-heptafluoropropan-2-yl | ethyl | $CH_3$ | O |
| H-2 | $CH_3$ | 1,1,1,2,3,3,3-heptafluoropropan-2-yl | ethyl | $CH_3$ | N(OH) |
| H-3 | $CH_3$ | 1,1,1,2,3,3,4,4,4-nonafluorobutan-2-yl | ethyl | $CH_3$ | O |
| H-4 | $CH_3$ | 1,1,1,2,3,3,4,4,4-nonafluorobutan-2-yl | ethyl | $CH_3$ | N(OH) |

TABLE H-continued

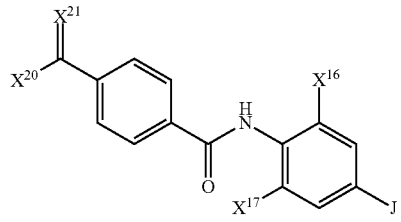

| Exa | $X^{16}$ | J | $X^{17}$ | $X^{20}$ | $X^{21}$ |
|---|---|---|---|---|---|
| H-5 | $CH_3$ | 1-bromo-1,1,2,3,3,3-hexafluoropropan-2-yl | ethyl | $CH_3$ | O |
| H-6 | $CH_3$ | 1-bromo-1,1,2,3,3,3-hexafluoropropan-2-yl | ethyl | $CH_3$ | N(OH) |

TABLE I

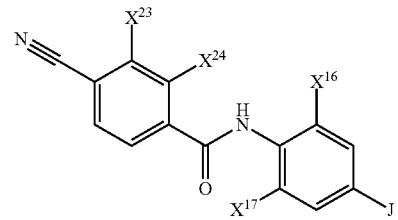

| Exa | $X^{16}$ | J | $X^{17}$ | $X^{24}$ | $X^{23}$ |
|---|---|---|---|---|---|
| I-1 | $CH_3$ | 1,1,1,2,3,3,3-heptafluoropropan-2-yl | $CH_3$ | fluoro | H |
| I-2 | $CH_3$ | 1,1,1,2,3,3,3-heptafluoropropan-2-yl | ethyl | H | H |
| I-3 | $CH_3$ | 1,1,1,2,3,3,3-heptafluoropropan-2-yl | ethyl | fluoro | H |
| I-4 | $CH_3$ | 1,1,1,2,3,3,3-heptafluoropropan-2-yl | ethyl | chloro | H |
| I-5 | $CH_3$ | 1,1,1,2,3,3,3-heptafluoropropan-2-yl | ethyl | H | methyl |
| I-6 | $CH_3$ | 1,1,1,3,3,3-hexafluoro-2-hydroxypropan-2-yl | ethyl | H | H |
| I-7 | $CH_3$ | 1,1,1,3,3,3-hexafluoro-2-[(methylsulfonyl)oxy]propan-2-yl | ethyl | H | H |
| I-8 | $CH_3$ | 1,1,1,2,3,3,4,4,4-nonafluorobutan-2-yl | ethyl | H | H |
| I-9 | $CH_3$ | 1,1,1,2,3,3,4,4,4-nonafluorobutan-2-yl | ethyl | H | H |
| I-10 | $CH_3$ | 1-bromo-1,1,2,3,3,3-hexafluoropropan-2-yl | ethyl | H | H |
| I-11 | $CH_3$ | 1-bromo-1,1,2,3,3,3-hexafluoropropan-2-yl | ethyl | H | H |
| I-12 | $CH_3$ | 1,1,1,2,3,3,3-heptafluoropropan-2-yl | difluoromethoxy | chloro | H |
| I-13 | $CH_3$ | 1,1,1,2,3,3,4,4,4-nonafluorobutan-2-yl | difluoromethoxy | chloro | H |
| I-14 | $CH_3$ | 1-bromo-1,1,2,3,3,3-hexafluoropropan-2-yl | difluoromethoxy | chloro | H |
| I-15 | chloro | 1,1,1,2,3,3,3-heptafluoropropan-2-yl | difluoromethoxy | chloro | H |
| I-16 | chloro | 1,1,1,2,3,3,4,4,4-nonafluorobutan-2-yl | difluoromethoxy | chloro | H |
| I-17 | chloro | 1-bromo-1,1,2,3,3,3-hexafluoropropan-2-yl | difluoromethoxy | chloro | H |
| I-18 | bromo | 1,1,1,2,3,3,3-heptafluoropropan-2-yl | difluoromethoxy | chloro | H |
| I-19 | bromo | 1,1,1,2,3,3,4,4,4-nonafluorobutan-2-yl | difluoromethoxy | chloro | H |
| I-20 | bromo | 1-bromo-1,1,2,3,3,3-hexafluoropropan-2-yl | difluoromethoxy | chloro | H |
| I-21 | $CH_3$ | 1-bromo-1,1,2,3,3,3-hexafluoropropan-2-yl | $CH_3$ | chloro | H |
| I-22 | chloro | 1-bromo-1,1,2,3,3,3-hexafluoropropan-2-yl | chloro | chloro | H |
| I-23 | bromo | 1-bromo-1,1,2,3,3,3-hexafluoropropan-2-yl | bromo | chloro | H |
| I-24 | chloro | 1,1,1,2,3,3,3-heptafluoropropan-2-yl | chloro | H | H |
| I-25 | chloro | 1,1,1,2,3,3,3-heptafluoropropan-2-yl | chloro | $CH_3$ | H |
| I-26 | bromo | 1,1,1,2,3,3,3-heptafluoropropan-2-yl | bromo | H | H |
| I-27 | chloro | 1,1,1,2,3,3,4,4,4-nonafluorobutan-2-yl | chloro | H | H |
| I-28 | $CH_3$ | 1,1,1,2,3,3,3-heptafluoropropan-2-yl | chloro | H | H |
| I-29 | $CH_3$ | 1,1,1,2,3,3,3-heptafluoropropan-2-yl | $CH_3$ | fluoro | H |
| I-30 | $CH_3$ | 1,1,1,2,3,3,3-heptafluoropropan-2-yl | ethyl | fluoro | H |
| I-31 | $CH_3$ | 1,1,1,2,3,3,3-heptafluoropropan-2-yl | ethyl | fluoro | H |
| I-32 | chloro | 1,1,1,2,3,3,4,4,4-nonafluorobutan-2-yl | chloro | chloro | H |
| I-33 | bromo | 1,1,1,2,3,3,3-heptafluoropropan-2-yl | bromo | H | H |
| I-34 | bromo | 1,1,1,2,3,3,3-heptafluoropropan-2-yl | bromo | chloro | H |
| I-35 | $CH_3$ | 1,1,1,2,3,3,3-heptafluoropropan-2-yl | chloro | chloro | H |
| I-36 | $CH_3$ | 1,1,1,2,3,3,3-heptafluoropropan-2-yl | ethyl | chloro | H |
| I-37 | bromo | 1,1,1,2,3,3,3-heptafluoropropan-2-yl | bromo | chloro | H |
| I-38 | chloro | 1,1,1,2,3,3,3-heptafluoropropan-2-yl | chloro | chloro | H |

TABLE J

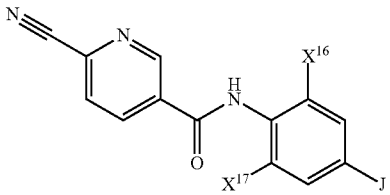

| Exa | $X^{16}$ | J | $X^{17}$ |
|---|---|---|---|
| J-1 | $CH_3$ | 1,1,1,2,3,3,3-heptafluoropropan-2-yl | ethyl |
| J-2 | $CH_3$ | 1,1,1,2,3,3,4,4,4-nonafluorobutan-2-yl | ethyl |
| J-3 | $CH_3$ | 1-bromo-1,1,2,3,3,3-hexafluoropropan-2-yl | ethyl |

TABLE K

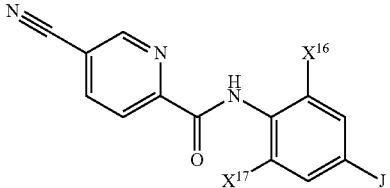

| Exa | $X^{16}$ | J | $X^{17}$ |
|---|---|---|---|
| K-1 | $CH_3$ | 1,1,1,2,3,3,3-heptafluoropropan-2-yl | ethyl |
| K-2 | $CH_3$ | 1,1,1,2,3,3,4,4,4-nonafluorobutan-2-yl | $CH_3$ |
| K-3 | $CH_3$ | 1,1,1,2,3,3,4,4,4-nonafluorobutan-2-yl | ethyl |
| K-4 | $CH_3$ | 1-bromo-1,1,2,3,3,3-hexafluoropropan-2-yl | $CH_3$ |
| K-5 | $CH_3$ | 1-bromo-1,1,2,3,3,3-hexafluoropropan-2-yl | ethyl |

TABLE L

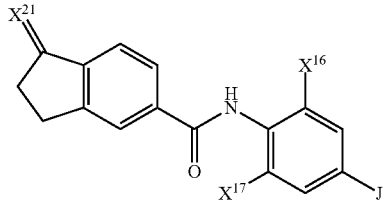

| Exa | $X^{16}$ | J | $X^{17}$ | $X^{21}$ |
|---|---|---|---|---|
| L-1 | $CH_3$ | 1,1,1,2,3,3,3-heptafluoropropan-2-yl | ethyl | O |
| L-2 | $CH_3$ | 1,1,1,2,3,3,3-heptafluoropropan-2-yl | ethyl | N(OH) |
| L-3 | $CH_3$ | 1,1,1,2,3,3,4,4,4-nonafluorobutan-2-yl | ethyl | O |
| L-4 | $CH_3$ | 1,1,1,2,3,3,4,4,4-nonafluorobutan-2-yl | ethyl | N(OH) |
| L-5 | $CH_3$ | 1-bromo-1,1,2,3,3,3-hexafluoropropan-2-yl | ethyl | O |
| L-6 | $CH_3$ | 1-bromo-1,1,2,3,3,3-hexafluoropropan-2-yl | ethyl | N(OH) |

TABLE M

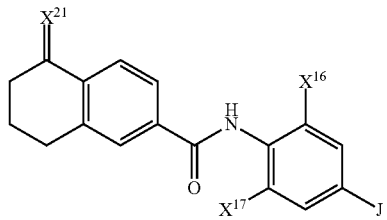

| Exa | $X^{16}$ | J | $X^{17}$ | $X^{21}$ |
|---|---|---|---|---|
| M-1 | $CH_3$ | 1,1,1,2,3,3,3-heptafluoropropan-2-yl | ethyl | O |
| M-2 | $CH_3$ | 1,1,1,2,3,3,3-heptafluoropropan-2-yl | ethyl | N(OH) |
| M-3 | $CH_3$ | 1,1,1,2,3,3,4,4,4-nonafluorobutan-2-yl | ethyl | O |
| M-4 | $CH_3$ | 1,1,1,2,3,3,4,4,4-nonafluorobutan-2-yl | ethyl | N(OH) |
| M-5 | $CH_3$ | 1-bromo-1,1,2,3,3,3-hexafluoropropan-2-yl | ethyl | O |
| M-6 | $CH_3$ | 1-bromo-1,1,2,3,3,3-hexafluoropropan-2-yl | ethyl | N(OH) |

TABLE N

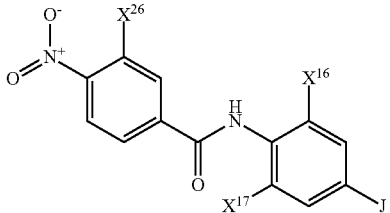

| Exa | $X^{16}$ | J | $X^{17}$ | $X^{26}$ |
|---|---|---|---|---|
| N-1 | chloro | 1,1,1,2,3,3,3-heptafluoropropan-2-yl | chloro | H |
| N-2 | chloro | 1,1,1,2,3,3,4,4,4-nonafluorobutan-2-yl | chloro | H |
| N-3 | chloro | 1-bromo-1,1,2,3,3,3-hexafluoropropan-2-yl | chloro | H |
| N-4 | chloro | 1,1,1,2,3,3,3-heptafluoropropan-2-yl | chloro | $CH_3$ |
| N-5 | chloro | 1,1,1,2,3,3,4,4,4-nonafluorobutan-2-yl | chloro | $CH_3$ |
| N-6 | chloro | 1-bromo-1,1,2,3,3,3-hexafluoropropan-2-yl | chloro | $CH_3$ |
| N-7 | $CH_3$ | 1,1,1,2,3,3,3-heptafluoropropan-2-yl | chloro | H |
| N-8 | $CH_3$ | 1,1,1,2,3,3,4,4,4-nonafluorobutan-2-yl | chloro | H |
| N-9 | $CH_3$ | 1-bromo-1,1,2,3,3,3-hexafluoropropan-2-yl | chloro | H |
| N-10 | $CH_3$ | 1,1,1,2,3,3,3-heptafluoropropan-2-yl | ethyl | H |
| N-11 | $CH_3$ | 1,1,1,2,3,3,4,4,4-nonafluorobutan-2-yl | ethyl | H |
| N-12 | $CH_3$ | 1-bromo-1,1,2,3,3,3-hexafluoropropan-2-yl | ethyl | H |
| N-13 | bromo | 1,1,1,2,3,3,3-heptafluoropropan-2-yl | bromo | H |
| N-14 | bromo | 1,1,1,2,3,3,4,4,4-nonafluorobutan-2-yl | bromo | H |
| N-15 | bromo | 1-bromo-1,1,2,3,3,3-hexafluoropropan-2-yl | bromo | H |

TABLE O

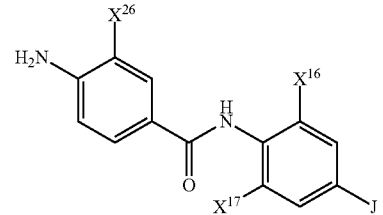

| Exa | $X^{16}$ | J | $X^{17}$ | $X^{26}$ |
|---|---|---|---|---|
| O-1 | chloro | 1,1,1,2,3,3,3-heptafluoropropan-2-yl | chloro | H |
| O-2 | chloro | 1,1,1,2,3,3,4,4,4-nonafluorobutan-2-yl | chloro | H |
| O-3 | chloro | 1-bromo-1,1,2,3,3,3-hexafluoropropan-2-yl | chloro | H |
| O-4 | chloro | 1,1,1,2,3,3,3-heptafluoropropan-2-yl | chloro | chloro |
| O-5 | chloro | 1,1,1,2,3,3,4,4,4-nonafluorobutan-2-yl | chloro | chloro |
| O-6 | chloro | 1-bromo-1,1,2,3,3,3-hexafluoropropan-2-yl | chloro | chloro |
| O-7 | chloro | 1,1,1,2,3,3,3-heptafluoropropan-2-yl | chloro | $CH_3$ |

TABLE O-continued

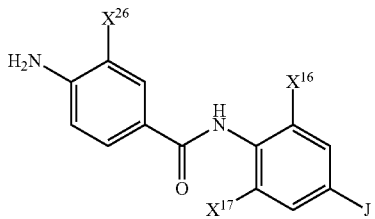

| Exa | $X^{16}$ | J | $X^{17}$ | $X^{26}$ |
|---|---|---|---|---|
| O-8 | chloro | 1,1,1,2,3,3,4,4,4-nonafluorobutan-2-yl | chloro | $CH_3$ |
| O-9 | chloro | 1-bromo-1,1,2,3,3,3-hexafluoropropan-2-yl | chloro | $CH_3$ |
| O-10 | $CH_3$ | 1,1,1,2,3,3,3-heptafluoropropan-2-yl | chloro | H |
| O-11 | $CH_3$ | 1,1,1,2,3,3,4,4,4-nonafluorobutan-2-yl | chloro | H |
| O-12 | $CH_3$ | 1-bromo-1,1,2,3,3,3-hexafluoropropan-2-yl | chloro | H |
| O-13 | $CH_3$ | 1,1,1,2,3,3,3-heptafluoropropan-2-yl | ethyl | H |
| O-14 | $CH_3$ | 1,1,1,2,3,3,4,4,4-nonafluorobutan-2-yl | ethyl | H |
| O-15 | $CH_3$ | 1-bromo-1,1,2,3,3,3-hexafluoropropan-2-yl | ethyl | H |
| O-16 | $CH_3$ | 1,1,1,2,3,3,3-heptafluoropropan-2-yl | ethyl | chloro |
| O-17 | $CH_3$ | 1,1,1,2,3,3,4,4,4-nonafluorobutan-2-yl | ethyl | chloro |
| O-18 | $CH_3$ | 1-bromo-1,1,2,3,3,3-hexafluoropropan-2-yl | ethyl | chloro |
| O-19 | $CH_3$ | 1,1,1,2,3,3,3-heptafluoropropan-2-yl | ethyl | bromo |
| O-20 | $CH_3$ | 1,1,1,2,3,3,4,4,4-nonafluorobutan-2-yl | ethyl | bromo |
| O-21 | $CH_3$ | 1-bromo-1,1,2,3,3,3-hexafluoropropan-2-yl | ethyl | bromo |

TABLE O-continued

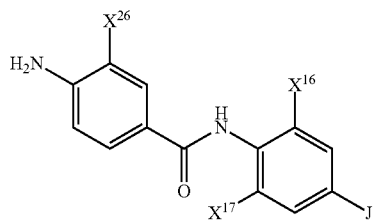

| Exa | $X^{16}$ | J | $X^{17}$ | $X^{26}$ |
|---|---|---|---|---|
| O-22 | bromo | 1,1,1,2,3,3,3-heptafluoropropan-2-yl | bromo | H |
| O-23 | bromo | 1,1,1,2,3,3,4,4,4-nonafluorobutan-2-yl | bromo | H |
| O-24 | bromo | 1-bromo-1,1,2,3,3,3-hexafluoropropan-2-yl | bromo | H |
| O-25 | bromo | 1,1,1,2,3,3,3-heptafluoropropan-2-yl | bromo | chloro |
| O-26 | bromo | 1,1,1,2,3,3,4,4,4-nonafluorobutan-2-yl | bromo | chloro |
| O-27 | bromo | 1-bromo-1,1,2,3,3,3-hexafluoropropan-2-yl | bromo | chloro |
| O-28 | bromo | 1,1,1,2,3,3,3-heptafluoropropan-2-yl | bromo | bromo |
| O-29 | bromo | 1,1,1,2,3,3,4,4,4-nonafluorobutan-2-yl | bromo | bromo |
| O-30 | bromo | 1-bromo-1,1,2,3,3,3-hexafluoropropan-2-yl | bromo | bromo |
| O-31 | $CH_3$ | 1,1,1,2,3,3,3-heptafluoropropan-2-yl | chloro | chloro |
| O-32 | $CH_3$ | 1,1,1,2,3,3,4,4,4-nonafluorobutan-2-yl | chloro | chloro |
| O-33 | $CH_3$ | 1-bromo-1,1,2,3,3,3-hexafluoropropan-2-yl | chloro | chloro |

NMR Table

| Exa | NMR |
|---|---|
| 1-1 | $^1$H-NMR (CDCl$_3$) δ: 2.33 (6H, s), 6.53 (1H, dd), 7.36 (2H, s), 7.57 (1H, s), 7.77 (1H, s), 7.84 (2H, d), 8.02-8.00 (3H, m). |
| 1-2 | $^1$H-NMR (CDCl$_3$) δ: 2.36 (6H, s), 7.37 (2H, s), 7.41 (1H, s), 7.70 (1H, s), 7.81 (2H, d), 8.01 (1H, s), 8.03 (2H, d). |
| 1-3 | $^1$H-NMR (CDCl$_3$) δ: 2.37 (6H, s), 7.38 (2H, s), 7.46 (1H, s), 7.88 (2H, d), 8.09 (2H, d), 8.16 (1H, s), 8.67 (1H, s). |
| 1-4 | $^1$H-NMR (CDCl$_3$) δ: 2.30 (6H, s), 3.35 (3H, s), 7.26 (3H, s), 7.39 (2H, d), 7.49 (2H, d), 8.07 (1H, s), 8.49 (1H, s). |
| 1-5 | $^1$H-NMR (CDCl$_3$) δ: 2.42 (6H, s), 7.39 (2H, s), 7.68 (1H, s), 7.75 (1H, dd), 7.93 (1H, d), 8.02 (1H, d), 8.16 (1H, s), 8.65 (1H, s). |
| 1-6 | $^1$H-NMR (CDCl$_3$) δ: 2.42 (6H, s), 7.18 (1H, s), 7.38 (2H, s), 7.90 (1H, d), 8.02 (1H, dd), 8.17-8.18 (2H, m), 8.70 (1H, s). |
| 1-7 | $^1$H-NMR (DMSO-d$_6$) δ: 2.40 (6H, s), 7.45 (2H, s), 7.95 (1H, s), 8.07 (1H, d), 8.38 (1H, s), 8.39 (1H, dd), 8.65 (1H, d), 9.57 (1H, s). |
| 1-8 | $^1$H-NMR (CDCl$_3$) δ: 2.36 (6H, s), 7.38 (2H, s), 7.51 (1H, s), 7.81 (1H, d), 7.96 (1H, dd), 8.16 (1H, d), 8.18 (1H, s), 8.70 (1H, s). |
| 1-9 | $^1$H-NMR (CDCl$_3$) δ: 2.34 (6H, s), 7.38 (2H, s), 7.69-7.71 (2H, m), 8.01 (1H, dd), 8.17 (1H, s), 8.34 (1H, d), 8.63 (1H, s). |
| 1-10 | $^1$H-NMR (CDCl$_3$) δ: 2.37 (6H, s), 7.39 (2H, s), 7.59 (1H, s), 7.75 (1H, d), 8.19 (1H, s), 8.27 (1H, d), 8.41 (2H, s). |
| 1-11 | $^1$H-NMR (CDCl$_3$) δ: 2.35 (6H, s), 7.39 (2H, s), 7.79 (1H, d), 7.84 (1H, s), 8.15 (1H, s), 8.34 (1H, dd), 8.48 (1H, s), 8.55 (1H, d). |
| 1-12 | $^1$H-NMR (CDCl$_3$) δ: 2.33 (6H, s), 7.38 (2H, s), 7.88 (1H, d), 7.98 (1H, d), 8.20 (1H, s), 8.33 (1H, dd), 8.44 (1H, d), 8.91 (1H, s). |
| 1-13 | $^1$H-NMR (CDCl$_3$) δ: 1.52 (3H, t), 2.36 (6H, s), 3.46 (2H, q), 7.38 (2H, s), 7.64 (1H, s), 7.78 (2H, d), 8.13 (2H, d). |
| 1-14 | $^1$H-NMR (CDCl$_3$) δ: 1.22 (3H, t), 2.33 (3H, s), 2.68 (2H, q), 6.42 (2H, d), 6.83 (2H, d), 7.39 (2H, s), 7.47-7.63 (2H, m), 8.24 (1H, m), 8.40 (1H, s) |
| 1-15 | $^1$H-NMR (CDCl$_3$) δ: 1.25 (3H, t), 2.36 (3H, s), 2.71 (2H, q), 6.41-6.43 (1H, m), 7.04-7.05 (2H, m), 7.40 (2H, s), 7.62 (1H, d), 7.78 (1H, s), 8.24 (1H, dd), 8.40 (1H, d). |
| 1-16 | $^1$H-NMR (CDCl$_3$) δ: 1.24 (3H, t), 2.36 (3H, s), 2.71 (2H, q), 6.54 (1H, dd), 7.38 (2H, s), 7.42 (1H, s), 7.78 (1H, d), 7.87 (2H, d), 8.04-8.01 (3H, m). |
| 1-17 | $^1$H-NMR (CDCl$_3$) δ: 1.23 (3H, t), 2.34 (3H, s), 2.69 (2H, q), 6.56 (1H, d), 7.39 (2H, s), 7.69-7.75 (4H, m), 8.24 (1H, d), 8.37 (1H, s). |
| 1-18 | $^1$H-NMR (CDCl$_3$) δ: 1.23 (3H, t), 2.38 (3H, s), 2.74 (2H, q), 6.60 (1H, t), 7.40 (2H, m), 7.56 (4H, tt), 7.92-8.03 (6H, m), 9.42 (1H, d), 11.92 (1H, s). |
| 1-19 | $^1$H-NMR (CDCl$_3$) δ: 1.23 (3H, t), 2.38 (3H, s), 2.69 (2H, q), 6.56-6.59 (1H, m), 7.14-7.34 (2H, m), 7.39 (2H, tt), 7.49-7.57 (2H, m), 7.71-7.77 (1H, m), 7.85-7.95 (3H, m), 8.06 (1H, t), 9.33 (1H, s), 11.44-11.51 (1H, d). |

-continued

| Exa | NMR |
|---|---|
| 1-20 | ¹H-NMR (CDCl₃) δ: 1.23 (3H, t), 2.39 (3H, s), 2.70 (2H, q), 3.454 (1H, d), 3.74 (1H, d), 6.58 (1H, d), 7.40 (3, m), 7.57 (1H, d), 7.72-7.83 (2H, m), 7.92-8.08 (3H, m), 8.54 (1H, d), 9.35 (1H, s), 11.63 (1H, s). |
| 1-21 | ¹H-NMR (CDCl₃) δ: 1.25 (3H, t), 2.36 (3H, s), 2.71 (2H, q), 7.38 (2H, s), 7.41 (1H, s), 7.70 (1H, s), 7.81 (2H, d), 8.01 (1H, s), 8.03 (2H, d). |
| 1-22 | ¹H-NMR (CDCl₃) δ: 1.23 (3H, t), 2.34 (3H, s), 2.69 (2H, q), 7.40 (2H, s), 7.76 (1H, s), 7.95 (1H, s), 8.02 (1H, s), 8.10 (2H, s), 8.33 (1H, dd), 8.51 (1H, d). |
| 1-23 | ¹H-NMR (CDCl₃) δ: 1.24 (3H, t), 2.35 (3H, s), 2.70 (2H, q), 7.41 (2H, s), 7.61 (1H, s), 7.80 (1H, d), 8.31 (1H, s), 8.34 (1H, dd), 8.54 (1H, d), 8.54 (1H, s). |
| 1-24 | ¹H-NMR (CDCl₃) δ: 1.24 (3H, t), 2.34 (3H, s), 2.69 (2H, q), 7.41 (2H, s), 7.65 (1H, s), 7.77 (1H, d), 8.04 (1H, s), 8.23 (1H, s), 8.33 (1H, dd), 8.51 (1H, d). |
| 1-25 | ¹H-NMR (CDCl₃) δ: 1.23 (3H, t), 2.35 (3H, s), 2.71 (2H, q), 7.24 (1H, s), 7.36 (1H, s), 7.39 (2H, s), 7.54 (2H, d), 7.78 (1H, s), 7.92 (1H, s), 8.07 (2H, d). |
| 1-26 | ¹H-NMR (CDCl₃) δ: 1.25 (3H, t), 2.37 (3H, s), 2.70 (2H, q), 7.11 (1H, d, J), 7.20 (1H, d), 7.42 (2H, s), 7.63-7.67 (2H, m), 8.36 (2H, m), 8.60 (1H, d). |
| 1-27 | ¹H-NMR (CDCl₃) δ: 1.24 (3H, t), 2.36 (3H, s), 2.71 (2H, q), 7.39 (2H, s), 7.63 (1H, s), 7.89-7.94 (3H, m), 8.13-8.10 (3H, m). |
| 1-28 | ¹H-NMR (CDCl₃) δ: 1.25 (3H, t), 2.33 (3H, s), 2.70 (2H, q), 7.22-7.32 (2H, m), 7.75-7.84 (3H, m), 7.89-7.96 (2H, m), 8.34-8.38 (2H, m), 8.59 (1H, s). |
| 1-29 | ¹H-NMR (CDCl₃) δ: 1.24 (3H, t), 2.36 (3H, s), 2.71 (2H, q), 7.39 (2H, s), 7.46 (1H, s), 7.88 (2H, s), 8.05 (2H, d), 8.25 (2H, d). |
| 1-30 | ¹H-NMR (CDCl₃) δ: 1.25 (3H, t), 2.37 (3H, s), 2.70 (2H, q), 7.41 (2H, s), 7.83 (2H, d), 7.94 (2H, d), 8.20 (1H, dd), 8.32 (1H, s). |
| 1-31 | ¹H-NMR (CDCl₃) δ: 1.24 (3H, t), 2.37 (3H, s), 2.71 (2H, q), 7.39 (2H, s), 7.44 (1H, s), 7.88 (2H, d), 8.09 (2H, d), 8.16 (1H, s), 8.67 (1H, s). |
| 1-32 | ¹H-NMR (CDCl₃) δ: 1.24 (3H, t), 2.34 (3H, s), 2.37 (3H, s), 2.70 (2H, q), 7.39 (2H, d), 7.48 (1H, d), 7.62 (1H, s), 7.86 (1H, d), 7.95 (1H, s), 8.16 (1H, s), 8.33 (1H, s). |
| 1-33 | ¹H-NMR (CDCl₃) δ: 1.25 (3H, t), 2.37 (3H, s), 2.71 (2H, q), 7.41 (2H, s), 7.63 (1H, s), 7.75 (1H, d), 8.19 (1H, s), 8.27 (1H, dd), 8.39-8.43 (2H, m). |
| 1-34 | ¹H-NMR (CDCl₃) δ: 1.24 (3H, t), 2.36 (3H, s), 2.70 (2H, q), 7.40 (2H, s), 7.50 (1H, s), 7.85 (1H, d), 7.92 (1H, d), 8.17-8.12 (2H, m), 8.80 (1H, d). |
| 1-35 | ¹H-NMR (CDCl₃) δ: 1.24 (3H, t), 2.35 (3H, s), 2.69 (2H, q), 7.39 (2H, s), 7.57 (1H, s), 7.80 (1H, d), 7.95 (1H, dd), 8.16-8.17 (2H, m), 8.70 (1H, s). |
| 1-36 | ¹H-NMR (CDCl₃) δ: 1.25 (3H, t), 2.35 (3H, s), 2.70 (2H, q), 7.40 (2H, s), 7.53 (1H, s), 7.71 (1H, d), 8.00 (1H, dd), 8.18 (1H, s), 8.33 (1H, d), 8.64 (1H, s). |
| 1-37 | ¹H-NMR (CDCl₃) δ: 1.23 (3H, t), 2.34 (3H, s), 2.69 (2H, q), 4.04 (3H, s), 7.37 (2H, s), 7.56-7.53 (2H, m), 7.75 (1H, s), 8.01 (1H, d), 8.09 (1H, s), 8.91 (1H, s). |
| 1-38 | ¹H-NMR (DMSO-d₆) δ: 1.25 (3H, t),, 2.31 (3H, s), 2.70 (2H, q), 5.75 (2H, s), 7.28 (1H, dd), 7.37-7.49 (4H, m), 8.29 (1H, s), 8.95 (1H, s), 9.92 (1H, s). |
| 1-39 | ¹H-NMR (CDCl₃) δ: 1.25 (3H, t), 2.37 (3H, s), 2.69 (H, q), 7.40 (2H, s), 7.79 (1H, dd), 7.91 (1H, s), 8.15 (1H, s), 8.34 (1H, dd), 8.48 (1H, s), 8.56 (1H, s). |
| 1-40 | ¹H-NMR (CDCl₃) δ: 1.08-1.35 (6H, m), 2.37 (3H, s), 2.46 (2H, q), 2.71 (2H, q), 7.39 (1H, d), 7.55 (1H, s), 7.87 (1H, dd), 8.29 (1H, s), 8.57 (1H, s), 9.15 (1H, s), 9.97 (1H, s). |
| 1-41 | ¹H-NMR (CDCl₃) δ: 1.25 (3H, t), 2.38 (3H, s), 2.70-2.78 (2H, q), 7.42 (2H, s), 7.51-7.65 (4H, m), 7.91-8.01 (4H, m), 8.36 (1H, s), 8.63 (1H, s), 9.37 (1H, s), 10.95 (1H, s). |
| 1-42 | ¹H-NMR (CDCl₃) δ: 1.25 (3H, t), 2.40 (3H, s), 2.70-2.78 (2H, q),, 7.19-7.38 (2H, m), 7.40 (2H, s), 7.51-7.62 (2H, m), 7.97 (2H, dd), 8.05-8.11 (1H, m), 8.30 (1H, s), 8.56 (1H, s), 9.28 (1H, s), 10.60 (1H, d). |
| 1-43 | ¹H-NMR (CDCl₃) δ: 1.25 (3H, t), 2.39 (3H, s), 2.74 (2H, q), 7.09-7.26 (2H, m), 7.39 (2H, s), 7.63 (1H, d), 7.94-8.04 (3H, m), 8.04-8.11 (1H, m), 8.36 (1H, s), 8.65 (1H, s,), 9.32 (1H, s), 10.97 (1H, s). |
| 1-44 | ¹H-NMR (CDCl₃) δ: 1.25 (3H, t), 2.39 (3H, s), 2.71-2.78 (2H, q), 7.14-7.33 (2H, m), 7.40 (2H, s), 7.58-7.65 (1H, m), 7.79 (1H, d), 7.88 (1H, d), 7.98 (1H, dd), 8.30 (1H, s), 8.56 (1H, s), 9.24 (1H, d), 10.67-10.73 (1H, d). |
| 1-45 | ¹H-NMR (CDCl₃) δ: 1.25 (3H, t), 2.39 (3H, s), 2.71-2.78 (2H, q), 7.43 (3H, m), 7.61 (1H, d), 7.83 (1H, s), 7.97 (1H, d), 8.34 (1H, s), 8.42 (1H, dd), 8.59 (2H, m), 9.26 (1H, s), 10.96 (1H, d). |
| 1-46 | ¹H-NMR (CDCl₃) δ: 1.25 (3H, t), 2.41 (3H, s), 2.75 (2H, q), 7.40-7.45 (3H, m), 7.62 (1H, d), 7.86 (1H, s), 8.03 (1H, dd), 8.24 (1H, s), 8.55-8.60 (2H, m), 9.28 (1H, s), 10.65 (1H, s). |
| 1-47 | ¹H-NMR (CDCl₃) δ: 1.24 (3H, t), 2.36 (3H, s), 2.71 (2H, q), 3.79 (3H, s), 7.38 (2H, s), 7.51 (1H, d), 7.79-7.84 (2H, m), 8.26 (1H, s), 8.54 (1H, s), 8.91 (1H, s), 9.30 (1H, s). |
| 1-48 | ¹H-NMR (acetone-d₆) δ: 1.21 (3H, t), 2.39 (3H, s), 2.79 (2H, q), 3.05 (3H, s), 7.48 (2H, s), 7.91 (1H, d), 8.04 (1H, dd), 8.31 (1H, s), 8.42 (1H, d), 9.03 (1H, s), 9.18 (1H, s), 9.48 (1H, s). |
| 1-49 | ¹H-NMR (CDCl₃) δ: 1.24 (3H, t), 2.35 (3H, s), 2.68 (2H, q), 7.41 (2H, s), 7.59 (1H, s), 8.01 (1H, d), 8.22 (1H, s), 8.31 (1H, dd), 8.42 (1H, d), 8.92 (1H, s). |
| 1-50 | ¹H-NMR (CDCl₃) δ: 1.25 (3H, t), 2.37 (3H, s), 2.71 (2H, q), 7.40 (2H, s), 7.46 (1H, s), 7.90 (2H, d), 8.12 (2H, d), 8.73 (1H, s). |
| 1-52 | ¹H-NMR (CDCl₃) δ: 1.23 (3H, td, J = 7.4, 4.9 Hz), 2.34 (3H, s), 2.69 (2H, q, J = 7.6 Hz), 7.40 (2H, s), 7.81 (1H, d, J = 8.2 Hz), 8.15 (1H, s), 8.41 (1H, dd, J = 8.2, 1.9 Hz), 8.54 (1H, s), 8.70 (1H, d, J = 1.8 Hz). |
| 1-53 | ¹H-NMR (CDCl₃) δ: 1.21 (3H, t), 2.33 (3H, s), 2.69 (2H, q), 3.99 (3H, s), 7.39 (2H, s), 7.78 (1H, d), 8.45 (1H, dd), 8.50 (1H, s), 8.74 (1H, d), 8.77 (1H, s). |
| 1-54 | ¹H-NMR (CDCl₃) δ: 1.24 (3H, t), 2.36 (3H, s), 2.71 (2H, q), 5.83 (1H, s), 7.10 (1H, s), 7.39 (2H, s), 7.58 (1H, s), 7.94 (2H, d), 8.12 (2H, d), 8.69 (1H, s). |
| 1-55 | ¹H-NMR (CDCl₃) δ: 1.24 (3H, t), 2.37 (3H, s), 2.71 (2H, q), 7.40 (2H, s), 7.63 (1H, s), 7.91 (2H, d), 8.17 (2H, d), 9.11 (1H, s). |
| 1-56 | ¹H-NMR (CDCl₃) δ: 1.25 (3H, t), 2.38 (3H, s), 2.73 (2H, q), 7.40 (2H, s), 7.70-7.82 (2H, m), 8.00 (1H, d), 8.44 (1H, dd), 9.13 (1H, s). |

-continued

NMR Table

| Exa | NMR |
|---|---|
| 1-57 | $^1$H-NMR (CDCl$_3$) δ: 1.25 (3H, t), 2.37 (3H, s), 2.69 (2H, q), 7.42 (2H, s), 7.47 (1H, s,), 7.79 (1H, d), 8.31 (1H, dd), 8.85 (1H, d), 9.64 (1H, d). |
| 1-58 | $^1$H-NMR (CDCl$_3$) δ: 1.25 (3H, t), 2.37 (3H, s), 2.72 (2H, q), 7.40 (2H, s), 7.48 (1H, s), 8.14 (2H, d), 8.34 (2H, d), 8.72 (1H, s). |
| 1-59 | $^1$H-NMR (CDCl$_3$) δ: 1.25 (3H, t), 2.37 (3H, s), 2.64-2.75 (2H, q), 7.40 (2H, s), 7.69 (1H, s), 7.83 (1H, d), 8.31 (1H, d), 8.84 (1H, s), 9.64 (1H, s). |
| 1-60 | $^1$H-NMR (CDCl$_3$) δ: 1.25 (3H, t), 2.39 (2H, d), 2.72 (2H, q), 2.90 (3H, s), 7.40 (2H, s), 7.45 (1H, s), 7.81 (2H, d), 8.13 (2H, d). |
| 1-61 | $^1$H-NMR (CDCl$_3$) δ: 1.24 (3H, t), 2.39 (3H, s), 2.75 (2H, q), 7.40 (2H, s), 7.68-7.54 (3H, m), 7.77 (2H, d), 7.88 (1H, d), 7.98 (1H, s), 8.23 (1H, d), 8.80 (1H, s). |
| 1-62 | $^1$H-NMR (CDCl$_3$) δ: 1.25 (3H, t), 2.38 (3H, s), 2.73 (2H, q), 7.42 (2H, s), 7.43-7.52 (2H, m), 7.61 (1H, dd), 7.92 (1H, d), 8.02 (1H, s), 8.09 (1H, d), 8.45 (1H, dd), 8.71 (1H, d). |
| 1-63 | $^1$H-NMR (CDCl$_3$) δ: 1.24 (3H, t), 2.35 (3H, s), 2.70 (2H, q), 7.41 (2H, s), 7.45-7.49 (2H, m), 7.63 (1H, s), 7.89-7.93 (2H, m), 8.41-8.28 (3H, m). |
| 1-64 | $^1$H-NMR (CDCl$_3$) δ: 1.24 (6H, dz), 3.25-3.11 (1H, m), 7.38 (1H, s), 7.44 (1H, s), 7.57 (1H, s), 7.87 (2H, d), 8.09 (2H, d), 8.16 (1H, s), 8.67 (1H, s). |
| 1-66 | $^1$H-NMR (CDCl$_3$) δ: 1.25 (6H, d), 3.21-3.08 (1H, m), 7.40 (1H, s), 7.46 (1H, s), 7.68 (1H, s), 7.80 (1H, d), 8.17 (1H, s), 8.34 (1H, dd), 8.49 (1H, s), 8.55 (1H, d). |
| 1-67 | $^1$H-NMR (CDCl$_3$) δ: 2.40 (3H, s), 3.43 (3H, s), 4.52 (2H, s), 7.39 (1H, s), 7.53 (1H, s), 7.88 (2H, d), 8.11 (2H, d), 8.16 (1H, s), 8.68 (1H, s), 8.88 (1H, s). |
| 1-68 | $^1$H-NMR (CDCl$_3$) δ: 2.39 (3H, s), 3.41 (3H, s), 4.51 (2H, s), 4.90 (2H, s), 7.26-7.39 (3H, m), 7.50-7.52 (2H, m), 8.20 (1H, s), 8.46 (1H, s), 8.77 (1H, s). |
| 1-69 | $^1$H-NMR (CDCl$_3$) δ: 2.40 (3H, s), 3.45 (3H, s), 4.55 (2H, s), 7.40 (1H, s), 7.55 (1H, s), 7.80 (1H, d), 8.17 (1H, s), 8.34 (1H, dd), 8.49 (1H, s), 8.57 (1H, d), 9.13 (1H, s). |
| 1-70 | $^1$H-NMR (CDCl$_3$) δ: 2.38 (3H, s), 3.87 (3H, s), 6.99 (1H, s), 7.16 (1H, s), 7.69 (1H, s), 7.86 (2H, d), 8.10 (2H, d), 8.16 (1H, s), 8.67 (1H, s). |
| 1-72 | $^1$H-NMR (CDCl$_3$) δ: 2.37 (3H, s), 3.89 (3H, s), 7.01 (1H, s), 7.17 (1H, s), 7.77 (1H, d), 7.84 (1H, s), 8.16 (1H, s), 8.32 (1H, dd), 8.48 (1H, s), 8.53 (1H, d). |
| 1-73 | $^1$H-NMR (CDCl$_3$) δ: 1.24 (6H, t, J = 7.6 Hz), 2.71 (4H, q, J = 7.6 Hz), 7.41 (2H, s), 7.46 (1H, s), 7.88 (2H, d), 8.08 (2H, d), 8.16 (1H, s), 8.67 (1H, s). |
| 1-74 | $^1$H-NMR (CDCl$_3$) δ: 1.24 (6H, t), 2.70 (4H, q), 7.41 (2H, s), 7.48 (1H, s), 7.81 (1H, d), 7.95 (1H, d), 8.16-8.18 (2H, m), 8.70 (1H, s). |
| 1-75 | $^1$H-NMR (CDCl$_3$) δ: 1.25 (6H, t), 2.70 (4H, q), 7.42 (2H, s), 7.44 (1H, s), 7.72 (1H, d), 7.99 (1H, dd), 8.18 (1H, s), 8.33 (1H, d), 8.64 (1H, s). |
| 1-77 | $^1$H-NMR (CDCl$_3$) δ: 1.25 (6H, t), 2.70 (4H, q), 7.43 (2H, s), 7.67 (1H, s), 7.80 (1H, d), 8.17 (1H, s), 8.33 (1H, dd), 8.49 (1H, s), 8.54 (1H, d). |
| 1-78 | $^1$H-NMR (CDCl$_3$) δ: 7.79 (1H, s), 7.89 (2H, s), 7.89 (2H, d), 8.13 (2H, d), 8.16 (1H, s), 8.68 (1H, s). |
| 1-79 | $^1$H-NMR (CDCl$_3$) δ: 7.92 (2H, d), 8.03 (1H, s), 8.14 (1H, s), 8.17 (2H, d), 8.69 (1H, s). |
| 1-80 | $^1$H-NMR (CDCl$_3$) δ: 7.86 (2H, d), 8.15-8.10 (6H, m), 8.66 (1H, s). |
| 1-81 | $^1$H-NMR (CDCl$_3$) δ: 7.82 (1H, d), 8.04-8.17 (4H, m), 8.38 (1H, d), 8.50 (1H, s), 8.60 (1H, s). |
| 1-86 | $^1$H-NMR (acetone-d$_6$) δ: 1.15 (3H, t), 2.35 (3H, s), 2.75 (2H, q), 7.26 (2H, d), 7.84 (1H, s), 7.95 (1H, s), 8.14 (2H, d), 8.33 (2H, d), 9.42 (1H, s), 9.85 (1H, s). |
| 1-87 | $^1$H-NMR (CDCl$_3$) δ: 2.39 (6H, s), 7.12 (2H, s), 7.73-7.77 (2H, m), 7.93 (1H, d), 8.01 (1H, d), 8.14 (1H, s), 8.15 (1H, s), 8.31 (1H, s), 8.65 (1H, s). |
| 1-89 | $^1$H-NMR (CDCl$_3$) δ: 1.23 (3H, t), 2.37 (3H, s), 2.71 (2H, q), 7.38 (2H, s), 7.45 (1H, s), 7.88 (2H, d), 8.09 (2H, d), 8.16 (1H, s), 8.67 (1H, s). |
| 1-96 | $^1$H-NMR (CDCl$_3$) δ: 1.25 (3H, t), 2.37 (3H, s), 2.71 (2H, q), 7.46 (2H, s), 7.52 (1H, s), 7.72 (1H, d), 8.00 (1H, dd), 8.18 (1H, s), 8.33 (1H, d), 8.64 (1H, s). |
| 1-99 | $^1$H-NMR (CDCl$_3$) δ: 1.24 (3H, t), 2.33 (3H, s), 2.68 (2H, q), 7.46 (2H, s), 7.46 (1H, s), 7.87 (2H, d), 8.08 (2H, d), 8.16 (1H, s), 8.67 (1H, s). |
| 1-101 | $^1$H-NMR (CDCl$_3$) δ: 1.22 (3H, t), 2.28 (3H, s), 2.64 (2H, q), 7.45 (2H, s), 7.77 (1H, d), 7.96 (1H, s), 8.13 (1H, s), 8.32 (1H, dd), 8.47 (1H, s), 8.54 (1H, d). |
| 1-102 | $^1$H-NMR (CDCl$_3$) δ: 1.24 (3H, t), 1.26 (3H, t), 2.33 (3H, s), 2.46 (2H, q), 2.68 (2H, q), 7.44 (2H, s), 7.55 (1H, d), 7.76 (1H, s), 7.90 (1H, dd), 8.28 (1H, s), 8.56 (1H, s), 9.15 (1H, d), 9.98 (1H, s). |
| 1-103 | $^1$H-NMR (CDCl$_3$) δ: 1.25 (3H, t), 2.34 (3H, s), 2.70 (2H, q), 7.19 (1H, dd), 7.31 (1H, dd), 7.45 (2H, s), 7.52-7.58 (2H, m), 7.88 (1H, s), 7.95 (1H, d), 8.08 (1H, dd), 8.28 (1H, s), 8.54 (1H, s), 9.27 (1H, d), 10.60 (1H, d). |
| 1-104 | $^1$H-NMR (CDCl$_3$) δ: 1.23 (3H, t), 2.32 (3H, s), 2.68 (2H, q), 3.80 (3H, s), 7.44 (2H, s), 7.51 (1H, d), 7.73 (1H, s), 7.82 (1H, dd), 8.26 (1H, s), 8.54 (1H, s), 8.92 (1H, d), 9.30 (1H, s). |
| 2-2 | $^1$H-NMR (CDCl$_3$) δ: 1.30 (3H, t), 2.49 (3H, s), 2.81 (2H, q), 7.44 (2H, s), 7.48 (1H, s), 7.59 (1H, d), 7.63-7.74 (2H, m), 7.80 (1H, dd), 7.89 (1H, d), 8.27 (1H, s), 8.46 (1H, s), 8.52 (1H, dd). |
| 4-1 | $^1$H-NMR (acetone-d$_6$) δ: 2.34 (6H, s), 7.23 (2H, s), 7.56 (1H, s), 7.64 (1H, d), 8.23 (1H, s), 8.41 (1H, dd), 8.67 (1H, s), 9.03 (1H, d). |
| 4-2 | $^1$H-NMR (CDCl$_3$) δ: 1.25 (3H, t), 2.37 (3H, s), 2.71 (2H, q), 7.40 (2H, s), 7.45 (1H, s), 8.07 (1H, d), 8.15 (1H, s), 8.44 (1H, d), 9.01 (1H, s), 9.25 (1H, s). |
| 5-1 | $^1$H-NMR (CDCl$_3$) δ: 2.33 (6H, s), 3.98 (2H, s), 7.35 (2H, s), 7.45-7.48 (3H, m), 7.89 (2H, d). |
| 5-2 | $^1$H-NMR (CDCl$_3$) δ: 2.04 (3H, s), 2.33 (6H, s), 4.51 (2H, d), 5.97 (1H, s), 7.35 (2H, s), 7.41 (2H, d), 7.53 (1H, s), 7.88 (2H, d). |
| 5-3 | $^1$H-NMR (CDCl$_3$) δ: 1.18 (3H, t), 2.27 (2H, q), 2.32 (6H, s), 4.51 (2H, d), 5.95 (1H, s), 7.35 (2H, s), 7.40 (2H, d), 7.59 (1H, s), 7.89 (2H, d). |
| 5-4 | $^1$H-NMR (CDCl$_3$) δ: 1.21 (6H, d), 2.34 (6H, s), 2.42-2.44 (1H, m), 4.53 (2H, d), 5.85 (1H, s), 7.37-7.41 (5H, m), 7.89 (2H, d). |
| 5-5 | $^1$H-NMR (CDCl$_3$) δ: 2.32 (6H, s), 4.11 (2H, s), 4.57 (2H, d), 7.04 (1H, s), 7.35 (2H, s), 7.42 (2H, d), 7.56 (1H, s), 7.90 (2H, d). |

-continued

NMR Table

| Exa | NMR |
|---|---|
| 5-6 | ¹H-NMR (CDCl₃) δ: 2.33 (6H, s), 4.60 (2H, d), 5.96 (1H, t), 6.75 (1H, s), 7.36 (2H, s), 7.42-7.45 (3H, m), 7.91 (2H, d). |
| 5-7 | ¹H-NMR (CDCl₃) δ: 2.34 (6H, s), 3.14 (2H, q), 4.58 (2H, d), 6.21 (1H, s), 7.38-7.41 (5H, m), 7.89 (2H, d). |
| 5-8 | ¹H-NMR (CDCl₃) δ: 0.21-0.23 (2H, m), 0.60-0.66 (2H, m), 0.98-1.00 (1H, m), 2.23 (2H, d), 2.34 (6H, s), 4.56 (2H, d), 6.32 (1H, s), 7.35 (2H, s), 7.43-7.46 (3H, m), 7.90 (2H, d). |
| 5-9 | ¹H-NMR (CDCl₃) δ: 1.98-2.21 (6H, m), 2.34 (6H, s), 3.04-3.07 (1H, m), 4.51 (2H, d), 5.78 (1H, s), 7.35 (2H, s), 7.40 (2H, d), 7.52 (1H, s), 7.89 (2H, d). |
| 5-10 | ¹H-NMR (CDCl₃) δ: 1.59-1.91 (8H, m), 2.34 (6H, s), 2.57-2.59 (1H, m), 4.53 (2H, d), 5.86 (1H, s), 7.35 (2H, s), 7.41-7.43 (3H, m), 7.89 (2H, d,). |
| 5-11 | ¹H-NMR (CDCl₃) δ: 1.37-1.79 (10H, m), 2.14 (1H, m), 2.34 (6H, s), 4.52 (2H, d), 5.85 (1H, s), 7.35 (2H, s), 7.40 (2H, d), 7.44 (1H, s), 7.89 (2H, d). |
| 5-12 | ¹H-NMR (CDCl₃) δ: 1.88 (3H, dd), 2.34 (6H, s), 4.59 (2H, d), 5.82-5.87 (2H, m), 6.92 (1H, dd), 7.34-7.37 (3H, m), 7.44 (2H, d), 7.89 (2H, d). |
| 5-13 | ¹H-NMR (CDCl₃) δ: 1.77 (3H, dd), 1.87-1.87 (3H, m), 2.33 (6H, s), 4.58 (2H, d), 6.13 (1H, s), 6.49 (1H, dd), 7.35 (2H, s), 7.42 (2H, d), 7.51 (1H, s), 7.89 (2H, d). |
| 5-14 | ¹H-NMR (CDCl₃) δ: 2.34 (6H, s), 3.43 (3H, s), 3.96 (2H, s), 4.57 (2H, d, J = 6.0 Hz), 6.95 (1H, s), 7.35 (2H, s), 7.43-7.45 (3H, m), 7.90 (2H, d, J = 8.1 Hz). |
| 5-15 | ¹H-NMR (CDCl₃) δ: 2.33 (6H, s), 2.53 (2H, tz), 3.38 (3H, s), 3.67 (2H, t), 4.53 (2H, d), 6.70 (1H, s), 7.35 (2H, s), 7.41 (2H, d), 7.49 (1H, s), 7.89 (2H, d). |
| 5-16 | ¹H-NMR (CDCl₃) δ: 1.21 (3H, d), 2.33 (6H, s), 2.43 (2H, d), 3.34 (3H, s), 3.72-3.75 (1H, m), 4.53 (2H, t), 6.74 (1H, s), 7.35 (2H, s), 7.41 (2H, d), 7.54 (1H, s), 7.89 (2H, d). |
| 5-17 | ¹H-NMR (CDCl₃) δ: 2.33 (6H, s), 4.52 (2H, d), 4.93 (2H, d), 6.97 (1H, s), 7.34-7.36 (4H, m), 7.57 (1H, s), 7.87 (2H, d), 8.00 (1H, s), 8.03 (1H, s). |
| 5-18 | ¹H-NMR (CDCl₃) δ: 2.33 (6H, s), 3.61 (2H, s), 4.49 (2H, d), 5.82 (1H, s), 7.05 (2H, dd), 7.24-7.27 (4H, m), 7.31-7.35 (4H, m), 7.41 (1H, s), 7.86 (2H, d,). |
| 5-19 | ¹H-NMR (CDCl₃) δ: 2.33 (6H, s), 4.76 (2H, d), 7.35 (2H, s), 7.37-7.42 (1H, m), 7.49-7.52 (3H, m), 7.92 (2H, d), 8.35-8.36 (1H, m), 8.57-8.64 (1H, m). |
| 5-21 | ¹H-NMR (CDCl₃) δ: 2.06 (3H, s), 2.35 (6H, s), 4.50 (2H, dz), 5.99 (1H, s), 7.16 (1H, d), 7.22 (1H, dd), 7.36 (2H, s), 7.96 (1H, d), 8.11 (1H, t). |
| 5-22 | ¹H-NMR (CDCl₃) δ: 1.21 (3H, t), 2.27-2.33 (8H, m), 4.51 (2H, d), 5.99 (1H, s), 7.15 (1H, d), 7.21 (1H, dd), 7.36 (2H, s), 7.97 (1H, d), 8.10 (1H, t). |
| 5-24 | ¹H-NMR (CDCl₃) δ: 0.23-0.26 (2H, m), 0.64-0.67 (2H, m), 1.00-1.03 (1H, m), 2.26 (2H, d), 2.35 (6H, s), 4.56 (2H, d), 6.36 (1H, s), 7.17 (1H, d), 7.24 (1H, d), 7.36 (2H, s), 7.96 (1H, d), 8.13 (1H, t). |
| 5-25 | ¹H-NMR (CDCl₃) δ: 2.35 (6H, s), 3.14 (2H, q), 4.55 (2H, d), 6.41 (1H, s), 7.13 (1H, d), 7.20 (1H, d), 7.36 (2H, s), 7.96 (1H, d), 8.09 (1H, t). |
| 5-27 | ¹H-NMR (CDCl₃) δ: 1.22 (3H, t), 2.34 (3H, s), 2.69 (2H, q), 3.98 (2H, s), 7.37 (2H, s), 7.47 (1H, s), 7.44 (2H, d), 7.90 (2H, d). |
| 5-28 | ¹H-NMR (acetone-d₆) δ: 1.17 (3H, t), 1.94 (3H, s), 2.35 (3H, s), 2.75 (2H, q), 4.45 (2H, d), 7.46-7.44 (4H, m), 7.61 (1H, s), 7.99 (2H), 9.17 (1H, s). |
| 5-29 | ¹H-NMR (CDCl₃) δ: 1.19-1.22 (6H, m), 2.28 (2H, q), 2.33 (3H, s), 2.68 (2H, q), 4.53 (2H, d), 5.88 (1H, s), 7.37 (2H, s), 7.42-7.45 (3H, m), 7.89 (2H, d). |
| 5-30 | ¹H-NMR (CDCl₃) δ: 0.75-1.08 (4H, m), 1.21 (3H, t), 1.36-1.44 (1H, m), 2.33 (3H, s), 2.68 (2H, q), 4.53 (2H, d), 6.10 (1H, s), 7.36 (2H, s), 7.42 (2H, d), 7.52 (1H, s), 7.88 (2H, d). |
| 5-31 | ¹H-NMR (CDCl₃) δ: 0.19-0.24 (2H, m), 0.61-0.64 (2H, m), 0.97-0.99 (1H, m), 1.21 (3H, t), 2.21 (2H, d), 2.33 (3H, s), 2.68 (2H, q), 4.55 (2H, d), 6.37 (1H, s), 7.36 (2H, s), 7.42 (2H, d), 7.59 (1H, s), 7.90 (2H, d). |
| 5-32 | ¹H-NMR (CDCl₃) δ: 1.21 (3H, t), 2.33 (3H, s), 2.68 (2H, q), 3.14 (2H, q), 4.57 (2H, d), 6.27 (1H, s), 7.38-7.41 (5H, m), 7.88 (2H, d). |
| 5-33 | ¹H-NMR (CDCl₃) δ: 1.21 (3H, t), 2.33 (3H, s), 2.69 (2H, q), 3.27 (2H, d), 4.57 (2H, d), 7.37 (2H, s), 7.44-7.46 (3H, m), 7.90 (2H, d). |
| 5-34 | ¹H-NMR (CDCl₃) δ: 1.21 (3H, t), 2.33 (3H, s), 2.68 (2H, q), 4.76 (2H, d), 7.14 (1H, dd), 7.29 (1H, d), 7.36 (2H, s), 7.46-7.54 (4H, m), 7.91 (2H, d), 8.12 (1H, td). |
| 5-35 | ¹H-NMR (CDCl₃) δ: 1.21 (3H, t,), 2.33 (3H, s), 2.67 (2H, q), 4.71 (2H, d), 6.63 (1H, s), 7.19-7.25 (1H, m), 7.41-7.51 (7H, m), 7.90 (2H, d). |
| 5-36 | ¹H-NMR (CDCl₃) δ: 1.19 (3H, t), 2.29 (3H, s), 2.66 (2H, q), 4.91 (2H, s), 6.99 (2H, t), 7.34 (2H, s), 7.49-7.54 (4H, m), 7.93 (3H, d). |
| 5-37 | ¹H-NMR (CDCl₃) δ: 1.21 (3H, t), 2.33 (3H, s), 2.68 (2H, q), 4.75 (2H, d), 6.70 (1H, s), 7.30-7.44 (4H, m), 7.53 (2H, d), 7.68-7.71 (1H, m), 7.92 (2H, d). |
| 5-38 | ¹H-NMR (CDCl₃) δ: 1.21 (3H, t), 2.33 (3H, s), 2.68 (2H, q), 4.71 (2H, d), 6.61 (1H, s), 7.36 (2H, s), 7.40 (1H, d), 7.47-7.52 (4H, m), 7.66-7.69 (1H, m), 7.79-7.80 (1H, m), 7.90 (2H, d). |
| 5-39 | ¹H-NMR (CDCl₃) δ: 1.21 (3H, t), 2.33 (3H, s), 2.68 (2H, q), 4.71 (2H, d), 6.56 (1H, s), 7.37 (2H, s), 7.43-7.48 (5H, m), 7.74 (2H, d), 7.90 (2H, d). |
| 5-40 | ¹H-NMR (CDCl₃) δ: 1.21 (3H, t), 2.34 (3H, s), 2.69 (2H, q), 4.77 (2H, d), 7.37-7.42 (4H, m), 7.51 (2H, d), 7.92 (2H, d), 8.35-8.37 (1H, m), 8.58-8.65 (1H, m). |
| 5-41 | ¹H-NMR (CDCl₃) δ: 1.21 (3H, t), 2.33 (3H, s), 2.68 (2H, q), 4.75 (2H, d), 7.05 (1H, s), 7.34-7.38 (3H, m), 7.54-7.51 (3H, m), 7.92 (2H, d), 8.14 (1H, dd), 8.48 (1H, dd). |
| 5-42 | ¹H-NMR (CDCl₃) δ: 1.22 (3H, t), 2.34 (3H, s), 2.69 (2H, q), 4.81-4.83 (4H, m), 7.37 (2H, s), 7.40 (1H, s), 7.46 (2H, d), 7.88 (2H, d). |
| 5-44 | ¹H-NMR (CDCl₃) δ: 1.21 (3H, t), 2.34 (3H, s), 2.70 (2H, q), 4.51 (2H, d), 5.96 (1H, s), 7.16 (1H, d), 7.22 (1H, d), 7.37 (2H, s), 7.97 (1H, d), 8.12 (1H, t). |
| 5-45 | ¹H-NMR (CDCl₃) δ: 1.19-1.26 (6H, m), 2.29 (2H, q), 2.34 (3H, s), 2.70 (2H, q), 4.52 (2H, d), 5.92 (1H, s), 7.16 (1H, d), 7.23 (1H, dd), 7.37 (2H, s), 7.97 (1H, d), 8.13 (1H, t). |

NMR Table

| Exa | NMR |
|---|---|
| 5-46 | ¹H-NMR (CDCl₃) δ: 0.23-0.26 (2H, m), 0.64-0.67 (2H, m), 1.00-1.03 (1H, m), 1.22 (3H, t), 2.26 (2H, d), 2.35 (3H, s), 2.70 (2H, q), 4.56 (2H, d), 6.36 (1H, s), 7.17 (1H, d), 7.24 (1H, d), 7.37 (2H, s), 7.97 (1H, d), 8.14 (1H, t). |
| 5-47 | ¹H-NMR (CDCl₃) δ: 1.22 (3H, t), 2.34 (3H, s), 2.70 (2H, q), 3.15 (2H, q), 4.56 (2H, d), 6.31 (1H, s), 7.14 (1H, d), 7.21 (1H, d), 7.37 (3H, s), 7.96 (1H, d), 8.11 (1H, t). |
| 5-48 | ¹H-NMR (CDCl₃) δ: 1.21 (3H, t), 2.35 (3H, d), 2.70 (2H, q), 4.76 (2H), 7.22 (1H, d), 7.32 (1H, d), 7.38 (2H, d), 7.41-7.42 (1H, m), 7.97 (1H, d), 8.17 (1H, t), 8.37 (1H, td), 8.59-8.66 (1H, m). |
| 5-49 | ¹H-NMR (CDCl₃) δ: 1.22 (3H, t), 1.48 (9H, s), 2.35 (3H, s), 2.70 (2H, q), 4.39 (2H, d), 5.02 (1H, s), 7.14-7.25 (2H, m), 7.37 (2H, s), 7.97 (1H, d), 8.14 (1H, dd). |
| 5-51 | ¹H-NMR (CDCl₃) δ: 1.22 (3H, t), 2.04 (3H, s), 2.34 (3H, s), 2.69 (2H, q), 4.56 (2H, d), 6.04 (1H, s), 7.27-7.29 (1H, m), 7.38 (2H, s), 7.81-7.88 (2H, m). |
| 5-52 | ¹H-NMR (CDCl₃) δ: 1.13-1.26 (6H, m), 2.28 (2H, q), 2.34 (3H, s), 2.70 (2H, q), 4.57 (2H, d), 5.94 (1H, s), 7.28-7.30 (1H, m), 7.38 (2H, s), 7.83-7.86 (2H, m). |
| 5-53 | ¹H-NMR (CDCl₃) δ: 0.77-0.81 (2H, m), 0.98-1.05 (2H, m), 1.22 (3H, t), 1.38-1.43 (1H, m), 2.34 (3H, s), 2.70 (2H, q), 4.58 (2H, d), 6.18 (1H, t), 7.28-7.30 (1H, m), 7.37 (2H, s), 7.83-7.86 (2H, m). |
| 5-54 | ¹H-NMR (CDCl₃) δ: 0.22-0.24 (2H, m), 0.64-0.67 (2H, m), 0.98-1.00 (1H, m), 1.23 (3H, t), 2.23 (2H, d), 2.35 (3H, s), 2.70 (2H, q), 4.61 (2H, d), 6.39 (1H, s), 7.30 (1H, d), 7.38 (2H, s), 7.83-7.88 (2H, m). |
| 5-55 | ¹H-NMR (CDCl₃) δ: 1.23 (3H, t), 2.35 (3H, s), 2.70 (2H, q), 3.14 (2H, q), 4.63 (2H, d), 6.25 (1H, s), 7.28-7.31 (1H, m), 7.38 (2H, s), 7.79-7.90 (2H, m). |
| 5-57 | ¹H-NMR (CDCl₃) δ: 1.22 (3H, t), 2.35 (3H, s), 2.70 (2H, q), 3.99 (2H, s), 7.32 (1H, dd), 7.38 (2H, s), 7.83 (1H, dd), 8.03 (1H, dz). |
| 5-58 | ¹H-NMR (CDCl₃) δ: 1.21 (3H, t), 2.05 (3H, s), 2.32 (3H, s), 2.68 (2H, q), 4.50 (2H, d), 6.05 (1H, t), 7.24-7.30 (1H, m), 7.37 (2H, s), 7.84 (1H, dd), 8.01 (1H, d). |
| 5-59 | ¹H-NMR (CDCl₃) δ: 1.16-1.24 (6H, m), 2.28 (2H, q), 2.33 (3H, s), 2.68 (2H, q), 4.51 (2H, d), 6.02 (1H, t), 7.24-7.29 (1H, m), 7.37 (2H, s), 7.84 (1H, dd), 8.01 (1H, d). |
| 5-61 | ¹H-NMR (CDCl₃) δ: 0.22-0.24 (2H, m), 0.63-0.69 (2H, m), 0.96-1.02 (1H, m), 1.21 (3H, t), 2.23 (2H, d), 2.33 (3H, s), 2.68 (2H, q), 4.55 (2H, d), 6.45 (1H, t), 7.27 (1H, dd), 7.37 (2H, s), 7.85 (1H, dd), 8.00 (1H, d). |
| 5-62 | ¹H-NMR (CDCl₃) δ: 1.21 (3H, t), 2.33 (3H, s), 2.68 (2H, q), 3.11 (2H, q), 4.55 (2H), 6.49 (1H, s), 7.23 (1H, dd), 7.38 (2H, s), 7.82 (1H, dd), 8.01 (1H, d). |
| 5-63 | ¹H-NMR (CDCl₃) δ: 1.22 (3H, t), 1.47 (9H, s), 2.34 (3H, s), 2.69 (2H, q), 4.40 (2H, d), 5.06 (1H, s), 7.22-7.24 (1H, m), 7.37 (2H, s), 7.84 (1H, dd), 8.01 (1H, d). |
| 5-64 | ¹H-NMR (CDCl₃) δ: 1.24 (3H, t), 2.40 (3H, s), 2.74 (2H, q), 3.95 (2H, s), 7.37-7.34 (3H, m), 7.49 (1H, s), 7.68 (1H, s), 7.83 (1H, s). |
| 5-65 | ¹H-NMR (CDCl₃) δ: 1.22 (3H, t), 2.04 (3H, s), 2.38 (3H, s), 2.73 (2H, q), 4.44 (2H, d), 6.21 (1H, s), 7.24-7.28 (1H, m), 7.35-7.38 (3H, m), 7.72-7.74 (2H, m). |
| 5-66 | ¹H-NMR (CDCl₃) δ: 1.18-1.23 (6H, m), 2.28 (2H, q), 2.39 (3H, s), 2.73 (2H, q), 4.46 (2H, dz), 6.05 (1H, s), 7.29-7.29 (1H, m), 7.35-7.39 (3H, m), 7.66 (1H, s), 7.76 (1H, d). |
| 5-67 | ¹H-NMR (CDCl₃) δ: 0.20-0.24 (2H, m), 0.56-0.68 (2H, m), 0.96-1.03 (1H, m), 1.23 (3H, t), 2.24 (2H, d), 2.40 (3H, s), 2.74 (2H, q), 4.51 (2H, d), 6.37 (1H, s), 7.31 (1H, dd), 7.38 (2H, s), 7.41 (1H, s), 7.62 (1H, s), 7.81 (1H, d). |
| 5-68 | ¹H-NMR (CDCl₃) δ: 1.21-1.24 (6H, m), 2.37 (3H, s), 2.72 (2H, q), 3.12 (2H, q), 4.49 (2H, d), 6.68 (1H, s), 7.23 (1H, d), 7.32 (1H, s), 7.37 (2H, s), 7.64 (1H, s), 7.70 (1H, d). |
| 5-69 | ¹H-NMR (CDCl₃) δ: 1.24 (3H, t), 1.47 (9H, s), 2.40 (3H, s), 2.74 (2H, q), 4.35 (2H, d), 5.01 (1H, s), 7.32 (1H, d), 7.38 (2H, s), 7.41 (1H, s), 7.61 (1H, s), 7.82 (1H, d). |
| 5-72 | ¹H-NMR (CDCl₃) δ: 1.12-1.25 (6H, m), 2.24 (2H, q), 2.32 (3H, s), 2.67 (2H, q), 4.53 (2H, d), 6.01 (1H, s), 7.36 (2H, s), 7.48 (1H, t), 7.64-7.66 (3H, m). |
| 5-76 | ¹H-NMR (CDCl₃) δ: 1.21 (3H, t), 2.33 (3H, s), 2.68 (2H, q), 4.56 (2H, s), 7.37 (2H, s), 7.44 (1H, s), 7.67 (1H, d), 7.77 (1H, d), 7.93 (1H, s). |
| 5-77 | ¹H-NMR (CDCl₃) δ: 1.21 (3H, t), 2.32 (3H, s), 2.67 (2H, q), 4.56 (2H, d), 6.10 (1H, s), 7.36 (2H, s), 7.52 (1H, d), 7.60 (1H, s), 7.75 (1H, dd), 7.96 (1H, d). |
| 5-78 | ¹H-NMR (CDCl₃) δ: 1.11-1.28 (6H, m), 2.24 (2H, q), 2.31 (3H, s), 2.67 (2H, q), 4.56 (2H, d), 6.10 (1H, t), 7.36 (2H, s), 7.49 (1H, d), 7.69 (1H, s), 7.75 (1H, dd), 7.96 (1H, d). |
| 5-79 | ¹H-NMR (CDCl₃) δ: 0.75-0.78 (2H, m), 0.92-0.97 (2H, m), 1.21 (3H, t), 1.38-1.44 (1H, m), 2.32 (3H, s), 2.67 (2H, q), 4.59 (2H, d), 6.24 (1H, s), 7.37 (2H, s), 7.51 (1H, d), 7.56 (1H, s), 7.74 (1H, d), 7.95 (1H, s). |
| 5-80 | ¹H-NMR (CDCl₃) δ: 0.19-0.23 (2H, m), 0.61-0.67 (2H, m), 0.95-0.98 (1H, m), 1.21 (3H, t), 2.19 (2H, d), 2.33 (3H, s), 2.67 (2H, q), 4.61 (2H, d), 6.54 (1H, s), 7.37 (2H, s), 7.53-7.55 (2H, m), 7.76 (1H, t), 7.97 (1H, d). |
| 5-81 | ¹H-NMR (CDCl₃) δ: 1.17-1.25 (6H, m), 2.30 (3H, s), 2.65 (2H, qz), 3.10 (2H, q), 4.59 (2H, d), 6.57 (1H, d), 7.36 (2H, s), 7.44 (1H, s), 7.58 (1H, s), 7.70 (1H, d), 7.91 (1H, s). |
| 5-82 | ¹H-NMR (CDCl₃) δ: 1.21 (3H, t), 2.32 (3H, s), 2.67 (2H, q), 4.82 (2H, d), 7.35-7.44 (4H, m), 7.62 (1H, d), 7.78 (1H, d), 7.98 (1H, d), 8.35-8.36 (1H, m), 8.58 (1H, dt). |
| 5-83 | ¹H-NMR (CDCl₃) δ: 1.22 (3H, t), 2.33 (3H, s), 2.68 (2H, q), 4.00 (2H, s), 7.37 (2H, s), 7.42 (1H, s), 7.57 (1H, d), 7.83 (1H, dd), 8.10 (1H, d). |
| 5-84 | ¹H-NMR (CDCl₃) δ: 1.21 (3H, t), 2.32 (3H, s), 2.66 (2H, q), 4.61 (2H, d), 6.23 (1H, s), 7.37 (2H, s), 7.52-7.54 (2H, m), 7.81 (1H, dd), 8.14 (1H, d), 8.29 (1H, s). |
| 5-85 | ¹H-NMR (CDCl₃) δ: 1.20 (3H, t), 2.31 (3H, s), 2.66 (2H, q), 4.54 (2H, d), 6.14 (1H, t), 7.36 (2H, s), 7.51 (1H, d), 7.65 (1H, s), 7.80 (1H, dd), 8.14 (1H, d). |
| 5-86 | ¹H-NMR (CDCl₃) δ: 1.14-1.24 (6H, m), 2.26 (2H, q), 2.32 (3H, s), 2.67 (2H, q), 4.56 (2H, d), 6.06 (1H, s), 7.37 (2H, s), 7.51-7.53 (2H, m), 7.80 (1H, dd), 8.14 (1H, d). |
| 5-88 | ¹H-NMR (CDCl₃) δ: 0.20-0.24 (2H, m), 0.61-0.67 (3H, m), 0.96-0.98 (1H, m), 1.22 (3H, t), 2.19 (2H, d), 2.33 (3H, s), 2.67 (2H, q), 4.59 (2H, d), 6.58 (1H, s), 7.37 (2H, s), 7.47 (1H, s), 7.54 (1H, d), 7.80 (1H, d), 8.14 (1H, s). |

-continued

NMR Table

| Exa | NMR |
|---|---|
| 5-89 | $^1$H-NMR (CDCl$_3$) δ: 1.22 (3H, t), 2.33 (3H, s), 2.67 (2H, q), 3.13 (2H, q), 4.61 (2H, d), 6.38 (1H, s), 7.37 (3H, s), 7.51 (1H, d), 7.79 (1H, d), 8.13 (1H, s). |
| 5-90 | $^1$H-NMR (CDCl$_3$) δ: 1.21 (3H, t), 1.87 (3H, dd,), 2.33 (3H, s), 2.67 (2H, q), 4.63 (2H, d), 5.85 (1H, d), 6.00 (1H, s), 6.89 (1H, dd), 7.35-7.38 (3H, m), 7.56 (1H, d), 7.78 (1H, d), 8.13 (1H, s). |
| 5-91 | $^1$H-NMR (CDCl$_3$) δ: 1.22 (3H, t), 2.32 (3H, s), 2.67 (2H, q), 3.43 (3H, s), 3.93 (2H, s), 4.62 (2H, d), 7.11 (1H, s), 7.37 (2H, s), 7.51-7.53 (2H, m), 7.82 (1H, dd), 8.15 (1H, d). |
| 5-92 | $^1$H-NMR (CDCl$_3$) δ: 1.21 (3H, t), 2.33 (3H, d), 2.67 (2H, q), 4.75 (2H, d), 6.74 (1H, s), 7.12 (2H, t), 7.37 (2H, s), 7.43 (1H, s), 7.61 (1H, d), 7.79-7.82 (3H, m), 8.16 (1H, d). |
| 5-93 | $^1$H-NMR (CDCl$_3$) δ: 1.21 (3H, t), 2.32 (3H, s), 2.67 (2H, q), 4.80 (2H), 7.36-7.39 (3H, m), 7.43 (1H, s), 7.50 (1H, t), 7.61 (1H, d), 7.83 (1H, dd), 8.16 (1H, d), 8.36 (1H, td), 8.57 (1H, ddd). |
| 5-94 | $^1$H-NMR (CDCl$_3$) δ: 1.16 (3H, t), 2.26 (3H, s), 2.62 (2H, q), 4.74 (2H, d), 7.28 (1H, dd), 7.34 (2H, s), 7.38 (1H, dd), 7.56 (1H, d), 7.82 (1H, dd), 7.94 (1H, s), 8.00 (1H, dd), 8.14 (1H, d), 8.42 (1H, dd). |
| 5-95 | $^1$H-NMR (acetone-d$_6$) δ: 1.07 (3H, t), 1.18 (3H, t), 2.76 (2H, q), 2.79 (3H, s), 3.22-3.13 (2H, m), 4.44 (2H, d), 5.66 (1H, s), 6.03 (1H, s), 7.46 (2H, s), 7.57 (1H, d), 8.00 (1H, dd), 8.19 (1H, d), 9.28 (1H, s). |
| 5-96 | $^1$H-NMR (CDCl$_3$) δ: 1.19 (3H, t), 2.28 (3H, s), 2.65 (2H, q), 2.93 (3H, s), 4.46 (2H, d), 5.14 (1H, t), 7.36 (2H, s), 7.61 (1H, d), 7.66 (1H, s), 7.84 (1H, dd), 8.14 (1H, d). |
| 5-97 | $^1$H-NMR (CDCl$_3$) δ: 1.23 (3H, t), 2.34 (3H, s), 2.68 (2H, q), 2.82 (6H, s), 4.41 (2H, d), 4.67 (1H, t), 7.33 (1H, s), 7.38 (2H, s), 7.64 (1H, d), 7.84 (1H, dd), 8.15 (1H, d). |
| 5-98 | $^1$H-NMR (CDCl$_3$) δ: 1.21 (3H, t), 2.33 (3H, s), 2.41 (3H, s), 2.69 (2H, q), 3.94 (2H, s), 7.36 (2H, s), 7.44-7.50 (2H, m), 7.74-7.72 (2H, m). |
| 5-99 | $^1$H-NMR (CDCl$_3$) δ: 1.21 (3H, t), 2.04 (1H, s), 2.33 (3H, s), 2.41 (3H, s), 2.68 (2H, q), 4.49 (2H, d), 5.80 (1H, s), 7.34-7.36 (3H, m), 7.47 (1H, s), 7.69-7.72 (2H, m). |
| 5-100 | $^1$H-NMR (CDCl$_3$) δ: 1.16-1.26 (6H, m), 2.27 (2H, q), 2.34 (3H, s), 2.42 (3H, s), 2.69 (2H, q), 4.51 (2H, d), 5.69 (1H, s), 7.36-7.39 (4H, m), 7.70 (1H, d), 7.75 (1H, s). |
| 5-101 | $^1$H-NMR (CDCl$_3$) δ: 0.21-0.25 (2H, m), 0.61-0.67 (2H, m), 0.98-1.01 (1H, m), 1.22 (3H, t), 2.24 (2H, d), 2.34 (3H, s), 2.43 (3H, s), 2.69 (2H, q), 4.55 (2H, d), 6.15 (1H, s), 7.37-7.39 (4H, m), 7.71 (1H, d), 7.75 (1H, s). |
| 5-102 | $^1$H-NMR (CDCl$_3$) δ: 1.22 (3H, t), 2.33 (3H, s), 2.41 (3H, s), 2.68 (2H, q), 3.13 (2H, q), 4.55 (2H, d), 6.11 (1H, s), 7.34-7.36 (4H, m), 7.68 (1H, d), 7.74 (1H, s). |
| 5-103 | $^1$H-NMR (CDCl$_3$) δ: 1.22 (3H, t), 2.34 (3H, s), 2.48 (3H, s), 2.69 (2H, q), 4.75 (2H, d), 7.15 (1H, s), 7.37-7.42 (4H, m), 7.46 (1H, d), 7.73 (1H, d), 7.79 (1H, s), 8.35-8.36 (1H, m), 8.62 (1H, ddd). |
| 5-104 | $^1$H-NMR (CDCl$_3$) δ: 1.21 (3H, t), 1.47 (9H, s), 2.33 (3H, s), 2.40 (3H, s), 2.68 (2H, q), 4.37 (2H, d), 4.85 (1H, s), 7.36-7.44 (4H, m), 7.70-7.73 (2H, m). |
| 5-106 | $^1$H-NMR (CDCl$_3$) δ: 1.21 (3H, t), 2.05 (3H, s), 2.34 (3H, s), 2.68 (2H, q), 4.69 (2H, d), 5.92 (1H, s), 7.38 (2H, s), 7.46 (1H, s), 7.77 (1H, d), 8.05 (1H, d), 8.23 (1H, s). |
| 5-107 | $^1$H-NMR (CDCl$_3$) δ: 1.16 (3H, t), 1.21 (3H, t), 2.26 (2H, q), 2.33 (3H, s), 2.68 (2H, q), 4.68 (2H, d), 5.94 (1H, s), 7.38 (2H, s), 7.61 (1H, s), 7.73 (1H, d), 8.05 (1H, d), 8.23 (1H, s). |
| 5-108 | $^1$H-NMR (CDCl$_3$) δ: 0.77-0.81 (2H, m), 0.97-1.02 (2H, m), 1.22 (3H, t), 1.37-1.43 (1H, m), 2.34 (3H, s), 2.68 (2H, q), 4.70 (2H, d), 6.11 (1H, s), 7.38 (2H, s), 7.53 (1H, s), 7.74 (1H, d), 8.05 (1H, d), 8.22 (1H, s). |
| 5-109 | $^1$H-NMR (CDCl$_3$) δ: 0.19-0.21 (2H, m), 0.60-0.66 (2H, m), 0.92-0.95 (1H, m), 1.22 (3H, t), 2.20 (2H, d), 2.34 (3H, s), 2.68 (2H, q), 4.72 (2H, d), 6.43 (1H, s), 7.38 (2H, s), 7.55 (1H, s), 7.76 (1H, d), 8.05 (1H, d), 8.24 (1H, s). |
| 5-110 | $^1$H-NMR (CDCl$_3$) δ: 1.23 (3H, t), 2.34 (3H, s), 2.67 (2H, q), 3.14 (2H, q), 4.75 (2H, d), 6.21 (1H, s), 7.37-7.40 (3H, m), 7.41 (1H, s), 7.73 (1H, d), 8.06 (1H, d), 8.24 (1H, s). |
| 5-111 | $^1$H-NMR (CDCl$_3$) δ: 1.22 (3H, t), 2.34 (3H, s), 2.67 (2H, q), 4.89 (2H, d), 6.56 (1H, s), 7.13 (2H, t), 7.38 (2H, s), 7.45 (1H, s), 7.77-7.85 (3H, m), 8.05 (1H, d), 8.26 (1H, s). |
| 5-112 | $^1$H-NMR (CDCl$_3$) δ: 1.22 (3H, t), 2.33 (3H, s), 2.68 (2H, q), 4.94 (2H, d), 7.38-7.41 (3H, m), 7.49 (1H, d), 7.81 (1H, d), 8.07 (1H, d), 8.26 (1H, s), 8.35-8.37 (1H, m), 8.59 (1H, ddd). |
| 5-113 | $^1$H-NMR (CDCl$_3$) δ: 1.20 (3H, t), 2.32 (3H, s), 2.66 (2H, q), 5.37 (2H, s), 7.37 (2H, s), 7.45 (1H, d), 7.60 (1H, s), 7.82-7.79 (2H, m), 7.93-7.91 (2H, m), 8.12 (1H, dd), 8.64 (1H, d). |
| 5-114 | $^1$H-NMR (CDCl$_3$) δ: 1.20 (3H, t), 1.95 (3H, s), 2.31 (3H, s), 2.67 (2H, q), 4.72 (2H, d), 6.44 (1H, t), 7.38 (2H, s), 7.81 (1H, d), 8.04 (1H, s), 8.18 (1H, dd), 8.64 (1H, d). |
| 5-115 | $^1$H-NMR (CDCl$_3$) δ: 1.09 (3H, t), 1.21 (3H, t), 2.20 (2H, q), 2.32 (3H, s), 2.67 (2H, q), 4.73 (2H, d), 6.41 (1H, t), 7.38 (2H, s), 7.80 (1H, d), 8.00 (1H, s), 8.17 (1H, dd), 8.64 (1H, d). |
| 5-116 | $^1$H-NMR (CDCl$_3$) δ: 0.69-0.74 (2H, m), 0.78-0.83 (2H, m), 1.18 (3H, t), 1.36-1.44 (1H, m), 2.29 (3H, s), 2.65 (2H, q), 4.72 (2H, d), 6.72 (1H, t), 7.36 (2H, s), 7.68 (1H, d), 8.16 (1H, dd), 8.38 (1H, s), 8.64 (1H, d). |
| 5-117 | $^1$H-NMR (CDCl$_3$) δ: 0.10-0.15 (2H, m), 0.56-0.62 (2H, m), 0.82-0.90 (1H, m), 1.20 (3H, t), 2.07 (2H, d), 2.32 (3H, s), 2.67 (2H, q), 4.76 (2H, d), 6.91 (1H, t), 7.38 (2H, s), 7.79 (1H, d), 8.23-8.19 (2H, m), 8.66 (1H, d). |
| 5-118 | $^1$H-NMR (acetone-d$_6$) δ: 1.06 (3H, t), 2.25 (3H, s), 2.66 (2H, q), 3.27 (2H, q), 4.71 (2H, d), 7.36 (2H, s), 7.72 (1H, s), 8.02 (1H, br s), 8.23 (1H, dd), 8.54 (1H, d), 9.44 (1H, s). |
| 5-127 | $^1$H-NMR (CDCl$_3$) δ: 1.19 (3H, q), 2.27 (2H, q), 2.33 (3H, s), 4.53 (2H, d), 5.87 (1H, s), 7.34 (2H, s), 7.41-7.43 (3H, m), 7.89 (2H, d). |
| 5-139 | $^1$H-NMR (CDCl$_3$) δ: 1.19-1.21 (6H, m), 2.25-2.33 (5H, m), 2.67 (2H, q, J = 25.8 Hz), 4.53 (2H, d, J = 5.9 Hz), 5.88 (1H, s), 7.35 (2H, s), 7.42-7.45 (3H, m), 7.89 (2H, d, J = 8.1 Hz). |
| 5-142 | $^1$H-NMR (CDCl$_3$) δ: 1.19 (3H, t, J = 7.6 Hz), 2.31 (3H, s), 2.67 (2H, q, J = 7.5 Hz), 3.11 (2H, q, J = 10.6 Hz), 4.55 (2H, d, J = 5.9 Hz), 6.52 (1H, s), 7.35-7.38 (4H, m), 7.53 (1H, s), 7.84 (2H, d, J = 8.1 Hz). |
| 5-144 | $^1$H-NMR (CDCl$_3$) δ: 1.11 (3H, t, J = 7.6 Hz), 1.81 (3H, s), 2.21 (3H, s), 2.60 (2H, q, J = 7.5 Hz), 4.40 (2H, d, J = 6.0 Hz), 6.79 (1H, t, J = 6.0 Hz), 7.28-7.29 (3H, m), 7.56-7.60 (2H, m), 8.72 (1H, s). |
| 5-145 | $^1$H-NMR (CDCl$_3$) δ: 1.17-1.21 (6H, m), 2.26 (2H, q, J = 7.6 Hz), 2.33 (3H, s), 2.67 (2H, q, J = 7.4 Hz), 4.55 (2H, d, J = 6.2 Hz), 5.92 (1H, s), 7.36 (2H, s), 7.43 (1H, s), 7.51 (1H, t, J = 7.6 Hz), 7.63-7.65 (2H, m). |

-continued

| | NMR Table |
|---|---|
| Exa | NMR |

5-146 $^1$H-NMR (CDCl$_3$) δ: 0.74-0.78 (2H, m), 0.92-0.96 (2H, m), 1.21 (3H, t, J = 12.6 Hz), 1.37-1.39 (1H, m), 2.32 (3H, s), 2.67 (2H, q, J = 7.5 Hz), 4.55 (2H, d, J = 6.0 Hz), 6.16 (1H, d, J = 6.2 Hz), 7.35 (2H, s), 7.48 (1H, t, J = 7.7 Hz), 7.61-7.65 (3H, m).

5-147 $^1$H-NMR (CDCl$_3$) δ: 0.19-0.21 (2H, m), 0.59-0.63 (2H, m), 0.92-0.97 (1H, m), 1.20 (3H, t, J = 7.6 Hz), 2.17 (2H, d, J = 3.6 Hz), 2.32 (3H, s), 2.67 (2H, q, J = 7.5 Hz), 4.57 (2H, d, J = 6.0 Hz), 6.45 (1H, s), 7.35 (2H, s), 7.49 (1H, t, J = 7.7 Hz), 7.65-7.67 (3H, m).

5-148 $^1$H-NMR (CDCl$_3$) δ: 1.21 (3H, t, J = 8.0 Hz), 2.33 (3H, s), 2.67 (2H, q, J = 7.3 Hz), 3.12 (2H, q, J = 10.6 Hz), 4.60 (2H, d, J = 5.9 Hz), 6.32 (1H, s), 7.36 (2H, s), 7.42 (1H, s), 7.49 (1H, t, J = 7.7 Hz), 7.63-7.65 (2H, m).

5-149 $^1$H-NMR (CDCl$_3$) δ: 1.20 (3H, t), 2.32 (3H, s), 2.67 (2H, q), 4.02 (2H, s), 7.35 (2H, s), 7.48 (1H, s), 7.57 (1H, d), 7.79 (1H, dd), 7.93 (1H, s).

5-150 $^1$H-NMR (CDCl$_3$) δ: 1.20 (3H, t), 2.01 (2H, s), 2.32 (3H, s), 2.66 (2H, q), 4.56 (2H, d), 6.13 (1H, s), 7.35 (2H, s), 7.52 (1H, d), 7.66 (1H, s), 7.76 (1H, dd), 7.96 (1H, d).

5-151 $^1$H-NMR (CDCl$_3$) δ: 1.14-1.25 (6H, m), 2.26 (2H, q), 2.32 (3H, s), 2.67 (2H, q), 4.58 (2H, d), 6.04 (1H, s), 7.35 (2H, s), 7.52-7.54 (2H, m), 7.76 (1H, dd), 7.96 (1H, d).

5-152 $^1$H-NMR (CDCl$_3$) δ: 0.76-0.80 (2H, m), 0.97-1.02 (2H, m), 1.21 (3H), 1.38-1.44 (1H, m), 2.33 (3H, s), 2.67 (2H, q), 4.61 (2H, d), 6.18 (1H, s), 7.36 (2H, s), 7.40 (1H, s), 7.55 (1H, d), 7.75 (1H, d), 7.95 (1H, s).

5-153 $^1$H-NMR (CDCl$_3$) δ: 0.19-0.22 (2H, m), 0.61-0.64 (2H, m), 0.93-0.98 (1H, m), 1.20 (3H, t), 2.18 (2H, d), 2.32 (3H, s), 2.67 (2H, q), 4.61 (2H, d), 6.56 (1H, s), 7.35 (2H, s), 7.53 (1H, d), 7.61 (1H, s), 7.77 (1H, dd), 7.97 (1H, d).

5-154 $^1$H-NMR (CDCl$_3$) δ: 1.21 (3H, t), 2.33 (3H, s), 2.67 (2H, q), 3.14 (2H, q), 4.64 (2H, d), 6.31 (1H, s), 7.36 (2H, s), 7.54 (1H, d), 7.76 (1H, d), 7.97 (1H, s).

5-155 $^1$H-NMR (CDCl$_3$) δ: 1.20 (3H, t), 2.32 (3H, s), 2.66 (2H, q), 4.82 (2H, d), 7.35-7.40 (3H, m), 7.47 (1H, s), 7.61 (1H, d), 7.78 (1H, dd), 7.98 (1H, d), 8.35-8.36 (1H, m), 8.57 (1H, ddd).

5-157 $^1$H-NMR (CDCl$_3$) δ: 1.20 (3H, t), 2.01 (3H, s), 2.32 (3H, s), 2.67 (2H, q), 4.55 (2H, d), 6.14 (1H, t), 7.35 (2H, s), 7.51 (1H, d), 7.65 (1H, s), 7.80 (1H, dd), 8.14 (1H).

5-158 $^1$H-NMR (CDCl$_3$) δ: 1.16-1.21 (6H, m), 2.27 (2H, q), 2.32 (3H, s), 2.67 (2H, q), 4.56 (2H, d), 6.05 (1H, t), 7.35 (2H, s), 7.50-7.52 (2H, m), 7.79 (1H, d), 8.13 (1H, s).

5-159 $^1$H-NMR (CDCl$_3$) δ: 0.77-0.80 (2H, m), 0.96-1.00 (2H, m), 1.21 (3H, t), 2.33 (3H, s), 2.68 (2H, q), 4.59 (2H, d), 6.21 (1H, s), 7.36 (2H, s), 7.40 (1H, s), 7.54 (1H, d), 7.80 (1H, d), 8.13 (1H, s).

5-160 $^1$H-NMR (acetone-d$_6$) δ: −0.02-0.01 (2H, m), 0.29-0.32 (3H, m), 0.94 (3H, t), 1.97 (2H, d), 2.59 (3H, s), 4.30 (2H, d), 7.24 (2H, s), 7.34 (1H, d), 7.80 (1H, dd), 8.00 (1H, d).

5-161 $^1$H-NMR (CDCl$_3$) δ: 1.21 (3H, t), 2.33 (3H, s), 2.66 (2H, q), 3.24 (2H, q), 4.62 (2H, d), 6.34 (1H, s), 7.36 (2H, s), 7.53 (1H, d), 7.81 (1H, d), 8.14 (1H, s).

5-174 $^1$H-NMR (CDCl$_3$) δ: 1.20 (3H, t), 2.32 (3H, s), 2.67 (2H, q), 4.79 (2H, d), 7.35-7.42 (4H, m), 7.58-7.69 (3H, m), 8.35-8.36 (1H, m), 8.55-8.62 (1H, m).

5-175 $^1$H-NMR (CDCl$_3$) δ: 1.21 (3H, t), 2.33 (3H, s), 2.67 (2H, q), 4.80 (2H, d), 7.36-7.37 (3H, m), 7.43 (1H, s), 7.67 (1H, d), 7.84 (1H, d), 8.15-8.18 (2H, m), 8.49 (1H, dd).

5-177 $^1$H-NMR (acetone-d$_6$) δ: 1.17 (3H, t), 2.69-2.80 (8H, m), 3.60 (1H, d), 3.79 (1H, d), 4.58 (2H, d), 7.46 (2H, s), 7.73 (1H, d), 7.99-8.03 (2H, m), 8.22 (1H, d), 9.32 (1H, s).

5-178 $^1$H-NMR (acetone-d$_6$) δ: 1.17 (3H, t), 2.73-2.79 (5H, m), 3.13 (3H, s), 4.16 (2H, s), 4.59 (2H, dz), 7.46 (2H, s), 7.69 (1H, d), 8.01 (1H, dd), 8.23 (1H, d), 9.32 (1H, s).

5-179 $^1$H-NMR (CDCl$_3$) δ: 1.21 (3H, t), 2.17 (2H, t), 2.34 (3H, d), 2.67 (2H, q), 3.23 (3H, s), 4.61 (2H, d), 7.36 (2H, s), 7.50-7.53 (2H, m), 7.81 (1H, dd), 8.15 (1H, d).

5-181 $^1$H-NMR (acetone-d$_6$) δ: 1.18 (3H, t), 2.36 (3H, s), 2.76 (2H, q), 3.14 (3H, d), 4.17 (2H, s), 4.61 (2H, d), 7.46 (2H, s), 7.69 (1H, d), 8.01-8.04 (2H, m), 8.25-8.25 (2H, m).

5-182 $^1$H-NMR (CDCl$_3$) δ: 2.35 (6H, s), 4.75 (2H, d), 7.12 (1H, s), 7.25-7.41 (5H, m), 7.98 (1H, d), 8.16-8.19 (2H, m), 8.50 (1H, dd).

5-183 $^1$H-NMR (CDCl$_3$) δ: 1.22 (3H, t), 2.34 (3H, s), 2.69 (2H, q), 4.75 (2H, d), 7.15 (1H, t), 7.37-7.41 (3H, m), 7.89 (1H, dd), 8.01 (1H, d), 8.17 (1H, dt), 8.50 (1H, dt).

5-184 $^1$H-NMR (CDCl$_3$) δ: 1.20 (3H, t), 2.31 (3H, s), 2.48 (2H, s), 2.67 (2H, q), 3.84 (2H, s), 7.36 (2H, s), 7.45 (2H, d), 7.57 (1H, s), 7.87 (2H, d).

5-185 $^1$H-NMR (CDCl$_3$) δ: 1.21 (3H, t), 2.34 (3H, s), 2.69 (2H, q), 2.98 (3H, s), 4.62-4.65 (2H, m), 7.32-7.38 (4H, m), 7.66-7.69 (1H, m), 7.90-7.96 (2H, m).

5-186 $^1$H-NMR (CDCl$_3$) δ: 1.13-1.21 (6H, m), 2.35 (3H, s), 2.42 (2H, s), 2.69 (2H, q), 2.98 (3H, d), 4.65 (2H, d), 7.31-7.38 (4H, m), 7.57 (1H, br s), 7.89-7.92 (2H, m).

5-187 $^1$H-NMR (CDCl$_3$) δ: 0.14-0.19 (2H, m), 0.55-0.58 (2H, m), 1.07-1.10 (1H, m), 1.22 (3H, t), 2.34 (3H, br s), 2.70 (2H, q), 2.97 (3H, d), 4.64 (2H, d), 7.31-7.39 (4H, m), 7.67 (1H, d), 7.93 (2H, dd).

5-188 $^1$H-NMR (CDCl$_3$) δ: 1.22 (3H, t), 2.34 (3H, s), 2.69 (2H, q), 3.03 (3H, d), 3.23-3.36 (2H, m), 4.67 (2H, d), 7.31-7.38 (4H, m), 7.54 (1H, br s), 7.94 (2H, dd).

5-189 $^1$H-NMR (CDCl$_3$) δ: 1.22 (3H, t), 2.32 (3H, d), 2.69 (2H, q), 2.84 (3H, s), 4.48 (2H, d), 7.35-7.38 (2H, m), 7.56 (1H, d), 7.65-7.68 (1H, m), 7.92-7.97 (2H, m), 8.45-8.46 (1H, m).

5-190 $^1$H-NMR (CDCl$_3$) δ: 1.21 (3H, t), 2.04 (3H, s), 2.32 (3H, s), 2.67 (2H, q), 4.51 (2H, d), 6.08 (1H, s), 7.37 (2H, s), 7.48-7.50 (2H, m), 7.83 (1H, d), 8.39 (1H, s).

5-191 $^1$H-NMR (CDCl$_3$) δ: 1.15-1.24 (6H, m), 2.26 (2H, q), 2.32 (3H, s), 2.67 (3H, q), 4.51 (2H, d), 6.06 (1H, s), 7.37 (2H, s), 7.47-7.49 (2H, m), 7.83 (1H, d), 8.39 (1H, s).

5-192 $^1$H-NMR (CDCl$_3$) δ: 1.22 (3H, tz), 2.33 (3H, s), 2.67 (2H, q), 3.15 (2H, q), 4.57 (2H, d), 6.38 (1H, s), 7.37 (3H, s), 7.49 (1H, d), 7.84 (1H, d), 8.40 (1H, d).

5-193 $^1$H-NMR (CDCl$_3$) δ: 1.21 (3H, t), 2.33 (3H, s), 2.67 (2H, q), 3.94 (2H, s), 7.35 (3H, s), 7.45 (1H, s), 7.54 (1H, d), 7.88 (1H, dd), 8.37 (1H, d).

5-194 $^1$H-NMR (CDCl$_3$) δ: 1.21 (3H, t), 2.05 (3H, s), 2.32 (3H, s), 2.67 (2H, q), 4.51 (2H, d), 6.05 (1H, s), 7.36 (2H, s), 7.42 (1H, s), 7.51 (1H, d), 7.84 (1H, d), 8.39 (1H, s).

5-195 $^1$H-NMR (CDCl$_3$) δ: 1.16-1.23 (6H, m), 2.27 (2H, q), 2.33 (3H, s), 2.67 (2H, q), 4.52 (2H, d), 6.04 (1H, s), 7.35 (2H, s), 7.40 (1H, s), 7.50 (1H, d), 7.83 (1H, d), 8.39 (1H, s).

NMR Table

| Exa | NMR |
|---|---|
| 5-196 | $^1$H-NMR (CDCl$_3$) δ: 0.77-0.80 (2H, m), 0.99-1.03 (2H, m), 1.21 (3H, t), 2.33 (3H, s), 2.67 (2H, q), 4.54 (2H, d), 6.19 (1H, s), 7.34-7.37 (3H, m), 7.51 (1H, d), 7.85 (1H, d), 8.39 (1H, s). |
| 5-197 | $^1$H-NMR (CDCl$_3$) δ: 0.21-0.25 (2H, m), 0.63-0.69 (2H, m), 0.97-1.00 (1H, m), 1.21 (3H, t), 2.21 (2H, d), 2.33 (3H, s), 2.67 (2H, q), 4.54 (2H, d), 6.61 (1H, s), 7.36 (2H, s), 7.44 (1H, s), 7.52 (1H, d), 7.85 (1H, d), 8.40 (1H, d). |
| 5-198 | $^1$H-NMR (CDCl$_3$) δ: 1.21 (3H, t), 2.33 (3H, s), 2.67 (2H, q), 3.15 (2H, q), 4.58 (2H, d), 7.36 (2H, s), 7.64-7.67 (1H, m), 7.85 (1H, d), 8.40 (1H, s). |
| 5-199 | $^1$H-NMR (CDCl$_3$) δ: 1.23 (3H, t), 2.35 (3H, s), 2.70 (2H, q), 4.81 (2H, d), 7.14 (1H, s), 7.36-7.43 (4H, m), 7.82-7.93 (2H, m), 8.18 (1H, dd), 8.50 (1H, dd). |
| 5-201 | $^1$H-NMR (CDCl$_3$) δ: 1.21 (3H, t), 2.05 (3H, s), 2.34 (3H, s), 2.69 (2H, q), 4.57 (2H, d), 5.98 (1H, s), 7.30 (1H, br s), 7.36 (2H, s), 7.84-7.87 (2H, m). |
| 5-202 | $^1$H-NMR (CDCl$_3$) δ: 1.16-1.24 (6H, m), 2.28 (2H, q), 2.34 (3H, s), 2.69 (2H, q), 4.58 (2H, d), 5.93 (1H, s), 7.30 (1H, d), 7.36 (2H, s), 7.81-7.89 (2H, m). |
| 5-203 | $^1$H-NMR (CDCl$_3$) δ: 0.78-0.81 (2H, m), 1.00-1.03 (2H, m), 1.21 (3H, t), 1.38-1.41 (1H, m), 2.34 (3H, s), 2.69 (2H, q), 4.59 (2H, d), 6.09 (1H, s), 7.30 (1H, d), 7.36 (2H, s), 7.82-7.87 (2H, m). |
| 5-204 | $^1$H-NMR (CDCl$_3$) δ: 0.20-0.26 (2H, m), 0.61-0.66 (2H, m), 0.97-1.02 (1H, m), 1.21 (3H, t), 2.24 (2H, d), 2.34 (3H, s), 2.70 (2H, q), 4.62 (2H, d), 6.38 (1H, s), 7.30 (1H, d), 7.36 (2H, s), 7.81-7.90 (2H, m). |
| 5-205 | $^1$H-NMR (CDCl$_3$) δ: 1.21 (3H, t), 2.34 (3H, s), 2.69 (2H, q), 3.14 (2H, q), 4.63 (2H, d), 6.26 (1H, s), 7.27 (1H, d), 7.37 (2H, s), 7.81-7.87 (2H, m). |
| 5-206 | $^1$H-NMR (CDCl$_3$) δ: 1.22 (3H, t), 2.35 (3H, s), 2.70 (2H, q), 4.81 (2H, d), 7.14 (1H, s), 7.36-7.43 (4H, m), 7.84-7.91 (2H, m), 8.18 (1H, dd), 8.50 (1H, dd). |
| 5-211 | $^1$H-NMR (CDCl$_3$) δ: 2.04 (3H, s), 2.33 (6H, s), 4.56 (2H, d), 6.07 (1H, s), 7.34 (2H, s), 7.47 (1H, s), 7.54 (1H, d), 7.81 (1H, d), 8.14 (1H, s). |
| 5-212 | $^1$H-NMR (CDCl$_3$) δ: 1.16 (3H, t), 2.26 (2H), 2.32 (6H, s), 4.56 (2H), 6.08 (1H, s), 7.34 (2H, s), 7.51 (1H, s), 7.57 (1H, s), 7.80 (1H, s), 8.13 (1H, s). |
| 5-213 | $^1$H-NMR (CDCl$_3$) δ: 1.26 (3H, t), 2.33 (6H, s), 3.14 (2H, q), 4.62 (2H, d), 6.36 (1H, s), 7.34-7.37 (3H, m), 7.52 (1H, d), 7.81 (1H, d), 8.14 (1H, s). |
| 5-219 | $^1$H-NMR (CDCl$_3$) δ: 1.16 (3H, t), 1.92 (3H, s), 2.26 (3H, s), 2.63 (2H, q), 4.47 (2H, d), 6.59 (1H, t), 7.34-7.37 (3H, m), 7.71 (1H, dd), 7.91 (1H, d), 8.39 (1H, s). |
| 5-220 | $^1$H-NMR (CDCl$_3$) δ: 1.14-1.24 (6H, m), 2.26 (2H, q), 2.33 (3H, s), 2.67 (2H, q), 4.58 (2H, d), 6.04 (1H, s), 7.37 (2H, s), 7.52-7.53 (2H, m), 7.75 (1H, d), 7.95 (1H, s). |
| 5-221 | $^1$H-NMR (CDCl$_3$) δ: 1.23 (3H, t), 2.34 (3H, s), 2.67 (2H, q), 3.14 (2H, q), 4.64 (2H, d), 6.30 (1H, s), 7.34 (1H, s), 7.38 (2H, s), 7.54 (1H, d), 7.76 (1H, d), 7.96 (1H, s). |
| 5-223 | $^1$H-NMR (CDCl$_3$) δ: 2.05 (3H, s), 4.52 (2H, d), 5.90 (1H, s), 7.43 (2H, d), 7.66 (2H, s), 7.73 (1H, s), 7.92 (2H, d). |
| 5-224 | $^1$H-NMR (CDCl$_3$) δ: 1.20 (3H, t), 2.29 (2H, q,), 4.54 (2H, d), 5.84 (1H, s), 7.44 (2H, d), 7.66-7.68 (3H, m), 7.93 (2H, d). |
| 5-225 | $^1$H-NMR (CDCl$_3$) δ: 0.21-0.25 (2H, m), 0.61-0.67 (2H, m), 0.97-1.00 (1H, m), 2.24 (2H, d), 4.58 (2H, d), 6.30 (1H, s), 7.45 (2H, d), 7.66-7.68 (3H, m), 7.93 (2H, d, J = 8.2 Hz). |
| 5-226 | $^1$H-NMR (CDCl$_3$) δ: 3.16 (2H, q), 4.59 (2H, d), 6.16 (1H, s), 7.43 (2H, d), 7.63 (1H, s), 7.67 (2H, s), 7.93 (2H, d). |
| 5-227 | $^1$H-NMR (CDCl$_3$) δ: 1.46 (9H, t), 4.40 (2H, d), 4.98 (1H, s), 7.43 (2H, d), 7.66 (2H, d), 7.69 (1H, s), 7.92 (2H, d). |
| 5-228 | $^1$H-NMR (CDCl$_3$) δ: 4.57 (2H, br s), 7.58 (1H, s), 7.66 (2H, s), 7.78-7.82 (2H, m), 7.96 (1H, d). |
| 5-229 | $^1$H-NMR (CDCl$_3$) δ: 2.04 (3H, s), 4.58 (2H, d), 6.05 (1H, t), 7.54 (1H, d), 7.67 (2H, s), 7.79 (1H, dd), 7.84 (1H, s), 7.98 (1H, d). |
| 5-230 | $^1$H-NMR (CDCl$_3$) δ: 1.17 (3H, t), 2.27 (2H, q), 4.59 (2H, d), 6.01 (1H, br s), 7.54 (1H, d), 7.67 (2H, s), 7.77-7.81 (2H, m), 7.98 (1H, d). |
| 5-231 | $^1$H-NMR (CDCl$_3$) δ: 0.75-1.06 (4H, m), 1.39-1.42 (1H, m), 4.61 (2H, d), 6.19 (1H, br s), 7.55 (1H, d), 7.67 (2H, s), 7.72 (1H, s), 7.79 (1H, dd), 7.98 (1H, d). |
| 5-232 | $^1$H-NMR (acetone-d$_6$) δ: 3.37 (2H, q), 4.60 (2H, d), 7.62 (1H, d), 7.86 (2H, d), 7.98 (1H, dd), 8.06-8.06 (2H, m), 9.76 (1H, s). |
| 6-1 | $^1$H-NMR (CDCl$_3$) δ: 1.26 (3H, t), 2.48 (3H, s), 2.79 (2H, q), 4.40 (2H, s), 7.35 (1H, s), 7.41 (2H, s), 7.55-7.64 (3H, m), 7.80 (1H, d), 8.13-8.15 (1H, m), 8.49-8.52 (1H, m). |
| 6-2 | $^1$H-NMR (CDCl$_3$) δ: 1.28 (3H, t), 2.03 (3H, s), 2.47 (3H, s), 2.78 (2H, q), 4.85 (2H, d), 5.93 (1H, s), 7.40-7.42 (4H, m), 7.62-7.64 (2H, m), 7.73 (1H, s), 8.03-8.04 (1H, m), 8.47-8.48 (1H, m). |
| 6-3 | $^1$H-NMR (CDCl$_3$) δ: 1.18 (3H, t), 1.29 (3H, t), 2.26 (2H, q), 2.48 (3H, s), 2.79 (2H, q), 4.91 (2H, d), 5.81 (1H, s), 7.35 (1H, s), 7.41 (2H, s), 7.46 (1H, d), 7.62-7.64 (2H, m), 7.76 (1H, d), 8.06-8.07 (1H, m), 8.48-8.49 (1H, m). |
| 6-4 | $^1$H-NMR (CDCl$_3$) δ: 0.76-0.81 (2H, m), 1.04-1.08 (2H, m), 1.29 (3H, t), 1.35-1.38 (1H, m), 2.49 (3H, s), 2.80 (2H, q), 4.96 (2H, d), 5.94 (1H, s), 7.29 (1H, s), 7.42 (2H, s), 7.52 (1H, d), 7.64-7.65 (2H, m), 7.79 (1H, d), 8.09-8.11 (1H, m), 8.49-8.51 (1H, m). |
| 6-5 | $^1$H-NMR (CDCl$_3$) δ: 0.17-0.18 (2H, m), 0.56-0.59 (2H, m), 0.92-0.97 (1H, m), 1.29 (2H, t), 2.22 (1H, d), 2.48 (3H, s), 2.80 (2H, q), 4.96 (2H, d), 6.23 (1H, s), 7.35 (1H, s), 7.42 (2H, s), 7.49 (1H, d), 7.63-7.65 (2H, m), 7.78 (1H, d), 8.07-8.09 (1H, m), 8.48-8.49 (1H, m). |
| 6-6 | $^1$H-NMR (CDCl$_3$) δ: 1.24 (3H, t), 2.45 (3H, s), 2.76 (2H, q), 3.12 (2H, q), 4.58 (2H, d), 6.83 (1H, d), 7.16 (1H, d), 7.41 (2H, s), 7.51 (1H, s), 7.55-7.59 (3H, m), 7.72-7.74 (1H, m), 8.35-8.36 (1H, m). |
| 6-7 | $^1$H-NMR (CDCl$_3$) δ: 1.24 (3H, t), 2.47 (3H, s), 2.79 (2H, q), 5.15 (2H, d), 7.35-7.38 (1H, m), 7.41 (2H, s), 7.47 (1H, d), 7.54 (1H, d), 7.61-7.66 (1H, m), 7.78 (0H, d), 8.08-8.13 (1H, m), 8.31-8.33 (1H, m), 8.47-8.52 (1H, m), 8.60 (1H, ddd). |
| 7-1 | $^1$H-NMR (CDCl$_3$) δ: 1.19 (3H, t), 2.30 (3H, s), 2.68 (2H, q), 4.06 (2H, s), 7.35 (2H, s), 7.95 (1H, d), 8.26 (1H, d), 8.60 (1H, s), 9.57 (1H, s). |
| 7-2 | $^1$H-NMR (CDCl$_3$) δ: 1.20 (3H, t), 2.01 (3H, s), 2.33 (3H, s), 2.69 (3H, q), 4.50 (2H, d), 6.50 (1H, t), 7.37 (2H, s), 7.81 (1H, dd), 8.18 (1H, d), 8.56 (1H, d), 9.55 (1H, s). |

| | NMR Table |
|---|---|
| Exa | NMR |
| 7-3 | ¹H-NMR (CDCl₃) δ: 1.18-1.23 (6H, m), 2.35-2.26 (5H, m), 2.70 (2H, q), 4.56 (2H, d), 5.94 (1H, s), 7.37 (2H, s), 7.84 (1H, dd), 8.25 (1H, d), 8.58 (1H, d), 9.52 (1H, s). |
| 7-5 | ¹H-NMR (CDCl₃) δ: 0.62-0.69 (2H, m), 0.63-0.69 (2H, m), 0.96-1.05 (1H, m), 1.18-1.29 (3H, m), 2.26 (2H, d), 2.35 (3H, s), 2.70 (2H, q), 4.61 (2H, d), 6.39 (1H, s), 7.37 (2H, s), 7.85 (1H, d), 8.26 (1H, d), 8.60 (1H, s), 9.52 (1H, s). |
| 7-6 | ¹H-NMR (CDCl₃) δ: 1.18-1.28 (3H, m), 2.34 (3H, s), 2.69 (2H, q), 3.19-3.08 (2H, m), 4.59 (2H, d), 6.49 (1H, s), 7.37 (2H, s), 7.82 (1H, dd), 8.21 (1H, d), 8.57 (1H, d), 9.51 (1H, s). |
| 7-19 | ¹H-NMR (CDCl₃) δ: 1.21 (3H, t), 1.47 (9H, s), 2.35 (3H, s), 2.70 (2H, q), 4.43 (2H, d), 5.12 (1H, s), 7.37 (2H, s), 7.84 (1H, dd), 8.25 (1H, d), 8.57 (1H, d), 9.54 (1H, s). |
| 8-2 | ¹H-NMR (CDCl₃) δ: 1.21 (3H, t), 2.08 (3H, s), 2.34 (3H, s), 2.69 (2H, q), 4.64 (2H, d), 6.71 (1H, s), 7.38 (2H, s), 7.42 (1H, d), 7.62 (1H, s), 8.22 (1H, dd), 9.08 (1H, d). |
| 8-3 | ¹H-NMR (CDCl₃) δ: 1.18-1.22 (6H, m), 2.28-2.36 (5H, m), 2.69 (2H, q), 4.63 (2H, d), 6.68 (1H, s), 7.38 (2H, s), 7.42 (1H, s), 7.71 (1H, s), 8.21 (1H, dd), 9.09 (1H, d). |
| 8-6 | ¹H-NMR (CDCl₃) δ: 1.23 (3H, t), 2.35 (3H, s), 2.70 (2H, q), 3.20 (3H, q), 4.71 (2H, d), 7.13 (1H, s), 7.40-7.43 (4H, m), 8.24 (1H, dd), 9.08 (1H, s). |
| 8-19 | ¹H-NMR (CDCl₃) δ: 1.20 (3H, t), 1.44 (9H, s), 2.30 (3H, s), 2.67 (2H, q), 4.50 (2H, d), 5.59 (1H, s), 7.38-7.40 (3H, m), 7.90 (1H, s), 8.21 (1H, d), 9.08 (1H, s). |
| 9-1 | ¹H-NMR (CDCl₃) δ: 1.18 (3H, t), 1.45 (3H, d), 2.27-2.33 (5H, m), 2.65 (2H, q), 4.29-4.22 (1H, m), 7.35 (2H, s), 7.50 (2H, d), 7.60 (1H, s), 7.89 (2H, d). |
| 9-2 | ¹H-NMR (CDCl₃) δ: 1.21 (3H, t), 1.52 (2H, d), 2.01 (3H, s), 2.33 (3H, s), 2.68 (2H, q), 5.12-5.21 (1H, m), 5.78 (1H, d), 7.36 (2H, s), 7.47-7.44 (3H, m), 7.89 (2H, d). |
| 9-3 | ¹H-NMR (CDCl₃) δ: 1.00 (3H, t), 1.10 (3H, t), 1.40 (3H, d), 2.08-2.19 (5H, m), 2.59 (2H, q), 5.00-5.11 (1H, m), 6.67 (1H, d), 7.34-7.28 (4H, m), 7.86 (2H, d), 8.61 (1H, s). |
| 9-5 | ¹H-NMR (DMSO-d₆) δ: 0.12-0.16 (2H, m), 0.41-0.45 (2H, m), 0.93-1.00 (1H, m), 1.11 (3H, t), 1.37 (3H, d), 2.01-2.06 (1H, m), 2.27 (3H, s), 2.65 (2H, q), 4.94-4.99 (1H, m), 7.48-7.40 (4H, m), 7.94 (2H, d), 8.25 (1H, d), 9.88 (1H, s). |
| 9-6 | ¹H-NMR (CDCl₃) δ: 1.19 (3H, t), 1.52 (3H, d), 2.30 (3H, s), 2.66 (2H, q), 3.00-3.11 (2H, m), 5.12-5.21 (1H, m), 6.35 (1H, d), 7.36 (2H, s), 7.41 (2H, d), 7.55 (1H, s), 7.86 (2H, d). |
| 9-7 | ¹H-NMR (CDCl₃) δ: 1.20 (3H, t), 1.41-1.46 (12H, m), 2.31 (3H, s), 2.67 (2H, q), 4.81-4.92 (2H, m), 7.36 (2H, s), 7.42 (1H, d), 7.56 (1H, br s), 7.89 (2H, d). |
| 10-2 | ¹H-NMR (CDCl₃) δ: 1.22 (3H, t), 1.84-1.87 (2H, m), 2.06 (3H, s), 2.35 (3H, s), 2.69 (2H, q), 2.95-3.05 (2H, m), 5.55-5.58 (1H, m), 5.67 (1H, s), 7.35-7.39 (3H, m), 7.43 (1H, d), 7.75 (1H, d), 7.81 (1H, s). |
| 10-3 | ¹H-NMR (acetone-d₆) δ: 1.09-1.20 (6H, m), 1.84-1.96 (1H, m), 2.23 (2H, q), 2.35 (3H, s), 2.50-2.53 (1H, m), 2.75 (2H, q), 2.91-3.01 (2H, m), 5.47 (1H, d), 7.27 (1H, s), 7.38 (1H, d), 7.45 (2H, s), 7.88 (2H, d), 9.14 (1H, s). |
| 10-5 | ¹H-NMR (CDCl₃) δ: 0.18-0.22 (2H, m), 0.54-0.65 (2H, m), 0.92-1.09 (1H, m), 1.22 (3H, t), 1.83-1.89 (1H, m), 2.24 (2H, d), 2.34 (3H, s), 2.70 (2H, q), 2.89-3.11 (2H, m), 5.57-5.60 (2H, m), 6.15 (1H, d), 7.37 (2H, s), 7.40 (1H, dz), 7.52 (1H, s), 7.77 (1H, d), 7.82 (1H, s). |
| 10-6 | ¹H-NMR (acetone-d₆) δ: 1.17 (3H, q), 1.92-1.96 (1H, m), 2.35 (3H, s), 2.52-2.63 (1H, m), 2.75 (2H, q), 2.89-3.10 (2H, m), 3.30 (2H, q), 5.49 (1H, q), 7.40 (1H, d), 7.45 (2H, s), 7.82 (1H, d), 7.89-7.91 (2H, m), 9.16 (1H, s). |
| 10-7 | ¹H-NMR (CDCl₃) δ: 1.20 (3H, t), 1.49 (9H, s), 1.81-1.87 (1H, m), 2.33 (3H, s), 2.62-2.68 (3H, m), 2.83-3.07 (2H, m), 4.79 (1H, d), 5.21 (1H, s), 7.36 (2H, s), 7.43 (1H, d), 7.52 (1H, s), 7.76-7.78 (2H, m). |
| 10-10 | ¹H-NMR (CDCl₃) δ: 1.21 (3H, t), 1.83-1.88 (1H, m), 2.25-2.32 (0H, m), 2.63 (3H, s), 2.69 (2H, q), 2.94-3.05 (2H, m), 5.58 (1H, q), 5.69 (1H, d), 7.35 (2H, s), 7.40 (1H, d), 7.45 (1H, s), 7.75 (1H, d), 7.81 (1H, s). |
| 10-22 | ¹H-NMR (CDCl₃) δ: 1.23 (3H, t), 1.88-1.95 (1H, m), 2.17 (3H, t), 2.35 (3H, s), 2.70 (2H, q), 2.99-3.07 (2H, m), 3.29 (3H, s), 5.58 (1H, q), 7.12 (1H, d), 7.38-7.41 (3H, m), 7.77 (1H, d), 7.83 (1H, s). |
| 11-2 | ¹H-NMR (CDCl₃) δ: 1.19 (3H, q), 1.47 (9H, s), 1.74-1.94 (4H, m), 2.30 (3H, s), 2.67 (2H, q), 2.77-2.89 (2H, m), 4.81-4.89 (2H, m), 7.35 (2H, s), 7.46 (1H, d), 7.78-7.61 (3H, m). |
| 11-6 | ¹H-NMR (CDCl₃) δ: 1.22 (3H, t), 1.81-2.16 (4H, m), 2.33 (3H, s), 2.68 (2H, q), 2.85-2.91 (2H, m), 3.06-3.17 (2H, m), 5.25-5.32 (1H, m), 6.07 (1H, d), 7.37-7.39 (4H, m), 7.69-7.64 (2H, m). |
| 11-7 | ¹H-NMR (CDCl₃) δ: 1.20 (3H, t), 1.47 (9H, s), 1.75-1.94 (4H, m), 2.30 (3H, s), 2.67 (2H, q), 2.76-2.94 (3H, m), 4.85 (1H, s), 7.35 (2H, s), 7.46 (1H, d), 7.60-7.78 (3H, m). |
| 12-1 | ¹H-NMR (CDCl₃) δ: 1.18 (3H, t), 1.39 (9H, s), 2.28 (3H, s), 2.66 (2H, q), 4.25 (2H, d), 5.67 (1H, t), 7.36 (2H, s), 7.43 (1H, d), 8.00 (1H, dd), 8.13 (1H, s), 8.23 (1H, d), 8.36 (1H, d), 8.46 (1H, s). |
| 12-2 | ¹H-NMR (CDCl₃) δ: 1.24 (3H, t), 2.36 (3H, s), 2.71 (2H, q), 3.85 (2H, s), 7.39 (2H, s), 7.54 (1H, d), 7.65 (1H, s), 7.95 (1H, dd), 8.17-8.18 (2H, m), 8.64 (1H, s). |
| 12-3 | ¹H-NMR (CDCl₃) δ: 1.23 (3H, t, J = 10.6 Hz), 1.99 (3H, s), 2.35 (3H, s), 2.70 (2H, q), 4.40 (2H, d), 6.85 (1H, t), 7.38 (2H, s), 7.50 (1H, d), 8.08-8.11 (2H, m), 8.22 (1H, s), 8.25 (1H, d), 8.49 (1H, s). |
| 12-4 | ¹H-NMR (CDCl₃) δ: 1.13 (3H, t), 1.23 (3H, t), 2.22 (2H, q), 2.35 (3H, s), 2.70 (2H, q), 4.42 (2H, d), 6.79 (1H, t), 7.38 (2H, s), 7.50 (1H, d), 7.94 (1H, s), 8.08 (1H, dd), 8.21 (1H, s), 8.24 (1H, d), 8.49 (1H, s). |
| 12-5 | ¹H-NMR (CDCl₃) δ: 1.25 (3H, t), 2.37 (3H, s), 2.71 (2H, q), 3.68 (3H, s), 4.35 (2H, d), 5.88 (1H, br s), 7.39 (2H, s), 7.50 (1H, d), 7.64 (1H, br s), 8.06 (1H, d), 8.19-8.20 (2H, m), 8.47 (1H, s). |
| 13-1 | ¹H-NMR (CDCl₃) δ: 0.96 (3H, t), 1.19 (3H, t), 2.09 (2H, q), 2.31 (3H, s), 2.69 (2H, q), 4.38 (2H, d), 6.52 (1H, dd), 7.17 (1H, t), 7.36 (2H, s), 7.71 (1H, d), 7.76 (1H, d), 7.84 (1H, d), 8.04-8.08 (2H, m), 8.84 (1H, s). |
| 13-2 | ¹H-NMR (CDCl₃) δ: 1.21 (3H, t), 1.91 (3H, s), 2.32 (3H, s), 2.68 (2H, q), 4.37 (2H, d), 6.82 (1H, t), 7.37 (2H, s), 7.84 (1H, d), 8.05-8.09 (2H, m), 8.19 (1H, s), 8.32 (1H, s), 8.52 (1H, s). |

-continued

| | NMR Table |
|---|---|
| Exa | NMR |
| 13-3 | $^1$H-NMR (CDCl$_3$) δ: 0.99 (3H, t), 1.19 (3H, t), 2.12 (4H, q), 2.30 (3H, s), 2.68 (2H, q), 4.37 (2H, d), 6.91 (1H, t), 7.36 (2H, s), 7.77 (1H, d), 8.08 (1H, d), 8.15 (1H, dd), 8.17 (1H, s), 8.51 (1H, s), 8.82 (1H, s). |
| 14-1 | $^1$H-NMR (CDCl$_3$) δ: 1.22 (3H, t), 2.33 (3H, s), 2.67 (2H, q), 6.60 (1H, dd), 7.38 (2H, s), 7.74 (1H, s), 7.84 (1H, d), 7.89-7.97 (2H, m), 8.28 (1H, d), 8.36 (1H, d). |
| 14-2 | $^1$H-NMR (CDCl$_3$) δ: 1.18 (3H, t), 2.27 (3H, s), 2.65 (2H, q), 7.38 (2H, s), 7.94 (1H, d), 8.08 (1H, dd), 8.13 (1H, s), 8.37 (1H, d), 8.49 (1H, s), 8.85 (1H, s). |
| A-1 | $^1$H-NMR (CDCl$_3$) δ: 2.32 (6H, s), 7.31-7.36 (3H, m), 7.50 (1H, s), 8.20-8.11 (2H, m). |
| A-2 | $^1$H-NMR (CDCl$_3$) δ: 1.22 (3H, t), 2.33 (3H, s), 2.67 (2H, q), 7.29-7.38 (4H, m), 7.67 (1H, br s), 7.78 (1H, dd). |
| A-3 | $^1$H-NMR (CDCl$_3$) δ: 2.33 (6H, s), 7.22-7.36 (4H, m), 7.81 (1H, br s), 8.00 (1H, d). |
| A-4 | $^1$H-NMR (CDCl$_3$) δ: 1.18 (3H, t), 2.27 (3H, s), 2.64 (2H, q), 7.21 (1H, t), 7.36 (2H, s), 7.61 (1H, s), 7.82-7.84 (1H, m), 8.14 (1H, dd). |
| A-5 | $^1$H-NMR (CDCl$_3$) δ: 1.21 (3H, t), 2.31 (3H, s), 2.66 (2H, q), 7.14 (1H, s), 7.33 (1H, d), 7.38 (2H, s), 7.62 (1H, s), 8.14 (1H, dd), 8.20 (1H, d). |
| B-1 | $^1$H-NMR (CDCl$_3$) δ: 2.39 (6H, s), 7.16-7.09 (1H, m), 7.24 (1H, dd), 7.37 (2H, s), 7.60 (1H, s), 7.87 (1H, dd). |
| B-2 | $^1$H-NMR (CDCl$_3$) δ: 2.38 (6H, s), 7.14 (1H, s), 7.39-7.33 (3H, m), 7.50 (1H, dd), 7.73 (1H, dd). |
| B-3 | $^1$H-NMR (CDCl$_3$) δ: 2.46 (6H, s), 7.20 (1H, s), 7.38 (2H, s), 7.44-7.50 (1H, m), 7.73 (1H, dd), 7.85 (1H, dd). |
| D-1 | $^1$H-NMR (CDCl$_3$) δ: 1.21 (3H, t), 2.34 (3H, s), 2.70 (2H, q), 7.37 (2H, s), 8.06 (1H, dd), 8.19 (1H, dd), 8.71 (1H, dd), 9.39 (1H, s). |
| E-1 | $^1$H-NMR (CDCl$_3$) δ: 1.28 (3H, t), 2.46 (3H, s), 2.77 (2H, q), 7.19 (1H, dd), 7.32 (1H, s), 7.41 (2H, s), 7.64-7.67 (2H, m), 7.80 (1H, dd), 8.18-8.22 (1H, m), 8.47-8.50 (1H, m). |
| F-1 | $^1$H-NMR (CDCl$_3$) δ: 2.34 (6H, s), 4.65 (2H, s), 7.36 (2H, s), 7.43 (1H, s), 7.54 (2H, d), 7.92 (2H, d). |
| F-2 | $^1$H-NMR (CDCl$_3$) δ: 2.31 (6H, s), 4.92 (2H, s), 7.33 (2H, s), 7.44 (1H, s), 7.56 (2H, d), 7.72-7.89 (6H, m). |
| F-3 | $^1$H-NMR (CDCl$_3$) δ: 1.22 (3H, t), 2.34 (3H, s), 2.69 (2H, q), 4.65 (2H, s), 7.37 (2H, s), 7.41 (1H, s), 7.55 (2H, d), 7.92 (2H, d). |
| F-4 | $^1$H-NMR (CDCl$_3$) δ: 1.19 (3H, t), 2.31 (3H, s), 2.66 (2H, q), 4.93 (2H, s), 7.35 (2H, s), 7.37 (1H, s), 7.57 (2H, d), 7.75-7.72 (2H, m), 7.89-7.85 (4H, m). |
| F-5 | $^1$H-NMR (CDCl$_3$) δ: 1.22 (3H, t), 2.32 (3H, s), 2.67 (2H, q), 4.76 (3H, s), 7.37 (2H, s), 7.43 (1H, s), 7.64 (1H, d), 7.80 (1H, dd), 7.96 (1H, d). |
| F-6 | $^1$H-NMR (CDCl$_3$) δ: 1.20 (3H, t), 2.32 (3H, s), 2.66 (2H, q), 5.06 (2H, s), 7.37 (3H, d), 7.76-7.78 (4H, m), 7.87-7.91 (3H, m), 7.96 (1H, d). |
| F-7 | $^1$H-NMR (CDCl$_3$) δ: 1.21 (3H, t), 2.31 (3H, s), 2.66 (2H, q), 4.75 (2H, s), 7.37 (2H, s), 7.48 (1H, s), 7.63 (1H, d), 7.84 (1H, dd), 8.14 (1H, d). |
| F-8 | $^1$H-NMR (CDCl$_3$) δ: 1.20 (3H, t), 2.31 (3H, s), 2.66 (2H, q), 5.04 (2H, s), 7.29-7.36 (4H, m), 7.75-7.80 (3H, m), 7.90-7.93 (2H, m), 8.15 (1H, d). |
| F-9 | $^1$H-NMR (CDCl$_3$) δ: 1.20 (3H, t), 2.32 (3H, s), 2.66 (2H, q), 5.37 (2H, s), 7.37 (2H, s), 7.45 (1H, d), 7.60 (1H, s), 7.82-7.79 (2H, m), 7.93-7.91 (2H, m), 8.12 (1H, dd), 8.64 (1H, d, J = 1.6 Hz). |
| F-14 | $^1$H-NMR (CDCl$_3$) δ: 1.21 (3H, t), 2.32 (3H, s), 2.67 (2H, q), 4.76 (2H, s), 7.36 (2H, s), 7.46 (1H, s), 7.64 (1H, d), 7.80 (1H, dd), 7.96 (1H, d). |
| F-15 | $^1$H-NMR (CDCl$_3$) δ: 1.17-1.22 (3H, m), 2.31 (3H, s), 2.65 (2H, q), 5.06 (2H, s), 7.36-7.39 (4H, m), 7.72-7.97 (6H, m). |
| F-16 | $^1$H-NMR (CDCl$_3$) δ: 1.19 (3H, t), 2.31 (3H, s), 2.65 (2H, q), 5.02 (2H, s), 7.31-7.43 (4H, m), 7.74-7.94 (5H, m), 8.15 (1H, d). |
| F-17 | $^1$H-NMR (CDCl$_3$) δ: 1.19 (3H, t), 2.31 (3H, s), 2.65 (2H, q), 5.04 (2H, s), 7.29-7.37 (4H, m), 7.75-7.82 (3H, m), 7.86-7.91 (3H, m), 8.15 (1H, d). |
| G-1 | $^1$H-NMR (CDCl$_3$) δ: 1.25 (2H, t), 2.45 (3H, s), 2.77 (2H, q), 5.07 (2H, d), 7.41 (2H, s), 7.55-7.75 (6H, m), 8.22 (1H, d), 8.45 (1H, d). |
| G-2 | $^1$H-NMR (CDCl$_3$) δ: 1.25 (3H, t), 2.46 (3H, s), 2.77 (2H, q), 5.36 (2H, s), 7.38 (2H, s), 7.59-7.88 (9H, m), 8.41 (1H, d), 8.47 (1H, d). |
| H-1 | $^1$H-NMR (CDCl$_3$) δ: 1.22-1.22 (3H, m), 2.34 (3H, s), 2.65-2.73 (5H, m), 7.38 (2H, s), 7.52 (1H, s), 8.00 (2H, d), 8.09 (2H, d). |
| H-2 | $^1$H-NMR (CDCl$_3$) δ: 1.23 (3H, t), 2.33-2.35 (6H, m), 2.70 (3H, q), 7.43-7.38 (4H, m), 7.79 (2H, d), 7.93 (2H, d). |
| I-1 | $^1$H-NMR (CDCl$_3$) δ: 2.36 (6H, s), 7.38 (2H, s), 7.56 (1H, dd), 7.65 (1H, dd), 7.92 (1H, d), 8.30 (1H, dd). |
| I-2 | $^1$H-NMR (CDCl$_3$) δ: 1.25 (3H, t), 2.27 (3H, s), 2.68 (1H, q), 7.39 (2H, s), 7.47 (2H, d), 7.81 (2H, d), 8.02 (2H, d). |
| I-3 | $^1$H-NMR (CDCl$_3$) δ: 1.23 (3H, t), 2.35 (3H, s), 2.70 (2H, q), 7.39 (2H, s), 7.56 (1H, dd), 7.66 (1H, dd), 7.93 (1H, d), 8.31 (1H, dd). |
| I-4 | $^1$H-NMR (CDCl$_3$) δ: 1.25 (3H, t), 2.40 (3H, s), 2.74 (2H, q), 7.40 (2H, s), 7.50 (1H, s), 7.70 (1H, dd), 7.81 (1H, d), 7.91 (1H, d). |
| I-5 | $^1$H-NMR (CDCl$_3$) δ: 1.22 (3H, t), 2.33 (3H, s), 2.65 (3H, s), 2.68 (2H, q), 7.38 (2H, s), 7.47 (1H, s), 7.74 (1H, d), 7.78 (1H, d), 7.88 (1H, s). |
| I-6 | $^1$H-NMR (acetone-d$_6$) δ: 1.17 (3H, t), 2.33 (3H, s), 2.73 (2H, q), 7.56 (1H, s), 7.58 (1H, s), 7.97 (2H, d), 8.21 (2H, d), 9.38 (1H, s). |
| J-1 | $^1$H-NMR (CDCl$_3$) δ: 1.24 (3H, t), 2.35 (3H, s), 2.67 (2H, t), 7.40 (2H, s), 7.50 (1H, s), 7.88 (1H, d), 8.40 (1H, dd), 9.22 (1H, d). |
| K-1 | $^1$H-NMR (CDCl$_3$) δ: 1.22 (3H, t), 2.34 (3H, t), 2.70 (2H, q), 7.39 (2H, s), 8.23 (1H, dd), 8.44 (1H, dd), 8.94 (1H, dd), 9.42 (1H, s). |
| L-1 | $^1$H-NMR (CDCl$_3$) δ: 1.23 (3H, t), 2.36 (3H, s), 2.70 (2H, q), 2.78-2.80 (2H, m), 3.24-3.26 (2H, m), 7.39 (2H, s), 7.61 (1H, s), 7.87 (2H, s), 8.06 (1H, s). |

-continued

| | NMR Table |
|---|---|
| Exa | NMR |
| L-2 | $^1$H-NMR (CDCl$_3$) δ: 1.23 (3H, t), 2.35 (3H, s), 2.70 (2H, q), 3.03-3.05 (2H, m), 3.15-3.18 (2H, m), 7.38 (2H, s), 7.41 (1H, s), 7.78 (2H, s), 7.90 (1H, s). |
| M-1 | $^1$H-NMR (CDCl$_3$) δ: 1.28-1.20 (5H, m), 2.35 (3H, s), 2.66-2.75 (4H, m), 3.07 (2H, t), 7.38 (2H, s), 7.49 (1H, s), 7.78 (1H, d), 7.85 (1H, s), 8.16 (1H, d). |
| M-2 | $^1$H-NMR (DMSO-d$_6$) δ: 1.11 (3H, t), 1.74-1.82 (2H, m), 2.27 (3H, s), 2.62-2.72 (4H, m), 2.81 (2H, q), 7.40 (1H, s), 7.45 (1H, s), 7.79-7.82 (2H, m), 7.99 (1H, d), 9.93 (1H, s), 11.35 (1H, s). |
| 5-119 | $^1$H-NMR (CDCl$_3$) δ: 3.97 (2H, s), 7.49 (2H, d), 7.86 (2H, d), 7.94 (2H, d). |
| 5-120 | $^1$H-NMR (CDCl$_3$) δ: 2.07 (3H, s), 4.53 (2H, d), 5.89 (1H, s), 7.44 (2H, d), 7.71 (1H, s), 7.87 (2H, s), 7.93 (2H, d). |
| 5-121 | $^1$H-NMR (CDCl$_3$) δ: 1.20 (3H, t), 2.29 (2H, q), 4.54 (2H, d), 5.87 (1H, s), 7.43 (2H, d), 7.73 (1H, s), 7.87 (2H, s), 7.93 (2H, d). |
| 5-123 | $^1$H-NMR (CDCl$_3$) δ: 0.22-0.24 (2H, m), 0.63-0.67 (2H, m), 0.99-1.02 (1H, m), 2.25 (2H, d), 4.58 (2H, d), 6.31 (1H, s), 7.46 (2H, d), 7.69 (1H, s), 7.87 (2H, s), 7.94 (2H, d). |
| 5-124 | $^1$H-NMR (CDCl$_3$) δ: 3.20 (2H, q), 4.59 (2H, d), 6.25 (1H, s), 7.43 (2H, d), 7.68 (1H, s), 7.87 (2H, s), 7.93 (2H, d). |
| 5-234 | $^1$H-NMR (CDCl$_3$) δ: 2.03 (3H, s), 4.57 (2H, d), 6.14 (1H, s), 7.50 (1H, dd), 7.79 (1H, dd), 7.87 (2H, s), 7.98 (1H, d). |
| 5-241 | $^1$H-NMR (CDCl$_3$) δ: 4.57 (2H, s), 7.67-7.88 (6H, m). |
| 5-242 | $^1$H-NMR (CDCl$_3$) δ: 2.04 (3H, s), 4.57 (2H, d), 6.08 (1H, t), 7.53 (1H, d), 7.65 (2H, s), 7.79 (1H, dd), 7.88 (1H, s), 7.98 (1H, d). |
| 5-243 | $^1$H-NMR (CDCl$_3$) δ: 1.18 (3H, t), 2.28 (2H, q), 4.59 (2H, d), 5.99 (1H, s), 7.56 (1H, d), 7.65 (2H, s), 7.69 (1H, s), 7.79 (1H, dd), 7.98 (1H, d). |
| 5-244 | $^1$H-NMR (CDCl$_3$) δ: 3.14 (2H, dd), 4.65 (2H, d), 6.29 (1H, s), 7.55 (1H, d), 7.61 (1H, s), 7.66 (2H, s), 7.81 (1H, d), 7.99 (1H, s). |
| 5-285 | $^1$H-NMR (CDCl$_3$) δ: 4.56 (2H, s), 6.58 (1H, t), 7.46 (1H, d), 7.67-7.79 (4H, m), 7.94 (1H, d). |
| 5-286 | $^1$H-NMR (CDCl$_3$) δ: 2.04 (3H, s), 4.58 (2H, d), 6.06 (1H, br s), 6.57 (1H, t), 7.50 (1H, s), 7.54 (1H, d), 7.75-7.78 (3H, m), 7.96 (1H, d). |
| 5-287 | $^1$H-NMR (CDCl$_3$) δ: 1.16 (3H, t), 2.28 (2H, q), 4.59 (2H, d), 6.00 (1H, d), 6.58 (1H, t), 7.50-7.57 (2H, m), 7.71-7.76 (3H, m), 7.96 (1H, d). |
| 5-288 | $^1$H-NMR (CDCl$_3$) δ: 3.14 (2H, q), 4.64 (2H, d), 6.30 (1H, d), 6.58 (1H, t), 7.52-7.55 (3H, m), 7.77-7.79 (2H, m), 7.97 (1H, d). |
| 5-293 | $^1$H-NMR (CDCl$_3$) δ: 1.70 (2H, s), 2.39 (3H, s), 4.03 (2H, d), 6.51 (1H, t), 7.32 (1H, s), 7.42 (1H, s), 7.59 (1H, d), 7.67 (1H, s), 7.78 (1H, dd), 7.92 (1H, d). |
| 5-294 | $^1$H-NMR (CDCl$_3$) δ: 2.04 (3H, s), 2.38 (3H, s), 4.57 (2H, d), 6.06 (1H, s), 6.51 (1H, t), 7.32 (1H, s), 7.42 (1H, s), 7.53 (1H, d), 7.73-7.76 (2H, m), 7.94 (1H, d). |
| 5-295 | $^1$H-NMR (CDCl$_3$) δ: 1.16 (3H, t), 2.27 (2H, q), 2.38 (3H, s), 4.57 (2H, d), 6.05 (1H, s), 6.51 (1H, t), 7.32 (1H, s), 7.42 (1H, s), 7.51 (1H, d), 7.74 (1H, dd), 7.80 (1H, s), 7.94 (1H, d). |
| 5-296 | $^1$H-NMR (CDCl$_3$) δ: 2.38 (3H, s), 3.14 (2H, q), 4.63 (2H, d), 6.40 (1H, s), 6.52 (1H, t), 7.32 (1H, s), 7.43 (1H, s), 7.52 (1H, d), 7.66 (1H, s), 7.75 (1H, d), 7.95 (1H, d). |
| 5-305 | $^1$H-NMR (CDCl$_3$) δ: 4.02 (1H, s), 4.56 (1H, s), 6.58 (2H, t), 7.46 (1H, s), 7.57-7.68 (3H, m), 7.77-7.81 (1H, m), 7.93 (1H, d). |
| 5-306 | $^1$H-NMR (CDCl$_3$) δ: 2.05 (3H, d), 4.57 (2H, d), 6.09 (1H, s), 6.58 (1H, t), 7.46 (1H, s), 7.53 (1H, d), 7.63 (1H, s), 7.77 (1H, dd), 7.84 (1H, s), 7.95 (1H, d). |
| 5-307 | $^1$H-NMR (CDCl$_3$) δ: 1.16 (3H, t), 2.26 (2H, q), 4.57 (2H, d), 6.07 (1H, t), 6.58 (1H, t), 7.46 (1H, s), 7.51 (1H, d), 7.63 (1H, s), 7.77 (1H, dd), 7.87 (1H, s), 7.95 (1H, d). |
| 5-308 | $^1$H-NMR (CDCl$_3$) δ: 3.14 (2H, q), 4.64 (2H, d), 6.58 (1H, t), 7.47 (1H, s), 7.54 (1H, d), 7.58 (1H, s), 7.64 (1H, s), 7.78 (1H, d), 7.97 (1H, s). |
| 5-310 | 1H-NMR (CDCl3) δ: 2.04 (3H, d), 4.57 (2H, d), 6.08 (1H, d), 6.57 (1H, t), 7.45 (1H, s), 7.53 (1H, d), 7.62 (1H, s), 7.77 (1H, dd), 7.80 (1H, s), 7.95 (1H, d). |
| 5-311 | 1H-NMR (CDCl3) δ: 1.18 (3H, t), 2.28 (2H, q), 4.59 (2H, d), 5.98 (1H, s), 6.57 (1H, t), 7.45 (1H, s), 7.56 (1H, d), 7.60 (1H, s), 7.62 (1H, s), 7.76 (1H, t), 7.95 (1H, d). |
| 5-312 | 1H-NMR (CDCl3) δ: 3.13 (2H, t), 4.65 (2H, d), 6.29 (1H, d), 6.57 (1H, t), 7.46 (1H, s), 7.54-7.57 (2H, m), 7.63 (1H, s), 7.78 (1H, d), 7.97 (1H, s). |
| 5-317 | $^1$H-NMR (CDCl$_3$) δ: 1.46 (9H, s), 4.47 (2H, d), 5.09 (1H, s), 7.55 (1H, d), 7.63 (1H, s), 7.67 (2H, s), 7.82 (1H, dd), 7.96 (1H, d). |
| 5-318 | $^1$H-NMR (CDCl$_3$) δ: 0.76-1.09 (4H, m), 1.61 (1H, td), 2.33 (3H, s), 2.67 (2H, q), 4.60 (2H, d), 6.21 (1H, s), 7.38 (2H, s), 7.46 (1H, s), 7.54 (1H, d), 7.75 (1H, d), 7.96 (1H, s). |
| 5-322 | $^1$H-NMR (CDCl$_3$) δ: 2.06 (3H, s), 4.52 (2H, d), 5.95 (1H, s), 7.42 (2H, d), 7.65 (2H, s), 7.79 (1H, s), 7.92 (2H, d). |
| 5-323 | $^1$H-NMR (CDCl$_3$) δ: 1.20 (3H, t), 2.29 (2H, q), 4.54 (2H, d), 5.85 (1H, s), 7.44 (2H, d), 7.65 (2H, s), 7.70 (1H, s), 7.92 (2H, d). |
| 5-324 | $^1$H-NMR (CDCl$_3$) δ: 3.22 (2H, q), 4.58 (2H, d), 6.26 (1H, s), 7.42 (2H, d), 7.65 (2H, s), 7.69 (1H, s), 7.91 (2H, d). |
| 5-325 | $^1$H-NMR (CDCl$_3$) δ: 0.21-0.25 (2H, m), 0.62-0.64 (2H, m), 0.98-1.02 (1H, m), 2.25 (2H, d, J = 7.1 Hz), 4.58 (2H, d), 6.30 (1H, s), 7.45 (2H, d), 7.65 (2H, s), 7.68 (1H, s), 7.93 (2H, d). |
| 5-326 | $^1$H-NMR (CDCl$_3$) δ: 0.77-0.81 (2H, m), 1.02 (2H, dd), 1.39-1.41 (1H, m), 4.54 (2H, d), 6.06 (1H, s), 7.44 (2H, d), 7.65 (2H, s), 7.73 (1H, s), 7.92 (2H, d). |
| 5-327 | $^1$H-NMR (CDCl$_3$) δ: 2.14 (3H, s), 3.28 (2H, s), 4.59 (2H, d), 7.46 (2H, d), 7.65 (3H, br s), 7.94 (2H, d). |
| 5-328 | $^1$H-NMR (CDCl$_3$) δ: 1.47 (9H, s), 4.40 (2H, d), 7.43 (2H, d), 7.65 (3H, br s), 7.92 (2H, d). |
| 5-329 | $^1$H-NMR (CDCl$_3$) δ: 1.44 (9H, s), 4.46 (2H, d), 5.14 (1H, s), 7.52 (1H, d), 7.65 (3H, br s), 7.82 (1H, d), 7.97 (1H, d). |
| 5-330 | $^1$H-NMR (CDCl$_3$) δ: 0.22 (2H, d), 0.63-0.66 (2H, m), 0.96-0.98 (1H, m), 2.21 (2H, d), 4.62 (2H), 6.51 (1H, s), 7.57 (1H, d), 7.65 (2H, s), 7.68 (1H, s), 7.80 (1H, dd), 7.99 (1H, d). |

-continued

| NMR Table | |
|---|---|
| Exa | NMR |

5-331  $^1$H-NMR (CDCl$_3$) δ: 2.14 (3H, s), 3.25 (2H, s), 4.64 (2H, d), 7.57 (1H, d), 7.63 (1H, s), 7.66 (2H, s), 7.81 (1H, dd), 7.99 (1H, d).

5-333  $^1$H-NMR (CDCl$_3$) δ: 2.02 (3H, s), 2.39 (3H, s), 4.50 (2H, d), 6.07 (1H, s), 7.40 (2H, d), 7.43 (1H, s), 7.56 (1H, s), 7.90 (2H, d).

5-334  $^1$H-NMR (CDCl$_3$) δ: 1.20 (3H, t), 2.28 (2H, q), 2.40 (3H, s), 4.53 (2H, d), 5.90 (1H, s), 7.41-7.44 (3H, m), 7.56 (1H, s), 7.76 (1H, s), 7.91 (2H, d).

5-335  $^1$H-NMR (CDCl$_3$) δ: 2.35 (3H, s), 3.09 (2H, q), 4.51 (2H, d), 6.64 (1H, s), 7.33 (2H, d), 7.41 (1H, s), 7.54 (1H, s), 7.83 (2H, d).

5-336  $^1$H-NMR (CDCl$_3$) δ: 0.18-0.26 (2H, m), 0.62 (2H, m), 0.98-1.02 (1H, m), 2.25 (2H, d), 2.41 (3H, s), 4.58 (2H, d), 6.31 (1H, s), 7.44-7.46 (3H, m), 7.56 (1H, s), 7.70 (1H, s), 7.92 (2H, d).

5-337  $^1$H-NMR (CDCl$_3$) δ: 2.11 (3H, s), 2.37 (3H, s), 3.24 (2H, s), 4.55 (2H, d), 7.32 (1H, s), 7.41-7.42 (3H, m), 7.54 (1H, s), 7.79 (1H, s), 7.90 (2H, d).

5-338  $^1$H-NMR (CDCl$_3$) δ: 0.68-1.02 (4H, m), 1.34-1.42 (1H, m), 2.35 (3H, s), 4.47 (2H, d), 6.39 (1H, s), 7.33 (2H, d), 7.40 (1H, s), 7.53 (1H, s), 7.84-7.87 (2H, m).

5-339  $^1$H-NMR (CDCl$_3$) δ: 1.47 (9H, s), 2.40 (3H, s), 4.40 (2H, d), 7.42-7.44 (3H, m), 7.56 (1H, s), 7.77 (1H, s), 7.92 (2H, d).

5-340  $^1$H-NMR (CDCl$_3$) δ: 0.21-0.22 (2H, m), 0.61-0.67 (2H, m), 0.93-0.99 (1H, m), 2.20 (2H, d), 2.39 (3H, s), 4.61 (2H, d), 6.52 (1H, t), 6.53 (1H, s), 7.32 (1H, s), 7.42 (1H, s), 7.53 (1H, d), 7.74-7.77 (2H, m), 7.95 (1H, d).

5-341  $^1$H-NMR (CDCl$_3$) δ: 0.75-1.09 (4H, m), 1.59-1.63 (1H, m), 2.39 (3H, s), 4.60 (2H, d), 6.19 (1H, s), 6.52 (1H, t), 7.32 (1H, s), 7.42 (1H, s), 7.54 (1H, d), 7.66 (1H, s), 7.75 (1H, t), 7.94 (1H, d).

5-342  $^1$H-NMR (CDCl$_3$) δ: 1.46 (9H, s), 2.39 (3H, s), 4.46 (2H, d), 5.11 (1H, s), 6.51 (1H, t), 7.32 (1H, s), 7.42 (1H, s), 7.52 (1H, s), 7.67 (1H, s), 7.77 (1H, d), 7.93 (1H, d).

5-344  1H-NMR (CDCl3) δ: 2.07 (3H, s), 2.42 (3H, s), 4.51 (2H, d), 5.70 (1H, s), 7.38 (1H, d), 7.65-7.66 (3H, m), 7.75-7.77 (2H, m).

5-345  $^1$H-NMR (CDCl$_3$) δ: 1.21 (3H, t), 2.29 (3H, q), 2.42 (3H, s), 4.51 (2H, d), 5.68 (1H, s), 7.37 (1H, d), 7.64-7.68 (3H, m), 7.74-7.76 (2H, m).

5-346  $^1$H-NMR (CDCl$_3$) δ: 2.42 (3H, s), 3.16 (2H, q), 4.57 (2H, d), 6.00 (1H, s), 7.37 (1H, d), 7.63 (1H, s), 7.67 (2H, s), 7.76 (1H, d), 7.79 (1H, s).

5-347  $^1$H-NMR (CDCl$_3$) δ: 1.47 (9H, s), 2.39 (3H, s), 4.37 (2H, d), 4.90 (1H, s), 7.39 (1H, d), 7.66 (3H, s), 7.76 (2H, d).

5-348  $^1$H-NMR (CDCl$_3$) δ: 4.61 (2H, d), 7.41 (2H, d), 7.65 (3H, s), 7.90 (2H, d).

5-349  $^1$H-NMR (CDCl$_3$) δ: 1.17 (3H, t), 2.27 (3H, s), 2.64 (2H, q), 4.63 (2H, d), 7.36 (2H, d), 7.43 (1H, d), 7.79 (1H, d), 8.13 (1H, s).

5-440  $^1$H-NMR (CDCl$_3$) δ: 1.46 (9H, s), 4.40 (2H, d), 4.98 (1H, s), 7.43 (2H, d), 7.72 (1H, s), 7.86 (2H, s), 7.93 (2H, d).

5-441  $^1$H-NMR (CDCl$_3$) δ: 1.16 (3H, t), 1.62-1.67 (1H, m), 1.99-2.08 (1H, m), 2.25 (3H, s), 2.32-2.36 (1H, m), 2.63 (2H, q), 4.50-4.52 (2H, m), 6.83 (1H, s), 7.31-7.33 (3H, m), 7.68 (1H, dd), 7.95 (1H, s), 8.04 (1H, d).

5-442  $^1$H-NMR (CDCl$_3$) δ: 1.23 (3H, t), 2.34 (3H, s), 2.68 (2H, q), 3.43 (2H, s), 4.63 (2H, d), 6.70 (1H, s), 7.36-7.39 (3H, m), 7.55 (1H, d), 7.82 (1H, d), 8.16 (1H, s).

5-443  $^1$H-NMR (CDCl$_3$) δ: 2.40 (3H, s), 4.03 (2H, s), 7.45 (1H, s), 7.58-7.60 (2H, m), 7.72 (1H, s), 7.82 (1H, dd), 7.95 (1H, d).

5-444  $^1$H-NMR (CDCl$_3$) δ: 2.17 (3H, s), 2.38 (3H, s), 4.56 (2H, d), 6.15 (1H, t), 7.44 (1H, s), 7.51 (1H, d), 7.57 (1H, s), 7.78 (1H, dd), 7.92 (1H, s), 7.97 (1H, d).

5-445  $^1$H-NMR (CDCl$_3$) δ: 1.18 (3H, t), 2.28 (2H, q), 2.40 (3H, s), 4.59 (2H, d), 5.98 (1H, s), 7.44 (1H, s), 7.54-7.57 (2H, m), 7.67 (1H, s), 7.78 (1H, dd), 7.97 (1H, d).

5-446  $^1$H-NMR (CDCl$_3$) δ: 2.40 (3H, s), 3.14 (2H, q), 4.64 (2H, d), 6.28 (1H, s), 7.45 (1H, s), 7.56-7.60 (2H, m), 7.79 (1H, d), 7.98 (1H, s).

5-447  $^1$H-NMR (CDCl$_3$) δ: 1.46 (9H, s), 2.40 (3H, s), 4.47 (2H, d), 5.09 (1H, s), 7.44 (1H, s), 7.54-7.56 (2H, m), 7.67 (1H, s), 7.80 (1H, dd), 7.95 (1H, d).

5-448  $^1$H-NMR (CDCl$_3$) δ: 1.45 (9H, s), 4.45 (2H, d), 5.14 (1H, t), 7.46 (1H, s), 7.51 (1H, d), 7.63 (1H, s), 7.79 (1H, dd), 7.94 (1H, d).

5-449  $^1$H-NMR (CDCl$_3$) δ: 1.47 (9H, s), 4.47 (2H, d), 5.10 (1H, s), 6.58 (1H, t), 7.52-7.57 (3H, m), 7.78-7.81 (2H, m), 7.94 (1H, d).

5-450  $^1$H-NMR (CDCl$_3$) δ: 0.19-0.22 (2H, m), 0.58-0.64 (2H, m), 0.97-1.04 (1H, m), 2.21 (2H, d), 4.62 (2H, d), 6.54 (1H, s), 6.58 (2H, t), 7.46 (1H, s), 7.55 (1H, d), 7.63 (1H, s), 7.73 (1H, s), 7.78 (1H, dd), 7.96 (1H, d).

5-451  $^1$H-NMR (CDCl$_3$) δ: 1.46 (9H, s), 4.47 (2H, d), 5.10 (1H, s), 7.54 (1H, d), 7.82 (1H, d), 7.87 (2H, s), 7.97 (1H, d).

5-452  1H-NMR (CDCl3) δ: 3.16 (2H, q), 4.59 (2H, d), 6.19 (1H, s), 6.58 (1H, t), 7.42-7.44 (3H, m), 7.61-7.62 (2H, m), 7.90 (2H, d).

5-453  1H-NMR (CDCl3) δ: 1.47 (9H, s), 4.39 (2H, d), 5.01 (1H, s), 6.58 (1H, t), 7.43 (3H, dq), 7.62 (1H, s), 7.71 (1H, s), 7.90 (2H, d).

5-454  1H-NMR (CDCl3) δ: 0.77-1.07 (4H, m), 1.60-1.63 (1H, m), 4.61 (2H, d), 6.17 (1H, s), 6.57 (1H, t), 7.46 (1H, s), 7.56 (1H, d), 7.60 (1H, s), 7.63 (1H, s), 7.77 (1H, d), 7.95 (1H, d).

5-455  1H-NMR (CDCl3) δ: 0.20-0.21 (2H, m), 0.57-0.66 (2H, m), 0.98 (1H, s), 2.22 (2H, d), 4.62 (2H, d), 6.52 (1H, s), 6.57 (1H, t), 7.45 (1H, s), 7.56 (1H, d), 7.63 (1H, s), 7.65 (1H, s), 7.77 (1H, dd), 7.96 (1H, d).

5-456  1H-NMR (CDCl3) δ: 1.46 (9H, s), 4.46 (2H, d), 5.09 (1H, s), 6.58 (1H, t), 7.45 (1H, s), 7.54 (1H, d), 7.62 (2H, s), 7.78 (1H, dd), 7.93 (1H, d).

A-6  $^1$H-NMR (CDCl$_3$) δ: 7.63-7.67 (5H, m), 7.89 (2H, d).

A-7  $^1$H-NMR (CDCl$_3$) δ: 7.49 (1H, dd), 7.60 (1H, s), 7.67 (2H, s), 8.00 (1H, d), 8.04 (1H, d).

A-8  $^1$H-NMR (CDCl$_3$) δ: 7.64 (1H, s), 7.68 (2H, d), 7.87 (2H, s), 7.90 (2H, d).

A-9  $^1$H-NMR (CDCl$_3$) δ: 7.49 (1H, dd), 7.65 (3H, br s), 8.00 (1H, d), 8.03 (1H, d).

-continued

NMR Table

| Exa | NMR |
|---|---|
| A-10 | $^1$H-NMR (CDCl$_3$) δ: 7.49 (1H, dd), 7.65 (3H, s), 8.00 (1H, d), 8.03 (1H, d). |
| A-11 | $^1$H-NMR (CDCl$_3$) δ: 2.40 (3H, s), 7.45 (1H, s), 7.49 (1H, dd), 7.57-7.60 (2H, m), 8.00 (1H, d), 8.04 (1H, d). |
| N-1 | $^1$H-NMR (CDCl$_3$) δ: 7.68 (2H, d), 7.80 (1H, s), 8.13 (2H, d), 8.39 (2H, d). |
| N-2 | $^1$H-NMR (CDCl$_3$) δ: 7.69 (2H, s), 8.11 (2H, d), 8.36 (2H, d), 8.58 (1H, br s). |
| N-4 | $^1$H-NMR (CDCl$_3$) δ: 2.67 (3H, s), 7.66-7.70 (2H, m), 7.89 (1H, dd), 7.94 (1H, s), 8.05 (1H, d), 8.12 (1H, s). |
| N-7 | $^1$H-NMR (CDCl$_3$) δ: 2.42 (3H, s), 7.47 (1H, s), 7.59 (1H, s), 7.82 (1H, s), 8.12 (2H, d), 8.38 (2H, d). |
| N-14 | $^1$H-NMR (CDCl$_3$) δ: 7.83 (1H, s), 7.88 (2H, s), 8.13 (1H, d), 8.37 (1H, d). |
| O-1 | $^1$H-NMR (CDCl$_3$) δ: 6.72 (2H, d), 7.56 (1H, s), 7.63 (2H, s), 7.78 (2H, d). |
| O-2 | $^1$H-NMR (CDCl$_3$) δ: 4.12 (2H, br s), 6.72 (2H, d), 7.55 (1H, s), 7.62 (2H, s), 7.79 (2H, d). |
| O-4 | $^1$H-NMR (CDCl$_3$) δ: 4.53 (2H, s), 6.82 (1H, d), 7.52 (1H, s), 7.64 (2H, s), 7.68 (1H, dd), 7.90 (1H, d). |
| O-5 | $^1$H-NMR (CDCl$_3$) δ: 4.53 (2H, br s), 6.81 (1H, d), 7.56 (1H, s), 7.63 (2H, s), 7.68 (1H, dd), 7.90 (1H, d). |
| O-7 | $^1$H-NMR (CDCl$_3$) δ: 2.23 (3H, s), 4.07 (2H, br s), 6.72 (1H, d), 7.54 (1H, s), 7.64-7.67 (2H, m), 7.70 (1H, s). |
| O-10 | $^1$H-NMR (CDCl$_3$) δ: 2.39 (3H, s), 4.11 (2H, br s), 6.72 (2H, d), 7.42 (1H, s), 7.54 (1H, s), 7.57 (1H, s), 7.78 (2H, d). |
| O-23 | $^1$H-NMR (CDCl$_3$) δ: 4.11 (2H, s), 6.73 (2H, d), 7.53 (1H, s), 7.78-7.83 (4H, m). |
| O-29 | $^1$H-NMR (CDCl$_3$) δ: 4.57 (2H, s), 6.81 (1H, d), 7.55 (1H, s), 7.72 (1H, dd), 7.83 (2H, s), 8.06 (1H, d). |
| O-31 | $^1$H-NMR (CDCl$_3$) δ: 2.38 (3H, s), 4.50 (2H, s), 6.82 (1H, d), 7.42 (1H, s), 7.52-7.54 (2H, m), 7.67 (1H, dd), 7.89 (1H, d). |
| I-12 | $^1$H-NMR (CDCl$_3$) δ: 2.40 (3H, s), 6.53 (1H, t), 7.33 (1H, s), 7.44 (1H, s), 7.66 (1H, s), 7.82-7.90 (2H, m), 8.06 (1H, d). |
| I-15 | $^1$H-NMR (CDCl$_3$) δ: 6.58 (1H, t), 7.47 (1H, s), 7.65 (1H, s), 7.82-7.93 (3H, m), 8.08 (1H, d). |
| I-16 | $^1$H-NMR (CDCl$_3$) δ: 6.57 (1H, t), 7.46 (1H, s), 7.64 (1H, s), 7.82-7.92 (3H, m), 8.07 (1H, d). |
| I-18 | $^1$H-NMR (CDCl$_3$) δ: 6.57 (1H, t), 7.51 (1H, s), 7.70 (1H, s), 7.81-7.92 (3H, m), 8.07 (1H, d). |
| I-29 | $^1$H-NMR (CDCl$_3$) δ: 2.33 (6H, s), 7.38 (2H, s), 7.48 (1H, s), 7.77-7.80 (3H, m). |
| I-30 | $^1$H-NMR (CDCl$_3$) δ: 1.23 (3H, t), 2.33 (3H, s), 2.66 (2H, t), 7.39 (2H, s), 7.43 (1H, s), 7.77-7.81 (3H, m). |
| I-31 | $^1$H-NMR (CDCl$_3$) δ: 1.23 (3H, t), 2.35 (3H, s), 2.69 (2H, q), 7.39 (2H, s), 7.55 (1H, dd), 7.95 (1H, d), 8.05 (1H, dd). |
| I-32 | $^1$H-NMR (CDCl$_3$) δ: 7.67 (2H, s), 7.75 (1H, s), 7.85 (1H, d), 7.93 (1H, dd), 8.09 (1H, d). |
| I-33 | $^1$H-NMR (CDCl$_3$) δ: 7.74 (1H, s), 7.84 (2H, d), 7.88 (2H, s), 8.07 (2H, d). |
| I-34 | $^1$H-NMR (CDCl$_3$) δ: 7.65 (1H, s), 7.86 (1H, d), 7.89 (2H, d), 7.93 (1H, dd), 8.10 (1H, d). |
| I-35 | $^1$H-NMR (CDCl$_3$) δ: 2.40 (3H, s), 7.47 (1H, s), 7.59 (1H, s), 7.70 (1H, s), 7.85 (1H, d), 7.92 (1H, dd), 8.09 (1H, d). |
| I-36 | $^1$H-NMR (CDCl$_3$) δ: 1.22 (3H, t), 2.33 (3H, s), 2.67 (2H, q), 7.38 (2H, s), 7.45 (1H, s), 7.83 (1H, d), 7.89 (1H, dd), 8.06 (1H, d). |
| I-37 | $^1$H-NMR (CDCl$_3$) δ: 7.84 (1H, d), 7.87 (2H, s), 7.94 (1H, dd), 7.98 (1H, s), 8.11 (1H, d). |
| I-38 | $^1$H-NMR (CDCl$_3$) d: 7.69 (2H, s), 7.72 (1H, s), 7.85 (1H, d), 7.93 (1H, dd), 8.09 (1H, d). |

The test preparations in Biological test examples 1 to 3 were prepared as follows.

Solvent: 3 parts by weight of dimethylformamide
Emulsifier: 1 part by weight of polyoxyethylene alkyl phenyl ether To prepare a suitable preparation containing the active compound, 1 part by weight of the active compound was mixed with the above amount of the solvent containing the above amount of the emulsifier, and the resulting mixture was diluted with water to a predetermined concentration.

Biological Test Example 1

Test Against Tobacco Cutworm (*Spodoptera litura*) Larvae

Leaves of sweet potato were immersed in the test solution at the appropriate concentration, and the leaves were dried in air. The leaves were then placed in a petri dish having a diameter of 9 cm, and ten *Spodoptera litura* at third instar larvae were released therein. The petri dishes were placed in a temperature-controlled chamber at 25° C. After 2 days and 4 days more sweet potato leaves were added. After 7 days, the number of dead larvae was counted to calculate the insecticidal activity. An insecticidal activity of 100% means that all larvae were killed, whereas an insecticidal activity of 0% means that no larva was killed. In the current test, the results of two petri dishes for each treatment were averaged.

In the biological test example 1, the compounds Nos. 1-3, 1-7, 1-8, 1-9, 1-11, 1-12, 1-17, 1-20, 1-24, 1-27, 1-28, 1-30, 1-31, 1-32, 1-33, 1-34, 1-35, 1-36, 1-37, 1-38, 1-39, 1-40, 1-41, 1-42, 1-43, 1-44, 1-47, 1-49, 1-50, 1-55, 1-56, 1-58, 1-64, 1-69, 1-73, 1-74, 1-75, 1-77, 1-78, 1-79, 1-80, 1-81, 1-89, 1-96, 1-103, 2-2, 4-2, 5-3, 5-7, 5-8, 5-19, 5-21, 5-22, 5-24, 5-28, 5-29, 5-30, 5-31, 5-32, 5-34, 5-35, 5-36, 5-37, 5-38, 5-39, 5-41, 5-45, 5-46, 5-51, 5-52, 5-53, 5-54, 5-55, 5-58, 5-59, 5-61, 5-62, 5-66, 5-67, 5-68, 5-72, 5-76, 5-77, 5-78, 5-79, 5-80, 5-81, 5-82, 5-83, 5-85, 5-86, 5-88, 5-89, 5-91, 5-93, 5-94, 5-96, 5-99, 5-100, 5-101, 5-102, 5-103, 5-106, 5-107, 5-108, 5-110, 5-112, 5-115, 5-116, 5-117, 5-139, 5-142, 5-144, 5-145, 5-146, 5-147, 5-148, 5-149, 5-150, 5-151, 5-152, 5-153, 5-154, 5-155, 5-157, 5-158, 5-159, 5-160, 5-161, 5-174, 5-175, 5-177, 5-178, 5-179, 5-181, 5-182, 5-183, 5-188, 5-189, 5-190, 5-191, 5-192, 5-194, 5-195, 5-196, 5-197, 5-198, 5-201, 5-202, 5-203, 5-204, 5-205, 5-206, 5-211, 5-212, 5-213, 5-219, 5-220, 5-221, 5-225, 5-229, 5-230, 5-231, 5-232, 5-242, 5-243, 5-244, 5-293, 5-294, 5-295, 5-296, 5-318, 5-319, 5-320, 5-322, 5-323, 5-324, 5-325, 5-326, 5-329, 5-330, 5-331, 5-335, 5-336, 5-340, 5-341, 5-349, 6-2, 6-3, 6-4, 6-5, 6-6, 6-7, 7-2, 7-3, 7-5, 7-6, 8-2, 8-6, 9-2, 9-3, 9-5, 9-6, 10-2, 10-3, 10-5, 10-6, 10-10, 10-22, 11-2, 11-6, 12-1, 12-3, 12-4, 12-5, A-3, A-4, A-7, A-8, A-10, I-2, I-3, I-5, I-12, I-24, I-25, I-26, I-27 and I-28 showed an insecticidal activity of 100% at an active compound concentration of 100 ppm.

Biological Test Example 2

Test Against Two-Spotted Spider Mite (*Tetranychus Urticae*)

50 to 100 adult mites of *Tetranychus urticae* were inoculated to leaves of kidney bean at two-leaf stage planted in a pot of 6 cm in diameter. After one day, test solution at the appropriate concentration was sprayed thereon in a sufficient amount using a spray gun. After the spraying, the plant pot was placed inside a greenhouse, and after 7 days, the acaricidal activity was calculated. An acaricidal activity of 100% means that all mites were killed, whereas an acaricidal activity of 0% means that no mite was killed. In the biological test example 2, the compound Nos. 1-11, 1-12, 1-27, 1-31, 1-32, 1-35, 1-36, 1-39, 1-41, 1-46, 1-49, 1-55, 1-73, 1-74, 1-75, 1-78, 1-80, 1-81, 1-89, 1-99, 5-28, 5-29, 5-30, 5-32, 5-33, 5-36, 5-40, 5-41, 5-44, 5-58, 5-61, 5-62, 5-72, 5-77, 5-78, 5-80, 5-81, 5-82, 5-85, 5-86, 5-88, 5-89, 5-91, 5-92, 5-93, 5-94, 5-102, 5-103, 5-110, 5-112, 5-147, 5-148, 5-150, 5-151, 5-153, 5-154, 5-155, 5-157, 5-175, 5-179, 5-186, 5-187, 5-188, 5-192, 5-213, 5-219, 5-220, 5-221, 5-224, 5-225, 5-242, 5-243, 5-244, 5-294, 5-295, 5-296, 5-319, 5-320, 5-331, 5-333, 5-340, 5-341, 9-2, 9-3, 10-3, 10-5, 10-6, 10-10, 11-2 and I-12 showed an acaricidal activity of 100% at an active compound concentration of 100 ppm.

Biological Test Example 3

Test Against Cucurbit Leaf Beetle (*Aulacophora Femoralis*)

Leaves of cucumber were immersed in the test solution at the appropriate concentration, and the leaves were dried in air. The leaves were then put in a plastic cup containing sterilized black soil and five *Aulacophora femoralis* at second instar larvae were released in the cup. The cups were placed in a temperature-controlled chamber at 25° C. After 7 days, the number of dead larvae was counted, and thus the insecticidal activity was calculated. An insecticidal activity of 100% means that all larvae were killed, whereas an insecticidal activity of 0% means that no larva was killed.

In the biological test example 3, the compounds Nos. 1-3, 1-5, 1-6, 1-7, 1-8, 1-11, 1-12, 1-25, 1-31, 1-32, 1-34, 1-37, 1-47, 1-49, 1-55, 1-56, 1-58, 1-67, 1-68, 1-69, 1-73, 1-77, 1-78, 1-79, 1-80, 1-101, 2-2, 4-2, 5-8, 5-21, 5-22, 5-30, 5-34, 5-35, 5-36, 5-40, 5-41, 5-44, 5-45, 5-46, 5-51, 5-58, 5-59, 5-61, 5-62, 5-65, 5-77, 5-78, 5-79, 5-81, 5-82, 5-85, 5-86, 5-89, 5-93, 5-96, 5-100, 5-102, 5-103, 5-127, 5-139, 5-142, 5-144, 5-145, 5-148, 5-150, 5-151, 5-152, 5-154, 5-155, 5-157, 5-161, 5-174, 5-175, 5-177, 5-178, 5-179, 5-181, 5-183, 5-198, 5-201, 5-202, 5-203, 5-204, 5-205, 5-206, 5-211, 5-212, 5-213, 5-219, 5-220, 5-221, 5-224, 5-225, 5-226, 5-229, 5-231, 5-242, 5-243, 5-244, 5-294, 5-295, 5-296, 5-320, 5-323, 5-324, 5-326, 5-331, 5-341, 6-6, 6-7, 7-2, 7-3, 7-5, 8-2, 9-2, 9-3, 9-6, 10-3, 10-6, 10-22, I-5, I-12, I-24, I-26 and I-27 showed an insecticidal activity of 100% at an active compound concentration of 100 ppm.

Biological Test Example 4

*Boophilus Microplus*—Test (Injection)

Solvent: dimethyl sulfoxide

To produce a suitable preparation of active compound, 10 mg of active compound are dissolved in 0.5 ml solvent, and the concentrate is diluted with solvent to the desired concentration. Five adult engorged female ticks (*Boophilus microplus*) are injected with 1 ml compound solution into the abdomen. Ticks are transferred into replica plates and incubated in a climate chamber for a period of time. Egg deposition of fertile eggs is monitored.

After 7 days mortality in % is determined. 100% means that all eggs are infertile; 0% means that all eggs are fertile.

In this test for example, the following compounds from the preparation examples showed good activity of 80% at application rate of 20 μg/animal: 1-104

In this test for example, the following compounds from the preparation examples showed good activity of 90% at application rate of 20 μg/animal: 1-27, 1-102

In this test for example, the following compounds from the preparation examples showed good activity of 95% at application rate of 20 μg/animal: 7-5, J-1

In this test for example, the following compounds from the preparation examples showed good activity of 98% at application rate of 20 μg/animal: 1-70, 1-87

In this test for example, the following compounds from the preparation examples showed good activity of 100% at application rate of 20 μg/animal: 1-8, 1-9, 1-10, 1-11, 1-12, 1-16, 1-23, 1-24, 1-25, 1-31, 1-32, 1-34, 1-35, 1-36, 1-37, 1-38, 1-39, 1-47, 1-49, 1-55, 1-56, 1-58, 1-66, 1-67, 1-68, 1-69, 1-72, 1-73, 1-74, 1-75, 1-77, 1-78, 1-79, 1-80, 1-81, 1-86, 1-89, 1-99, 1-101, 1-103, 2-2, 4-2, 5-8, 5-19, 5-21, 5-24, 5-28, 5-29, 5-30, 5-31, 5-32, 5-34, 5-35, 5-36, 5-37, 5-40, 5-41, 5-44, 5-45, 5-46, 5-48, 5-58, 5-59, 5-61, 5-62, 5-78, 5-79, 5-80, 5-81, 5-82, 5-85, 5-86, 5-88, 5-89, 5-90, 5-91, 5-92, 5-93, 5-94, 5-96, 5-100, 5-101, 5-102, 5-103, 5-110, 5-112, 5-117, 5-127, 5-142, 5-144, 5-145, 5-146, 5-147, 5-148, 5-149, 5-150, 5-151, 5-152, 5-153, 5-154, 5-155, 5-157, 5-158, 5-159, 5-160, 5-161, 5-174, 5-175, 5-177, 5-178, 5-179, 5-181, 5-183, 5-187, 5-188, 5-190, 5-192, 5-194, 5-197, 5-198, 5-201, 5-202, 5-203, 5-204, 5-205, 5-206, 5-211, 5-212, 5-213, 5-219, 5-220, 5-221, 6-2, 6-3, 6-4, 6-5, 6-6, 6-7, 9-3, 9-5, 9-6, 10-3, 10-5, 10-6, 10-22, 12-1, A-2, A-3, A-4, F-4, I-5, I-24

After 42 days mortality in % is determined. 100% means that all eggs are infertile; 0% means that all eggs are fertile.

In this test for example, the following compounds from the preparation examples showed good activity of 80% at application rate of 20 μg/animal: 1-7

Biological Test Example 5

*Boophilus Microplus* (dip)

Solvent: dimethyl sulfoxide

To produce a suitable preparation of active compound, 10 mg of active compound are dissolved in 0.5 ml solvent, and the concentrate is diluted with water to the desired concentration. Eight to ten adult engorged female *Boophilus microplus* ticks are placed in perforated plastic beakers and immersed in aqueous compound solution for one minute. Ticks are transferred to a filter paper in a plastic tray. Egg deposition of fertile eggs is monitored after. After 7 days mortality in % is determined 100% means that all the ticks have been killed; 0% means that none of the ticks have been killed. In this test for example, the following compounds from the preparation examples showed good activity of 98% at application rate of 100 ppm: 1-3

Biological Test Example 6

*Ctenocephalides Felis*—Test (CTECFE)

Solvent: dimethyl sulfoxide

To produce a suitable preparation of active compound, 10 mg of active compound are dissolved in 0.5 ml solvent, and the concentrate is diluted with cattle blood to the desired concentration. Approximately 20 adult unfed (*Ctenocepahlides felis*) are placed in flea chambers. The blood chamber, sealed with parafilm on the bottom, are filled with cattle blood supplied with compound solution and placed on top of the flea chamber, so that the fleas are able to suck the blood. The blood chamber is heated to 37° C. whereas the flea chamber is kept at room temperature. After 2 days mortality in % is determined 100% means that all the fleas have been killed; 0% means that none of the fleas have been killed.

In this test for example, the following compounds from the preparation examples showed good activity of 80% at application rate of 100 ppm: 1-3, 1-11, 1-58, 1-75, 1-86, 1-101, 5-46, 5-61, 5-93, 5-100, 5-103, 5-155

In this test for example, the following compounds from the preparation examples showed good activity of 90% at application rate of 100 ppm: 1-9, 1-27, 1-31, 1-32, 1-35, 1-36, 1-47, 1-55, 1-69, 1-79, 2-2, 5-19, 5-21, 5-30, 5-62, 5-67, 5-72, 5-80, 5-82, 5-85, 5-94, 5-96, 5-174, 5-203, 7-5

In this test for example, the following compounds from the preparation examples showed good activity of 95% at application rate of 100 ppm: 1-8, 1-34, 1-49, 1-81, 5-8, 5-24, 5-29, 5-32, 5-65, 5-79, 5-88, 5-89, 5-91, 5-145, 5-147, 5-151, 5-152, 5-175, 5-177, 5-179, 5-181, 5-190, 5-192, 5-198, 5-201, 5-202, 5-221, 9-3, 9-5

In this test for example, the following compounds from the preparation examples showed good activity of 98% at application rate of 100 ppm: 5-139, 5-159

In this test for example, the following compounds from the preparation examples showed good activity of 100% at application rate of 100 ppm: 1-12, 1-38, 1-39, 1-73, 1-77, 1-78, 1-80, 1-89, 5-22, 5-28, 5-31, 5-44, 5-58, 5-77, 5-78, 5-81, 5-86, 5-101, 5-117, 5-127, 5-144, 5-146, 5-148, 5-150, 5-153, 5-154, 5-157, 5-158, 5-160, 5-161, 5-178, 5-194, 5-197, 5-204, 5-205, 5-211, 5-212, 5-213, 5-219, 5-220, 6-2, 6-3, 6-4, 6-5, 6-7, 9-6, 10-3, 10-5, 10-6, 10-22

Biological Test Example 7

*Lucilia Cuprina* (48 h)

species: *Lucilia cuprina* 1$^{st}$ instar larvae (age 24 hrs)
solvent: dimethyl sulfoxide 10 mg active compound are dissolve in 0.5 ml Dimethylsulfoxid. Serial dilutions are made to obtain the desired rates. Approximately 20 *Lucilia* cuprina 1$^{st}$ instar larvae are transferred into a test tube containing 1 cm$^3$ of minced horse meat and 0.5 ml aqueous dilution of test compound. After 48 hrs percentage of larval mortality are recorded. 100% efficacy=all larvae are killed, % efficacy=normally developed larvae after 48 hrs.

In this test for example, the following compounds from the preparation examples showed good activity of 80% at application rate of 100 ppm: 1-27, 1-56, 1-58, 1-72, 5-19, 5-32, 5-80, 5-88, 5-89, 5-91, 5-101, 5-110, 5-117, 5-127, 5-139, 5-187, 5-197, 5-198, 5-201, 6-5, 6-7

In this test for example, the following compounds from the preparation examples showed good activity of 90% at application rate of 100 ppm: 1-35, 1-55, 1-99, 1-103, 5-36, 5-62, 5-81, 5-152, 5-153, 5-179, 5-190, 5-202, 5-204, F-4

In this test for example, the following compounds from the preparation examples showed good activity of 95% at application rate of 100 ppm: 1-12, 5-82, 5-142, 5-146, 5-174, 5-194

In this test for example, the following compounds from the preparation examples showed good activity of 100% at application rate of 100 ppm: 1-3, 1-8, 1-9, 1-11, 1-25, 1-31, 1-35, 1-36, 1-38, 1-39, 1-49, 1-68, 1-69, 1-73, 1-74, 1-75, 1-77, 1-78, 1-79, 1-80, 1-81, 1-89, 2-2, 5-8, 5-22, 5-24, 5-61, 5-72, 5-77, 5-78, 5-85, 5-86, 5-100, 5-144, 5-145, 5-147, 5-148, 5-150, 5-151, 5-154, 5-155, 5-157, 5-158, 5-160, 5-161, 5-211, 5-212, 5-213, 5-219, 5-220, 5-221, 6-2, 6-2, 6-6, 9-3, 9-5, 9-6, 10-3, 10-5, 10-6, A-2, A-3, A-4, I-5, I-24

Biological Test Example 8

*Musca Domestica*—Test

Solvent: dimethyl sulfoxide

To produce a suitable preparation of active compound, 10 mg of active compound are dissolved in 0.5 ml solvent, and the concentrate is diluted with water to the desired concentration. Prior to the assay, a piece of kitchen sponge is soaked with a mixture of sugar and compound solution and placed into a container. 10 adults (*Musca domestica*) are placed into the container and closed with a perforated lid. After 2 days mortality in % is determined 100% means that all the flies have been killed; 0% means that none of the flies have been killed. In this test for example, the following compounds from the preparation examples showed good activity of 80% at application rate of 100 ppm: 1-3, 1-8,1-12, 1-58, 1-73, 1-75, 5-77, 5-88,5-91, 5-103,5-110,5-146, 5-155, 9-6, A-3

In this test for example, the following compounds from the preparation examples showed good activity of 90% at application rate of 100 ppm: 1-11, 1-32, 1-55, 5-78, 5-127, 5-152, 5-153,5-177, 5-198, 5-220

In this test for example, the following compounds from the preparation examples showed good activity of 100% at application rate of 100 ppm: 1-9, 1-39, 1-78, 1-79, 1-80, 1-81, 1-89, 2-2, 5-81, 5-85, 5-89, 5-93, 5-142, 5-148, 5-150, 5-151, 5-154, 5-157, 5-161, 5-175, 5-179, 5-181, 5-192, 5-212, 5-213, 5-211, 5-219, 5-221, 9-3, 10-3, 10-5, 10-6

Preparation Example 1 (Granules)

To a mixture containing 10 parts of the compound of the present invention (No. 1-78), 30 parts of bentonite (montmorillonite), 58 parts of talc and 2 parts of lignin sulfonate was added 25 parts of water, and the mixture was well kneaded and granulated with 10 to 40 meshes by an extruding granulator and dried at 40 to 50° C. to obtain granules.

Preparation Example 2 (Granules)

95 parts of clay mineral granules having particle diameter distribution within the range of 0.2 to 2 mm were put into a rotary mixer, and then wetted evenly by spraying of 5 parts of the compound of the present invention (No. 1-31) together with a liquid diluent under rotating condition and dried at 40 to 50° C. to obtain granules.

Preparation Example 3 (Emulsion)

30 parts of the compound of the present invention (No. 1-31), 55 parts of xylene, 8 parts of polyoxyethylene alkyl phenyl ether and 7 parts of calcium alkylbenzenesulfonate were mixed together to obtain the emulsion.

Preparation Example 4 (Wettable Agent)

15 parts of the compound of the present invention (No. 5-102), 80 parts of a mixture of white carbon (hydrated amorphous silicon oxide fine powder) and powdered clay (1:5), formalin condensate of 2 parts of sodium alkylbenzenesulfonate and 3 parts of sodium alkylnaphthalenesulfonate were mixed together and the mixture was crushed to obtain a wettable agent.

Preparation Example 5 (Wettable Granules)

20 parts of the active compound of the present invention (No. 5-28), 30 parts of lignin sodium sulfonate, 15 parts of bentonite and 35 parts of calcined diatomaceous earth powder were well mixed, and after addition of water, the mixture was then extruded with a screen of 0.3 mm and dried to obtain wettable granules.

Industrial Applicability

The novel pesticidal carboxamides of the present invention have excellent pesticidal activity as shown in the above examples.

The invention claimed is:
1. A carboxamide compound of Formula (I-V):

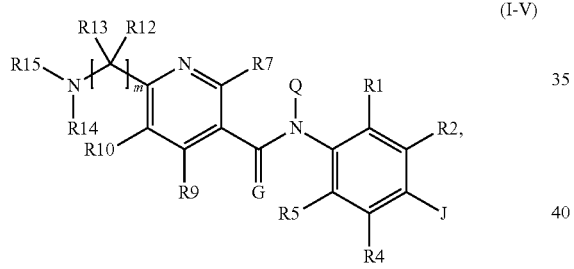

wherein
G represents oxygen or sulfur;
Q represents hydrogen, $C_{1-12}$ haloalkyl, ($C_{1-12}$ alkyl)carbonyl, ($C_{1-12}$ haloalkyl)carbonyl, ($C_{1-12}$ alkoxy)carbonyl or ($C_{1-12}$ hloalkxy)carbonyl;
J represents $C_{1-12}$ haloalkyl, $C_{1-12}$ haloalkyl-O—, $C_{1-12}$ haloalkyl-S—, $C_{1-12}$ haloalkyl-S(=O), $C_{1-12}$ haloalkyl-S(=O)$_2$—, $C_{3-8}$ halocycloalkyl, —C($J^1$) ($J^2$) ($J^3$) or —C($J^1$) ($J^2$) ($OJ^4$),
wherein
$J^1$ and $J^2$ each independently represents $C_{1-12}$ haloalkyl,
$J^3$ represents a heterocyclic group, and
$J^4$ represents hydrogen, $C_{1-12}$ alkyl, $C_{1-12}$ haloalkyl, alkylsulfonyl, $C_{1-12}$ haloalkylsulfonyl, arylsulfonyl, an aryl group or a heterocyclic group;
R1, R2, R4, R5, R7, R8, R9 and R10 each independently represents hydrogen, cyano, halogen, nitro, hydroxy, mercapto, amino, formyl, oxide, $C_{1-12}$ alkyl, $C_{1-12}$ haloalkyl, aryl-($C_{1-12}$)alkyl, heterocyclyl-($C_{1-12}$)alkyl, $C_{1-12}$ alkyl-O—, $C_{1-12}$ alkyl-NH—, $C_{1-12}$ alkyl-S—, $C_{1-12}$ alkyl-S(O)—, $C_{1-12}$ alkyl-S(O)$_2$—, $C_{1-12}$ alkyl-S(O)$_2$O—, $C_{1-12}$ haloalkyl-O—, $C_{1-12}$ haloalkyl-NH—, $C_{1-12}$ haloalkyl-S—, $C_{1-12}$ haloalkyl-S(O)—, $C_{1-12}$ haloalkyl-S(O)$_2$—, $C_{1-12}$ haloalkyl-S(=O)$_2$O—, aryl-O—, aryl-NH—, aryl-S—, aryl-S(O)—, aryl-S(O)$_2$—, aryl-S(O)$_2$O—, heterocyclyl-O—, heterocyclyl-NH—, heterocyclyl-S—, heterocyclyl-S(O)—, heterocyclyl-S(O)$_2$—, heterocyclyl-S(O)$_2$O—, $C_{1-12}$ alkyl-O—($C_{1-12}$)alkyl, $C_{1-12}$ alkyl-NH—($C_{1-12}$)alkyl, $C_{1-12}$ alkyl-S—($C_{1-12}$)alkyl, $C_{1-12}$ alkyl-S(O)—($C_{1-12}$)alkyl, $C_{1-12}$ alkyl-S(O)$_2$—($C_{1-12}$)alkyl, $C_{1-12}$ alkyl-S(O)$_2$O—($C_{1-12}$)alkyl, $C_{1-12}$ haloalkyl-O—($C_{1-12}$)alkyl, $C_{1-12}$ haloalkyl-NH—($C_{1-12}$)alkyl, $C_{1-12}$ haloalkyl-S—($C_{1-12}$)alkyl, $C_{1-12}$ haloalkyl-S(O)—($C_{1-12}$)alkyl, $C_{1-12}$ haloalkyl-S(O)$_2$—($C_{1-12}$)alkyl, $C_{1-12}$ haloalkyl-S(O)$_2$O—($C_{1-12}$)alkyl, aryl-O—($C_{1-12}$)alkyl, aryl-NH—($C_{1-12}$)alkyl, aryl-S—($C_{1-12}$)alkyl, aryl-S (O)—($C_{1-12}$)alkyl, aryl-S(O)$_2$—($C_{1-12}$)alkyl, aryl-S(O)$_2$O—($C_{1-12}$)alkyl, heterocyclyl-O—($C_{1-12}$)alkyl, heterocyclyl-NH—($C_{1-12}$)alkyl, heterocyclyl-S—($C_{1-12}$)alkyl, heterocyclyl-S(O)—($C_{1-12}$)alkyl, heterocyclyl-S(O)$_2$—($C_{1-12}$)alkyl, heterocyclyl-S(O)$_2$O—($C_{1-12}$)alkyl, $C_{3-8}$ cycloalkyl, $C_{3-8}$ cycloalkyl-($C_{1-12}$)alkyl-, $C_{3-8}$ halocycloalkyl, $C_{3-8}$ halocycloalkyl-($C_{1-12}$)alkyl-, $C_{2-12}$ alkenyl, $C_{2-12}$ haloalkenyl, $C_{2-12}$ alkynyl, $C_{2-12}$ haloalkynyl, di($C_{1-12}$ alkyl)amino, di($C_{1-12}$ haloalkyl)amino, $C_{3-36}$ trialkylsilyl, hydroxyimino($C_{1-12}$)alkyl, $C_{1-12}$ alkyl-O—N=($C_{1-12}$)alkyl, $C_{1-12}$ alkyl-NH—N=($C_{1-12}$)alkyl, $C_{1-12}$ alkyl-S—N=($C_{1-12}$)alkyl, $C_{1-12}$ alkyl-S(O)—N=($C_{1-12}$)alkyl, $C_{1-12}$ alkyl-S(O)$_2$—N=($C_{1-12}$)alkyl, $C_{1-12}$ alkyl-S(O)$_2$O—N=($C_{1-12}$)alkyl, $C_{1-12}$ haloalkyl-O—N=($C_{1-12}$)alkyl, $C_{1-12}$ haloalkyl-NH—N=($C_{1-12}$)alkyl, $C_{1-12}$ haloalkyl-S—N=($C_{1-12}$)alkyl, $C_{1-12}$ haloalkyl-S(O)—N=($C_{1-12}$)alkyl, $C_{1-12}$ haloalkyl-S(O)$_2$—N=($C_{1-12}$)alkyl, $C_{1-12}$ haloalkyl-S(O)$_2$O—N=($C_{1-12}$)alkyl, ($C_{1-12}$ alkoxy)carbonyl, ($C_{1-12}$ haloalkoxy)carbonyl, ($C_{3-8}$ cycloalkoxy)carbonyl, ($C_{3-8}$ halocycloalkoxy)carbonyl, $C_{3-8}$ cycloalkyl-($C_{1-12}$ alkoxy)carbonyl, $C_{3-8}$ halocycloalkyl-($C_{1-12}$ alkoxy)carbonyl, ($C_{1-12}$ alkyl)carbonyl, ($C_{1-12}$ haloalkyl)carbonyl, ($C_{3-8}$ cycloalkyl)carbonyl, ($C_{3-8}$ halocycloalkyl)carbonyl, $C_{3-8}$ cycloalkyl-($C_{1-12}$)alkyl-carbonyl, ($C_{3-8}$ halocycloalkyl)-($C_{1-12}$)alkyl-carbonyl, an aryl group, a heterocyclic group, sulfur pentafluoride, or one of the groups of Formulae (X1-1) to (X1-5):

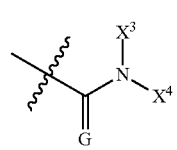

X1-1

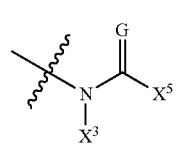

X1-2

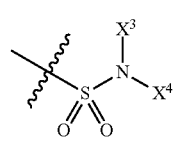

X1-3

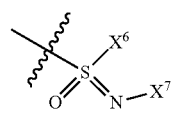

X1-4

-continued

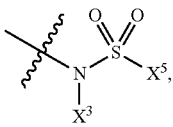
X1-5 wherein
G is as defined above;
$X^3$, $X^4$ and $X^5$ each independently represents hydrogen, cyano, halogen, nitro, hydroxy, mercapto, amino, formyl, $C_{1-12}$ alkyl, $C_{1-12}$ haloalkyl, aryl-($C_{1-12}$)alkyl, heterocyclyl-($C_{1-12}$)alkyl, $C_{1-12}$ alkyl-NH—$C_{1-12}$ alkyl-S—, $C_{1-12}$ alkyl-S(O)—, $C_{1-12}$ alkyl-S(O)$_2$—, $C_{1-12}$ alkyl-S(O)$_2$O—, $C_{1-12}$ haloalkyl-O—, $C_{1-12}$ haloalkyl-NH—, $C_{1-12}$ haloalkyl-S—, $C_{1-12}$ haloalkyl-S(O)—, $C_{1-12}$ haloalkyl-S(O)$_2$—, $C_{1-12}$ haloalkyl-S(O)$_2$O—, aryl-O—, aryl-NH—, aryl-S—, aryl-S(O)—, aryl-S(O)$_2$—, aryl-S(O)$_2$O—, heterocyclyl-O—, heterocyclyl-NH—, heterocyclyl-S—, heterociyl-S(O)—, heterocyclyl-S(O)$_2$—, heterocyclyl-S(O)$_2$O—, $C_{1-12}$ alkyl-O—($C_{1-12}$)alkyl-NH—($C_{1-12}$)alkyl, $C_{1-12}$ alkyl-S—($C_{1-12}$)alkyl, $C_{1-12}$alkyl-S(O)—($C_{1-12}$)alkyl, $C_{1-12}$ alkyl-S(O)$_2$—($C_{1-12}$)alkyl, $C_{1-12}$ alkyl-S(O)$_2$O—($C_{1-12}$)alkyl, $C_{1-12}$ haloalkyl-O—($C_{1-12}$)alkyl, $C_{1-12}$ haloalkyl-NH—($C_{1-12}$)alkyl, $C_{1-12}$ haloalkyl-S—($C_{1-12}$)alkyl, $C_{1-12}$ haloalkyl-S(O)—($C_{1-12}$)alkyl, $C_{1-12}$ haloalkyl-S(O)$_2$—($C_{1-12}$) alkyl, $C_{1-12}$ haloalkyl-S(O)$_2$O—($C_{1-12}$)alkyl, aryl-O—($C_{1-12}$)alkyl, aryl-NH—($C_{1-12}$)alkyl, aryl-S—($C_{1-12}$)alkyl, aryl-S(O)—($C_{1-12}$)alkyl, aryl-S(O)$_2$—($C_{1-12}$)alkyl, aryl-S(O)$_2$O—($C_{1-12}$)alkyl, heterocyclyl-O—($C_{1-12}$)alkyl, heterocyclyl-NH—($C_{1-12}$)alkyl, heterocyclyl-S—($C_{1-12}$)alkyl, heterocyclyl-S(O)—($C_{1-12}$)alkyl, heterocyclyl-S(O)$_2$—($C_{1-12}$)alkyl, heterocyclyl-S(O)$_2$O—($C_{1-12}$)alkyl, $C_{3-8}$ cycloalkyl, $C_{3-8}$ cycloalkyl-($C_{1-12}$)alkyl-, $C_{3-8}$ halocycloalkyl, $C_{3-8}$ halocycloalkyl-($C_{1-12}$)alkyl-, $C_{2-12}$ alkenyl, $C_{2-12}$ haloalkenyl, $C_{2-12}$ alkynyl, $C_{2-12}$ haloalkynyl, di($C_{1-12}$ alkyl)amino, di($C_{1-12}$ haloalkyl) amino, $C_{3-36}$ trialkylsilyl, hydroxyimino($C_{1-12}$)alkyl, $C_{1-12}$ alkyl-O—N=($C_{1-12}$)alkyl, $C_{1-12}$ alkyl-NH—N=($C_{1-12}$)alkyl, $C_{1-12}$ alkyl-S—N=($C_{1-12}$)alkyl, $C_{1-12}$ alkyl-S(O)—N=($C_{1-12}$)alkyl, $C_{1-12}$ alkyl-S(O)$_2$—N=($C_{1-12}$)alkyl, $C_{1-12}$ alkyl-S(O)$_2$O—N=($C_{1-12}$)alkyl, $C_{1-12}$ haloalkyl-O—N=($C_{1-12}$)alkyl, $C_{1-12}$ haloalkyl-NH—N=($C_{1-12}$)alkyl, $C_{1-12}$ haloalkyl-S—N—($C_{1-12}$)alkyl, $C_{1-12}$ haloalkyl-S(O)—N=($C_{1-12}$)alkyl, $C_{1-12}$ haloalkyl-S(O)$_2$—N=($C_{1-12}$)alkyl, $C_{1-12}$ haloalkyl-S(O)$_2$O—N=($C_{1-12}$) alkyl, ($C_{1-12}$ haloalkoxy)carbonyl, ($C_{3-8}$ cycloalkoxy)carbonyl, ($C_{3-8}$ halocycloalkoxy)carbonyl, $C_{3-8}$ cycloalkyl-($C_{1-12}$ alkoxy)carbonyl, $C_{3-8}$ halocycloalkyl-($C_{1-12}$ alkoxy)carbonyl, ($C_{1-12}$ alkyl)carbonyl, ($C_{1-12}$ haloalkyl)carbonyl, ($C_{3-8}$ cycloalkyl)carbonyl, ($C_{3-8}$ halocycloalkyl)carbonyl, $C_{3-8}$ cycloalkyl-($C_{1-12}$)alkyl-carbonyl, $C_{3-8}$ halocycloalkyl-($C_{1-12}$)alkyl-carbonyl, aryl-carbonyl, heterocyclyl-carbonyl, aryl-($C_{1-12}$)alkyl-carbonyl, heterocyclyl-($C_{1-12}$)alkyl-carbonyl, sulfur pentafluoride, or an aryl group, or
$X^3$ and $X^4$ optionally forms a heterocycle together with the nitrogen atom, carbon atom, oxygen atom or sulfur atom to which they are bonded, or
$X^3$ and $X^5$ optionally forms a heterocycle together with the nitrogen atom, carbon atom, oxygen atom or sulfur atom to which they are bonded,
$X^6$ represents hydrogen, $C_{1-12}$ alkyl, $C_{1-12}$ haloalkyl, $C_{3-8}$ cycloalkyl, $C_{2-12}$ alkenyl, $C_{2-12}$ haloalkenyl, an aryl group, a heterocyclic group, aryl-($C_{1-12}$)alkyl or heterocyclyl-($C_{1-12}$)alkyl,
$X^7$ represents hydrogen, nitro, cyano, formyl, $X^8$-carbonyl or $X^8$-oxycarbonyl, and wherein $X^8$ independently has the same meaning as $X^6$ defined above;
R12 has the same meaning as $X^3$ defined above;
R13 has the same meaning as $X^4$ defined above;
m represents an integer of 1 to 4;
R14 has the same meaning as $X^3$ defined above; and
R15 represents hydrogen or has the same meaning as —C(=G)-$X^5$, and wherein G and $X^5$ are as defined above.

2. The carboxamide compound according to claim 1, wherein
the heterocyclic group represents any one of groups W1 to W9:

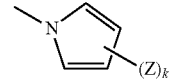
W1

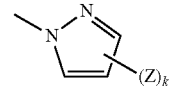
W2

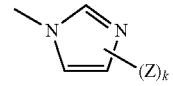
W3

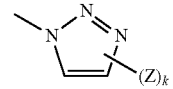
W4

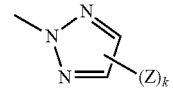
W5

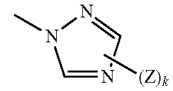
W6

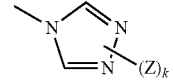
W7

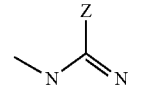
W8

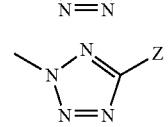
W9 wherein
Z each independently represents hydrogen, halogen, nitro, cyano, hydroxy, thio, $C_{1-6}$ haloalkyl, $C_{1-6}$ haloalkoxy, $C_{1-6}$ alkylthio, $C_{1-6}$ alkylsulfinyl, $C_{1-6}$ alkylsulfonyl, $C_{1-6}$ haloalkylthio, $C_{1-6}$ haloalkylsulfinyl or $C_{1-6}$ haloalkylsulfonyl; and k represents an integer from 1 to 4.

3. The carboxamide compound according to claim 1, wherein

G represents oxygen or sulfur;

Q represents hydrogen, $C_{1-4}$ haloalkyl, ($C_{1-4}$ alkyl)carbonyl, ($C_{1-4}$ haloalkyl)carbonyl, ($C_{1-4}$ alkoxy)carbonyl or ($C_{1-4}$ haloalkoxy)carbonyl;

J represents $C_{1-4}$ haloalkyl, $C_{1-4}$ haloalkyl-O—, $C_{1-4}$ haloalkyl-S—, $C_{1-4}$ haloalkyl-S(=O)—, $C_{1-4}$ haloalkyl-S(=O)$_2$—, $C_{3-6}$ halocycloalkyl, —C($J^1$)($J^2$)($J^3$) or —C($J^1$)($J^2$)(O$J^4$), wherein $J^1$ and $J^2$ each independently represent $C_{1-4}$ haloalkyl,
$J^3$ represents any one of groups W1 to W9:

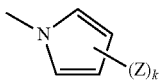
W1

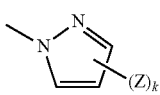
W2

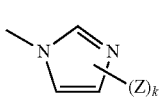
W3

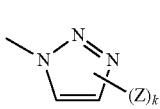
W4

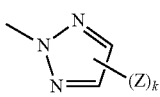
W5

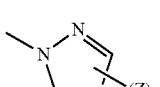
W6

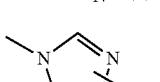
W7

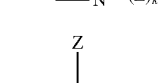
W8

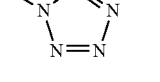
W9 wherein

Z each independently represents hydrogen, halogen, nitro, cyano, hydroxy, thio, $C_{1-6}$ haloalkyl, $C_{1-6}$ haloalkoxy, $C_{1-6}$ alkylthio, $C_{1-6}$ alkylsulfinyl, $C_{1-6}$ alkylsulfonyl, $C_{1-6}$ haloalkylthio, $C_{1-6}$ haloalkylsulfinyl or $C_{1-6}$ haloalkylsulfonyl, and k represents an integer from 1 to 4, $J^4$ represents hydrogen, $C_{1-4}$ alkyl, $C_{1-4}$ haloalkyl, $C_{1-4}$ alkylsulfonyl, $C_{1-4}$ haloalkylsulfonyl, aryl sulfonyl, an aryl group or a heterocyclic group;

R1, R2, R4, R5, R7, R8, R9 and R10 each independently represents hydrogen, cyano, halogen, nitro, hydroxy, mercapto, amino, formyl, oxide, $C_{1-4}$ alkyl, $C_{1-4}$ haloalkyl, aryl-($C_{1-4}$)alkyl, heterocyclyl-($C_{1-4}$)alkyl, $C_{1-4}$ alkyl-O—, $C_{1-4}$ alkyl-NH—, $C_{1-4}$ alkyl-S—, $C_{1-4}$ alkyl-S(O)—, $C_{1-4}$ alkyl-S(O)$_2$—, $C_{1-4}$ alkyl-S(O)$_2$O—, $C_{1-4}$ haloalkyl-O—, $C_{1-4}$ haloalkyl-NH—, $C_{1-4}$ haloalkyl-S—, $C_{1-4}$ haloalkyl-S(O)—, $C_{1-4}$ haloalkyl-S(O)$_2$—, $C_{1-4}$ haloalkyl-S(=O)$_2$O—, aryl-O—, aryl-NH—, aryl-S—, aryl-S(O)—, aryl-S(O)$_2$—, aryl-S(O)$_2$O—, heterocyclyl-O—, heterocyclyl-NH—, heterocyclyl-S—, heterocyclyl-S(O)—, heterocyclyl-S(O)$_2$—, heterocyclyl-S(O)$_2$O—, $C_{1-4}$ alkyl-O—($C_{1-4}$)alkyl, $C_{1-4}$ alkyl-NH—($C_{1-4}$)alkyl, $C_{1-4}$ alkyl-S—($C_{1-4}$)alkyl, $C_{1-4}$ alkyl-S(O)—($C_{1-4}$)alkyl, $C_{1-4}$ alkyl-S(O)$_2$—($C_{1-4}$)alkyl, $C_{1-4}$ alkyl-S(O)$_2$O—($C_{1-4}$)alkyl, $C_{1-4}$ haloalkyl-O—($C_{1-4}$)alkyl, $C_{1-4}$ haloalkyl-NH—($C_{1-4}$)alkyl, $C_{1-4}$ haloalkyl-S—($C_{1-4}$)alkyl, $C_{1-4}$ haloalkyl-S(O)—($C_{1-4}$)alkyl, $C_{1-4}$ haloalkyl-S(O)$_2$—($C_{1-4}$)alkyl, $C_{1-4}$ haloalkyl-S(O)$_2$O—($C_{1-4}$)alkyl, aryl-O—($C_{1-4}$)alkyl, aryl-NH—($C_{1-4}$)alkyl, aryl-S—($C_{1-4}$)alkyl, aryl-S(O)—($C_{1-4}$)alkyl, aryl-S(O)$_2$—($C_{1-4}$)alkyl, aryl-S(O)$_2$O—($C_{1-4}$)alkyl, heterocyclyl-O—($C_{1-4}$)alkyl, heterocyclyl-NH—($C_{1-4}$)alkyl, heterocyclyl-S—($C_{1-4}$)alkyl, heterocyclyl-S(O)—($C_{1-4}$)alkyl, heterocyclyl-S(O)$_2$—($C_{1-4}$)alkyl, heterocyclyl-S(O)$_2$O—($C_{1-4}$)alkyl, $C_{3-6}$ cycloalkyl, $C_{3-6}$ cycloalkyl-($C_{1-4}$)alkyl-, $C_{3-6}$ halocycloalkyl, $C_{3-6}$ halocycloalkyl-($C_{1-4}$)alkyl-, $C_{2-4}$ alkenyl, $C_{2-4}$ haloalkenyl, $C_{2-4}$ alkynyl, $C_{2-4}$ haloalkynyl, di($C_{1-4}$ alkyl)amino, di($C_{1-4}$ haloalkyl)amino, $C_{3-12}$ trialkylsilyl, hydroxyimino($C_{1-4}$)alkyl, $C_{1-4}$ alkyl-O—N=($C_{1-4}$)alkyl, $C_{1-4}$ alkyl-NH—N=($C_{1-4}$)alkyl, $C_{1-4}$ alkyl-S—N=($C_{1-4}$)alkyl, $C_{1-4}$ alkyl-S(O)—N=($C_{1-4}$)alkyl, $C_{1-4}$ alkyl-S(O)$_2$—N=($C_{1-4}$)alkyl, $C_{1-4}$ alkyl-S(O)$_2$O—N=($C_{1-4}$)alkyl, $C_{1-4}$ haloalkyl-O—N=($C_{1-4}$)alkyl, $C_{1-4}$ haloalkyl-NH—N=($C_{1-4}$)alkyl, $C_{1-4}$ haloalkyl-S—N=($C_{1-4}$)alkyl, $C_{1-4}$ haloalkyl-S(O)—N=($C_{1-4}$)alkyl, $C_{1-4}$ haloalkyl-S(O)$_2$—N=($C_{1-4}$)alkyl, $C_{1-4}$ haloalkyl-S(O)$_2$O—N=($C_{1-4}$)alkyl, ($C_{1-4}$ alkoxy)carbonyl, ($C_{1-4}$ haloalkoxy)carbonyl, ($C_{3-6}$ cycloalkoxy)carbonyl, ($C_{3-6}$ halocycloalkoxy)carbonyl, $C_{3-6}$ cycloalkyl-($C_{1-4}$ alkoxy)carbonyl, $C_{3-6}$ halocycloalkyl-($C_{1-4}$ alkoxy)carbonyl, ($C_{1-4}$ alkyl)carbonyl, ($C_{1-4}$ haloalkyl)carbonyl, ($C_{3-6}$ cycloalkyl)carbonyl, ($C_{3-6}$ halocycloalkyl)carbonyl, $C_{3-6}$ cycloalkyl-($C_{1-4}$)alkyl-carbonyl, ($C_{3-6}$ halocycloalkyl)-($C_{1-4}$)alkyl-carbonyl, an aryl group, sulfur pentafluoride, or one of the groups of Formulae (X1-1) to (X1-5):

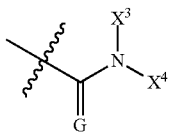
X1-1

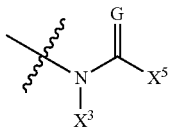
X1-2

-continued

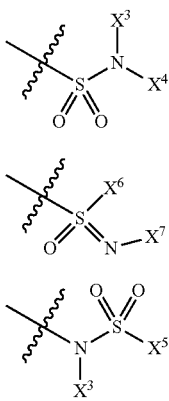

wherein
G is as defined above;
$X^3$, $X^4$ and $X^5$ each independently represent hydrogen, cyano, halogen, nitro, hydroxy, mercapto, amino, formyl, $C_{1-4}$ alkyl, $C_{1-4}$ haloalkyl, aryl-($C_{1-4}$)alkyl, heterocyclyl-($C_{1-4}$)alkyl, $C_{1-4}$ alkyl-NH—, $C_{1-4}$ alkyl-S—, $C_{1-4}$ alkyl-S(O)—, $C_{1-4}$ alkyl-S(O)$_2$—, $C_{1-4}$ alkyl-S(O)$_2$O—, $C_{1-4}$ haloalkyl-O—, $C_{1-4}$ haloalkyl-NH—, $C_{1-4}$ haloalkyl-S—, $C_{1-4}$ haloalkyl-S(O)—, $C_{1-4}$ haloalkyl-S(O)$_2$—, $C_{1-4}$ haloalkyl-S(O)$_2$O—, aryl-O—, aryl-NH—, aryl-S—, aryl-S(O)—, aryl-S(O)$_2$—, aryl-S(O)$_2$O—, heterocyclyl-O—, heterocyclyl-NH—, heterocyclyl-S—, heterocyclyl-S(O)—, heterocyclyl-S(O)$_2$-, heterocyclyl-S(O)$_2$O—, $C_{1-4}$ alkyl-O—($C_{1-4}$)alkyl, $C_{1-4}$ alkyl-NH—($C_{1-4}$)alkyl, $C_{1-4}$ alkyl-S—($C_{1-4}$)alkyl, $C_{1-4}$ alkyl-S(O)—($C_{1-4}$)alkyl, $C_{1-4}$ alkyl-S(O)$_2$—($C_{1-4}$)alkyl, $C_{1-4}$ alkyl-S(O)$_2$O—($C_{1-4}$)alkyl, $C_{1-4}$ haloalkyl-O—($C_{1-4}$)alkyl, $C_{1-4}$ haloalkyl-NH—($C_{1-4}$)alkyl, $C_{1-4}$ haloalkyl-S—($C_{1-4}$)alkyl, $C_{1-4}$ haloalkyl-S(O)—($C_{1-4}$)alkyl, $C_{1-4}$ haloalkyl-S(O)$_2$—($C_{1-4}$)alkyl, $C_{1-4}$ haloalkyl-S(O)$_2$O—($C_{1-4}$) alkyl, aryl-O—($C_{1-4}$)alkyl, aryl-NH—($C_{1-4}$)alkyl, aryl-S—($C_{1-4}$)alkyl, aryl-S(O)—($C_{1-4}$)alkyl, aryl-S(O)$_2$—($C_{1-4}$)alkyl, aryl-S(O)$_2$O—($C_{1-4}$)alkyl, heterocyclyl-O—($C_{1-4}$)alkyl, heterocyclyl-NH—($C_{1-4}$) alkyl, heterocyclyl-S—($C_{1-4}$)alkyl, heterocyclyl-S(O)—($C_{1-4}$)alkyl, heterocyclyl-S(O)$_2$—($C_{1-4}$)alkyl, heterocyclyl-S(O)$_2$O—($C_{1-4}$)alkyl, $C_{3-6}$ cycloalkyl, $C_{3-6}$ cycloalkyl-($C_{1-4}$)alkyl-, $C_{3-6}$ halocycloalkyl, $C_{3-6}$ halocycloalkyl-($C_{1-4}$)alkyl-, $C_{2-4}$ alkenyl, $C_{2-4}$ haloalkenyl, $C_{2-4}$ alkynyl, $C_{2-4}$ haloalkynyl, di($C_{1-4}$ alkyl)amino, di($C_{1-4}$ haloalkyl)amino, $C_{3-12}$ trialkylsilyl, hydroxyimino($C_{1-4}$)alkyl, $C_{1-4}$ alkyl-O—N=($C_{1-4}$)alkyl, $C_{1-4}$ alkyl-NH—N=($C_{1-4}$)alkyl, $C_{1-4}$ alkyl-S—N=($C_{1-4}$)alkyl, $C_{1-4}$ alkyl-S(O)—N=($C_{1-4}$)alkyl, $C_{1-4}$ alkyl-S(O)$_2$—N=($C_{1-4}$)alkyl, $C_{1-4}$ alkyl-S(O)$_2$O—N=($C_{1-4}$)alkyl, $C_{1-4}$ haloalkyl-O—N=($C_{1-4}$)alkyl, $C_{1-4}$ haloalkyl-NH—N=($C_{1-4}$) alkyl, $C_{1-4}$ haloalkyl-S—N=($C_{1-4}$)alkyl, $C_{1-4}$ haloalkyl-S(O)—N=($C_{1-4}$)alkyl, $C_{1-4}$ haloalkyl-S(O)$_2$—N=($C_{1-4}$)alkyl, $C_{1-4}$ haloalkyl-S(O)$_2$O—N=($C_{1-4}$) alkyl, ($C_{1-4}$ haloalkoxy)carbonyl, ($C_{3-6}$ cycloalkoxy)carbonyl, ($C_{3-6}$ halocycloalkoxy)carbonyl, $C_{3-6}$ cycloalkyl-($C_{1-4}$alkoxy)carbonyl, $C_{3-6}$ halocycloalkyl-($C_{1-4}$ alkoxy)carbonyl, ($C_{1-4}$ alkyl)carbonyl, ($C_{1-4}$ haloalkyl)carbonyl, ($C_{3-6}$ cycloalkyl)carbonyl, ($C_{3-6}$ halocycloalkyl)carbonyl, $C_{3-6}$ cycloalkyl-($C_{1-4}$)alkyl-carbonyl, $C_{3-6}$ halocycloalkyl-($C_{1-4}$)alkyl-carbonyl, aryl-carbonyl, heterocyclyl-carbonyl, aryl-($C_{1-4}$alkyl-carbonyl, heterocyclyl-($C_{1-4}$)alkyl-carbonyl, sulfur pentafluoride, or an aryl group, or $X^3$ and $X^4$ optionally form a heterocycle together with the nitrogen atom, carbon atom, oxygen atom or sulfur atom to which they are bonded, or $X^3$ and $X^5$ optionally form a heterocycle together with the nitrogen atom, carbon atom, oxygen atom or sulfur atom to which they are bonded, $X^6$ represents hydrogen, $C_{1-4}$ alkyl, $C_{1-4}$ haloalkyl, $C_{3-6}$ cycloalkyl, $C_{2-4}$ alkenyl, $C_{2-4}$ haloalkenyl, an aryl group, a heterocyclic group, aryl-($C_{1-4}$)alkyl or heteroeyelyl-($C_{1-4}$)alkyl, and $X^7$ represents hydrogen, nitro, cyano, formyl, $X^8$-carbonyl or $X^8$-oxycarbonyl, and wherein $X^8$ independently has the same meaning as $X^6$ defined above.

4. The carboxamide compound according to claim 1, wherein

J represents $C_{1-4}$ perfluoroalkyl, $C_{1-4}$ monobromoperfluoroalkyl, $C_{3-6}$ perfluorocycloalkyl, —C ($J^1$) ($J^2$) ($J^3$) or —C($J^1$) ($J^2$) (O$J^4$), $J^1$ and $J^2$ each independently represent $C_{1-4}$ perfluoroalkyl, $J^3$ represents any one of groups W1 to W9:

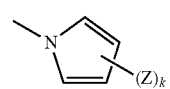 W1

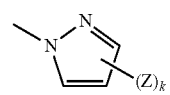 W2

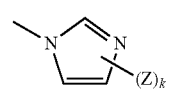 W3

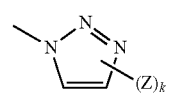 W4

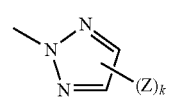 W5

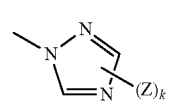 W6

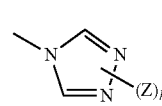 W7

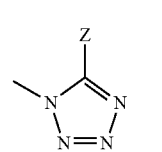 W8

-continued

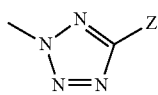

W9 wherein
Z each independently represents hydrogen, halogen, nitro, cyano, hydroxy, thio, $C_{1-6}$ haloalkyl, $C_{1-6}$ haloalkoxy, $C_{1-6}$ alkylthio, $C_{1-6}$ alkylsulfinyl, $C_{1-6}$ alkylsulfonyl, $C_{1-6}$ haloalkylthio, $C_{1-6}$ haloalkylsulfinyl or $C_{1-6}$ haloalkylsulfonyl, and
K represents an integer from 1 to 4;
and
$J^4$ represents $C_{1-4}$ alkyl, $C_{1-4}$ haloalkyl or a phenyl group.

5. The carboxamide compound according to claim 1, wherein
G represents oxygen;
m represents an integer of 1; and
R9, R12 and R13 each represents hydrogen.

6. A composition comprising at least one compound according to any one of claims 1 to 5, and an extender and/or a surfactant.

7. An animal parasite-controlling agent comprising at least one compound according to any one of claims 1 to 5.

8. A carboxamide compound of Formula (I-V):

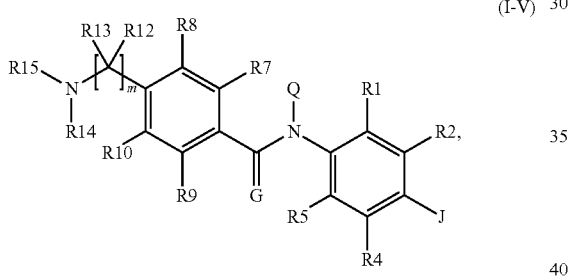

(I-V)

wherein
G represents oxygen or sulfur;
Q represents $C_{1-12}$ alkyl;
J represents $C_{1-12}$ haloalkyl, $C_{1-12}$ haloalkyl-O—, $C_{1-12}$ haloalkyl-S—, $C_{1-12}$ haloalkyl-S(=O), $C_{1-12}$ haloalkyl-S(=O)$_2$—, $C_{3-8}$ halocycloalkyl, —C($J^1$) ($J^2$) ($J^3$) or —C($J^1$) ($J^2$) (O$J^4$),
wherein
$J^1$ and $J^2$ each independently represents $C_{1-12}$ haloalkyl,
$J^3$ represents a heterocyclic group, and
$J^4$ represents hydrogen, $C_{1-12}$ alkyl, $C_{1-12}$ haloalkyl, alkylsulfonyl, $C_{1-12}$ haloalkylsulfonyl, arylsulfonyl, an aryl group or a heterocyclic group;
R1, R2, R4, R5, R7, R8, R9 and R10 each independently represents hydrogen, cyano, halogen, nitro, hydroxy, mercapto, amino, formyl, oxide, $C_{1-12}$ alkyl, $C_{1-12}$ haloalkyl, aryl-($C_{1-12}$)alkyl, heterocyclyl-($C_{1-12}$)alkyl, $C_{1-12}$ alkyl-O—, $C_{1-12}$ alkyl-NH—, $C_{1-12}$ alkyl-S—, $C_{1-12}$ alkyl-S(O)—, $C_{1-12}$ alkyl-S(O)$_2$—, $C_{1-12}$ alkyl-S(O)$_2$O—, $C_{1-12}$ haloalkyl-O—, $C_{1-12}$ haloalkyl-NH—, $C_{1-12}$ haloalkyl-S—, $C_{1-12}$ haloalkyl-S(O)—, $C_{1-12}$ haloalkyl-S(O)$_2$—, $C_{1-12}$ haloalkyl-S(=O)$_2$O—, aryl-O—, aryl-NH—, aryl-S—, aryl-S(O)—, aryl-S(O)$_2$—, aryl-S(O)$_2$O—, heterocyclyl-O—, heterocyclyl-NH—, heterocyclyl-S—, heterocyclyl-S(O)—, heterocyclyl-S(O)$_2$—, heterocyclyl-S(O)$_2$O—, $C_{1-12}$ alkyl-O—($C_{1-12}$)alkyl, $C_{1-12}$ alkyl-NH—($C_{1-12}$)alkyl, $C_{1-12}$ alkyl-S—($C_{1-12}$)alkyl, $C_{1-12}$ alkyl-S(O)—($C_{1-12}$)alkyl, $C_{1-12}$ alkyl-S(O)$_2$—($C_{1-12}$)alkyl, $C_{1-12}$ alkyl-S(O)$_2$O—($C_{1-12}$)alkyl, $C_{1-12}$ haloalkyl-O—($C_{1-12}$)alkyl, $C_{1-12}$ haloalkyl-NH—($C_{1-12}$)alkyl, $C_{1-12}$ haloalkyl-S—($C_{1-12}$)alkyl, $C_{1-12}$ haloalkyl-S(O)—($C_{1-12}$)alkyl, $C_{1-12}$ haloalkyl-S(O)$_2$—($C_{1-12}$)alkyl, $C_{1-12}$ haloalkyl-S(O)$_2$O—($C_{1-12}$)alkyl, aryl-O—($C_{1-12}$)alkyl, aryl-NH—($C_{1-12}$)alkyl, aryl-S—($C_{1-12}$)alkyl, aryl-S(O)—($C_{1-12}$)alkyl, aryl-S(O)$_2$—($C_{1-12}$)alkyl, aryl-S(O)$_2$O—($C_{1-12}$)alkyl, heterocyclyl-O—($C_{1-12}$)alkyl, heterocyclyl-NH—($C_{1-12}$)alkyl, heterocyclyl-S—($C_{1-12}$)alkyl, heterocyclyl-S(O)—($C_{1-12}$)alkyl, heterocyclyl-S(O)$_2$—($C_{1-12}$)alkyl, heterocyclyl-S(O)$_2$O—($C_{1-12}$)alkyl, $C_{3-8}$ cycloalkyl, $C_{3-8}$ cycloalkyl-($C_{1-12}$)alkyl-, $C_{3-8}$ halocycloalkyl, $C_{3-8}$ halocycloalkyl-($C_{1-12}$)alkyl-, $C_{2-12}$ alkenyl, $C_{2-12}$ haloalkenyl, $C_{2-12}$ alkynyl, $C_{2-12}$ haloalkynyl, di($C_{1-12}$ alkyl)amino, di($C_{1-12}$ haloalkyl)amino, $C_{3-36}$ trialkylsilyl, hydroxyimino($C_{1-12}$)alkyl, $C_{1-12}$ alkyl-O—N=($C_{1-12}$)alkyl, $C_{1-12}$ alkyl-NH—N=($C_{1-12}$)alkyl, $C_{1-12}$ alkyl-S—N=($C_{1-12}$)alkyl, $C_{1-12}$ alkyl-S(O)—N=($C_{1-12}$)alkyl, $C_{1-12}$ alkyl-S(O)$_2$—N=($C_{1-12}$)alkyl, $C_{1-12}$ alkyl-S(O)$_2$O—N=($C_{1-12}$)alkyl, $C_{1-12}$ haloalkyl-O—N=($C_{1-12}$)alkyl, $C_{1-12}$ haloalkyl-NH—N=($C_{1-12}$)alkyl, $C_{1-12}$ haloalkyl-S—N=($C_{1-12}$)alkyl, $C_{1-12}$ haloalkyl-S(O)—N=($C_{1-12}$)alkyl, $C_{1-12}$ haloalkyl-S(O)$_2$—N=($C_{1-12}$)alkyl, $C_{1-12}$ haloalkyl-S(O)$_2$O—N=($C_{1-12}$)alkyl, ($C_{1-12}$ alkoxy)carbonyl, ($C_{1-12}$ haloalkoxy)carbonyl, ($C_{3-8}$ cycloalkoxy)carbonyl, ($C_{3-8}$ halocycloalkoxy)carbonyl, $C_{3-8}$ cycloalkyl-($C_{1-12}$ alkoxy)carbonyl, $C_{3-8}$ halocycloalkyl-($C_{1-12}$ alkoxy)carbonyl, ($C_{1-12}$ alkyl)carbonyl, ($C_{1-12}$ haloalkyl)carbonyl, ($C_{3-8}$ cycloalkyl)carbonyl, ($C_{3-8}$ halocycloalkyl)carbonyl, $C_{3-8}$ cycloalkyl-($C_{1-12}$)alkyl-carbonyl, ($C_{3-8}$ halocycloalkyl)-($C_{1-12}$)alkyl-carbonyl, an aryl group, a heterocyclic group, sulfur pentafluoride, or one of the groups of Formulae (X1-1) to (X1-5):

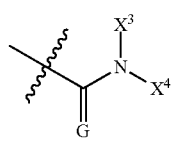

X1-1

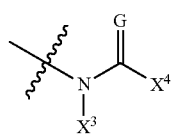

X1-2

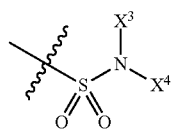

X1-3

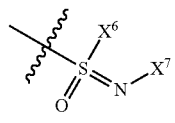

X1-4

-continued

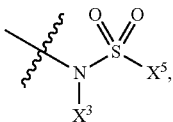

X1-5 wherein

G is as defined above;

$X^3$ independently represents hydrogen, cyano, halogen, nitro, hydroxy, mercapto, amino, formyl, $C_{1-12}$ alkyl, $C_{1-12}$ haloalkyl, aryl-$(C_{1-12})$alkyl, heterocyclyl-$(C_{1-12})$alkyl, $C_{1-12}$ alkyl-O—, $C_{1-12}$ alkyl-NH—, $C_{1-12}$ alkyl-S—, $C_{1-12}$ alkyl-S(O)—, $C_{1-12}$ alkyl-S(O)$_2$—, $C_{1-12}$ alkyl-S(O)$_2$O—, $C_{1-12}$ haloalkyl-O—, $C_{1-12}$ haloalkyl-NH—, $C_{1-12}$ haloalkyl-S—, $C_{1-12}$ haloalkyl-S(O)—, $C_{1-12}$ haloalkyl-S(O)$_2$O—, $C_{1-12}$ haloalkyl-S(O)$_2$O—, aryl-O—, aryl-NH—, aryl-S—, aryl-S(O)—, aryl-S(O)$_2$O—, aryl-S(O)$_2$O—, heterocyclyl-O—, heterocyclyl-NH—, heterocyclyl-S—, heterocyclyl-S(O)—, heterocyclyl-S(O)$_2$—, heterocyclyl-S(O)$_2$O—, $C_{1-12}$ alkyl-O—$(C_{1-12})$alkyl, $C_{1-12}$ alkyl-NH—$(C_{1-12})$alkyl, $C_{1-12}$ alkyl-S—$(C_{1-12})$alkyl, $C_{1-12}$ alkyl-S(O)—$(C_{1-12})$alkyl, $C_{1-12}$ alkyl-S(O)$_2$—$(C_{1-12})$alkyl, $C_{1-12}$ alkyl-S(O)$_2$O—$(C_{1-12})$alkyl, $C_{1-12}$ haloalkyl-O—$(C_{1-12})$alkyl, $C_{1-12}$ haloalkyl-NH—$(C_{1-12})$alkyl, $C_{1-12}$ haloalkyl-S—$(C_{1-12})$alkyl, $C_{1-12}$ haloalkyl-S(O)—$(C_{1-12})$alkyl, $C_{1-12}$ haloalkyl-S(O)$_2$—$(C_{1-12})$alkyl, $C_{1-12}$ haloalkyl-S(O)$_2$O—$(C_{1-12})$alkyl, aryl-O—$(C_{1-12})$alkyl, aryl-NH—$(C_{1-12})$alkyl, aryl-S—$(C_{1-12})$alkyl, aryl-S(O)—$(C_{1-12})$alkyl, aryl-S(O)$_2$—$(C_{1-12})$alkyl, aryl-S(O)$_2$O—$(C_{1-12})$alkyl, heterocyclyl-O—$(C_{1-12})$alkyl, heterocyclyl-NH—$(C_{1-12})$alkyl, heterocyclyl-S—$(C_{1-12})$alkyl, heterocyclyl-S(O)—$(C_{1-12})$alkyl, heterocyclyl-S(O)$_2$—$(C_{1-12})$alkyl, heterocyclyl-S(O)$_2$O—$(C_{1-12})$alkyl, $C_{3-8}$ cycloalkyl, $C_{3-8}$ cycloalkyl-$(C_{1-12})$alkyl-, $C_{3-8}$ halocycloalkyl, $C_{3-8}$ halocycloalkyl-$(C_{1-12})$alkyl-, $C_{2-12}$ alkenyl, $C_{2-12}$ haloalkenyl, $C_{2-12}$ alkynyl, $C_{2-12}$ haloalkynyl, di($C_{1-12}$ alkyl)amino, di($C_{1-12}$ haloalkyl)amino, $C_{3-36}$ trialkylsilyl, hydroxyimino($C_{1-12}$)alkyl, $C_{1-12}$ alkyl-O—N=$(C_{1-12})$alkyl, $C_{1-12}$ alkyl-NH—N=$(C_{1-12})$alkyl, $C_{1-12}$ alkyl-S—N=$(C_{1-12})$alkyl, $C_{1-12}$ alkyl-S(O)—N=$(C_{1-12})$alkyl, $C_{1-12}$ alkyl-S(O)$_2$—N=$(C_{1-12})$alkyl, $C_{1-12}$ alkyl-S(O)$_2$O—N=$(C_{1-12})$alkyl, $C_{1-12}$ haloalkyl-O—N=$(C_{1-12})$alkyl, $C_{1-12}$ haloalkyl-NH—N=$(C_{1-12})$alkyl, $C_{1-12}$ haloalkyl-S—N=$(C_{1-12})$alkyl, $C_{1-12}$ haloalkyl-S(O)—N=$(C_{1-12})$alkyl, $C_{1-12}$ haloalkyl-S(O)$_2$—N=$(C_{1-12})$alkyl, $C_{1-12}$ haloalkyl-S(O)$_2$O—N=$(C_{1-12})$alkyl, $(C_{1-12}$ alkoxy)carbonyl, $(C_{1-12}$ haloalkoxy)carbonyl, $(C_{3-8}$ cycloalkoxy)carbonyl, $(C_{3-8}$ halocycloalkoxy)carbonyl, $C_{3-8}$ cycloalkyl-$(C_{1-12}$ alkoxy)carbonyl, $C_{3-8}$ halocycloalkyl-$(C_{1-12}$ alkoxy)carbonyl, $(C_{1-12}$ alkyl)carbonyl, $(C_{1-12}$ haloalkyl)carbonyl, $(C_{3-8}$ cycloalkyl)carbonyl, $(C_{3-8}$ halocycloalkyl)carbonyl, $C_{3-8}$ cycloalkyl-$(C_{1-12})$alkyl-carbonyl, $C_{3-8}$ halocycloalkyl-$(C_{1-12})$alkyl-carbonyl, aryl-carbonyl, aryl-$(C_{1-12})$alkyl-carbonyl, heterocyclyl-carbonyl, heterocyclyl-$(C_{1-12})$alkyl-carbonyl, or sulfur pentafluoride, or a heterocyclic group, $X^4$ independently represents hydrogen, cyano, halogen, nitro, hydroxy, mercapto, amino, formyl, $C_{1-12}$ alkyl, $C_{1-12}$ haloalkyl, heterocyclyl-$(C_{1-12})$alkyl, $C_{1-12}$ alkyl-O—, $C_{1-12}$ alkyl-NH—, $C_{1-12}$ alkyl-S—, $C_{1-12}$ alkyl-S(O)—, $C_{1-12}$ alkyl-S(O)$_2$—, $C_{1-12}$ alkyl-S(O)$_2$O—, $C_{1-12}$ haloalkyl-O—, $C_{1-12}$ haloalkyl-NH—, $C_{1-12}$ haloalkyl-S—, $C_{1-12}$ haloalkyl-S(O)—, $C_{1-12}$ haloalkyl-S(O)$_2$—, $C_{1-12}$ haloalkyl-S(O)$_2$O—, aryl-O—, aryl-NH—, aryl-S—, aryl-S(O)—, aryl-S(O)$_2$—, aryl-S(O)$_2$O—, heterocyclyl-O—, heterocyclyl-NH—, heterocyclyl-S—, heterocyclyl-S(O)—, heterocyclyl-S(O)$_2$—, heterocyclyl-S(O)$_2$O—, $C_{1-12}$alkyl-O—$(C_{1-12})$alkyl, $C_{1-12}$ alkyl-NH—$(C_{1-12})$alkyl, $C_{1-12}$ alkyl-S—$(C_{1-12})$alkyl, $C_{1-12}$ alkyl-S(O)—$(C_{1-12})$alkyl, $C_{1-12}$ alkyl-S(O)$_2$—$(C_{1-12})$alkyl, $C_{1-12}$ alkyl-S(O)$_2$O—$(C_{1-12})$alkyl, $C_{1-12}$ haloalkyl-O—$(C_{1-12})$alkyl, $C_{1-12}$ haloalkyl-NH—$(C_{1-12})$alkyl, $C_{1-12}$ haloalkyl-S—$(C_{1-12})$alkyl, $C_{1-12}$ haloalkyl-S(O)—$(C_{1-12})$alkyl, $C_{1-12}$ haloalkyl-S(O)$_2$—$(C_{1-12})$alkyl, $C_{1-12}$ haloalkyl-S(O)$_2$O—$(C_{1-12})$alkyl, aryl-O—$(C_{1-12})$alkyl, aryl-NH—$(C_{1-12})$alkyl, aryl-S—$(C_{1-12})$alkyl, aryl-S(O)—$(C_{1-12})$alkyl, aryl-S(O)$_2$—$(C_{1-12})$alkyl, aryl-S(O)$_2$O—$(C_{1-12})$alkyl, heterocyclyl-O—$(C_{1-12})$alkyl, heterocyclyl-NH—$(C_{1-12})$alkyl, heterocyclyl-S—$(C_{1-12})$alkyl, heterocyclyl-S(O)—$(C_{1-12})$alkyl, heterocyclyl-S(O)$_2$—$(C_{1-12})$alkyl, heterocyclyl-S(O)$_2$O—$(C_{1-12})$alkyl, $C_{3-8}$ cycloalkyl, $C_{3-8}$ cycloalkyl-$(C_{1-12})$alkyl-, $C_{3-8}$ halocycloalkyl, $C_{3-8}$ halocycloalkyl-$(C_{1-12})$alkyl-, $C_{2-12}$ alkenyl, $C_{2-12}$ haloalkenyl, $C_{2-12}$ alkynyl, $C_{2-12}$ haloalkynyl, di($C_{1-12}$ alkyl)amino, di($C_{1-12}$ haloalkyl)amino, $C_{3-36}$ trialkylsilyl, hydroxyimino($C_{1-12}$)alkyl, $C_{1-12}$ alkyl-O—N=$(C_{1-12})$alkyl, $C_{1-12}$ alkyl-NH—N=$(C_{1-12})$alkyl, $C_{1-12}$ alkyl-S—N=$(C_{1-12})$alkyl, $C_{1-12}$ alkyl-S(O)—N=$(C_{1-12})$alkyl, $C_{1-12}$ alkyl-S(O)$_2$—N=$(C_{1-12})$alkyl, $C_{1-12}$ alkyl-S(O)$_2$O—N=$(C_{1-12})$alkyl, $C_{1-12}$ haloalkyl-O—N=$(C_{1-12})$alkyl, $C_{1-12}$ haloalkyl-NH—N=$(C_{1-12})$alkyl, $C_{1-12}$ haloalkyl-S—N=$(C_{1-12})$alkyl, $C_{1-12}$ haloalkyl-S(O)—N=$(C_{1-12})$alkyl, $C_{1-12}$ haloalkyl-S(O)$_2$—N=$(C_{1-12})$alkyl, $C_{1-12}$ haloalkyl-S(O)$_2$O—N=$(C_{1-12})$alkyl, $(C_{1-12}$ alkoxy)carbonyl, $(C_{1-12}$ haloalkoxy)carbonyl, $(C_{3-8}$ cycloalkoxy)carbonyl, $(C_{3-8}$ halocycloalkoxy)carbonyl, $C_{3-8}$ cycloalkyl-$(C_{1-12}$ alkoxy)carbonyl, $C_{3-8}$ halocycloalkyl-$(C_{1-12}$ alkoxy)carbonyl, $(C_{1-12}$ alkyl)carbonyl, $(C_{1-12}$ haloalkyl)carbonyl, $(C_{3-8}$ cycloalkyl)carbonyl, $(C_{3-8}$ halocycloalkyl)carbonyl, $C_{3-8}$ cycloalkyl-$(C_{1-12})$alkyl-carbonyl, $C_{3-8}$ halocycloalkyl-$(C_{1-12})$alkyl-carbonyl, aryl-carbonyl, heterocyclyl-carbonyl, aryl-$(C_{1-12})$alkyl-carbonyl, heterocyclyl-$(C_{1-12})$alkyl-carbonyl, or sulfur pentafluoride, an aryl group or a heterocyclic group, $X^5$ independently represents hydrogen, cyano, halogen, nitro, hydroxy, mercapto, amino, formyl, $C_{1-12}$ alkyl, $C_{1-12}$ haloalkyl, aryl-$(C_{1-12})$alkyl, heterocyclyl-$(C_{1-12})$alkyl, $C_{1-12}$ alkyl-NH—, $C_{1-12}$ alkyl-S—, $C_{1-12}$ alkyl-S(O)—, $C_{1-12}$ alkyl-S(O)$_2$—, $C_{1-12}$ alkyl-S(O)$_2$O—, $C_{1-12}$ haloalkyl-O—, $C_{1-12}$ haloalkyl-NH—, $C_{1-12}$ haloalkyl-S—, $C_{1-12}$ haloalkyl-S(O)—, $C_{1-12}$ haloalkyl-S(O)$_2$—, $C_{1-12}$ haloalkyl-S(O)$_2$O—, aryl-O—, aryl-NH—, aryl-S—, aryl-S(O)—, aryl-S(O)$_2$—, aryl-S(O)$_2$O—, heterocyclyl-O—, heterocyclyl-NH—, heterocyclyl-S—, heterocyclyl-S(O)—, heterocyclyl-S(O)$_2$—, heterocyclyl-S(O)$_2$O—, $C_{1-12}$ alkyl-O—$(C_{1-12})$alkyl, $C_{1-12}$ alkyl-NH—$(C_{1-12})$alkyl, $C_{1-12}$ alkyl-S—$(C_{1-12})$alkyl, $C_{1-12}$ alkyl-S(O)—$(C_{1-12})$alkyl, $C_{1-12}$ alkyl-S(O)$_2$—$(C_{1-12})$alkyl, $C_{1-12}$ alkyl-S(O)$_2$O—$(C_{1-12})$alkyl, $C_{1-12}$ haloalkyl-O—$(C_{1-12})$alkyl, $C_{1-12}$ haloalkyl-NH—$(C_{1-12})$alkyl, $C_{1-12}$ haloalkyl-S—$(C_{1-12})$alkyl, $C_{1-12}$ haloalkyl-S(O)—$(C_{1-12})$alkyl, $C_{1-12}$ haloalkyl-S(O)$_2$—$(C_{1-12})$ alkyl, $C_{1-12}$ haloalkyl-$S(O)_2O$—$(C_{1-12})$alkyl, aryl-O—$(C_{1-12})$alkyl, aryl-NH—$(C_{1-12})$alkyl, aryl-S—$(C_{1-12})$alkyl, aryl-S(O)—$(C_{1-12})$alkyl, aryl-$S(O)_2$—$(C_{1-12})$alkyl, aryl-$S(O)_2O$—$(C_{1-12})$alkyl, heterocyclyl-O—$(C_{1-12})$alkyl, heterocyclyl-NH—$(C_{1-12})$alkyl, heterocyclyl-S—$(C_{1-12})$alkyl, heterocyclyl-S(O)—$(C_{1-12})$alkyl, heterocyclyl-$S(O)_2$—$(C_{1-12})$alkyl, heterocyclyl-$S(O)_2O$—$(C_{1-12})$alkyl, $C_{3-8}$ cycloalkyl, $C_{3-8}$ cycloalkyl-$(C_{1-12})$alkyl-, $C_{3-8}$ halocycloalkyl, $C_{3-8}$ halocycloalkyl-$(C_{1-12})$alkyl-, $C_{2-12}$ alkenyl, $C_{2-12}$ haloalkenyl, $C_{2-12}$ alkynyl, $C_{2-12}$ haloalkynyl, di($C_{1-12}$ alkyl)amino, di($C_{1-12}$haloalkyl)amino, $C_{3-36}$ trialkylsilyl, hydroxyimino($C_{1-12}$)alkyl, $C_{1-12}$ alkyl-O—N═$(C_{1-12})$alkyl, $C_{1-12}$ alkyl-NH—N═$(C_{1-12})$alkyl, $C_{1-12}$ alkyl-S—N═$(C_{1-12})$alkyl, $C_{1-12}$ alkyl-S(O)—N═$(C_{1-12})$alkyl, $C_{1-12}$ alkyl-$S(O)_2$—N═$(C_{1-12})$alkyl, $C_{1-12}$ alkyl-$S(O)_2O$—N═$(C_{1-12})$alkyl, $C_{1-12}$ haloalkyl-O—N═$(C_{1-12})$alkyl, $C_{1-12}$ haloalkyl-NH—N═$(C_{1-12})$alkyl, $C_{1-12}$ haloalkyl-S—N═$(C_{1-12})$alkyl, $C_{1-12}$ haloalkyl-S(O)—N═$(C_{1-12})$alkyl, $C_{1-12}$ haloalkyl-$S(O)_2$—N═$(C_{1-12})$alkyl, $C_{1-12}$ haloalkyl-$S(O)_2O$—N═$(C_{1-12})$alkyl, $(C_{1-12}$ alkoxy)carbonyl, $(C_{1-12}$ haloalkoxy)carbonyl, $(C_{3-8}$ cycloalkoxy)carbonyl, $(C_{3-8}$ halocycloalkoxy)carbonyl, $C_{3-8}$ cycloalkyl-$(C_{1-12}$ alkoxy)carbonyl, $C_{3-8}$ halocycloalkyl-$(C_{1-12}$ alkoxy)carbonyl, $(C_{1-12}$ alkyl)carbonyl, $(C_{1-12}$haloalkyl)carbonyl, $(C_{3-8}$ cycloalkyl)carbonyl, $(C_{3-8}$ halocycloalkyl)carbonyl, $C_{3-8}$ cycloalkyl-$(C_{1-12})$alkyl-carbonyl, $C_{3-8}$ halocycloalkyl-$(C_{1-12})$alkyl-carbonyl, aryl-carbonyl, aryl-$(C_{1-12})$alkyl-carbonyl, heterocyclyl-carbonyl, heterocyclyl-$(C_{1-12})$alkyl-carbonyl, or sulfur pentafluoride, an aryl group, or $X^3$ and $X^4$ optionally forms a heterocycle together with the nitrogen atom, carbon atom, oxygen atom or sulfur atom to which they are bonded, or $X^3$ and $X^5$ optionally forms a heterocycle together with the nitrogen atom, carbon atom, oxygen atom or sulfur atom to which they are bonded, $X^6$ represents hydrogen, $C_{1-12}$ alkyl, $C_{1-12}$ haloalkyl, $C_{3-8}$ cycloalkyl, $C_{2-12\ alkenyl}$, $C_{2-12}$ haloalkenyl, an aryl group, a heterocyclic group, aryl-$(C_{1-12})$alkyl or heterocyclyl-$(C_{1-12})$alkyl, $X^7$ represents hydrogen, nitro, cyano, formyl, $X^8$-carbonyl or $X^8$-oxycarbonyl, and wherein $X^8$ independently has the same meaning as $X^6$ defined above;

R12 has the same meaning as $X^3$ defined above;

R13 has the same meaning as $X^4$ defined above;

m represents an integer of 1 to 4;

R14 has the same meaning as $X^3$ defined above; and

R15 represents —C(═G)—$X^5$, and wherein G and $X^5$ are as defined above.

* * * * *